US007816083B2

(12) United States Patent
Grupe et al.

(10) Patent No.: US 7,816,083 B2
(45) Date of Patent: Oct. 19, 2010

(54) GENETIC POLYMORPHISMS ASSOCIATED WITH NEURODEGENERATIVE DISEASES, METHODS OF DETECTION AND USES THEREOF

(75) Inventors: Andrew Grupe, Orinda, CA (US); Yonghong Li, Palo Alto, CA (US)

(73) Assignee: Celera Corporation, Alameda, CA (US)

( * ) Notice: Subject to any disclaimer, the term of this patent is extended or adjusted under 35 U.S.C. 154(b) by 29 days.

(21) Appl. No.: 12/151,163

(22) Filed: May 1, 2008

(65) Prior Publication Data

US 2008/0286796 A1 Nov. 20, 2008

Related U.S. Application Data

(60) Provisional application No. 60/927,864, filed on May 3, 2007.

(51) Int. Cl.
*C12Q 1/68* (2006.01)
*C12P 19/34* (2006.01)

(52) U.S. Cl. .......................................... 435/6; 435/91.2

(58) Field of Classification Search ....................... None
See application file for complete search history.

(56) References Cited

U.S. PATENT DOCUMENTS

2004/0265849 A1 12/2004 Cargill et al.
2005/0123524 A1 6/2005 Morimoto et al.

OTHER PUBLICATIONS

Hegele R.A. Arterioscler Thromb Vasc Biol. 2002;22:1058-1061.*
Hacker UT et al. Gut; May 1997; vol. 40, p. 623-627.*
Lucentini J. The Scientist, Dec 20, 2004, p. 20.*
'Datta Changes that Occur between Builds', from The SNP FAQ Archive, www.ncbi.nlm.nih.gov, printed Oct. 28, 2008, pp. 1-3.*
Tedde A. et al. Neuroscience Letters (2010), pritned pp. 1-3 from www.elsevier.com.*
Chapuis, J., et al., "Association Study of the NEDD9 Gene with the Risk of Developing Alzheimer's and Parkinson's Disease," Human Molecular Genetics, vol. 17, No. 18, pp. 2863-2867, Jun. 25, 2008.
Li, Y., et al., "Evidence that Common Variation in NEDD9 is Associated with Susceptibility to Late-Onset Alzheimer's and Parkinson's Disease," Human Molecular Genetics, vol. 17, No. 5, pp. 759-767, Dec. 6, 2007.
Bertram L., et al., "Meta-Analysis of All Published PD Association Studies (Case-Control Only) RS760678," [http://www.pdgene.org/meta.asp?geneID=294], Available at: http://www.pdgene.org/. Accessed on Aug. 31, 2009.
Bertram L., et al., "Meta-analysis of All Published AD Association Studies (Case-Control Only) RS760678," [http://www.alzgene.org/meta.asp?geneID=589], Available at http://www.alzgene.org. Accessed on Aug. 31, 2009.
NCBI Database Submission ss44758870 [online] Jul. 19, 2005, <URL:htp://www.ncbi.nlm.nih.gov/SNP/snp_ss.cgi?subsnp_id=44758870>.
International Search Report and Written Opinion dated Sep. 25, 2008.

* cited by examiner

*Primary Examiner*—Stephen Kapushoc

(57) ABSTRACT

The present invention is based on the discovery of genetic polymorphisms that are associated with neurodegenerative disease, particularly Alzheimer's disease and Parkinson's disease. In particular, the present invention relates to nucleic acid molecules containing the polymorphisms, variant proteins encoded by such nucleic acid molecules, reagents for detecting the polymorphic nucleic acid molecules and proteins, and methods of using the nucleic acid and proteins as well as methods of using reagents for their detection.

32 Claims, 1 Drawing Sheet

Figure 1

Exemplary genomic sequence surrounding rs760678 (hCV10039123) (S = G/C):

AGTTCTATAAAGTTACTAATAGGGAAATATATAAAGTGGAAAAAGCTGTTTATAAAAGT
CTGAGTAAATGACTATATATGTACATAGATATGATTTTGAAAAGAACTTAATAGGATAC
ACAAACATTAATAAGAATGCTTATTTCTGAGTAATTAAGGGGCGATTTTGTTGTATTCCT
TATACATTTTAAATGTTTTAATCCAAAATTTTTTACAGTGAGTATGTATTATCTTTTGTCA
TCTGAAAAATAACACAAATAAATAAGTTAAAATAGAATTAACTGAATTTGTACAAATCG
GG
S
AAGATAAGGGTGCCCCTGTTTTCTCTATTCATGCCACCGCTACCACTGTTTAGACTATTG
GTCATAATTTTTTTCTCACCTGCAAATATCTCCTTGCCTGTTACTTTCTCTTCAGTTTCTTT
CCCCATTATTCATTCTCTCTGAAAATATTAGGTTGGAGCAAACGTTAATTGCATTTTTGC
ATTGTTGGAATTTGCTGTTTGATATTGGAATACATTCTTAAATAAATGTGGTTATGTTAT
ACATCATTTTAATGGGCATTTCTCGCTTTATGTTTTTTGCTAATGACTTACTACTTG
(SEQ ID NO:24)

GENETIC POLYMORPHISMS ASSOCIATED WITH NEURODEGENERATIVE DISEASES, METHODS OF DETECTION AND USES THEREOF

FIELD OF THE INVENTION

The present invention is in the field of neurodegenerative disease diagnosis and therapy. In particular, the present invention relates to specific single nucleotide polymorphisms (SNPs) in the human genome, and their association with neurodegenerative disease, particularly Alzheimer's disease and Parkinson's disease, and related pathologies. Based on differences in allele frequencies in the neurodegenerative disease patient population relative to normal individuals, the naturally-occurring SNPs disclosed herein can be used as targets for the design of diagnostic reagents and the development of therapeutic agents, as well as for disease association and linkage analysis. In particular, the SNPs of the present invention are useful for identifying an individual who is at an increased or decreased risk of developing neurodegenerative disease and for early detection of the disease, for providing clinically important information for the prevention and/or treatment of neurodegenerative disease, and for screening and selecting therapeutic agents. The SNPs disclosed herein are also useful for human identification applications. Methods, assays, kits, and reagents for detecting the presence of these polymorphisms and their encoded products are provided.

BACKGROUND OF THE INVENTION

Neurodegenerative Diseases

A variety of central nervous system disorders (neurodegenerative diseases) are associated with aging. Neurodegenerative diseases are typically characterized by a gradual and progressive loss of neural tissue or nerve cells. These diseases, directly or indirectly, affect millions of people worldwide. The number of individuals affected by neurodegenerative diseases is anticipated to grow attendant with the increase in human life expectancy.

Specific diseases exemplifying this class of disorders include: age-related dementia, such as Alzheimer's disease (AD); leukodystrophies, such as adrenoleukodystrophy, metachromatic leukodystrophy, Krabbe disease (globoid cell leukodystrophy), Canavan disease, Alexander disease, Pelizaeus-Merzbacher Disease, and the like; and others such as Parkinson's disease (PD), neuronal ceroid lipofuscinoses, amyotrophic lateral sclerosis (ALS, or Lou Gehrig's disease), Huntington's disease (HD), dentatorubral-pallidoluysian atrophy (DRPLA), stroke and the like.

PD affects 1-2% of people over the age of 50, and 10-15% of those over the age of 80. Huntington's Disease and ALS each afflict approximately 30,000 in the United States. Stroke is the leading cause of neurological impairment, with half a million new stroke victims surviving each year with some degree of permanent neurological damage.

AD (described in greater detail in the following section) alone affects 20 million people worldwide. AD is the fourth leading cause of death in industrialized societies, afflicting 5-11% of the population over the age of 65 and 30% of those over the age of 85. AD is fast becoming the paramount healthcare problem as the world's geriatric population continues to grow.

Alzheimer's Disease

Alzheimer's disease (AD) is the most significant and common cause of dementia in developed countries, accounting for 60% or more of all cases of dementia. AD is a progressive neurodegenerative disorder characterized clinically by memory loss of subtle onset, followed by a slowly progressive dementia that has a course of several years. Brain pathology of AD is characterized by gross, diffuse atrophy of the cerebral cortex with secondary enlargement of the ventricular system. Microscopically, there are neuritic plaques containing Aβ amyloid, silver-staining neurofibrillary tangles in neuronal cytoplasm, and accumulation of Aβ amyloid in arterial walls of cerebral blood vessels. A definite diagnosis of AD can only occur at autopsy, where the presence of amyloid plaques and neurofibrillary tangles is confirmed.

The frequency of AD increases with each decade of adult life, reaching 20-40% of the population over the age of 85. Because more and more people will live into their 80's and 90's, the number of patients is expected to triple over the next 20 years. More than 4 million people suffer from AD in the USA, where 800,000 deaths per year are associated with AD. It is estimated that the cost of AD in the USA is $80 billion to $100 billion a year in medical care, personal caretaking and lost productivity. AD also puts a heavy emotional toll on family members and caregivers: about 2.7 million people care for AD patients in the USA. AD patients live for 7 to 10 years after diagnosis and spend an average of 5 years under care either at home or in a nursing home.

Despite the high prevalence of AD today and its expected prevalence increase in an aging population, there are currently no diagnostic tests available that determine the cause of dementia and adequately differentiate between AD and other types of dementias. A diagnostic test that, for example, enables physicians to identify AD early in the disease process, or identify individuals who are at high risk of developing the disease, will provide the option to intervene at an early stage in the disease process. Early intervention in disease processes does generally result in better treatment results by delaying disease onset or progression compared to later intervention.

AD is presumed to have a genetic component, as evidenced by an increased risk for AD among first degree relatives of affected individuals. So far, three genes have been identified in patients with early onset AD that lead to the less common, dominantly inherited form of dementia. Mutations in the three genes, beta-amyloid precursor protein (Goate et al., *Nature* 1991, 349:704-706), presenilin 1 (Sherrington et al., *Nature* 1995, 375:754-760), and presenilin 2 (Levy-Lahad et al., *Science* 1996, 269:973-977) lead to an increase in the production of long amyloid beta (Aβ42), the main component in amyloid plaques. Although early onset AD makes up less than 5% of all AD cases, the identification of these genes has contributed substantially to the understanding of the disease process.

Late onset Alzheimer's disease (LOAD), the much more common form of this dementia, is inherited in a non-Mendelian pattern and involves genetic susceptibility factors and environmental factors. Early genetic studies of AD demonstrated association and linkage to the same region on chromosome 19 containing the ApoE gene (Schellenberg et al., *J. Neurogenet.* 1987, 4:97-108, Pericak-Vance et al., *Am. J. Hum. Gen.* 1991, 48:1034-1050). Three common alleles were identified for the ApoE gene, ϵ2, ϵ3, ϵ4. The ϵ4 allele frequency is increased to 50% in affected individuals vs. 14% in controls (Corder et al., *Science* 1993, 281:921-923). Although there is strong association with the ApoE-ϵ4 allele, which has been replicated in many studies, most investigators consider the ApoE-ϵ4 allele to be neither necessary nor sufficient for the development of AD. ApoE is considered a major risk factor, but ApoE testing does not provide enough sensitivity and specificity for use as an independent diagnostic test and therefore is not recommended as a diagnostic marker for the prediction of AD (National Institute on Aging/Alzheimer's Association Working Group, 1996).

Thus, there is a definite need for novel diagnostic markers that, for example, enable the detection of AD at an early stage of the disease or that identify individuals who are at high risk of developing AD. For example, the availability of a genetic test may provide a non-invasive method to assess an individual's risk for developing AD. Furthermore, there is an urgent need for new and improved treatments for AD to prevent or delay the onset of the disease, or to reverse or slow down disease progression after onset.

Parkinson's Disease

Parkinson's disease (PD) is the second most prevalent neurodegenerative disease after AD, affecting as many as one million individuals in the US. PD pathology results from a loss of dopaminergic neurons in the substantia nigra and is characterized by resting tremor, rigidity, bradykinesia and postural instability. Susceptibility to PD depends on both environmental and genetic factors, as familial aggregation of the disease has been well documented, however risk factors for PD remain largely unknown.

SNPs

The genomes of all organisms undergo spontaneous mutation in the course of their continuing evolution, generating variant forms of progenitor genetic sequences (Gusella, *Ann. Rev. Biochem.* 55, 831-854 [1986]). A variant form may confer an evolutionary advantage or disadvantage relative to a progenitor form or may be neutral. In some instances, a variant form confers an evolutionary advantage to the species and is eventually incorporated into the DNA of many or most members of the species and effectively becomes the progenitor form. Additionally, the effects of a variant form may be both beneficial and detrimental, depending on the circumstances. For example, a heterozygous sickle cell mutation confers resistance to malaria, but a homozygous sickle cell mutation is usually lethal. In many cases, both progenitor and variant forms survive and co-exist in a species population. The coexistence of multiple forms of a genetic sequence gives rise to genetic polymorphisms, including SNPs.

Approximately 90% of all polymorphisms in the human genome are SNPs. SNPs are single base positions in DNA at which different alleles, or alternative nucleotides, exist in a population. The SNP position (interchangeably referred to herein as SNP, SNP site, SNP locus, SNP marker, or marker) is usually preceded by and followed by highly conserved sequences of the allele (e.g., sequences that vary in less than 1/100 or 1/1000 members of the populations). An individual may be homozygous or heterozygous for an allele at each SNP position. A SNP can, in some instances, be referred to as a "cSNP" to denote that the nucleotide sequence containing the SNP is an amino acid coding sequence.

A SNP may arise from a substitution of one nucleotide for another at the polymorphic site. Substitutions can be transitions or transversions. A transition is the replacement of one purine nucleotide by another purine nucleotide, or one pyrimidine by another pyrimidine. A transversion is the replacement of a purine by a pyrimidine, or vice versa. A SNP may also be a single base insertion or deletion variant referred to as an "indel" (Weber et al., "Human diallelic insertion/deletion polymorphisms," *Am. J. Hum. Genet.* 71 [4]:854-62 [October 2002]).

A synonymous codon change, or silent mutation/SNP (terms such as "SNP," "polymorphism," "mutation," "mutant," "variation," and "variant" are used herein interchangeably), is one that does not result in a change of amino acid due to the degeneracy of the genetic code. A substitution that changes a codon coding for one amino acid to a codon coding for a different amino acid (i.e., a non-synonymous codon change) is referred to as a missense mutation. A nonsense mutation results in a type of non-synonymous codon change in which a stop codon is formed, thereby leading to premature termination of a polypeptide chain and a truncated protein. A read-through mutation is another type of non-synonymous codon change that causes the destruction of a stop codon, thereby resulting in an extended polypeptide product. While SNPs can be bi-, tri-, or tetra-allelic, the vast majority of SNPs are bi-allelic, and are thus often referred to as "bi-allelic markers," or "di-allelic markers."

As used herein, references to SNPs and SNP genotypes include individual SNPs and/or haplotypes, which are groups of SNPs that are generally inherited together. Haplotypes can have stronger correlations with diseases or other phenotypic effects compared with individual SNPs, and therefore may provide increased diagnostic accuracy in some cases (Stephens et al., *Science* 293, 489-493 [20 Jul. 2001]).

Causative SNPs are those SNPs that produce alterations in gene expression or in the expression, structure, and/or function of a gene product, and therefore are most predictive of a possible clinical phenotype. One such class includes SNPs falling within regions of genes encoding a polypeptide product, i.e. cSNPs. These SNPs may result in an alteration of the amino acid sequence of the polypeptide product (i.e., non-synonymous codon changes) and give rise to the expression of a defective or other variant protein. Furthermore, in the case of nonsense mutations, a SNP may lead to premature termination of a polypeptide product. Such variant products can result in a pathological condition, e.g. genetic disease. Examples of genes in which a SNP within a coding sequence causes a genetic disease include sickle cell anemia and cystic fibrosis.

Causative SNPs do not necessarily occur in coding regions; causative SNPs can occur in, for example, any genetic region that can ultimately affect the expression, structure, and/or activity of the protein encoded by a nucleic acid. Such genetic regions include, for example, those involved in transcription, such as SNPs in transcription factor binding domains, SNPs in promoter regions, in areas involved in transcript processing, such as SNPs at intron-exon boundaries that may cause defective splicing, or SNPs in mRNA processing signal sequences such as polyadenylation signal regions. Some SNPs that are not causative SNPs nevertheless are in close association with, and therefore segregate with, a disease-causing sequence. In this situation, the presence of a SNP correlates with the presence of, or predisposition to, or an increased risk in developing the disease. These SNPs, although not causative, are nonetheless also useful for diagnostics, disease predisposition screening, and other uses.

An association study of a SNP and a specific disorder involves determining the presence or frequency of the SNP allele in biological samples from individuals with the disorder of interest, such as neurodegenerative disease, and comparing the information to that of controls (i.e., individuals who do not have the disorder; controls may be also referred to as "healthy" or "normal" individuals) who are preferably of similar age and race. The appropriate selection of patients and controls is important to the success of SNP association studies. Therefore, a pool of individuals with well-characterized phenotypes is extremely desirable.

A SNP may be screened in diseased tissue samples or any biological sample obtained from a diseased individual, and compared to control samples, and selected for its increased (or decreased) occurrence in a specific pathological condition, such as pathologies related to neurodegenerative disease. Once a statistically significant association is established between one or more SNPs and a pathological condition (or other phenotype) of interest, then the regions around the SNPs can optionally be thoroughly screened to identify the causative genetic locus or sequences (e.g., the causative SNP/mutation, gene, regulatory region, etc.) that influences the pathological condition or phenotype. Association studies may be conducted within the general population and are not limited to studies performed on related individuals in affected families (linkage studies).

Clinical trials have shown that patient response to treatment with pharmaceuticals is often heterogeneous. There is a continuing need to improve pharmaceutical agent design and therapy. In that regard, SNPs can be used to identify patients most suited to therapy with particular pharmaceutical agents (this is often termed "pharmacogenomics"). Similarly, SNPs can be used to exclude patients from certain treatments due to the patient's increased likelihood of developing toxic side effects or their likelihood of not responding to the treatment. Pharmacogenomics can also be used in pharmaceutical research to assist the drug development and selection process (Linder et al., *Clinical Chemistry* 43, 254 [1997]; Marshall, *Nature Biotechnology* 15, 1249 [1997]; International Patent Application WO 97/40462, Spectra Biomedical; and Schafer et al., *Nature Biotechnology* 16, 3 [1998]).

SUMMARY OF THE INVENTION

The present invention relates to the identification of novel SNPs, unique combinations of such SNPs, and haplotypes of SNPs that are associated with neurodegenerative disease, particularly AD and PD, and related neurological pathologies. The polymorphisms disclosed herein are directly useful as targets for the design of diagnostic reagents, as druggable targets in the development of therapeutic agents for use in the treatment and diagnosis of neurodegenerative disease and also other neurological pathologies.

Based on the identification of SNPs associated with neurodegenerative disease, the present invention also provides methods of detecting these variants as well as the design and preparation of detection reagents needed to accomplish this task. The invention specifically provides, for example, novel SNPs in genetic sequences involved in neurodegenerative disease, isolated nucleic acid molecules (including, for example, DNA or RNA molecules) containing these SNPs, variant proteins encoded by nucleic acid molecules containing SNPs, antibodies to the encoded variant proteins, computer-based and data storage systems containing the novel SNP information, methods of detecting these SNPs in a test sample, methods of identifying individuals who have an altered (i.e., increased or decreased) risk of developing neurodegenerative disease based on the presence or absence of one or more particular nucleotides (alleles) at one or more SNP sites disclosed herein or the detection of one or more encoded variant products (e.g., variant mRNA transcripts or variant proteins), methods of identifying individuals who are more or less likely to respond to a treatment (or more or less likely to experience undesirable side effects from a treatment, etc.), methods of screening for compounds useful in the treatment of a disorder associated with a variant gene/protein, compounds identified by these methods, methods of treating disorders mediated by a variant gene/protein, methods of using the novel SNPs of the present invention for human identification, etc.

In Table 1, the present invention provides gene information, genomic sequences (SEQ ID NO:1), and genomic-based context sequences (SEQ ID NOS:2-11) that contain the SNPs of the present invention, and extensive SNP information that includes observed alleles, allele frequencies, populations/ethnic groups in which alleles have been observed, and information about the type of SNP. The genomic sequences (SEQ ID NO:1) and genomic-based context sequences (SEQ ID NOS: 2-11) are provided in the Sequence Listing.

In a specific embodiment of the present invention, SNPs which occur naturally in the human genome are provided as isolated nucleic acid molecules. These SNPs are associated with neurodegenerative disease such that they can have a variety of uses in the diagnosis and/or treatment of neurodegenerative disease and related pathologies. One aspect of the present invention relates to an isolated nucleic acid molecule comprising a nucleotide sequence in which at least one nucleotide is a SNP disclosed in Table 1. In an alternative embodiment, a nucleic acid of the invention is an amplified polynucleotide, which is produced by amplification of a SNP-containing nucleic acid template.

In yet another embodiment of the invention, a reagent for detecting a SNP in the context of its naturally-occurring flanking nucleotide sequences (which can be, e.g., either DNA or mRNA) is provided. In particular, such a reagent may be in the form of, for example, a hybridization probe or an amplification primer that is useful in the specific detection of a SNP of interest.

Various embodiments of the invention also provide kits comprising SNP detection reagents, and methods for detecting the SNPs disclosed herein by employing detection reagents. In a specific embodiment, the present invention provides for a method of identifying an individual having an increased or decreased risk of developing neurodegenerative disease by detecting the presence or absence of one or more SNP alleles disclosed herein. In another embodiment, a method for diagnosis of neurodegenerative disease by detecting the presence or absence of one or more SNP alleles disclosed herein is provided.

The nucleic acid molecules of the invention can be inserted in an expression vector, such as to produce a variant protein in a host cell. Thus, the present invention also provides for a vector comprising a SNP-containing nucleic acid molecule, genetically-engineered host cells containing the vector, and methods for expressing a recombinant variant protein using such host cells.

In another specific embodiment, the host cells, SNP-containing nucleic acid molecules, and/or variant proteins can be used as targets in a method for screening and identifying therapeutic agents or pharmaceutical compounds useful in the treatment of neurodegenerative disease and other neurological pathologies.

One aspect of this invention is a method for treating neurodegenerative disease in a human subject wherein said subject harbors a SNP or gene identified in Table 1, which method comprises administering to said subject a therapeutically or prophylactically effective amount of one or more agents counteracting the effects of the disease, such as by inhibiting (or stimulating) the activity of the gene identified in Table 1.

Another aspect of this invention is a method for identifying an agent useful in therapeutically or prophylactically treating neurodegenerative disease in a human subject wherein said subject harbors a SNP or gene identified in Table 1, which method comprises contacting the gene, transcript, or encoded protein with a candidate agent under conditions suitable to allow formation of a binding complex between the gene, transcript, or encoded protein and the candidate agent and detecting the formation of the binding complex, wherein the presence of the complex identifies said agent.

Another aspect of this invention is a method for treating neurodegenerative disease in a human subject, which method comprises:

(i) determining that said subject harbors a SNP or gene identified in Table 1, and (ii) administering to said subject a therapeutically or prophylactically effective amount of one or more agents counteracting the effects of the disease.

Another aspect of the invention is a method for selecting a human with neurodegenerative disease for a drug treatment or for selecting a drug treatment for a given human having neurodegenerative disease, the method comprising determining whether said human harbors a NEDD9 SNP, and administering an appropriate drug to said human in an amount to effect treatment of the neurodegenerative disease. In certain embodiments, selecting a human comprises predicting whether the human is likely to positively respond to the drug treatment. In exemplary embodiments, the NEDD9 SNP is rs760678 (the identifier "rs760678" is a publicly known reference identification number for the SNP, and this SNP may be interchangeably referred to herein by identification number hCV10039123). Determining whether said human harbors a NEDD9 SNP can comprise, for example, determining which nucleotide is present at SNP rs760678 (which may be referred to as "genotyping" SNP rs760678). In certain specific embodiment, determining whether said human harbors a NEDD9 SNP comprises determining whether a 'G' nucleotide (based on the sequence orientation of SEQ ID NOS:2 and 24), or the complement thereof, is present at SNP rs760678. In other exemplary embodiments, the NEDD9 SNP is a SNP disclosed in Table 1, Table 5, and/or Table 6. In further embodiments, the drug is a drug selected from Tables 8-10, or a drug that targets a NEDD9-binding protein disclosed in Table 7. In yet further exemplary embodiments, a drug selected from Tables 8-10, or a drug that targets a NEDD9-binding protein disclosed in Table 7, is administered to a human having a 'G' nucleotide (based on the sequence orientation of SEQ ID NOS:2 and 24), or the complement thereof, at SNP rs760678.

Another aspect of this invention is a method for identifying an agent useful for therapeutically or prophylactically treating neurodegenerative disease in a human subject harboring the NEDD9 SNP, said method comprising contacting a gene, transcript, or encoded protein of NEDD9 with a candidate agent under conditions suitable to allow formation of a binding complex between the gene, transcript, or encoded protein of NEDD9 and the candidate agent and detecting the formation of the binding complex, wherein the presence of the complex identifies said agent.

Another aspect of the invention is a method of treating a human having neurodegenerative disease, comprising administering to said human an agent which modulates (e.g., inhibits) the function of NEDD9, thereby ameliorating the symptoms of neurodegenerative disease. In certain specific embodiments, the human has a 'G' nucleotide (based on the sequence orientation of SEQ ID NOS:2 and 24), or the complement thereof, at SNP rs760678.

Another aspect of the invention is a method of treating a human having neurodegenerative disease, comprising administering to said human an agent which modulates (e.g., inhibits) the function of FAK, integrin, or src protein, which in turn modulates (e.g., inhibits) the function of NEDD9, thereby ameliorating the symptoms of neurodegenerative disease. In certain specific embodiments, the human has a 'G' nucleotide (based on the sequence orientation of SEQ ID NOS:2 and 24), or the complement thereof, at SNP rs760678.

In certain exemplary embodiments, the compound or agent used in treating neurodegenerative disease is selected from the group consisting TAE-226, PF-914222, and other inhibitors listed in Tables 8-10. In further embodiments, the compound or agent targets one or more NEDD9-binding proteins listed in Table 7. In certain specific embodiments, the compound or agent is used to treat a human having a 'G' nucleotide (based on the sequence orientation of SEQ ID NOS:2 and 24), or the complement thereof, at SNP rs760678.

In the various exemplary embodiments described herein which relate to neurodegenerative disease, the neurodegenerative disease can be, but is not limited to, AD or PD.

In the various exemplary embodiments described herein which relate to determining which nucleotide is present at SNP rs760678 (i.e., "genotyping" SNP rs760678), such as for diagnostic, prognostic, therapeutic, or any other purposes, these embodiments can comprise, for example, determining whether a 'G' nucleotide (based on the sequence orientation of SEQ ID NOS:2 and 24), or the complement thereof, is present at SNP rs760678. These embodiments can also comprise, for example, determining whether a 'C' nucleotide (based on the sequence orientation of SEQ ID NOS:2 and 24), or the complement thereof, is present at SNP rs760678. These embodiments can further comprise, for example, determining whether an individual has a 'GG', 'CG', or 'CC' genotype (based on the sequence orientation of SEQ ID NOS:2 and 24), or the complement thereof, at SNP rs760678. Further, these embodiments can comprise determining whether the reverse complement of these nucleotides and/or genotypes is present.

Many other uses and advantages of the present invention will be apparent to those skilled in the art upon review of the detailed description of the exemplary embodiments herein. Solely for clarity of discussion, the invention is described in the sections below by way of non-limiting examples.

Description of the Files Contained on CD-R Named CD000015ORD CDR

The CD-R named CD000015ORD CDR contains the following text (ASCII) file:

File CD000015_SEQLIST.txt provides the Sequence Listing. The Sequence Listing provides an exemplary genomic sequence (SEQ ID NO:1) as shown in Table 1 for each neurodegenerative disease-associated gene that contains one or more SNPs of the present invention. Also provided in the Sequence Listing are genomic-based context sequences flanking each SNP (SEQ ID NOS:2-11). The context sequences generally provide 100 bp upstream (5') and 100 bp downstream (3') of each SNP, with the SNP in the middle of the context sequence, for a total of 200 bp of context sequence surrounding each SNP. File CD000015 SEQLIST.txt is 269 KB in size, and was created on Apr. 29, 2008.

The information recorded in the CRF CDR is identical to the sequence listing as provided on the CDR Duplicate Copy 1 and Duplicate Copy 2. The material contained on the CD-R labeled CD000015CDR is hereby incorporated by reference pursuant to 37 CFR 1.77(b)(4).

Description of Table 1

Tables 1-6 are found at the end of the specification herein.

Table 1 discloses exemplary SNP and associated gene information of the present invention. For each gene, Table 1 provides a header containing gene information, followed by a genomic sequence, and then SNP information regarding each SNP found in that gene.

The gene information includes:

a gene number (1 through n, where n=the total number of genes in the Table);

a Celera hCG and UID internal identification numbers for the gene;

an art-known gene symbol;

an art-known gene/protein name;

Celera genomic axis position (indicating start nucleotide position-stop nucleotide position);

the chromosome number of the chromosome on which the gene is located;

an OMIM (Online Mendelian Inheritance in Man, Johns Hopkins University/NCBI) public reference number for obtaining further information regarding the medical significance of each gene; and the alternative gene/protein name(s) and/or symbol(s) in the OMIM entry.

Following the gene information is a genomic sequence for each gene, with SNPs identified by their IUB codes, including 6 kb on each side of the gene boundaries (i.e., 6 kb on the 5' side of the gene plus 6 kb on the 3' side of the gene) (corresponding to SEQ ID NO:1 of the Sequence Listing).

The genomic and genomic-based SNP context sequences are identified in Table 1 by SEQ ID NO and the actual sequences are provided in the Sequence Listing (the genomic sequence is SEQ ID NO:1 and genomic-based context sequences are SEQ ID NOS:2-11).

The SNP information includes:

context sequence (taken from the genomic sequence) with the SNP represented by its IUB code, including 100 nucleotides upstream (5') of the SNP position plus 100 nucleotides downstream (3') of the SNP position (the genomic-based SNP context sequences in Table 1 are provided in the Sequence Listing as SEQ ID NOS:2-11);

Celera hCV internal identification number for the SNP (in some instances, an "hDV" number is given instead of an "hCV" number);

SNP position (position of the SNP within the given genomic sequence);

SNP source (may include any combination of one or more of the following five codes, depending on which internal sequencing projects and/or public databases the SNP has been observed in: "Applera"=SNP observed during the re-sequencing of genes and regulatory regions of 39 individuals, "Celera"=SNP observed during shotgun sequencing and assembly of the Celera human genome sequence, "Celera Diagnostics"=SNP observed during re-sequencing of nucleic acid samples from individuals who have neurodegenerative disease or a related pathology, "dbSNP"=SNP observed in the dbSNP public database, "HGBASE"=SNP observed in the HGBASE public database, "HGMD"=SNP observed in the Human Gene Mutation Database [HGMD] public database, "HapMap"=SNP observed in the International HapMap Project public database, "CSNP"=SNP observed in an internal Applied Biosystems [Foster City, Calif.] database of coding SNPS [cSNPs]);

NOTE: multiple "Applera" source entries for a single SNP indicate that the same SNP was covered by multiple overlapping amplification products and the re-sequencing results (e.g., observed allele counts) from each of these amplification products is being provided.

Population/allele/allele count information in the format of [population1 (first_allele count|second_allele,count) population2(first_allele,count|second_allele,coun t) total (first_allele,total count|second_allele,total count)]. The information in this field includes populations/ethnic groups in which particular SNP alleles have been observed ("cau"=Caucasian, "his"=Hispanic, "chn"=Chinese, and "afr"=African-American, "jpn"=Japanese, "ind"=Indian, "mex"=Mexican, "ain"="American Indian, "cra"=Celera donor, "no_pop"=no population information available), identified SNP alleles, and observed allele counts (within each population group and total allele counts), where available ["–" in the allele field represents a deletion allele of an insertion/deletion ("indel") polymorphism (in which case the corresponding insertion allele, which may be comprised of one or more nucleotides, is indicated in the allele field on the opposite side of the "|"); "–" in the count field indicates that allele count information is not available]. For certain SNPs from the public dbSNP database, population/ethnic information is indicated as follows (this population information is publicly available in dbSNP): "HISP1"= human individual DNA (anonymized samples) from 23 individuals of self-described HISPANIC heritage; "PAC1"=human individual DNA (anonymized samples) from 24 individuals of self-described PACIFIC RIM heritage; "CAUC1"=human individual DNA (anonymized samples) from 31 individuals of self-described CAUCASIAN heritage; "AFR1"=human individual DNA (anonymized samples) from 24 individuals of self-described AFRICAN/AFRICAN AMERICAN heritage; "P1"=human individual DNA (anonymized samples) from 102 individuals of self-described heritage; "PA130299515"; "SC__12_A"=SANGER 12 DNAs of Asian origin from Corielle cell repositories, 6 of which are male and 6 female; "SC__12_C"=SANGER 12 DNAs of Caucasian origin from Corielle cell repositories from the CEPH/UTAH library. Six male and 6 female; "SC__12_AA"=SANGER 12 DNAs of African-American origin from Corielle cell repositories 6 of which are male and 6 female; "SC__95_C"=SANGER 95 DNAs of Caucasian origin from Corielle cell repositories from the CEPH/UTAH library; and "SC__12_CA"=Caucasians—12 DNAs from Corielle cell repositories that are from the CEPH/UTAH library. Six male and 6 female;

NOTE: For SNPs of "Applera" SNP source, genes/regulatory regions of 39 individuals (20 Caucasians and 19 African Americans) were re-sequenced and, since each SNP position is represented by two chromosomes in each individual (with the exception of SNPs on X and Y chromosomes in males, for which each SNP position is represented by a single chromosome), up to 78 chromosomes were genotyped for each SNP position. Thus, the sum of the African-American ("afr") allele counts is up to 38, the sum of the Caucasian allele counts ("cau") is up to 40, and the total sum of all allele counts is up to 78.

NOTE: semicolons separate population/allele/count information corresponding to each indicated SNP source; i.e., if four SNP sources are indicated, such as "Celera," "dbSNP," "HGBASE," and "HGMD," then population/allele/count information is provided in four groups which are separated by semicolons and listed in the same order as the listing of SNP sources, with each population/allele/count information group corresponding to the respective SNP source based on order; thus, in this example, the first population/allele/count information group would correspond to the first listed SNP source (Celera) and the third population/allele/count information group separated by semicolons would correspond to the third listed SNP source (HGBASE); if population/allele/count information is not available for any particular SNP source, then a pair of semicolons is still inserted as a place-holder in order to maintain correspondence between the list of SNP sources and the corresponding listing of population/allele/count information.

SNP type (e.g., location within gene/transcript and/or predicted functional effect) ("MIS-SENSE MUTATION"=SNP causes a change in the encoded amino acid [i.e., a non-synonymous coding SNP]; "SILENT MUTATION"=SNP does not cause a change in the encoded amino acid [i.e., a synonymous coding SNP]; "STOP CODON MUTATION"=SNP is located in a stop codon; "NONSENSE MUTATION"=SNP creates or destroys a stop codon; "UTR 5"=SNP is located in a 5' UTR of a transcript; "UTR 3"=SNP is located in a 3' UTR of a transcript; "PUTATIVE UTR 5"=SNP is located in a putative 5' UTR; "PUTATIVE UTR 3"=SNP is located in a putative 3' UTR; "DONOR SPLICE SITE"=SNP is located in a donor splice site [5' intron boundary]; "ACCEPTOR SPLICE SITE"=SNP is located in an acceptor splice site [3' intron boundary]; "CODING REGION"=SNP is located in a protein-coding region of the transcript; "EXON"=SNP is located in an exon; "INTRON"=SNP is located in an intron; "hmCS"=SNP is located in a human-mouse conserved segment; "TFBS"=SNP is located in a transcription factor binding site; "UNKNOWN"=SNP type is not defined; and "INTERGENIC"=SNP is intergenic, i.e., outside of any gene boundary).

Description of Table 2

Table 2 provides sequences (SEQ ID NOS:12-23) of primers that have been synthesized and used in the laboratory to assay the SNPs disclosed in Tables 3-5 by allele-specific PCR during the course of association studies to verify the association of these SNPs with neurodegenerative disease (see Examples section).

Table 2 provides the following:

- the columns labeled "Marker" provide an identification number (e.g., a public "rs" number and/or internal "hCV" number) for each SNP site.
- the column labeled "Alleles" designates the two alternative alleles (i.e., nucleotides) at the SNP site. These alleles are targeted by the allele-specific primers (the allele-specific primers are shown as Primer 1 and Primer 2). Note that alleles may be presented in Table 2 based on a different orientation (i.e., the reverse complement) relative to how the same alleles are presented in Table 1.
- the column labeled "Primer 1 (Allele-Specific Primer)" provides an allele-specific primer that is specific for an allele designated in the "Alleles" column.
- the column labeled "Primer 2 (Allele-Specific Primer)" provides an allele-specific primer that is specific for the other allele designated in the "Alleles" column.
- the column labeled "Common Primer" provides a common primer that is used in conjunction with each of the allele-specific primers (i.e., Primer 1 and Primer 2) and which hybridizes at a site away from the SNP position.

All primer sequences are given in the 5' to 3' direction.

Each of the nucleotides designated in the "Alleles" column matches or is the reverse complement of (depending on the orientation of the primer relative to the designated allele) the 3' nucleotide of the allele-specific primer (i.e., either Primer 1 or Primer 2) that is specific for that allele.

Description of Tables 3-5

Table 3 shows the results of statistical analysis (allelic test and genotypic test) for the association of SNP rs760678 (interchangeably referred to as hCV10039123) with Alzheimer's disease (AD) and Parkinson's disease (PD). "P" refers to allelic P value. "$P_{2df}$" refers to two-degree freedom P value. "$P_{recessive}$" refers to recessive genotypic P value. "OR [95% CI]" refers to odds ratio with 95% confidence intervals.

Table 4 shows the genotype (CC, GC, and GG, based on the sequence orientation of SEQ ID NOS:2 and 24) counts for SNP rs760678 SNP in AD and PD cases and controls, along with p-values from Hardy Weinberg equilibrium (HWE) tests. Here, "Sum" refers to the total number of samples. UK1, UK2, UK3, WU, and SD refer to case-control sample sets from Cardiff University and King's College London (UK1, UK2), University of Cambridge (UK3), Washington University in St. Louis (WU), and the University of California, San Diego (SD). "Celera" refers to a PD case-control sample set constructed from the NINDS Human Genetics Resources at the Coriell Institute. These sample sets are further described in the Examples section.

Table 5 shows characteristics and results of statistical analysis for exemplary SNPs (identified by their publicly known "rs" reference identification numbers) that have a statistically significant association with AD.

Further description of Tables 3-5 is provided in the Examples section herein.

Throughout Tables 3-5, "OR" refers to the odds ratio and "95% CI" refers to the 95% confidence interval for the odds ratio. Odds ratios (OR) that are greater than one indicate that a given allele (or combination of alleles such as a haplotype, diplotype, or two-locus diplotype) is a risk allele (which may also be referred to as a susceptibility allele), whereas odds ratios that are less than one indicate that a given allele is a non-risk allele (which may also be referred to as a protective allele). For a given risk allele, the other alternative allele at the SNP position (which can be derived from the information provided in Table 1, for example) may be considered a non-risk allele. For a given non-risk allele, the other alternative allele at the SNP position may be considered a risk allele.

Thus, with respect to disease risk (e.g., risk for neurodegenerative disease), if the odds ratio for a particular allele at a SNP position is greater than one, this indicates that an individual with this particular allele has a higher risk for the disease than an individual who has the other allele at the SNP position. In contrast, if the odds ratio for a particular allele is less than one, this indicates that an individual with this particular allele has a reduced risk for the disease compared with an individual who has the other allele at the SNP position.

Description of Table 6

Table 6 provides a list of LD SNPs that are related to and derived from interrogated SNPs. The interrogated SNPs were SNP rs760678, as well as SNPs rs2950, rs6940151, and rs2064112 (which are statistically significantly associated with AD) shown in Table 5. These LD SNPs are provided as an example of SNPs which can also serve as markers for disease association based on their being in LD with an interrogated SNP. The criteria and process of selecting such LD SNPs, including the calculation of the $r^2$ value and the $r^2$ threshold value, are described in Example Two, below.

In Table 6, the column labeled "Interrogated SNP" presents each marker as identified by its unique hCV identification number. The column labeled "Interrogated rs" presents the publicly known identifier rs number for the corresponding hCV number. The column labeled "LD SNP" presents the hCV numbers of the LD SNPs that are derived from their corresponding interrogated SNPs. The column labeled "LD SNP rs" presents the publicly known rs number for the corresponding hCV number. The column labeled "Power" presents the level of power where the $r^2$ threshold is set. For example, when power is set at 0.51, the threshold $r^2$ value calculated therefrom is the minimum $r^2$ that an LD SNP must have in reference to an interrogated SNP, in order for the LD SNP to be classified as a marker capable of being associated with a disease phenotype at greater than 51% probability. The column labeled "Threshold $r_T^2$" presents the minimum value of $r^2$ that an LD SNP must meet in reference to an interrogated SNP in order to qualify as an LD SNP. The column labeled "$r^2$" presents the actual $r^2$ value of the LD SNP in reference to the interrogated SNP to which it is related.

DESCRIPTION OF THE FIGURE

FIG. 1 shows an exemplary genomic sequence (SEQ ID NO:24) surrounding SNP rs760678. SNP rs760678 is located in a region containing clusters of TATA (underlined) and GATA (dashed underlined) binding motifs. The GATA motif immediately adjacent to this SNP (AGATAA) is predicted to be strongly associated with site occupancy for it matches the consensus sequence (A/T)GATA(A/G).

DETAILED DESCRIPTION OF EXEMPLARY EMBODIMENTS OF THE INVENTION

The present invention provides SNPs associated with neurodegenerative disease, particularly AD and PD, nucleic acid molecules containing these SNPs, methods and reagents for the detection of the SNPs disclosed herein, uses of these SNPs for the development of detection reagents, and assays or kits that utilize such reagents. The neurodegenerative disease-associated SNPs disclosed herein are useful for diagnosing, screening for, and evaluating predisposition to neurodegenerative disease and other neurological pathologies in humans. Furthermore, such SNPs and their encoded products are useful targets for the development of therapeutic agents in treating neurodegenerative disease and other neurological pathologies.

A large number of SNPs have been identified from re-sequencing DNA from 39 individuals, and they are indicated as "Applera" SNP source in Table 1. Their allele frequencies, observed in each of the Caucasian and African-American ethnic groups, are provided. Additional SNPs included herein were previously identified during shotgun sequencing and assembly of the human genome, and they are indicated as "Celera" SNP source in Table 1. Furthermore, the information provided in Table 1, particularly the allele frequency information obtained from 39 individuals and the identification of the precise position of each SNP within each gene, allows haplotypes (i.e., groups of SNPs that are co-inherited) to be readily inferred. The present invention encompasses SNP haplotypes, as well as individual SNPs.

Thus, the present invention provides individual SNPs associated with neurodegenerative disease, as well as combinations of SNPs and haplotypes in genetic regions associated with neurodegenerative disease, genomic sequences (SEQ ID NO:1) and genomic-based context sequences (SEQ ID NOS: 2-11), methods of detecting these polymorphisms in a test sample, methods of determining the risk of an individual of having or developing neurodegenerative disease, methods of screening for compounds useful for treating neurological pathologies such as neurodegenerative disease associated with a variant gene/protein, compounds identified by these screening methods, methods of using the disclosed SNPs to select a treatment strategy, methods of treating a disorder associated with a variant gene/protein (i.e., therapeutic methods), and methods of using the SNPs of the present invention for human identification.

The present invention provides novel SNPs associated with neurodegenerative disease, as well as SNPs that were previously known in the art, but were not previously known to be associated with neurodegenerative disease. Accordingly, the present invention provides novel compositions and methods based on the novel SNPs disclosed herein, and also provides novel methods of using the known, but previously unassociated, SNPs in methods relating to neurodegenerative disease (e.g., for diagnosing neurodegenerative disease). In Table 1, known SNPs are identified based on the public database in which they have been observed, which is indicated as one or more of the following SNP types: "dbSNP"=SNP observed in dbSNP, "HGBASE"=SNP observed in HGBASE, and "HGMD"=SNP observed in the Human Gene Mutation Database (HGMD).

Particular SNP alleles of the present invention can be associated with either an increased risk of having or developing neurodegenerative disease, or a decreased risk of having or developing neurodegenerative disease. SNP alleles that are associated with a decreased risk of having or developing neurodegenerative disease may be referred to as "protective" alleles, and SNP alleles that are associated with an increased risk of having or developing neurodegenerative disease may be interchangeably referred to as "susceptibility" alleles, "risk" alleles, or "risk factors." Thus, whereas certain SNPs (or their encoded products) can be assayed to determine whether an individual possesses a SNP allele that is indicative of an increased risk of having or developing neurodegenerative disease (i.e., a susceptibility allele), other SNPs (or their encoded products) can be assayed to determine whether an individual possesses a SNP allele that is indicative of a decreased risk of having or developing neurodegenerative disease (i.e., a protective allele). Similarly, particular SNP alleles of the present invention can be associated with either an increased or decreased likelihood of responding to a particular treatment or therapeutic compound, or an increased or decreased likelihood of experiencing toxic effects from a particular treatment or therapeutic compound, for example. The term "altered" may be used herein to encompass either of these two possibilities (e.g., an increased or a decreased risk/likelihood).

Those skilled in the art will readily recognize that nucleic acid molecules may be double-stranded molecules (as well as single-stranded molecules) and that reference to a particular site on one strand inherently refers, as well, to the corresponding site on a complementary strand. In defining a SNP position, SNP allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular SNP position, SNP allele, or nucleotide sequence. Oligonucleotides such as probes and primers may be designed to hybridize to either strand, and SNP genotyping methods disclosed herein may generally target either strand. Throughout the specification, in identifying a SNP position, reference is generally made to the protein-encoding strand, only for the purpose of convenience.

References to variant peptides, polypeptides, or proteins of the present invention include peptides, polypeptides, proteins, or fragments thereof, that contain at least one amino acid residue that differs from the corresponding amino acid sequence of the art-known peptide/polypeptide/protein (the art-known protein may be interchangeably referred to as the "wild-type," "reference," or "normal" protein). Such variant peptides/polypeptides/proteins can result from a codon change caused by a nonsynonymous nucleotide substitution at a protein-coding SNP position (i.e., a missense mutation). Variant peptides/polypeptides/proteins can also result from a nonsense mutation (i.e., a SNP that creates a premature stop codon), a SNP that generates a read-through mutation by abolishing a stop codon, or due to any SNP disclosed by the present invention that otherwise alters the structure, function/activity, or expression of a protein, such as a SNP in a regulatory region (e.g. a promoter or enhancer) or a SNP that leads to alternative or defective splicing, such as a SNP in an intron or a SNP at an exon/intron boundary. As used herein, the terms "polypeptide," "peptide," and "protein" are used interchangeably.

As used herein, an "allele" may refer to a nucleotide at a SNP position (wherein at least two alternative nucleotides are present in the population at the SNP position, in accordance with the inherent definition of a SNP) or, for cSNPs, may refer to an amino acid residue that is encoded by the codon which contains the SNP position (where the alternative nucleotides that are present in the population at the SNP position form alternative codons that encode different amino acid residues). Using rs760678 (hCV10039123) as an example, the term "allele" can refer to, for example, a 'G' or 'C' nucleotide (based on the sequence orientation of SEQ ID NOS:2 and 24), or the reverse complements thereof, at the SNP position. An "allele" may also be referred to herein as a "variant". Also, an amino acid residue that is encoded by a codon containing a particular SNP may simply be referred to as being encoded by the SNP.

The results of a test (e.g., an individual's risk for neurodegenerative disease based on assaying one or more SNPs disclosed herein, and/or an individual's genotype for one or more SNPs disclosed herein, etc.), and/or any other information pertaining to a test, may be referred to herein as a "report". A tangible report can optionally be generated as part of a testing process (which may be interchangeably referred to herein as "reporting", or as "providing" a report, "producing" a report, or "generating" a report). Examples of tangible reports may include, but are not limited to, reports in paper (such as computer-generated printouts of test results) or equivalent formats and reports stored on computer readable medium (such as a CD, computer hard drive, or computer network server, etc.). Reports, particularly those stored on computer readable medium, can be part of a database (such as a database of patient records, which may be a "secure database" that has security features that limit access to the report, such as to allow only the patient and the patient's medical practitioners to view the report, for example). In addition to, or as an alternative to, generating a tangible report, reports can also be displayed on a computer screen (or the display of another electronic device or instrument).

A report can further be "transmitted" or "communicated" (these terms may be used herein interchangeably), such as to the individual who was tested, a medical practitioner (e.g., a doctor, nurse, clinical laboratory practitioner, genetic counselor, etc.), a healthcare organization, a clinical laboratory, and/or any other party intended to view or possess the report. The act of "transmitting" or "communicating" a report can be by any means known in the art, based on the form of the report. Furthermore, "transmitting" or "communicating" a report can include delivering a report ("pushing") and/or retrieving ("pulling") a report. For example, reports can be transmitted/communicated by such means as being physically transferred between parties (such as for reports in paper format), such as by being physically delivered from one party to another, or by being transmitted electronically or in signal form (e.g., via e-mail or over the internet, by facsimile, and/or by any wired or wireless communication methods known in the art), such as by being retrieved from a database stored on a computer network server, etc.

In certain exemplary embodiments, the invention further provides methods of doing business. For example, exemplary methods of doing business can comprise assaying one or more SNPs disclosed herein and reporting an individual's risk for neurodegenerative disease based on which allele(s) are present at the assayed SNP(s), and optionally transmitting the report.

NEDD9, Including Protein Interactions, Disease Pathways, and Therapeutic Intervention Thereof Exemplary embodiments of the invention provide SNPs in NEDD9 that are associated with neurodegenerative disease, particularly AD and PD. Tables 7-10 below provide NEDD9-binding proteins (Table 7) and compounds that target proteins that interact with NEDD9 or are otherwise in NEDD9 pathways (Tables 8-10). The NEDD9-binding proteins provided in Table 7 are examples of NEDD9-binding proteins that can be targeted by therapeutic agents to treat neurodegenerative disease (particularly AD and PD), such as by directly or indirectly modulating (e.g., inhibiting) NEDD9, in accordance with exemplary embodiments of the invention. Similarly, the compounds provided in Tables 8-10, which are generally used for disease indications other than neurodegenerative disease, are examples of compounds that can be used to treat neurodegenerative disease (particularly AD and PD), such as by directly or indirectly modulating (e.g., inhibiting) NEDD9, in accordance with exemplary embodiments of the invention.

NEDD9 ("neural precursor cell expressed, developmentally down-regulated 9") is also known by such aliases as CASL ("cellular apoptosis susceptibility gene homolog (like)"), CAS-L ("Csk-associated substrate, lymphocyte type"), and HEF1 ("human enhancer of filamentation 1").

NEDD9 is a docking protein with several structural domains that mediate intracellular protein-protein interactions (O'Neill G M, et al., 2000, "Integrin signalling: a new Cas(t) of characters enters the stage", *Trends in Cell Biology* 10:111-119; Seo S, et al., 2006, "Structure and function of Cas-L and integrin-mediated signaling", *Critical Reviews in Immunology* 26(5):391-406).

NEDD9 plays a key coordinating role for signaling related to cell adhesion, morphology, migration, and apoptosis. In neurite development, the adhesion of regions of the cell membrane to the extracellular matrix and subsequent extension of the membrane (lamellipodia) is a part of axon and dendrite formation. This adhesion occurs at focal adhesion sites that typically involve many, proteins, including NEDD9.

In AD, extracellular plaques composed of aggregated amyloid β peptides (Aβ) and intracellular neurofibrillar tangles (NFT) of hyperphosphorylated tau proteins are found. One disease hypothesis is that the association of external Aβ with integrins stimulates the formation of intracellular NFTs by signaling through proteins in focal adhesion sites. NEDD9 can be found in the Aβ to NFT signaling pathway.

The NEDD9 protein typically has 4 functional domains, an N-terminal SH3 domain, a substrate domain for tyrosine phosphorylation and docking of SH2 containing proteins, a serine-rich region, and a C-terminal helix-loop-helix. See Seo et al., *ibid*. Proteins that bind to NEDD9 include signaling molecules (kinases, phosphatases), adaptor proteins, and factors involved in ubiquitination and degradation of proteins by the proteasome. Examples of NEDD9-binding proteins are listed in Table 7 below:

TABLE 7

| | |
|---|---|
| ABL1 | Cytoplasmic and nuclear protein tyrosine kinase |
| AURKA | Aurora kinase A |
| BCAR1 | Adaptor protein, NEDD9 paralog (P130CAS) |
| BCAR3 | Adaptor protein, SH2 domain and SH3 interacting domain |
| CDH1 | Cadherin, cell to cell adhesion glycoprotein |
| CHAT | Choline acetyltransferase, synthesis of acetylcholine |
| CRK | Adaptor protein, SH2 and SH3 domains |
| CRKL | Adaptor protein, SH2 and SH3 domains |
| CSK | c-src tyrosine kinase |
| DIMT1L | enzyme dimethylates two adjacent adenosines, substrate rRNA |
| ELSPBP1 | Transcription factor |
| FYN | Protein tyrosine kinase |
| FZR1 | Subunit of the anophase promoting complex, protein degradation |
| ID2 | Transcriptional regulator, binds transcription factors |
| ITCH | E3 ubiquitin-ligase, targets proteins for degradation |
| LCK | Lymphocyte-specific protein tyrosine kinase |
| LYN | SRC family protein tyrosine kinase |
| MICAL1 | Microtubule associated monoxygenase, interacts with the neuronal plexin A, likely to function in neuronal guidance |
| NCK1 | Adaptor protein, SH2 and SH3 domains |
| PTK2 | Protein tyrosine kinase (FAK: focal adhesion kinase) |
| PTK2B | Protein tyrosine kinase (FAK paralog, PYK2) |
| PTPN11 | Protein tyrosine phosphatase, non-receptor type 11 |
| PTPN12 | Protein tyrosine phosphatase, non-receptor type 12 |
| PXN | Cytoskeletal protein involved in actin-membrane attachment at sites of cell adhesion to the extracellular matrix (focal adhesion) |
| SMAD1 | Signal transduction, receptor-regulated R-Smad, TGF-β cascades |
| SMAD2 | Signal transduction, receptor-regulated R-Smad, TGF-β cascades |
| SMAD3 | Signal transduction, receptor-regulated R-Smad, TGF-β cascades |

TABLE 7-continued

| | |
|---|---|
| TCF3 | Transcription factor |
| TRIP6 | Adaptor protein, docking protein, lim domains |
| ZYX | Adaptor protein, docking protein, lim domains, TRIP6 homolog |

NEDD9 functions in the signal transduction cascade that promotes formation of focal adhesion sites and lamellipodia along with the tyrosine kinase FAK (focal adhesion kinase, gene symbol PTK2; Parsons J T, 2003, "Focal adhesion kinase: the first ten years", *J Cell Sci* 116:1409-1416). Following stimulation of neurons by integrin clustering or receptor activation, FAK autophosphorylation (at tyr397) creates an SH2 binding site for the recruitment of Src family kinases. The association of FAK and a Src family kinase initiates phosphorylation of additional sites on FAK and phosphorylation of other focal adhesion proteins, including NEDD9. See Parsons J T, ibid.

In a study by Wright et al., ("α2β1 and αVβ1 integrin signaling pathways mediate amyloid-β-induced neurotoxicity", 2007, *Neurobiology of Aging* 28:226-237), integrin-blocking antibodies were used to disrupt Aβ signaling in a human cortical neuron model system. These authors proposed that α2β1 and αVβ1 integrins were the primary receptors that initiate the signal transduction cascades associated with AD. This conclusion was based on assays that demonstrated inhibition of Aβ stimulated toxicity by a spectrum of integrin antibodies. Other α2β1 or αVβ1 integrin inhibitors are listed in Table 8 below.

TABLE 8

| Drug | Action | Company | Indication | Highest Development Status | Technology |
|---|---|---|---|---|---|
| ATN-161 | Anticancer, Integrin alpha-V/beta-1 antagonist, Integrin alpha-5/beta-3 antagonist, Angiogenesis inhibitor, Metastasis inhibitor | University of Michigan | Glioma, Cancer | Phase 2 Clinical | Intravenous formulation, Peptide |
| alpha-2/beta-1 integrin antagonists | Anticancer, Integrin alpha-2/beta-1 antagonists | BioTie Therapies Corp | Thrombosis, Cancer | Discovery | |
| MN-447 | Cardioprotectant, Integrin alpha-V/beta-1 antagonist, Platelet aggregation inhibitor, GP IIb/IIIa antagonist | Meiji Seika Kaisha Ltd | Thrombosis, Myocardial infarction | Discovery | |
| SJ-749 | Anticancer, FGF receptor antagonist, Integrin alpha-V/beta-1 antagonist, Angiogenesis inhibitor | Bristol-Myers Squibb Pharma Co | Inflammation, Cancer | Discovery | Monoclonal antibody |
| EMS-16 | Anticancer, Integrin alpha-2/beta-1 antagonist | Biogen Inc | Cancer | Discontinued | Natural product |
| F-200 | Integrin alpha-V/beta-1 antagonist, Angiogenesis inhibitor | Eos Biotechnology Inc | Ocular disease | Discontinued | Antibody fragment |

A second potential point of inhibition is the enzyme FAK kinase (PTK2 kinase). As published by Toutant et al. ("Autophosphorylation of Tyr397 and its phosphorylation by Src-family kinases are altered in focal-adhesion-kinase neuronal isoforms", 2000, *Biochem J.* 348:119-128), activation of FAK by integrin clustering or by seven-transmembrane domain receptors leads to autophosphorylation of Tyr397 on FAK, which allows the binding of the Src-homology 2 (SH2) domain of Src, Fyn, or phosphatidylinositol 3-kinase (PI3K). Additional residues on FAK are then phosphorylated, Tyr407, Tyr576, and Tyr577 of the catalytic domain and Tyr871, and Tyr925 at the C-terminus are modified. Phosphorylation of Tyr576 and Tyr577 increases enzyme activity (Parsons J T, ibid.). For further information regarding FAK kinase and other tyrosine kinases, particularly as targets for drug development, see McCulloch et al., "Signalling platforms that modulate the inflammatory response: new targets for drug development", *Nat Rev Drug Discov.* 2006 October; 5(10): 864-76.

Inhibitors of FAK kinase are under development in various academic and industry laboratories, as shown in Table 9 below. Most research groups are exploring this target for cancer treatments.

TABLE 9

| Drug | Actions | Company | Therapy Areas | Highest Development Status | Technologies |
|---|---|---|---|---|---|
| NVP-TAE-226 | Anticancer; Insulin-like growth factor 1 receptor modulator; Focal adhesion kinase inhibitor | Novartis AG | Cancer | Discovery | Oral formulation |
| FAK inhibitors (cancer) | Anticancer; Focal adhesion kinase inhibitor | Pfizer Inc | Cancer | Discovery | |
| TAC, Medexis/Bionature | Anticancer, Apoptosis stimulator, Androgen receptor agonist, Phosphoinositide 3-kinase stimulator, Focal adhesion kinase stimulator | University of Crete | Prostate tumor | Discovery | Protein (conjugated) |
| FAK inhibitors | FAK inhibitors | Poniard/ Scripps Research Institute | Cancer | Discovery | small molecules/ press release Jan. 9, 2007 |
| ISIS-15421 | Anticancer; Focal adhesion kinase inhibitor; Metastasis inhibitor; Antisense oligonucleotide inhibitor | Isis Pharmaceuticals Inc | Metastasis; Melanoma | No Development Reported | Oligonucleotide (antisense) |
| anti-FAK oligonucleotides | Anticancer; Focal adhesion kinase-1 inhibitor; Antisense oligonucleotide inhibitor | Genta Inc | Cancer | Discontinued | Oligonucleotide (antisense) |

Another druggable target upstream of NEDD9 phosphorylation is the Src kinase that binds to the FAK SH2 domain. Williamson et al. (*J Neurosci*., "Rapid tyrosine phosphorylation of neuronal proteins including tau and focal adhesion kinase in response to amyloid-beta peptide exposure: involvement of Src family protein kinases", 2002 Jan. 1; 22(1):10-20) demonstrated with immunoprecipitation that the kinase Fyn was associated with FAK in Aβ-treated neurons. These authors and others have noted that application of Src kinase inhibitors prevents Tau phosphorylation, indicating that intervention at the FAK-FYN complex may be an effective AD therapy. Inhibitors of Fyn, Src, and Lyn are listed in Table 10 below. These compounds target the kinases in the Src family with varying specificity.

TABLE 10

| Drug | Highest Development Status | Company | Therapy Areas | Actions | Technologies |
|---|---|---|---|---|---|
| dasatinib | Launched | Bristol-Myers Squibb Co | Acute lymphoblastic leukemia; Chronic myelocytic leukemia; Multiple myeloma; Solid tumor | Anticancer; Abl tyrosine kinase inhibitor; Fyn tyrosine kinase inhibitor; Src tyrosine kinase inhibitor; Lck tyrosine kinase inhibitor | Oral formulation |
| AZD-0530 | Phase 2 Clinical | AstraZeneca plc | Colorectal tumor; Hematological disease; Solid tumor | Anticancer; Abl tyrosine kinase inhibitor; Src tyrosine kinase inhibitor; Metastasis inhibitor; Cell cycle inhibitor | Oral formulation |
| bosutinib | Phase 2 Clinical | Wyeth Research | Leukemia; Intracranial hemorrhage; Chronic myelocytic leukemia; Cancer; Solid tumor | Anticancer; Neuroprotectant; Abl tyrosine kinase inhibitor; Src tyrosine kinase inhibitor; DNA gyrase inhibitor | Oral formulation |
| Src tyrosine kinase inhibitors (cancer) | Phase 1 Clinical | AstraZeneca plc | Metastasis; Cancer | Anticancer; Src tyrosine kinase inhibitor; Metastasis inhibitor | Oral formulation |
| INNO-406 | Phase 1 Clinical | Nippon Shinyaku Co Ltd | Acute lymphoblastic leukemia; Leukemia; Chronic myelocytic leukemia | Anticancer; Abl tyrosine kinase inhibitor; Lyn tyrosine kinase inhibitor | Oral formulation |
| AZD-0424 | Discovery | AstraZeneca plc | Solid tumor | Anticancer; Src tyrosine kinase inhibitor | |
| dual Abl/Src inhibitors (cancer) | Discovery | ARIAD Pharmaceuticals Inc | Leukemia; Solid tumor | Anticancer; ABL family tyrosine kinase inhibitor; Src tyrosine kinase inhibitor; Metastasis inhibitor | |
| kinase inhibitors (edema, cancer) | Discovery | TargeGen Inc | Edema; Cancer | Anticancer; Protein kinase inhibitor; Abl tyrosine kinase inhibitor; Src tyrosine kinase inhibitor; Angiogenesis inhibitor; Metastasis inhibitor | Oral formulation |
| KX-2377 | Discovery | Kinex Pharmaceuticals LLC | Cancer | Anticancer; Src tyrosine kinase inhibitor | Oral formulation |
| SKS-927 | Discovery | Wyeth | Cerebrovascular ischemia | Neuroprotectant; Src tyrosine kinase inhibitor; | Intravenous formulation |

TABLE 10-continued

| Drug | Highest Development Status | Company | Therapy Areas | Actions | Technologies |
|---|---|---|---|---|---|
| | | | | Cardiovascular agent | |
| src family kinase inhibitors (cancer) | Discovery | Pfizer Inc | Cancer | Anticancer; Apoptosis inhibitor; SRC-A family tyrosine kinase inhibitor | |
| Src inhibitors (kinase domain) | Discovery | ARIAD Pharmaceuticals Inc | Osteoporosis; Bone metastases | Anticancer; Src tyrosine kinase inhibitor; Bone resorption inhibitor | |
| Src kinase inhibitors | Discovery | SIRENADE Pharmaceuticals AG | Colorectal tumor; Cerebrovascular ischemia; Metastasis; Immune disorder; Osteoporosis; Cancer | Anticancer; Neuroprotectant; Src tyrosine kinase inhibitor | |
| Lck inhibitors | Discovery | GlaxoSmithKline plc | Rheumatoid arthritis | Anti-inflammatory; Lck tyrosine kinase inhibitor; reference states also Fyn inhibition | |
| Lck tyrosine kinase inhibitors | Discovery | Bristol-Myers Squibb Co | Atherosclerosis; Rheumatoid arthritis; Transplant rejection; Delayed hypersensitivity; Multiple sclerosis; Cardiac failure; Psoriasis; Cancer | Anticancer; Antiarteriosclerotic; Lck tyrosine kinase inhibitor, reference states also Fyn inhibition | |
| KRX-123 | Discovery | Keryx Biopharmaceuticals Inc | Prostate tumor | peptide inhibitor of Lyn, Protein kinase modulator; Protein tyrosine kinase modulator; Anticancer; Apoptosis stimulator | |
| Src kinase inhibitors | No Development Reported | Sunesis Pharmaceuticals Inc | Cancer | Anticancer; Src tyrosine kinase inhibitor | |
| SRPK-1 inhibitors (hepatitis B virus infection) | No Development Reported | Axxima Pharmaceuticals AG | Hepatitis B virus infection | Protein serine-threonine kinase inhibitor; Antiviral | |
| p56lck inhibitors (dihydroquinazolines) | No Development Reported | UCB Celltech | Immune disorder | Immunomodulator, some Fyn inhibition from reference | |
| T-102 | Discontinued | TargeGen Inc | Cerebrovascular ischemia | Neuroprotectant; Src tyrosine kinase inhibitor; Non-viral vector based gene therapy | Gene transfer system, non-viral |

TABLE 10-continued

| Drug | Highest Development Status | Company | Therapy Areas | Actions | Technologies |
|---|---|---|---|---|---|
| p56lck inhibitors (phenylaminopyrimidines) | Discontinued | UCB Celltech | Rheumatoid arthritis; Autoimmune disease; Graft versus host disease | Immunomodulator; Zap70 tyrosine kinase inhibitor, some Fyn inhibition from reference | |

Isolated Nucleic Acid Molecules and SNP Detection Reagents & Kits

Table 1 provides a variety of information about each SNP of the present invention that is associated with neurodegenerative disease, including the genomic sequences (SEQ ID NO:1) and SNP context sequences, which generally include 100 nucleotide upstream (5') plus 100 nucleotides downstream (3') of each SNP position (SEQ ID NOS:2-11 correspond to genomic-based context sequences disclosed in Table 1), the alternative nucleotides (alleles) at each SNP position, and additional information about the variant where relevant, such as SNP type (intron, etc.), human populations in which the SNP was observed, observed allele frequencies, etc.

Isolated Nucleic Acid Molecules

The present invention provides isolated nucleic acid molecules that contain one or more SNPs disclosed Table 1. Isolated nucleic acid molecules containing one or more SNPs disclosed in Table 1 may be interchangeably referred to throughout the present text as "SNP-containing nucleic acid molecules." Isolated nucleic acid molecules may optionally encode a full-length variant protein or fragment thereof. The isolated nucleic acid molecules of the present invention also include oligonucleotides such as probes and primers (which are described in greater detail below in the section entitled "SNP Detection Reagents"), which may be used for assaying the disclosed SNPs, and isolated full-length genes, transcripts, cDNA molecules, and fragments thereof, which may be used for such purposes as expressing an encoded protein.

As used herein, an "isolated nucleic acid molecule" generally is one that contains a SNP of the present invention or one that hybridizes to such molecule such as a nucleic acid with a complementary sequence, and is separated from most other nucleic acids present in the natural source of the nucleic acid molecule. Moreover, an "isolated" nucleic acid molecule, such as a cDNA molecule containing a SNP of the present invention, can be substantially free of other cellular material, or culture medium when produced by recombinant techniques, or chemical precursors or other chemicals when chemically synthesized. A nucleic acid molecule can be fused to other coding or regulatory sequences and still be considered "isolated." For example, recombinant DNA molecules contained in a vector are considered "isolated." Nucleic acid molecules present in non-human transgenic animals, which do not naturally occur in the animal, are also considered "isolated." Further examples of "isolated" DNA molecules include recombinant DNA molecules maintained in heterologous host cells, and purified (partially or substantially) DNA molecules in solution. Isolated RNA molecules include in vivo or in vitro RNA transcripts of the isolated SNP-containing DNA molecules of the present invention. Isolated nucleic acid molecules according to the present invention further include such molecules produced synthetically.

Generally, an isolated SNP-containing nucleic acid molecule comprises one or more SNP positions disclosed by the present invention with flanking nucleotide sequences on either side of the SNP positions. A flanking sequence can include nucleotide residues that are naturally associated with the SNP site and/or heterologous nucleotide sequences. In exemplary embodiments, the flanking sequence is up to about 500, 300, 100, 60, 50, 30, 25, 20, 15, 10, 8, or 4 nucleotides (or any other length in-between) on either side of a SNP position, or as long as the full-length gene or entire protein-coding sequence (or any portion thereof such as an exon), especially if the SNP-containing nucleic acid molecule is to be used to produce a protein or protein fragment.

For full-length genes and entire protein-coding sequences, a SNP flanking sequence can be, for example, up to about 5 KB, 4 KB, 3 KB, 2 KB, 1 KB on either side of the SNP. Furthermore, in such instances, the isolated nucleic acid molecule comprises exonic sequences (including protein-coding and/or non-coding exonic sequences), but may also include intronic sequences. Thus, any protein coding sequence may be either contiguous or separated by introns. The important point is that the nucleic acid is isolated from remote and unimportant flanking sequences and is of appropriate length such that it can be subjected to the specific manipulations or uses described herein such as recombinant protein expression, preparation of probes and primers for assaying the SNP position, and other uses specific to the SNP-containing nucleic acid sequences.

An isolated SNP-containing nucleic acid molecule can comprise, for example, a full-length gene or transcript, such as a gene isolated from genomic DNA (e.g., by cloning or PCR amplification), a cDNA molecule, or an mRNA transcript molecule. Polymorphic genomic sequences are provided in Table 1 and in the Sequence Listing (SEQ ID NO:1). Furthermore, fragments of such full-length genes or transcripts that contain one or more SNPs disclosed herein are also encompassed by the present invention, and such fragments may be used, for example, to express any part of a protein, such as a particular functional domain or an antigenic epitope.

Thus, the present invention also encompasses fragments of the nucleic acid sequences provided in Table 1 (genomic sequences are provided in Table 1 as SEQ ID NO:1 and genomic-based SNP context sequences are provided in Table 1 as SEQ ID NOS:2-11) and their complements. A fragment typically comprises a contiguous nucleotide sequence at least about eight or more nucleotides, or at least about 12 or more nucleotides, or at least about 16 or more nucleotides. Further, a fragment could comprise at least about 18, 20, 22, 25, 30, 40, 50, 60, 80, 100, 150, 200, 250 or 500 nucleotides in length, or any other number in between. The length of the fragment may be based on its intended use. For example, the fragment can encode epitope-bearing regions of a variant peptide or regions of a variant peptide that differ from the normal/wild-type protein, or can be useful as a polynucleotide probe or primer. Such fragments can be isolated using the nucleotide sequences provided in Table 1 for the synthesis of a polynucleotide probe. A labeled probe can then be used, for example, to screen a cDNA library, genomic DNA library, or mRNA to isolate nucleic acid corresponding to the coding region. Further, primers can be used in amplification reactions, such as for purposes of assaying one or more SNP sites or for cloning specific regions of a gene.

An isolated nucleic acid molecule of the present invention further encompasses a SNP-containing polynucleotide that is the product of any one of a variety of nucleic acid amplification methods, which are used to increase the copy numbers of a polynucleotide of interest in a nucleic acid sample. Such amplification methods are well known in the art, and they include but are not limited to, polymerase chain reaction (PCR) (U.S. Pat. Nos. 4,683,195 and 4,683,202; *PCR Technology: Principles and Applications for DNA Amplification*, ed. H. A. Erlich, Freeman Press, New York, N.Y. [1992]), ligase chain reaction (LCR) (Wu and Wallace, *Genomics* 4:560 [1989]; Landegren et al., *Science* 241:1077 [1988]), strand displacement amplification (SDA) (U.S. Pat. Nos. 5,270,184 and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., *Proc. Natl. Acad. Sci. USA* 87: 1874 [1990]). Based on such methodologies, a person skilled in the art can readily design primers in any suitable regions 5' and 3' to a SNP disclosed herein (these regions may optionally include the SNP site). Such primers may be used to amplify DNA of any length so long that it contains the SNP of interest in its sequence.

As used herein, an "amplified polynucleotide" of the invention is a SNP-containing nucleic acid molecule whose amount has been increased at least two-fold by any nucleic acid amplification method performed in vitro as compared to its starting amount in a test sample. In other exemplary embodiments, an amplified polynucleotide is the result of at least 10-fold, 15-fold, 20-fold, 25-fold, 30-fold, 35-fold, 40-fold, 50-fold, 100-fold, 1000-fold, or even 10.000-fold increase as compared to its starting amount in a test sample. In certain PCR amplifications, a polynucleotide of interest is often amplified at least 50,000-fold in amount over the unamplified genomic DNA, but the precise amount of amplification needed for an assay typically depends on the sensitivity of the subsequent detection method used.

Generally, an amplified polynucleotide is at least about 16 nucleotides in length. More typically, an amplified polynucleotide is at least about 20 nucleotides in length. In an exemplary embodiment of the invention, an amplified polynucleotide is at least about 30 nucleotides in length. In other exemplary embodiments of the invention, an amplified polynucleotide is at least about 32, 40, 45, 50, or 60 nucleotides in length. In yet other exemplary embodiments of the invention, an amplified polynucleotide is at least about 100, 200, 300, 400, or 500 nucleotides in length. While the total length of an amplified polynucleotide of the invention can be as long as, for example, an exon, an intron, or the entire gene where the SNP of interest resides, an amplified product is typically up to about 1,000 nucleotides in length (although certain amplification methods may generate amplified products greater than 1000 nucleotides in length). In certain exemplary embodiments, an amplified polynucleotide is not greater than about 600-700 nucleotides in length. It is understood that irrespective of the length of an amplified polynucleotide, a SNP of interest may be located anywhere along its sequence.

In a specific embodiment of the invention, the amplified product is at least about 201 nucleotides in length, and comprises one of the genomic-based context sequences shown in Table 1. Such a product may have additional sequences on its 5' end or 3' end or both. In another embodiment, the amplified product is about 101 nucleotides in length, and it contains a SNP disclosed herein. In exemplary embodiments, the SNP is located at the middle of the amplified product (e.g., at position 101 in an amplified product that is 201 nucleotides in length, or at position 51 in an amplified product that is 101 nucleotides in length), or within 1, 2, 3, 4, 5, 6, 7, 8, 9, 10, 12, 15, or 20 nucleotides from the middle of the amplified product (however, as indicated above, the SNP of interest may be located anywhere along the length of the amplified product).

The present invention provides isolated nucleic acid molecules that comprise, consist of, or consist essentially of one or more polynucleotide sequences that contain one or more SNPs disclosed herein, complements thereof, and SNP-containing fragments thereof.

Accordingly, the present invention provides nucleic acid molecules that consist of any of the nucleotide sequences shown in Table 1 (genomic sequences are provided in Table 1 as SEQ ID NO:1, and genomic-based SNP context sequences are provided in Table 1 as SEQ ID NOS:2-11). A nucleic acid molecule consists of a nucleotide sequence when the nucleotide sequence is the complete nucleotide sequence of the nucleic acid molecule.

The present invention further provides nucleic acid molecules that consist essentially of any of the nucleotide sequences shown in Table 1 (genomic sequences are provided in Table 1 as SEQ ID NO:1, and genomic-based SNP context sequences are provided in Table 1 as SEQ ID NOS:2-11). A nucleic acid molecule consists essentially of a nucleotide sequence when such a nucleotide sequence is present with only a few additional nucleotide residues in the final nucleic acid molecule.

The present invention further provides nucleic acid molecules that comprise any of the nucleotide sequences shown in Table 1 or a SNP-containing fragment thereof (genomic sequences are provided in Table 1 as SEQ ID NO:1 and genomic-based SNP context sequences are provided in Table 1 as SEQ ID NOS:2-11). A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleotide residues, such as residues that are naturally associated with it or heterologous nucleotide sequences. Such a nucleic acid molecule can have one to a few additional nucleotides or can comprise many more additional nucleotides. A brief description of how various types of these nucleic acid molecules can be readily made and isolated is provided below, and such techniques are well known to those of ordinary skill in the art (*Molecular Cloning: A Laboratory Manual*, Sambrook and Russell, Cold Spring Harbor Press, New York [2000]).

The isolated nucleic acid molecules can encode mature proteins plus additional amino or carboxyl-terminal amino acids or both, or amino acids interior to the mature protein (when the mature form has more than one peptide chain, for instance). Such sequences may play a role in processing of a protein from precursor to a mature form, facilitate protein trafficking, prolong or shorten protein half-life, or facilitate manipulation of a protein for assay or production. As generally is the case in situ, the additional amino acids may be processed away from the mature protein by cellular enzymes.

Thus, the isolated nucleic acid molecules include, but are not limited to, nucleic acid molecules having a sequence encoding a protein alone, a sequence encoding a mature protein and additional coding sequences such as a leader or secretory sequence (e.g., a pre-pro or pro-protein sequence), a sequence encoding a mature protein with or without additional coding sequences, plus additional non-coding sequences, for example introns and non-coding 5' and 3' sequences such as transcribed but untranslated sequences that play a role in, for example, transcription, mRNA processing (including splicing and polyadenylation signals), ribosome binding, and/or stability of mRNA. In addition, the nucleic acid molecules may be fused to heterologous marker sequences encoding, for example, a peptide that facilitates purification.

Isolated nucleic acid molecules can be in the form of RNA, such as mRNA, or in the form of DNA, including cDNA and genomic DNA, which may be obtained, for example, by molecular cloning or produced by chemical synthetic techniques or by a combination thereof (*Molecular Cloning: A Laboratory Manual*, Sambrook and Russell, Cold Spring Harbor Press, New York [2000]). Furthermore, isolated nucleic acid molecules, particularly SNP detection reagents such as probes and primers, can also be partially or completely in the form of one or more types of nucleic acid analogs, such as peptide nucleic acid (PNA) (U.S. Pat. Nos. 5,539,082; 5,527,675; 5,623,049; 5,714,331). The nucleic acid, especially DNA, can be double-stranded or single-stranded. Single-stranded nucleic acid can be the coding strand (sense strand) or the complementary non-coding strand (anti-sense strand). DNA, RNA, or PNA segments can be assembled, for example, from fragments of the human genome (in the case of DNA or RNA) or single nucleotides, short oligonucleotide linkers, or from a series of oligonucleotides, to provide a synthetic nucleic acid molecule. Nucleic acid molecules can be readily synthesized using the sequences provided herein as a reference; oligonucleotide and PNA oligomer synthesis techniques are well known in the art (see, e.g., Corey, "Peptide nucleic acids: expanding the scope of nucleic acid recognition," *Trends Biotechnol.* 15[6]: 224-9 [June 1997], and Hyrup et al., "Peptide nucleic acids [PNA]: synthesis, properties and potential applications," *Bioorg. Med. Chem.* 4[1]:5-23 [January 1996]). Furthermore, large-scale automated oligonucleotide/PNA synthesis (including synthesis on an array or bead surface or other solid support) can readily be accomplished using commercially available nucleic acid synthesizers, such as the Applied Biosystems (Foster City, Calif.) 3900 High-Throughput DNA Synthesizer or Expedite 8909 Nucleic Acid Synthesis System, and the sequence information provided herein.

The present invention encompasses nucleic acid analogs that contain modified, synthetic, or non-naturally occurring nucleotides or structural elements or other alternative/modified nucleic acid chemistries known in the art. Such nucleic acid analogs are useful, for example, as detection reagents (e.g., primers/probes) for detecting one or more SNPs identified in Table 1. Furthermore, kits/systems (such as beads, arrays, etc.) that include these analogs are also encompassed by the present invention. For example, PNA oligomers that are based on the polymorphic sequences of the present invention are specifically contemplated. PNA oligomers are analogs of DNA in which the phosphate backbone is replaced with a peptide-like backbone (Lagriffoul et al., *Bioorganic & Medicinal Chemistry Letters* 4:1081-1082 [1994], Petersen et al., *Bioorganic & Medicinal Chemistry Letters* 6:793-796 [1996], Kumar et al., *Organic Letters* 3[9]:1269-1272 [2001], WO96/04000). PNA hybridizes to complementary RNA or DNA with higher affinity and specificity than conventional oligonucleotides and oligonucleotide analogs. The properties of PNA enable novel molecular biology and biochemistry applications.

Additional examples of nucleic acid modifications that improve the binding properties and/or stability of a nucleic acid include the use of base analogs such as inosine, intercalators (U.S. Pat. No. 4,835,263) and the minor groove binders (U.S. Pat. No. 5,801,115). Thus, references herein to nucleic acid molecules, SNP-containing nucleic acid molecules, SNP detection reagents (e.g., probes and primers), and oligonucleotides/polynucleotides include PNA oligomers and other nucleic acid analogs. Other examples of nucleic acid analogs and alternative/modified nucleic acid chemistries known in the art are described in *Current Protocols in Nucleic Acid Chemistry*, John Wiley & Sons, New York (2002).

Also provided are nucleic acid molecules that encode fragments of variant polypeptides as well as nucleic acid molecules that encode obvious variants of such variant polypeptides. Such nucleic acid molecules may be naturally occurring, such as paralogs (different locus) and orthologs (different organism), or may be constructed by recombinant DNA methods or by chemical synthesis. Non-naturally occurring variants may be made by mutagenesis techniques, including those applied to nucleic acid molecules, cells, or organisms. Accordingly, the variants can contain nucleotide substitutions, deletions, inversions and insertions (in addition to the SNPs disclosed in Table 1). Variation can occur in either or both the coding and non-coding regions. The variations can produce conservative and/or non-conservative amino acid substitutions.

Further variants of the nucleic acid molecules disclosed in Table 1, such as naturally occurring allelic variants (as well as orthologs and paralogs) and synthetic variants produced by mutagenesis techniques, can be identified and/or produced using methods well known in the art. Such further variants can comprise a nucleotide sequence that shares at least 70-80%, 80-85%, 85-90%, 91%, 92%, 93%, 94%, 95%, 96%, 97%, 98%, or 99% sequence identity with a nucleic acid sequence disclosed in Table 1 (or a fragment thereof) and that includes a novel SNP allele disclosed in Table 1. Thus, an aspect of the present invention that is specifically contemplated is isolated nucleic acid molecules that have a certain degree of sequence variation compared with the sequences shown in Tables 1, but that contain a novel SNP allele disclosed herein. In other words, as long as an isolated nucleic acid molecule contains a novel SNP allele disclosed herein, other portions of the nucleic acid molecule that flank the novel SNP allele can vary to some degree from the specific genomic and context sequences shown in Table 1.

To determine the percent identity of two amino acid sequences or two nucleotide sequences of two molecules that share sequence homology, the sequences are aligned for optimal comparison purposes (e.g., gaps can be introduced in one or both of a first and a second amino acid or nucleic acid sequence for optimal alignment and non-homologous sequences can be disregarded for comparison purposes). In exemplary embodiments, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm (*Computational Molecular Biology*, ed. A. M. Lesk, Oxford University Press, New York [1988]; *Biocomputing: Informatics and Genome Projects*, ed. Smith, D. W., Academic Press, New York [1993]; *Computer Analysis of Sequence Data, Part* 1, ed. A. M. Griffin, and H. G. Griffin, Humana Press, New Jersey [1994]; *Sequence Analysis in Molecular Biology*, G. von Heinje, Academic Press [1987]; and *Sequence Analysis Primer*, eds. M. Gribskov and J. M. Devereux, Stockton Press, New York [1991]). In an exemplary embodiment, the percent identity between two amino acid sequences is determined using the Needleman and Wunsch algorithm (*J. Mol. Biol.* 48:444-453 [1970]) which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

In yet another exemplary embodiment, the percent identity between two nucleotide sequences is determined using the GAP program in the GCG software package (J. Devereux et al., *Nucleic Acids Res.* 12[1]:387 [1984]), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11-17 [1989]) which has been incorporated into the ALIGN program (version 2.0), using a PAM120 weight residue table, a gap length penalty of 12, and a gap penalty of 4.

The nucleotide and amino acid sequences of the present invention can further be used as a "query sequence" to perform a search against sequence databases to, for example, identify other family members or related sequences. Such searches can be performed using the NBLAST and XBLAST programs (version 2.0) of Altschul et al. (*J. Mol. Biol.* 215: 403-10 [1990]). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25[17]:3389-3402 [1997]). When utilizing BLAST and gapped BLAST programs, the default parameters of the respective programs (e.g., XBLAST and NBLAST) can be used. In addition to BLAST, examples of other search and sequence comparison programs used in the art include, but are not limited to, FASTA (Pearson, *Methods Mol. Biol.* 25, 365-389 [1994]) and KERR (Dufresne et al., *Nat. Biotechnol.* 20[12]:1269-71 [December 2002]). For further information regarding bioinformatics techniques, see *Current Protocols in Bioinformatics*, John Wiley & Sons, Inc., New York.

The present invention further provides non-coding fragments of the nucleic acid molecules disclosed in Table 1. Exemplary non-coding fragments include, but are not limited to, promoter sequences, enhancer sequences, intronic sequences, 5' untranslated regions (UTRs), 3' untranslated regions, gene modulating sequences and gene termination sequences. Such fragments are useful, for example, in controlling heterologous gene expression and in developing screens to identify gene-modulating agents.

SNP Detection Reagents

In a specific aspect of the present invention, the SNPs disclosed in Table 1 and their associated genomic sequences (provided in Table 1 as SEQ ID NO:1), and context sequences (genomic-based context sequences are provided in Table 1 as SEQ ID NOS:2-11), can be used for the design of SNP detection reagents. As used herein, a "SNP detection reagent" is a reagent that specifically detects a specific target SNP position disclosed herein, and that is preferably specific for a particular nucleotide (allele) of the target SNP position (i.e., the detection reagent preferably can differentiate between different alternative nucleotides at a target SNP position, thereby allowing the identity of the nucleotide present at the target SNP position to be determined). Typically, such detection reagent hybridizes to a target SNP-containing nucleic acid molecule by complementary base-pairing in a sequence-specific manner, and discriminates the target variant sequence from other nucleic acid sequences such as an art-known form in a test sample. An example of a detection reagent is a probe that hybridizes to a target nucleic acid containing one or more of the SNPs provided in Table 1. In an exemplary embodiment, such a probe can differentiate between nucleic acids having a particular nucleotide (allele) at a target SNP position from other nucleic acids that have a different nucleotide at the same target SNP position, or enables the identity of which nucleotide is present at a target SNP position to be determined in a given individual's nucleic acid. In addition, a detection reagent may hybridize to a specific region 5' and/or 3' to a SNP position, particularly a region corresponding to the context sequences provided in Table 1 (genomic-based context sequences are provided in Table 1 as SEQ ID NOS:2-11). Another example of a detection reagent is a primer which acts as an initiation point of nucleotide extension along a complementary strand of a target polynucleotide. The SNP sequence information provided herein is also useful for designing primers, e.g. allele-specific primers, to amplify (e.g., using PCR) any SNP of the present invention.

In certain exemplary embodiments of the invention, a SNP detection reagent is an isolated or synthetic DNA or RNA polynucleotide probe or primer or PNA oligomer, or a combination of DNA, RNA and/or PNA, that hybridizes to a segment of a target nucleic acid molecule containing a SNP identified in Table 1. A detection reagent in the form of a polynucleotide may optionally contain modified base analogs, intercalators or minor groove binders. Multiple detection reagents such as probes may be, for example, affixed to a solid support (e.g., arrays or beads) or supplied in solution (e.g., probe/primer sets for enzymatic reactions such as PCR, RT-PCR, TaqMan assays, or primer-extension reactions) to form a SNP detection kit.

A probe or primer typically is a substantially purified oligonucleotide or PNA oligomer. Such oligonucleotide typically comprises a region of complementary nucleotide sequence that hybridizes under stringent conditions to at least about 8, 10, 12, 16, 18, 20, 22, 25, 30, 40, 50, 55, 60, 65, 70, 80, 90, 100, 120 (or any other number in-between) or more consecutive nucleotides in a target nucleic acid molecule. Depending on the particular assay, the consecutive nucleotides can either include the target SNP position, or be a specific region in close enough proximity 5' and/or 3' to the SNP position to carry out the desired assay.

Other exemplary primer and probe sequences can readily be determined using the genomic sequences (SEQ ID NO:1) and SNP context sequences (genomic-based context sequences are provided in Table 1 as SEQ ID NOS:2-11)

disclosed in the Sequence Listing and in Table 1. It will be apparent to one of skill in the art that such primers and probes are directly useful as reagents for genotyping the SNPs of the present invention, and can be incorporated into any kit/system format.

In order to produce a probe or primer specific for a target SNP-containing sequence, the gene/transcript and/or context sequence surrounding the SNP of interest is typically examined using a computer algorithm which starts at the 5' or at the 3' end of the nucleotide sequence. Typical algorithms can then, for example, identify oligomers of defined length that are unique to the gene/SNP context sequence, have a GC content within a range suitable for hybridization, lack predicted secondary structure that may interfere with hybridization, and/or possess other desired characteristics or that lack other undesired characteristics.

An exemplary primer or probe of the present invention is typically at least about 8, 10, 12, 14, 15, 16, 17, 18, 19, 20, 21, 22, 23, 24 or 25 nucleotides in length. While the maximal length of a probe can be as long as the target sequence to be detected, depending on the type of assay in which it is employed, a probe can typically be less than about 50, 60, 65, or 70 nucleotides in length, for example. A primer can typically be less than about 30 nucleotides in length, for example. In a specific exemplary embodiment of the invention, a primer or a probe is between about 18 and about 28 nucleotides in length. However, in other embodiments, such as nucleic acid arrays and other embodiments in which probes are affixed to a substrate, the probes can be longer, such as on the order of 30-70, 75, 80, 90, 100, or more nucleotides in length (see the section below entitled “SNP Detection Kits and Systems”).

For analyzing SNPs, it may be appropriate to use oligonucleotides specific for alternative SNP alleles. Such oligonucleotides which detect single nucleotide variations in target sequences may be referred to by such terms as “allele-specific oligonucleotides,” “allele-specific probes,” or “allele-specific primers.” The design and use of allele-specific probes for analyzing polymorphisms is described in, e.g., *Mutation Detection: A Practical Approach*, ed. Cotton et al., Oxford University Press [1998]; Saiki et al., *Nature* 324, 163-166 [1986]; Dattagupta, EP235, 726; and Saiki, WO 89/11548.

While the design of each allele-specific primer or probe depends on variables such as the precise composition of the nucleotide sequences flanking a SNP position in a target nucleic acid molecule, and the length of the primer or probe, another factor in the use of primers and probes is the stringency of the condition under which the hybridization between the probe or primer and the target sequence is performed. Higher stringency conditions typically utilize buffers with lower ionic strength and/or a higher reaction temperature, and tend to require a more perfect match between probe/primer and a target sequence in order to form a stable duplex. If the stringency is too high, however, hybridization may not occur at all. In contrast, lower stringency conditions typically utilize buffers with higher ionic strength and/or a lower reaction temperature, and permit the formation of stable duplexes with more mismatched bases between a probe/primer and a target sequence. By way of example and not limitation, exemplary conditions for high stringency hybridization conditions using an allele-specific probe are as follows: prehybridization with a solution containing 5× standard saline phosphate EDTA (SSPE), 0.5% $NaDodSO_4$ (SDS) at 55° C., and incubating probe with target nucleic acid molecules in the same solution at the same temperature, followed by washing with a solution containing 2×SSPE, and 0.1% SDS at 55° C. or room temperature.

Moderate stringency hybridization conditions may be used for allele-specific primer extension reactions with a solution containing, e.g., about 50 mM KCl at about 46° C. Alternatively, the reaction may be carried out at an elevated temperature such as 60° C. In another embodiment, a moderately stringent hybridization condition suitable for oligonucleotide ligation assay (OLA) reactions wherein two probes are ligated if they are completely complementary to the target sequence may utilize a solution of about 100 mM KCl at a temperature of 46° C.

In an exemplary hybridization-based assay, allele-specific probes can be designed that hybridize to a segment of target DNA from one individual but do not hybridize to the corresponding segment from another individual due to the presence of different polymorphic forms (e.g., alternative SNP alleles/nucleotides) in the respective DNA segments from the two individuals. Hybridization conditions should be sufficiently stringent that there is a significant detectable difference in hybridization intensity between alleles, and preferably an essentially binary response, whereby a probe hybridizes to only one of the alleles or significantly more strongly to one allele. While a probe may be designed to hybridize to a target sequence that contains a SNP site such that the SNP site aligns anywhere along the sequence of the probe, a probe can be specifically designed to hybridize to a segment of the target sequence such that the SNP site aligns with a central position of the probe (e.g., a position within the probe that is at least three nucleotides from either end of the probe). This design of probe generally achieves good discrimination in hybridization between different allelic forms.

In another embodiment, a probe or primer may be designed to hybridize to a segment of target DNA such that the SNP aligns with either the 5'-most end or the 3'-most end of the probe or primer. In a specific exemplary embodiment, which is particularly suitable for use in an oligonucleotide ligation assay (U.S. Pat. No. 4,988,617), the 3'-most nucleotide of the probe aligns with the SNP position in the target sequence.

Oligonucleotide probes and primers may be prepared by methods well known in the art. Chemical synthetic methods include, but are not limited to, the phosphotriester method described by Narang et al., *Methods in Enzymology* 68:90 [1979]; the phosphodiester method described by Brown et al., *Methods in Enzymology* 68:109 [1979], the diethylphosphoamidate method described by Beaucage et al., *Tetrahedron Letters* 22:1859 [1981]; and the solid support method described in U.S. Pat. No. 4,458,066.

Allele-specific probes are often used in pairs (or, for example, in sets of 3 or 4, such as if a SNP position is known to have 3 or 4 alleles, respectively, or to assay both strands of a nucleic acid molecule for a target SNP allele), and such pairs may be identical except for a one nucleotide mismatch that represents the allelic variants at the SNP position. Commonly, one member of a pair perfectly matches a reference form of a target sequence that has a more common SNP allele (i.e., the allele that is more frequent in the target population) and the other member of the pair perfectly matches a form of the target sequence that has a less common SNP allele (i.e., the allele that is rarer in the target population). In the case of an array, multiple pairs of probes can be immobilized on the same support for simultaneous analysis of multiple different polymorphisms.

In one type of PCR-based assay, an allele-specific primer hybridizes to a region on a target nucleic acid molecule that overlaps a SNP position and only primes amplification of an allelic form to which the primer exhibits perfect complementarity (Gibbs, *Nucleic Acid Res.* 17:2427-2448 [1989]). Typically, the primer's 3'-most nucleotide is aligned with and complementary to the SNP position of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works particularly effectively when the mismatch is at the 3'-most position of the oligonucleotide (i.e., the 3'-most position of the oligonucleotide aligns with the target SNP position) because this position is most destabilizing to elongation from the primer (see, e.g., WO 93/22456). This PCR-based assay can be utilized as part of the TaqMan assay, described below.

In a specific embodiment of the invention, a primer of the invention contains a sequence substantially complementary to a segment of a target SNP-containing nucleic acid molecule except that the primer has a mismatched nucleotide in one of the three nucleotide positions at the 3'-most end of the primer, such that the mismatched nucleotide does not base pair with a particular allele at the SNP site. In an exemplary embodiment, the mismatched nucleotide in the primer is the second from the last nucleotide at the 3'-most position of the primer. In another exemplary embodiment, the mismatched nucleotide in the primer is the last nucleotide at the 3'-most position of the primer.

In another embodiment of the invention, a SNP detection reagent of the invention is labeled with a fluorogenic reporter dye that emits a detectable signal. While an exemplary reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

In yet another embodiment of the invention, the detection reagent may be further labeled with a quencher dye such as Tamra, especially when the reagent is used as a self-quenching probe such as a TaqMan (U.S. Pat. Nos. 5,210,015 and 5,538,848) or Molecular Beacon probe (U.S. Pat. Nos. 5,118,801 and 5,312,728), or other stemless or linear beacon probe (Livak et al., *PCR Method Appl.* 4:357-362 [1995]; Tyagi et al., *Nature Biotechnology* 14:303-308 [1996]; Nazarenko et al., *Nucl. Acids Res.* 25:2516-2521 [1997]; U.S. Pat. Nos. 5,866,336 and 6,117,635).

Exemplary detection reagents of the invention may also contain other labels, including but not limited to, biotin for streptavidin binding, hapten for antibody binding, and oligonucleotide for binding to another complementary oligonucleotide such as pairs of zipcodes.

Exemplary embodiments of the invention also provide reagents that do not contain (or that are complementary to) a SNP nucleotide identified herein but that are used to assay one or more SNPs disclosed herein. For example, primers that flank, but do not hybridize directly to a target SNP position provided herein are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can be detected in order to determine which SNP allele is present at the target SNP site. For example, particular ddNTPs can be used in the primer extension reaction to terminate primer extension once a ddNTP is incorporated into the extension product (a primer extension product which includes a ddNTP at the 3'-most end of the primer extension product, and in which the ddNTP is a nucleotide of a SNP disclosed herein, is a composition that is specifically provided in an exemplary embodiment of the invention). Thus, reagents that bind to a nucleic acid molecule in a region adjacent to a SNP site and that are used for assaying the SNP site, even though the bound sequences do not necessarily include the SNP site itself, are also contemplated by the present invention.

SNP Detection Kits and Systems

A person skilled in the art will recognize that, based on the SNP and associated sequence information disclosed herein, detection reagents can be developed and used to assay any SNP of the present invention individually or in combination, and such detection reagents can be readily incorporated into one of the established kit or system formats which are well known in the art. The terms "kits" and "systems", as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.). Accordingly, the present invention further provides SNP detection kits and systems, including but not limited to, packaged probe and primer sets (e.g., TaqMan probe/primer sets), arrays/microarrays of nucleic acid molecules, and beads that contain one or more probes, primers, or other detection reagents for detecting one or more SNPs of the present invention. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more SNP detection reagents (along with, optionally, other biochemical reagents) packaged in one or more containers.

In some embodiments, a SNP detection kit typically contains one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction, such as amplification and/or detection of a SNP-containing nucleic acid molecule. A kit may further contain means for determining the amount of a target nucleic acid, and means for comparing the amount with a standard, and can comprise instructions for using the kit to detect the SNP-containing nucleic acid molecule of interest. In one embodiment of the present invention, kits are provided which contain the necessary reagents to carry out one or more assays to detect one or more SNPs disclosed herein. In an exemplary embodiment of the present invention, SNP detection kits/systems are in the form of nucleic acid arrays, or compartmentalized kits, including microfluidic/lab-on-a-chip systems.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is a SNP of the present invention. In some kits/systems, the allele-specific probes are immobilized to a substrate such as an array or bead. For example, the same substrate can comprise allele-specific probes for detecting at least 1; 10; 100; 1000; 10,000; 100,000 (or any other number in-between) or substantially all of the SNPs shown in Table 1.

The terms "arrays," "microarrays," and "DNA chips" are used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In one embodiment, the microarray is prepared and used according to the methods described in U.S. Pat. No. 5,837,832 (Chee et al.), PCT application WO95/11995 (Chee et al.), Lockhart, D. J. et al. (*Nat. Biotech.* 14:1675-1680 [1996]) and Schena, M. et al. (*Proc. Natl. Acad. Sci.* 93:10614-10619 [1996]), all of which are incorporated herein in their entirety by reference. In other embodiments, such arrays are produced by the methods described by Brown et al., U.S. Pat. No. 5,807,522.

Nucleic acid arrays are reviewed in the following references: Zammatteo et al., "New chips for molecular biology and diagnostics," *Biotechnol. Annu. Rev.* 8:85-101 (2002); Sosnowski et al., "Active microelectronic array system for DNA hybridization, genotyping and pharmacogenomic applications," *Psychiatr. Genet.* 12(4):181-92 (December 2002); Heller, "DNA microarray technology: devices, systems, and applications," *Annu. Rev. Biomed. Eng.* 4:129-53 (2002); Epub Mar. 22, 2002; Kolchinsky et al., "Analysis of SNPs and other genomic variations using gel-based chips," *Hum. Mutat.* 19(4):343-60 (April 2002); and McGall et al., "High-density genechip oligonucleotide probe arrays," *Adv. Biochem. Eng. Biotechnol.* 77:21-42 (2002).

Any number of probes, such as allele-specific probes, may be implemented in an array, and each probe or pair of probes can hybridize to a different SNP position. In the case of polynucleotide probes, they can be synthesized at designated areas (or synthesized separately and then affixed to designated areas) on a substrate using a light-directed chemical process. Each DNA chip can contain, for example, thousands to millions of individual synthetic polynucleotide probes arranged in a grid-like pattern and miniaturized (e.g., to the size of a dime). Probes can be attached to a solid support in an ordered, addressable array.

A microarray can be composed of a large number of unique, single-stranded polynucleotides, usually either synthetic antisense polynucleotides or fragments of cDNAs, fixed to a solid support. Typical polynucleotides are about 6-60 nucleotides in length, or about 15-30 nucleotides in length, or about 18-25 nucleotides in length. For certain types of microarrays or other detection kits/systems, it may be preferable to use oligonucleotides that are only about 7-20 nucleotides in length. In other types of arrays, such as arrays used in conjunction with chemiluminescent detection technology, exemplary probe lengths can be, for example, about 15-80 nucleotides in length, or about 50-70 nucleotides in length, or about 55-65 nucleotides in length, or about 60 nucleotides in length. The microarray or detection kit can contain polynucleotides that cover the known 5' or 3' sequence of a gene/transcript or target SNP site, sequential polynucleotides that cover the full-length sequence of a gene/transcript; or unique polynucleotides selected from particular areas along the length of a target gene/transcript sequence, particularly areas corresponding to one or more SNPs disclosed in Table 1. Polynucleotides used in the microarray or detection kit can be specific to a SNP or SNPs of interest (e.g., specific to a particular SNP allele at a target SNP site, or specific to particular SNP alleles at multiple different SNP sites), or specific to a polymorphic gene/transcript or genes/transcripts of interest.

Hybridization assays based on polynucleotide arrays rely on the differences in hybridization stability of the probes to perfectly matched and mismatched target sequence variants. For SNP genotyping, it is generally preferable that stringency conditions used in hybridization assays are high enough such that nucleic acid molecules that differ from one another at as little as a single SNP position can be differentiated (e.g., typical SNP hybridization assays are designed so that hybridization will occur only if one particular nucleotide is present at a SNP position, but will not occur if an alternative nucleotide is present at that SNP position). Such high stringency conditions may be preferable when using, for example, nucleic acid arrays of allele-specific probes for SNP detection. Such high stringency conditions are described in the preceding section, and are well known to those skilled in the art and can be found in, for example, *Current Protocols in Molecular Biology* 6.3.1-6.3.6, John Wiley & Sons, New York (1989).

In other embodiments, the arrays are used in conjunction with chemiluminescent detection technology. The following patents and patent applications, which are all hereby incorporated by reference, provide additional information pertaining to chemiluminescent detection: U.S. patent application Ser. Nos. 10/620,332 and 10/620,333 describe chemiluminescent approaches for microarray detection; U.S. Pat. Nos. 6,124,478, 6,107,024, 5,994,073, 5,981,768, 5,871,938, 5,843,681, 5,800,999, and 5,773,628 describe methods and compositions of dioxetane for performing chemiluminescent detection; and U.S. published application US2002/0110828 discloses methods and compositions for microarray controls.

In one embodiment of the invention, a nucleic acid array can comprise an array of probes of about 15-25 nucleotides in length. In further embodiments, a nucleic acid array can comprise any number of probes, in which at least one probe is capable of detecting one or more SNPs disclosed in Table 1, and/or at least one probe comprises a fragment of one of the sequences selected from the group consisting of those disclosed in Table 1, the Sequence Listing, and sequences complementary thereto, said fragment comprising at least about 8, 10, 12, 15, 16, 18, 20, 22, 25, 30, 40, 47, 50, 55, 60, 65, 70, 80, 90, 100, or more consecutive nucleotides (or any other number in-between) and containing (or being complementary to) a novel SNP allele disclosed in Table 1. In some embodiments, the nucleotide complementary to the SNP site is within 5, 4, 3, 2, or 1 nucleotide from the center of the probe, or at the center of said probe.

A polynucleotide probe can be synthesized on the surface of the substrate by using a chemical coupling procedure and an inkjet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more polynucleotides, or any other number which lends itself to the efficient use of commercially available instrumentation.

Using such arrays or other kits/systems, the present invention provides methods of identifying the SNPs disclosed herein in a test sample. Such methods typically involve incubating a test sample of nucleic acids with an array comprising one or more probes corresponding to at least one SNP position of the present invention, and assaying for binding of a nucleic acid from the test sample with one or more of the probes. Conditions for incubating a SNP detection reagent (or a kit/system that employs one or more such SNP detection reagents) with a test sample vary. Incubation conditions depend on such factors as the format employed in the assay, the detection methods employed, and the type and nature of the detection reagents used in the assay. One skilled in the art will recognize that any one of the commonly available hybridization, amplification and array assay formats can readily be adapted to detect the SNPs disclosed herein.

A SNP detection kit/system of the present invention may include components that are used to prepare nucleic acids from a test sample for the subsequent amplification and/or detection of a SNP-containing nucleic acid molecule. Such sample preparation components can be used to produce nucleic acid extracts (including DNA and/or RNA), proteins or membrane extracts from any bodily fluids (such as blood, serum, plasma, urine, saliva, phlegm, gastric juices, semen, tears, sweat, etc.), skin, hair, cells (especially nucleated cells), biopsies, buccal swabs or tissue specimens. The test samples used in the above-described methods will vary based on such factors as the assay format, nature of the detection method, and the specific tissues, cells or extracts used as the test sample to be assayed. Methods of preparing nucleic acids, proteins, and cell extracts are well known in the art and can be readily adapted to obtain a sample that is compatible with the system utilized. Automated sample preparation systems for extracting nucleic acids from a test sample are commercially available, and examples are Qiagen's BioRobot 9600, Applied Biosystems' PRISM 6700, and Roche Molecular Systems' COBAS AmpliPrep System.

Another form of kit contemplated by the present invention is a compartmentalized kit. A compartmentalized kit includes any kit in which reagents are contained in separate containers. Such containers include, for example, small glass containers, plastic containers, strips of plastic, glass or paper, or arraying material such as silica. Such containers allow one to efficiently transfer reagents from one compartment to another compartment such that the test samples and reagents are not cross-contaminated, or from one container to another vessel not included in the kit, and the agents or solutions of each container can be added in a quantitative fashion from one compartment to another or to another vessel. Such containers may include, for example, one or more containers which will accept the test sample, one or more containers which contain at least one probe or other SNP detection reagent for detecting one or more SNPs of the present invention, one or more containers which contain wash reagents (such as phosphate buffered saline, Tris-buffers, etc.), and one or more containers which contain the reagents used to reveal the presence of the bound probe or other SNP detection reagents. The kit can optionally further comprise compartments and/or reagents for, for example, nucleic acid amplification or other enzymatic reactions such as primer extension reactions, hybridization, ligation, electrophoresis (e.g., capillary electrophoresis), mass spectrometry, and/or laser-induced fluorescent detection. The kit may also include instructions for using the kit. Exemplary compartmentalized kits include microfluidic devices known in the art (see, e.g., Weigl et al., "Lab-on-a-chip for drug development," *Adv. Drug Deliv. Rev.* 24, 55-[3]: 349-77 [February 2003]). In such microfluidic devices, the containers may be referred to as, for example, microfluidic "compartments," "chambers," or "channels."

Microfluidic devices, which may also be referred to as "lab-on-a-chip" systems, biomedical micro-electro-mechanical systems (bioMEMs), or multicomponent integrated systems, are exemplary kits/systems of the present invention for analyzing SNPs. Such systems miniaturize and compartmentalize processes such as probe/target hybridization, nucleic acid amplification, and capillary electrophoresis reactions in a single functional device. Such microfluidic devices typically utilize detection reagents in at least one aspect of the system, and such detection reagents may be used to detect one or more SNPs of the present invention. One example of a microfluidic system is disclosed in U.S. Pat. No. 5,589,136, which describes the integration of PCR amplification and capillary electrophoresis in chips. Exemplary microfluidic systems comprise a pattern of microchannels designed onto a glass, silicon, quartz, or plastic wafer included on a microchip. The movements of the samples may be controlled by electric, electroosmotic or hydrostatic forces applied across different areas of the microchip to create functional microscopic valves and pumps with no moving parts. Varying the voltage can be used as a means to control the liquid flow at intersections between the micro-machined channels and to change the liquid flow rate for pumping across different sections of the microchip. See, for example, U.S. Pat. Nos. 6,153,073, Dubrow et al., and 6,156,181, Parce et al.

For genotyping SNPs, an exemplary microfluidic system may integrate, for example, nucleic acid amplification, primer extension, capillary electrophoresis, and a detection method such as laser induced fluorescence detection. In a first step of an exemplary process for using such an exemplary system, nucleic acid samples are amplified, such as by PCR. Then, the amplification products are subjected to automated primer extension reactions using ddNTPs (specific fluorescence for each ddNTP) and the appropriate oligonucleotide primers to carry out primer extension reactions which hybridize just upstream of the targeted SNP. Once the extension at the 3' end is completed, the primers are separated from the unincorporated fluorescent ddNTPs by capillary electrophoresis. The separation medium used in capillary electrophoresis can be, for example, polyacrylamide, polyethyleneglycol or dextran. The incorporated ddNTPs in the single nucleotide primer extension products are identified by laser-induced fluorescence detection. Such an exemplary microchip can be used to process, for example, at least 96 to 384 samples, or more, in parallel.

Uses of Nucleic Acid Molecules

The nucleic acid molecules of the present invention have a variety of uses, especially in the diagnosis and treatment of neurodegenerative disease. For example, the nucleic acid molecules are useful as hybridization probes, such as for genotyping SNPs in genomic DNA, amplified DNA, or other nucleic acid molecules.

A probe can hybridize to any nucleotide sequence along the entire length of a nucleic acid molecule provided in Table 1. Typically, a probe of the present invention hybridizes to a region of a target sequence that encompasses a SNP position indicated in Table 1. For example, a probe can hybridize to a SNP-containing target sequence in a sequence-specific manner such that it distinguishes the target sequence from other nucleotide sequences which vary from the target sequence only by which nucleotide is present at the SNP site. Such a probe is particularly useful for detecting the presence of a SNP-containing nucleic acid in a test sample, or for determining which nucleotide (allele) is present at a particular SNP site (i.e., genotyping the SNP site).

A nucleic acid hybridization probe may be used for determining the presence, level, form, and/or distribution of nucleic acid expression. The nucleic acid whose level is determined can be DNA or RNA. Accordingly, probes specific for the SNPs described herein can be used to assess the presence, expression and/or gene copy number in a given cell, tissue, or organism. These uses are relevant for diagnosis of disorders involving an increase or decrease in gene expression relative to normal levels. In vitro techniques for detection of mRNA include, for example, Northern blot hybridizations and in situ hybridizations. In vitro techniques for detecting DNA include Southern blot hybridizations and in situ hybridizations (Sambrook and Russell, *Molecular Cloning: A Laboratory Manual*, Cold Spring Harbor Press, Cold Spring Harbor, N.Y. [2000]).

Probes can be used as part of a diagnostic test kit for identifying cells or tissues in which a variant protein is expressed, such as by measuring the level of a variant protein-encoding nucleic acid (e.g., mRNA) in a sample of cells from a subject or determining if a polynucleotide contains a SNP of interest.

Thus, the nucleic acid molecules of the invention can be used as hybridization probes to detect the SNPs disclosed herein, thereby determining whether an individual with the polymorphisms is at risk for neurodegenerative disease or has developed early stage neurodegenerative disease. Detection of a SNP associated with a disease phenotype provides a diagnostic tool for an active disease and/or genetic predisposition to the disease.

Furthermore, the nucleic acid molecules of the invention are therefore useful for detecting a gene (gene information is disclosed in Table 1, for example) which contains a SNP disclosed herein. The nucleic acid molecules can optionally be implemented in, for example, an array or kit format.

The nucleic acid molecules of the invention are also useful as primers to amplify any given region of a nucleic acid molecule, particularly a region containing a SNP identified in Table 1.

The nucleic acid molecules of the invention are also useful for constructing recombinant vectors (described in greater detail below). Such vectors include expression vectors. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced SNPs.

The nucleic acid molecules of the invention are also useful for constructing vectors containing a gene regulatory region of the nucleic acid molecules of the present invention.

The nucleic acid molecules of the invention are also useful for designing ribozymes corresponding to all, or a part, of an mRNA molecule expressed from a SNP-containing nucleic acid molecule described herein.

The nucleic acid molecules of the invention are also useful for constructing host cells expressing a part, or all, of the nucleic acid molecules and variant peptides.

The nucleic acid molecules of the invention are also useful for constructing transgenic animals expressing all, or a part, of the nucleic acid molecules and variant peptides. The production of recombinant cells and transgenic animals having nucleic acid molecules which contain the SNPs disclosed in Table 1 allow, for example, effective clinical design of treatment compounds and dosage regimens.

The nucleic acid molecules of the invention are also useful in assays for drug screening to identify compounds that, for example, modulate nucleic acid expression.

The nucleic acid molecules of the invention are also useful in gene therapy in patients whose cells have aberrant gene expression. Thus, recombinant cells, which include a patient's cells that have been engineered ex vivo and returned to the patient, can be introduced into an individual where the recombinant cells produce the desired protein to treat the individual.

SNP Genotyping Methods

The process of determining which specific nucleotide (i.e., allele) is present at each of one or more SNP positions, such as a SNP position in a nucleic acid molecule disclosed in Table 1, is referred to as SNP genotyping. The present invention provides methods of SNP genotyping, such as for use in screening for neurodegenerative disease or related pathologies, or determining predisposition thereto, or determining responsiveness to a form of treatment, or in genome mapping or SNP association analysis, etc.

Nucleic acid samples can be genotyped to determine which allele(s) is/are present at any given genetic region (e.g., SNP position) of interest by methods well known in the art. The neighboring sequence can be used to design SNP detection reagents such as oligonucleotide probes, which may optionally be implemented in a kit format. Exemplary SNP genotyping methods are described in Chen et al., "Single nucleotide polymorphism genotyping: biochemistry, protocol, cost and throughput," *Pharmacogenomics J.* 3(2):77-96 (2003); Kwok et al., "Detection of single nucleotide polymorphisms," *Curr. Issues Mol. Biol.* 5(2):43-60 (April 2003); Shi, "Technologies for individual genotyping: detection of genetic polymorphisms in drug targets and disease genes," *Am. J. Pharmacogenomics* 2(3):197-205 (2002); and Kwok, "Methods for genotyping single nucleotide polymorphisms," *Annu. Rev. Genomics Hum. Genet.* 2:235-58 (2001). Exemplary techniques for high-throughput SNP genotyping are described in Marnellos, "High-throughput SNP analysis for genetic association studies," *Curr. Opin. Drug Discov. Devel.* 6(3):317-21 (May 2003). Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Various methods for detecting polymorphisms include, but are not limited to, methods in which protection from cleavage agents is used to detect mismatched bases in RNA/RNA or RNA/DNA duplexes (Myers et al., *Science* 230:1242 [1985]; Cotton et al., *PNAS* 85:4397 [1988]; and Saleeba et al., *Meth. Enzymol.* 217:286-295 [1992]), comparison of the electrophoretic mobility of variant and wild type nucleic acid molecules (Orita et al., *PNAS* 86:2766 [1989]; Cotton et al, *Mutat. Res.* 285:125-144 [1993]; and Hayashi et al., *Genet. Anal.*

*Tech. Appl.* 9:73-79 [1992]), and assaying the movement of polymorphic or wild-type fragments in polyacrylamide gels containing a gradient of denaturant using denaturing gradient gel electrophoresis (DGGE) (Myers et al., *Nature* 313:495 [1985]). Sequence variations at specific locations can also be assessed by nuclease protection assays such as RNase and S1 protection or chemical cleavage methods.

In an exemplary embodiment, SNP genotyping is performed using the TaqMan assay, which is also known as the 5' nuclease assay (U.S. Pat. Nos. 5,210,015 and 5,538,848). The TaqMan assay detects the accumulation of a specific amplified product during PCR. The TaqMan assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5'-most and the 3'-most ends, respectively, or vice versa. Alternatively, the reporter dye may be at the 5'- or 3'-most end while the quencher dye is attached to an internal nucleotide, or vice versa. In yet another embodiment, both the reporter and the quencher may be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Exemplary TaqMan primer and probe sequences can readily be determined using the SNP and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the SNPs of the present invention are useful in diagnostic assays for neurodegenerative disease and related pathologies, and can be readily incorporated into a kit format. The present invention also includes modifications of the Taqman assay well known in the art such as the use of Molecular Beacon probes (U.S. Pat. Nos. 5,118,801 and 5,312,728) and other variant formats (U.S. Pat. Nos. 5,866,336 and 6,117,635).

Another exemplary method for genotyping the SNPs of the present invention is the use of two oligonucleotide probes in an OLA (see, e.g., U.S. Pat. No. 4,988,617). In this method, one probe hybridizes to a segment of a target nucleic acid with its 3'-most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the SNP site. If there is a mismatch, ligation would not occur. After the reaction, the ligated probes are separated from the target nucleic acid molecule, and detected as indicators of the presence of a SNP.

The following patents, patent applications, and published international patent applications, which are all hereby incorporated by reference, provide additional information pertaining to techniques for carrying out various types of OLA: U.S. Pat. Nos. 6,027,889, 6,268,148, 5,494,810, 5,830,711, and 6,054,564 describe OLA strategies for performing SNP detection; WO 97/31256 and WO 00/56927 describe OLA strategies for performing SNP detection using universal arrays, wherein a zipcode sequence can be introduced into one of the hybridization probes, and the resulting product, or amplified product, hybridized to a universal zip code array; U.S. application US01/17329 (and Ser. No. 09/584,905) describes OLA (or LDR) followed by PCR, wherein zipcodes are incorporated into OLA probes, and amplified PCR products are determined by electrophoretic or universal zipcode array readout; U.S. applications 60/427,818, 60/445,636, and 60/445,494 describe SNPlex methods and software for multiplexed SNP detection using OLA followed by PCR, wherein zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for SNP genotyping is based on mass spectrometry. Mass spectrometry takes advantage of the unique mass of each of the four nucleotides of DNA. SNPs can be unambiguously genotyped by mass spectrometry by measuring the differences in the mass of nucleic acids having alternative SNP alleles. MALDI-TOF (Matrix Assisted Laser Desorption Ionization—Time of Flight) mass spectrometry technology is useful for extremely precise determinations of molecular mass, such as SNPs. Numerous approaches to SNP analysis have been developed based on mass spectrometry. Exemplary mass spectrometry-based methods of SNP genotyping include primer extension assays, which can also be utilized in combination with other approaches, such as traditional gel-based formats and microarrays.

Typically, the primer extension assay involves designing and annealing a primer to a template PCR amplicon upstream (5') from a target SNP position. A mix of dideoxynucleotide triphosphates (ddNTPs) and/or deoxynucleotide triphosphates (dNTPs) are added to a reaction mixture containing template (e.g., a SNP-containing nucleic acid molecule which has typically been amplified, such as by PCR), primer, and DNA polymerase. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the SNP position. If the primer is several nucleotides removed from the target SNP position, the only limitation is that the template sequence between the 3' end of the primer and the SNP position cannot contain a nucleotide of the same type as the one to be detected, or this will cause premature termination of the extension primer. Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer.

The extended primers can then be purified and analyzed by MALDI-TOF mass spectrometry to determine the identity of the nucleotide present at the target SNP position. In one method of analysis, the products from the primer extension reaction are combined with light absorbing crystals that form a matrix. The matrix is then hit with an energy source such as a laser to ionize and desorb the nucleic acid molecules into the gas-phase. The ionized molecules are then ejected into a flight tube and accelerated down the tube towards a detector. The time between the ionization event, such as a laser pulse, and collision of the molecule with the detector is the time of flight of that molecule. The time of flight is precisely correlated with the mass-to-charge ratio (m/z) of the ionized molecule. Ions with smaller m/z travel down the tube faster than ions with larger m/z and therefore the lighter ions reach the detector before the heavier ions. The time-of-flight is then converted into a corresponding, and highly precise, m/z. In this manner, SNPs can be identified based on the slight differences in mass, and the corresponding time of flight differences, inherent in nucleic acid molecules having different nucleotides at a single base position. For further information regarding the use of primer extension assays in conjunction with MALDI-TOF mass spectrometry for SNP genotyping, see, e.g., Wise et al., "A standard protocol for single nucleotide primer extension in the human genome using matrix-assisted laser desorption/ionization time-of-flight mass spectrometry," *Rapid Commun. Mass Spectrom.* 17(11):1195-202 (2003).

The following references provide further information describing mass spectrometry-based methods for SNP genotyping: Bocker, "SNP and mutation discovery using base-specific cleavage and MALDI-TOF mass spectrometry," *Bioinformatics* 19 Suppl 1:I44-I53 (July 2003); Storm et al., "MALDI-TOF mass spectrometry-based SNP genotyping," *Methods Mol. Biol.* 212:241-62 (2003); Jurinke et al., "The use of MassARRAY technology for high throughput genotyping," *Adv. Biochem. Eng. Biotechnol.* 77:57-74 (2002); and Jurinke et al., "Automated genotyping using the DNA MassArray technology," *Methods Mol. Biol.* 187:179-92 (2002).

SNPs can also be scored by direct DNA sequencing. A variety of automated sequencing procedures can be utilized (*Biotechniques* 19:448 [1995]), including sequencing by mass spectrometry (see, e.g., PCT International Publication No. WO94/16101; Cohen et al., *Adv. Chromatogr.* 36:127-162 [1996]; and Griffin et al., *Appl. Biochem. Biotechnol.* 38:147-159 [1993]). The nucleic acid sequences of the present invention enable one of ordinary skill in the art to readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing.

Other methods that can be used to genotype the SNPs of the present invention include single-strand conformational polymorphism (SSCP), and denaturing gradient gel electrophoresis (DGGE) (Myers et al., *Nature* 313:495 [1985]). SSCP identifies base differences by alteration in electrophoretic migration of single stranded PCR products, as described in Orita et al., *Proc. Nat. Acad.* Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel ("PCR Technology," *Principles and Applications for DNA Amplification Chapter* 7, ed. Erlich, W.H. Freeman and Co., New York, [1992]).

Sequence-specific ribozymes (U.S. Pat. No. 5,498,531) can also be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis.

SNP genotyping can include the steps of, for example, collecting a biological sample from a human subject (e.g., sample of tissues, cells, fluids, secretions, etc.), isolating nucleic acids (e.g., genomic DNA, mRNA or both) from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

SNP genotyping is useful for numerous practical applications, as described below. Examples of such applications include, but are not limited to, SNP-disease association analysis, disease predisposition screening, disease diagnosis, disease prognosis, disease progression monitoring, determining therapeutic strategies based on an individual's genotype ("pharmacogenomics"), developing therapeutic agents based on SNP genotypes associated with a disease or likelihood of responding to a drug, stratifying a patient population for clinical trials of a treatment regimen, predicting the likelihood that an individual will experience toxic side effects from a therapeutic agent, and human identification applications such as forensics.

Analysis of Genetic Association Between SNPs and Phenotypic Traits

SNP genotyping for disease diagnosis, disease predisposition screening, disease prognosis, determining drug responsiveness (pharmacogenomics), drug toxicity screening, and other uses described herein, typically relies on initially establishing a genetic association between one or more specific SNPs and the particular phenotypic traits of interest.

Different study designs may be used for genetic association studies (*Modern Epidemiology* 609-622, Lippincott Williams & Wilkins [1998]). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is case-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-control studies are considerably less than those for prospective studies, case-control studies are the more commonly used study design in genetic association studies, at least during the exploration and discovery stage.

In both types of observational studies, there may be potential confounding factors that should be taken into consideration. Confounding factors are those that are associated with both the real cause(s) of the disease and the disease itself, and they include demographic information such as age, gender, ethnicity as well as environmental factors. When confounding factors are not matched in cases and controls in a study, and are not controlled properly, spurious association results can arise. If potential confounding factors are identified, they should be controlled for by analysis methods explained below.

In a genetic association study, the cause of interest to be tested is a certain allele or a SNP or a combination of alleles or a haplotype from several SNPs. Thus, tissue specimens (e.g., whole blood) from the sampled individuals may be collected and genomic DNA genotyped for the SNP(s) of interest. In addition to the phenotypic trait of interest, other information such as demographic (e.g., age, gender, ethnicity, etc.), clinical, and environmental information that may influence the outcome of the trait can be collected to further characterize and define the sample set. In many cases, these factors are known to be associated with diseases and/or SNP allele frequencies. There are likely gene-environment and/or gene-gene interactions as well. Analysis methods to address gene-environment and gene-gene interactions (for example, the effects of the presence of both susceptibility alleles at two different genes can be greater than the effects of the individual alleles at two genes combined) are discussed below.

After all the relevant phenotypic and genotypic information has been obtained, statistical analyses are carried out to determine if there is any significant correlation between the presence of an allele or a genotype with the phenotypic characteristics of an individual. Data inspection and cleaning can first be performed before carrying out statistical tests for genetic association. Epidemiological and clinical data of the samples can be summarized by descriptive statistics with tables and graphs. Data validation can be performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively. To ensure genotyping quality, Hardy-Weinberg disequilibrium tests can be performed on cases and controls separately. Significant deviation from Hardy-Weinberg equilibrium (HWE) in both cases and controls for individual markers can be indicative of genotyping errors. If HWE is violated in a majority of markers, it is indicative of population substructure that should be further investigated. Moreover, Hardy-Weinberg disequilibrium in cases only can indicate genetic association of the markers with the disease (*Genetic Data Analysis*, Weir B., Sinauer [1990]).

To test whether an allele of a single SNP is associated with the case or control status of a phenotypic trait, one skilled in the art can compare allele frequencies in cases and controls. Standard chi-squared tests and Fisher exact tests can be carried out on a 2×2 table (2 SNP alleles×2 outcomes in the categorical trait of interest). To test whether genotypes of a SNP are associated, chi-squared tests can be carried out on a 3×2 table (3 genotypes×2 outcomes). Score tests are also carried out for genotypic association to contrast the three genotypic frequencies (major homozygotes, heterozygotes and minor homozygotes) in cases and controls, and to look for trends using 3 different modes of inheritance, namely dominant (with contrast coefficients 2, −1, −1), additive (with contrast coefficients 1, 0, −1) and recessive (with contrast coefficients 1, 1, −2). Odds ratios for minor versus major alleles, and odds ratios for heterozygote and homozygote variants versus the wild type genotypes are calculated with the desired confidence limits, usually 95%.

In order to control for confounders and to test for interaction and effect modifiers, stratified analyses may be performed using stratified factors that are likely to be confounding, including demographic information such as age, ethnicity, and gender, or an interacting element or effect modifier, such as a known major gene (e.g., APOE for AD or HLA genes for autoimmune diseases), or environmental factors such as smoking in lung cancer. Stratified association tests may be carried out using Cochran-Mantel-Haenszel tests that take into account the ordinal nature of genotypes with 0, 1, and 2 variant alleles. Exact tests by StatXact may also be performed when computationally possible. Another way to adjust for confounding effects and test for interactions is to perform stepwise multiple logistic regression analysis using statistical packages such as SAS or R. Logistic regression is a model-building technique in which the best fitting and most parsimonious model is built to describe the relation between the dichotomous outcome (for instance, getting a certain disease or not) and a set of independent variables (for instance, genotypes of different associated genes, and the associated demographic and environmental factors). The most common model is one in which the logit transformation of the odds ratios is expressed as a linear combination of the variables (main effects) and their cross-product terms (interactions) (Applied Logistic Regression, Hosmer and Lemeshow, Wiley [2000]). To test whether a certain variable or interaction is significantly associated with the outcome, coefficients in the model are first estimated and then tested for statistical significance of their departure from zero.

In addition to performing association tests one marker at a time, haplotype association analysis may also be performed to study a number of markers that are closely linked together. Haplotype association tests can have better power than genotypic or allelic association tests when the tested markers are not the disease-causing mutations themselves but are in linkage disequilibrium with such mutations. The test will even be more powerful if the disease is indeed caused by a combination of alleles on a haplotype (e.g., APOE is a haplotype formed by 2 SNPs that are very close to each other). In order to perform haplotype association effectively, marker-marker linkage disequilibrium measures, both D' and $R^2$, are typically calculated for the markers within a gene to elucidate the haplotype structure. Recent studies (Daly et al., *Nature Genetics* 29, 232-235 [2001]) in linkage disequilibrium indicate that SNPs within a gene are organized in block pattern, and a high degree of linkage disequilibrium exists within blocks and very little linkage disequilibrium exists between blocks. Haplotype association with the disease status can be performed using such blocks once they have been elucidated.

Haplotype association tests can be carried out in a similar fashion as the allelic and genotypic association tests. Each haplotype in a gene is analogous to an allele in a multi-allelic marker. One skilled in the art can either compare the haplotype frequencies in cases and controls or test genetic association with different pairs of haplotypes. It has been proposed (Schaid et al., *Am. J. Hum. Genet.* 70, 425-434 [2002]) that score tests can be done on haplotypes using the program "haplo.score." In that method, haplotypes are first inferred by EM algorithm and score tests are carried out with a generalized linear model (GLM) framework that allows the adjustment of other factors.

An important decision in the performance of genetic association tests is the determination of the significance level at which significant association can be declared when the P value of the tests reaches that level. In an exploratory analysis where positive hits will be followed up in subsequent confirmatory testing, an unadjusted P value <0.1 (a significance level on the lenient side) may be used for generating hypotheses for significant association of a SNP with certain phenotypic characteristics of a disease. It is preferred that a P value <0.05 (a significance level traditionally used in the art) is achieved in order for a SNP to be considered to have an association with a disease. It is more preferred that a P value <0.01 (a significance level on the stringent side) is achieved for an association to be declared. When hits are followed up in confirmatory analyses in more samples of the same source or in different samples from different sources, adjustment for multiple testing will be performed as to avoid excess number of hits while maintaining the experiment-wise error rates at 0.05. While there are different methods to adjust for multiple testing to control for different kinds of error rates, a commonly used but rather conservative method is Bonferroni correction to control the experiment-wise or family-wise error rate (Westfall et al., *Multiple comparisons and multiple tests*, SAS Institute [1999]). Permutation tests to control for the false discovery rates, FDR, can be more powerful (Benjamini and Hochberg, *Journal of the Royal Statistical Society* Series B 57, 1289-1300 [1995*], Resampling-based Multiple Testing*, Westfall and Young, Wiley [1993]). Such methods to control for multiplicity would be preferred when the tests are dependent and controlling for false discovery rates is sufficient as opposed to controlling for the experiment-wise error rates.

In replication studies using samples from different populations after statistically significant markers have been identified in the exploratory stage, meta-analyses can then be performed by combining evidence of different studies (*Modern Epidemiology* 643-673, Lippincott Williams & Wilkins [1998]). If available, association results known in the art for the same SNPs can be included in the meta-analyses.

Since both genotyping and disease status classification can involve errors, sensitivity analyses may be performed to see how odds ratios and P values would change upon various estimates on genotyping and disease classification error rates.

It has been well known that subpopulation-based sampling bias between cases and controls can lead to spurious results in case-control association studies (Ewens and Spielman, *Am. J. Hum. Genet.* 62, 450-458 [1995]) when prevalence of the disease is associated with different subpopulation groups. Such bias can also lead to a loss of statistical power in genetic association studies. To detect population stratification, Pritchard and Rosenberg (Pritchard et al., *Am. J. Hum. Gen.* 65:220-228 [1999]) suggested typing markers that are unlinked to the disease and using results of association tests on those markers to determine whether there is any population stratification. When stratification is detected, the genomic control (GC) method as proposed by Devlin and Roeder (Devlin et al., *Biometrics* 55:997-1004 [1999]) can be used to adjust for the inflation of test statistics due to population stratification. GC method is robust to changes in population structure levels as well as being applicable to DNA pooling designs (Devlin et al., *Genet. Epidem.* 21:273-284 [2001]).

While Pritchard's method recommended using 15-20 unlinked microsatellite markers, it suggested using more than 30 biallelic markers to get enough power to detect population stratification. For the GC method, it has been shown (Bacanu et al., *Am. J. Hum. Genet.* 66:1933-1944 [2000]) that about 60-70 biallelic markers are sufficient to estimate the inflation factor for the test statistics due to population stratification. Hence, 70 intergenic SNPs can be chosen in unlinked regions as indicated in a genome scan (Kehoe et al., *Hum. Mol. Genet.* 8:237-245 [1999]).

Once individual risk factors, genetic or non-genetic, have been found for the predisposition to disease, the next step is to set up a classification/prediction scheme to predict the category (for instance, disease or no-disease) that an individual will be in depending on his genotypes of associated SNPs and other non-genetic risk factors. Logistic regression for discrete trait and linear regression for continuous trait are standard techniques for such tasks (*Applied Regression Analysis*, Draper and Smith, Wiley [1998]). Moreover, other techniques can also be used for setting up classification. Such techniques include, but are not limited to, MART, CART, neural network, and discriminant analyses that are suitable for use in comparing the performance of different methods (*The Elements of Statistical Learning*, Hastie, Tibshirani & Friedman, Springer [2002]).

Disease Diagnosis and Predisposition Screening

Information on association/correlation between genotypes and disease-related phenotypes can be exploited in several ways. For example, in the case of a highly statistically significant association between one or more SNPs with predisposition to a disease for which treatment is available, detection of such a genotype pattern in an individual may justify immediate administration of treatment, or at least the institution of regular monitoring of the individual. Detection of the susceptibility alleles associated with serious disease in a couple contemplating having children may also be valuable to the couple in their reproductive decisions. In the case of a weaker but still statistically significant association between a SNP and a human disease, immediate therapeutic intervention or monitoring may not be justified after detecting the susceptibility allele or SNP. Nevertheless, the subject can be motivated to begin simple life-style changes (e.g., diet, exercise) that can be accomplished at little or no cost to the individual but would confer potential benefits in reducing the risk of developing conditions for which that individual may have an increased risk by virtue of having the susceptibility allele(s).

The SNPs of the invention may contribute to neurodegenerative disease in an individual in different ways. Some polymorphisms occur within a protein coding sequence and contribute to disease phenotype by affecting protein structure. Other polymorphisms occur in noncoding regions but may exert phenotypic effects indirectly via influence on, for example, replication, transcription, and/or translation. A single SNP may affect more than one phenotypic trait. Likewise, a single phenotypic trait may be affected by multiple SNPs in different genes.

As used herein, the terms "diagnose," "diagnosis," and "diagnostics" include, but are not limited to any of the following: detection of neurodegenerative disease that an individual may presently have, predisposition/susceptibility screening (i.e., determining the increased risk of an individual in developing neurodegenerative disease in the future, or determining whether an individual has a decreased risk of developing neurodegenerative disease in the future), determining a particular type or subclass of neurodegenerative disease in an individual known to have neurodegenerative disease, confirming or reinforcing a previously made diagnosis of neurodegenerative disease, pharmacogenomic evaluation of an individual to determine which therapeutic strategy that individual is most likely to positively respond to or to predict whether a patient is likely to respond to a particular treatment, predicting whether a patient is likely to experience toxic effects from a particular treatment or therapeutic compound, and evaluating the future prognosis of an individual having neurodegenerative disease. Such diagnostic uses are based on the SNPs individually or in a unique combination or SNP haplotypes of the present invention.

Haplotypes are particularly useful in that, for example, fewer SNPs can be genotyped to determine if a particular genomic region harbors a locus that influences a particular phenotype, such as in linkage disequilibrium-based SNP association analysis.

Linkage disequilibrium (LD) refers to the co-inheritance of alleles (e.g., alternative nucleotides) at two or more different SNP sites at frequencies greater than would be expected from the separate frequencies of random occurrence of each allele in a given population. The expected frequency of co-occurrence of two alleles that are inherited independently is the frequency of the first allele multiplied by the frequency of the second allele. Alleles that co-occur at expected frequencies are said to be in "linkage equilibrium." In contrast, LD refers to any non-random genetic association between allele(s) at two or more different SNP sites, which is generally due to the physical proximity of the two loci along a chromosome. LD can occur when two or more SNPs sites are in close physical proximity to each other on a given chromosome and therefore alleles at these SNP sites will tend to remain unseparated for multiple generations, with the consequence that a particular nucleotide (allele) at one SNP site will show a non-random association with a particular nucleotide (allele) at another SNP site located nearby. Hence, genotyping one of the SNP sites will give almost the same information as genotyping the other SNP site that is in LD. The physical area of the chromosome that contains SNPs in LD with each other is referred to as an LD block.

Various degrees of LD can be encountered between two or more SNPs with the result being that some SNPs are more closely associated (i.e., in stronger LD) than others. Furthermore, the physical distance over which LD extends along a chromosome differs between different regions of the genome, and therefore the degree of physical separation between two or more SNP sites necessary for LD to occur can differ between different regions of the genome.

For diagnostic purposes and similar uses, if a particular SNP site is found to be useful for diagnosing neurodegenerative disease (e.g., has a significant statistical association with the condition and/or is recognized as a causative polymorphism for the condition), then the skilled artisan would recognize that other SNP sites which are in LD with this SNP site would also be useful for diagnosing the condition. Thus, polymorphisms (e.g., SNPs and/or haplotypes) that are not the actual disease-causing (causative) polymorphisms, but are in LD with such causative polymorphisms, are also useful. In such instances, the genotype of the polymorphism(s) that is/are in LD with the causative polymorphism is predictive of the genotype of the causative polymorphism and, consequently, predictive of the phenotype (e.g., neurodegenerative disease) that is influenced by the causative SNP(s). Therefore, polymorphic markers that are in LD with causative polymorphisms are useful as diagnostic markers, and are particularly useful when the actual causative polymorphism(s) is/are unknown.

Examples of polymorphisms that can be in LD with one or more causative polymorphisms (and/or in LD with one or more polymorphisms that have a significant statistical association with a condition) and therefore useful for diagnosing the same condition that the causative/associated SNP(s) is used to diagnose, include, for example, other SNPs in the same gene, protein-coding, or mRNA transcript-coding region as the causative/associated SNP, other SNPs in the same exon or same intron as the causative/associated SNP, other SNPs in the same haplotype block as the causative/associated SNP, other SNPs in the same intergenic region as the causative/associated SNP, SNPs that are outside but near a gene (e.g., within 6 kb on either side, 5' or 3', of a gene boundary) that harbors a causative/associated SNP, etc. Such useful LD SNPs can be selected from among the SNPs disclosed in Table 1, for example.

Linkage disequilibrium in the human genome is reviewed in: Wall et al., "Haplotype blocks and linkage disequilibrium in the human genome", *Nat Rev Genet.* 2003 August; 4(8): 587-97; Garner et al., "On selecting markers for association studies: patterns of linkage disequilibrium between two and three diallelic loci", *Genet Epidemiol.* 2003 January; 24(1): 57-67; Ardlie et al., "Patterns of linkage disequilibrium in the human genome", *Nat Rev Genet.* 2002 April; 3(4):299-309 (erratum in *Nat Rev Genet* 2002 July; 3(7):566); and Remm et al., "High-density genotyping and linkage disequilibrium in the human genome using chromosome 22 as a model"; *Curr Opin Chem. Biol.* 2002 February; 6(1):24-30; Haldane J B S (1919) The combination of linkage values, and the calculation of distances between the loci of linked factors. *J Genet* 8:299-309; Mendel, G. (1866) Versuche über Pflanzen-Hybriden. Verhandlungen des naturforschenden Vereines in Brünn [Proceedings of the Natural History Society of Brünn]; Lewin B (1990) *Genes IV.* Oxford University Press, New York, USA; Hartl D L and Clark A G (1989) *Principles of Population Genetics* 2*nd ed.* Sinauer Associates, Inc. Sunderland, Mass., USA; Gillespie J H (2004) *Population Genetics: A Concise Guide.* 2nd ed. Johns Hopkins University Press. USA; Lewontin R C (1964) The interaction of selection and linkage. I. General considerations; heterotic models. *Genetics* 49:49-67; Hoel P G (1954) *Introduction to Mathematical Statistics* 2*nd ed.* John Wiley & Sons, Inc. New York, USA; Hudson R R (2001) Two-locus sampling distributions and their application. *Genetics* 159:1805-1817; Dempster A P, Laird N M, Rubin D B (1977) Maximum likelihood from incomplete data via the EM algorithm. J R Stat Soc 39:1-38; Excoffier L, Slatkin M (1995) Maximum-likelihood estimation of molecular haplotype frequencies in a diploid population. *Mol Biol Evol* 12(5):921-927; Tregouet D A, Escolano S, Tiret L, Mallet A, Golmard J L (2004) A new algorithm for haplotype-based association analysis: the Stochastic-EM algorithm. *Ann Hum Genet* 68(Pt 2):165-177; Long A D and Langley C H (1999) The power of association studies to detect the contribution of candidate genetic loci to variation in complex traits. *Genome Research* 9:720-731; Agresti A (1990) *Categorical Data Analysis*. John Wiley & Sons, Inc. New York, USA; Lange K (1997) *Mathematical and Statistical Methods for Genetic Analysis*. Springer-Verlag New York, Inc. New York, USA; The International HapMap Consortium (2003) The International HapMap Project. *Nature* 426:789-796; The International HapMap Consortium (2005) A haplotype map of the human genome. *Nature* 437:1299-1320; Thorisson G A, Smith A V, Krishnan L, Stein L D (2005), The International HapMap Project Web Site. Genome Research 15:1591-1593; McVean G, Spencer C C A, Chaix R (2005) Perspectives on human genetic variation from the HapMap project. *PLoS Genetics* 1(4):413-418; Hirschhorn J N, Daly M J (2005) Genome-wide association studies for common diseases and complex traits. Nat Genet 6:95-108; Schrodi S J (2005) A probabilistic approach to large-scale association scans: a semi-Bayesian method to detect disease-predisposing alleles. *SAGMB* 4(1):31; Wang W Y S, Barratt B J, Clayton D G, Todd J A (2005) Genome-wide association studies: theoretical and practical concerns. *Nat Rev Genet* 6:109-118. Pritchard J K, Przeworski M (2001) Linkage disequilibrium in humans: models and data. *Am J Hum Genet* 69:1-14.

As discussed above, one aspect of the present invention is the discovery that SNPs which are in certain LD distance with the interrogated SNP can also be used as valid markers for identifying an increased or decreased risk of having or developing neurodegenerative disease. As used herein, the term "interrogated SNP" refers to SNPs that have been found to be associated with an increased or decreased risk of disease using genotyping results and analysis, or other appropriate experimental method as exemplified in the working examples described in this application. As used herein, the term "LD SNP" refers to a SNP that has been characterized as a SNP associating with an increased or decreased risk of diseases due to their being in LD with the "interrogated SNP" under the methods of calculation described in the application. Below, applicants describe the methods of calculation with which one of ordinary skilled in the art may determine if a particular SNP is in LD with an interrogated SNP. The parameter $r^2$ is commonly used in the genetics art to characterize the extent of linkage disequilibrium between markers (Hudson, 2001). As used herein, the term "in LD with" refers to a particular SNP that is measured at above the threshold of a parameter such as $r^2$ with an interrogated SNP.

It is now common place to directly observe genetic variants in a sample of chromosomes obtained from a population. Suppose one has genotype data at two genetic markers located on the same chromosome, for the markers A and B. Further suppose that two alleles segregate at each of these two markers such that alleles $A_1$ and $A_2$ can be found at marker A and alleles $B_1$ and $B_2$ at marker B. Also assume that these two markers are on a human autosome. If one is to examine a specific individual and find that they are heterozygous at both markers, such that their two-marker genotype is $A_1A_2B_1B_2$, then there are two possible configurations: the individual in question could have the alleles $A_1B_1$ on one chromosome and $A_2B_2$ on the remaining chromosome; alternatively, the individual could have alleles $A_1B_2$ on one chromosome and $A_2B_1$ on the other. The arrangement of alleles on a chromosome is called a haplotype. In this illustration, the individual could have haplotypes $A_1B_1/A_2B_2$ or $A_1B_2/A_2B_1$ (see Hartl and Clark (1989) for a more complete description). The concept of linkage equilibrium relates the frequency of haplotypes to the allele frequencies.

Assume that a sample of individuals is selected from a larger population. Considering the two markers described above, each having two alleles, there are four possible haplotypes: $A_1B_1$, $A_1B_2$, $A_2B_1$ and $A_2B_2$. Denote the frequencies of these four haplotypes with the following notation.

$$P_{11}=\text{freq}(A_1B_1) \quad (1)$$

$$P_{12}=\text{freq}(A_1B_2) \quad (2)$$

$$P_{21}=\text{freq}(A_2B_1) \quad (3)$$

$$P_{22}=\text{freq}(A_2B_2) \quad (4)$$

The allele frequencies at the two markers are then the sum of different haplotype frequencies, it is straightforward to write down a similar set of equations relating single-marker allele frequencies to two-marker haplotype frequencies:

$$p_1=\text{freq}(A_1)=P_{11}+P_{12} \quad (5)$$

$$p_2=\text{freq}(A_2)=P_{21}+P_{22} \quad (6)$$

$$q_1=\text{freq}(B_1)=P_{11}+P_{21} \quad (7)$$

$$q_2=\text{freq}(B_2)=P_{12}+P_{22} \quad (8)$$

Note that the four haplotype frequencies and the allele frequencies at each marker must sum to a frequency of 1.

$$P_{11}+P_{12}+P_{21}+P_{22}=1 \quad (9)$$

$$p_1+p_2=1 \quad (10)$$

$$q_1+q_2=1 \quad (11)$$

If there is no correlation between the alleles at the two markers, one would expect that the frequency of the haplotypes would be approximately the product of the composite alleles. Therefore, $$P_{11}\approx p_1q_1 \quad (12)$$

$$P_{12}\approx p_1q_2 \quad (13)$$

$$P_{21}\approx p_2q_1 \quad (14)$$

$$P_{22}\approx p_2q_2 \quad (15)$$

These approximating equations (12)-(15) represent the concept of linkage equilibrium where there is independent assortment between the two markers—the alleles at the two markers occur together at random. These are represented as approximations because linkage equilibrium and linkage disequilibrium are concepts typically thought of as properties of a sample of chromosomes; and as such they are susceptible to stochastic fluctuations due to the sampling process. Empirically, many pairs of genetic markers will be in linkage equilibrium, but certainly not all pairs.

Having established the concept of linkage equilibrium above, applicants can now describe the concept of linkage disequilibrium (LD), which is the deviation from linkage equilibrium. Since the frequency of the $A_1B_1$ haplotype is approximately the product of the allele frequencies for $A_1$ and $B_1$ under the assumption of linkage equilibrium as stated mathematically in (12), a simple measure for the amount of departure from linkage equilibrium is the difference in these two quantities, D, $$D=P_{11}-p_1q_1 \quad (16)$$

D=0 indicates perfect linkage equilibrium. Substantial departures from D=0 indicates LD in the sample of chromosomes examined. Many properties of D are discussed in Lewontin (1964) including the maximum and minimum values that D can take. Mathematically, using basic algebra, it can be shown that D can also be written solely in terms of haplotypes:

$$D=P_{11}P_{22}-P_{12}P_{21} \quad (17)$$

If one transforms D by squaring it and subsequently dividing by the product of the allele frequencies of $A_1$, $A_2$, $B_1$ and $B_2$, the resulting quantity, called $r^2$, is equivalent to the square of the Pearson's correlation coefficient commonly used in statistics (e.g. Hoel, 1954).

$$r^2 = \frac{D^2}{p_1 p_2 q_1 q_2} \quad (18)$$

As with D, values of $r^2$ close to 0 indicate linkage equilibrium between the two markers examined in the sample set. As values of $r^2$ increase, the two markers are said to be in linkage disequilibrium. The range of values that $r^2$ can take are from 0 to 1. $r^2=1$ when there is a perfect correlation between the alleles at the two markers.

In addition, the quantities discussed above are sample-specific. And as such, it is necessary to formulate notation specific to the samples studied. In the approach discussed here, three types of samples are of primary interest: (i) a sample of chromosomes from individuals affected by a disease-related phenotype (cases), (ii) a sample of chromosomes obtained from individuals not affected by the disease-related phenotype (controls), and (iii) a standard sample set used for the construction of haplotypes and calculation pairwise linkage disequilibrium. For the allele frequencies used in the development of the method described below, an additional subscript will be added to denote either the case or control sample sets.

$$p_{1,cs}=\text{freq}(A_1 \text{ in cases}) \quad (19)$$

$$P_{2,cs}=\text{freq}(A_2 \text{ in cases}) \quad (20)$$

$$q_{1,cs}=\text{freq}(B_1 \text{ in cases}) \quad (21)$$

$$q_{2,cs}=\text{freq}(B_2 \text{ in cases}) \quad (22)$$

Similarly, $$p_{1,ct}=\text{freq}(A_1 \text{ in controls}) \quad (23)$$

$$p_{2,ct}=\text{freq}(A_2 \text{ in controls}) \quad (24)$$

$$q_{1,ct}=\text{freq}(B_1 \text{ in controls}) \quad (25)$$

$$q_{2,ct}=\text{freq}(B_2 \text{ in controls}) \quad (26)$$

As a well-accepted sample set is necessary for robust linkage disequilibrium calculations, data obtained from the International HapMap project (The International HapMap Consortium 2003, 2005; Thorisson et al, 2005; McVean et al, 2005) can be used for the calculation of pairwise $r^2$ values. Indeed, the samples genotyped for the International HapMap Project were selected to be representative examples from various human sub-populations with sufficient numbers of chromosomes examined to draw meaningful and robust conclusions from the patterns of genetic variation observed. The International HapMap project website (hapmap.org) contains a description of the project, methods utilized and samples examined. It is useful to examine empirical data to get a sense of the patterns present in such data.

Haplotype frequencies were explicit arguments in equation (18) above. However, knowing the 2-marker haplotype frequencies requires that phase to be determined for doubly heterozygous samples. When phase is unknown in the data examined, various algorithms can be used to infer phase from the genotype data. This issue was discussed earlier where the doubly heterozygous individual with a 2-SNP genotype of $A_1A_2B_1B_2$ could have one of two different sets of chromosomes: $A_1B_1/A_2B_2$ or $A_1B_2/A_2B_1$. One such algorithm to estimate haplotype frequencies is the expectation-maximization (EM) algorithm first formalized by Dempster et al (1977). This algorithm is often used in genetics to infer haplotype frequencies from genotype data (e.g., Excoffier and Slatkin, 1995; Tregouet et al, 2004). It should be noted that for the two-SNP case explored here, EM algorithms have very little error provided that the allele frequencies and sample sizes are not too small. The impact on $r^2$ values is typically negligible.

As correlated genetic markers share information, interrogation of SNP markers in LD with a disease-associated SNP marker can also have sufficient power to detect disease association (Long and Langley, 1999). The relationship between the power to directly find disease-associated alleles and the power to indirectly detect disease-association was investigated by Pritchard and Przeworski (2001). In a straight-forward derivation, it can be shown that the power to detect disease association indirectly at a marker locus in linkage disequilibrium with a disease-association locus is approximately the same as the power to detect disease-association directly at the disease-association locus if the sample size is increased by a factor of $$\frac{1}{r^2}$$

(the reciprocal of equation 18) at the marker in comparison with the disease-association locus.

Therefore, if one calculated the power to detect disease-association indirectly with an experiment having N samples, then equivalent power to directly detect disease-association (at the actual disease-susceptibility locus) would necessitate an experiment using approximately $r^2N$ samples. This elementary relationship between power, sample size and linkage disequilibrium can be used to derive an $r^2$ threshold value useful in determining whether or not genotyping markers in linkage disequilibrium with a SNP marker directly associated with disease status has enough power to indirectly detect disease-association.

To commence a derivation of the power to detect disease-associated markers through an indirect process, define the effective chromosomal sample size as $$n = \frac{4N_{cs}N_{ct}}{N_{cs}+N_{ct}}; \quad (27)$$

where $N_{cs}$ and $N_{ct}$ are the numbers of diploid cases and controls, respectively. This is necessary to handle situations where the numbers of cases and controls are not equivalent. For equal case and control sample sizes, $N_{cs}=N_{ct}=N$, the value of the effective number of chromosomes is simply $n=2N$—as expected. Let power be calculated for a significance level $\alpha$ (such that traditional P-values below $\alpha$ will be deemed statistically significant). Define the standard Gaussian distribution function as $\Phi(\cdot)$. Mathematically, $$\Phi(x) = \frac{1}{\sqrt{2\pi}} \int_{-\infty}^{x} e^{-\frac{\theta^2}{2}} d\theta \tag{28}$$

Alternatively, the following error function notation (Erf) may also be used, $$\Phi(x) = \frac{1}{2}\left[1 + \mathrm{Erf}\left(\frac{x}{\sqrt{2}}\right)\right] \tag{29}$$

For example, $\Phi(1.644854)=0.95$. The value of $r^2$ may be derived to yield a pre-specified minimum amount of power to detect disease association though indirect interrogation. Noting that the LD SNP marker could be the one that is carrying the disease-association allele, therefore that this approach constitutes a lower-bound model where all indirect power results are expected to be at least as large as those interrogated.

Denote by $\beta$ the error rate for not detecting truly disease-associated markers. Therefore, $1-\beta$ is the classical definition of statistical power. Substituting the Pritchard-Pzreworski result into the sample size, the power to detect disease association at a significance level of $\alpha$ is given by the approximation $$1 - \beta \cong \Phi\left[\frac{|q_{1,cs} - q_{1,ct}|}{\sqrt{\frac{q_{1,cs}(1 - q_{1,cs}) + q_{1,ct}(1 - q_{1,ct})}{r^2 n}}} - Z_{1-\alpha/2}\right]; \tag{30}$$

where $Z_u$ is the inverse of the standard normal cumulative distribution evaluated at $u(u\in(0,1))$. $Z_u=\Phi^{-1}(u)$, where $\Phi(\Phi^{-1}(u))=\Phi^{-1}(\Phi(u))=u$. For example, setting $\alpha=0.05$, and therefore $1-\alpha/2=0.975$, $Z_{0.975}=1.95996$ is obtained. Next, setting power equal to a threshold of a minimum power of T, $$T = \Phi\left[\frac{|q_{1,cs} - q_{1,ct}|}{\sqrt{\frac{q_{1,cs}(1 - q_{1,cs}) + q_{1,ct}(1 - q_{1,ct})}{r^2 n}}} - Z_{1-\alpha/2}\right] \tag{31}$$

and solving for $r^2$, the following threshold $r^2$ is obtained:

$$r_T^2 = \frac{[q_{1,cs}(1 - q_{1,cs}) + q_{1,ct}(1 - q_{1,ct})]}{n(q_{1,cs} - q_{1,ct})^2}[\Phi^{-1}(T) + Z_{1-\alpha/2}] \tag{32}$$

Or, $$r_T^2 = \left(\frac{Z_T + Z_{1-\alpha/2}}{n}\right)\left[\frac{q_{1,cs} - (q_{1,cs})^2 + q_{1,ct} - (q_{1,ct})^2}{(q_{1,cs} - q_{1,ct})^2}\right] \tag{33}$$

Suppose that $r^2$ is calculated between an interrogated SNP and a number of other SNPs with varying levels of LD with the interrogated SNP. The threshold value $r_T^2$ is the minimum value of linkage disequilibrium between the interrogated SNP and the potential LD SNPs such that the LD SNP still retains a power greater or equal to T for detecting disease-association. For example, suppose that SNP rs200 is genotyped in a case-control disease-association study and it is found to be associated with a disease phenotype. Further suppose that the minor allele frequency in 1,000 case chromosomes was found to be 16% in contrast with a minor allele frequency of 10% in 1,000 control chromosomes. Given those measurements one could have predicted, prior to the experiment, that the power to detect disease association at a significance level of 0.05 was quite high—approximately 98% using a test of allelic association. Applying equation (32) one can calculate a minimum value of $r^2$ to indirectly assess disease association assuming that the minor allele at SNP rs200 is truly disease-predisposing for a threshold level of power. If one sets the threshold level of power to be 80%, then $r_T^2=0.489$ given the same significance level and chromosome numbers as above. Hence, any SNP with a pairwise $r^2$ value with rs200 greater than 0.489 is expected to have greater than 80% power to detect the disease association. Further, this is assuming the conservative model where the LD SNP is disease-associated only through linkage disequilibrium with the interrogated SNP rs200.

The contribution or association of particular SNPs and/or SNP haplotypes with disease phenotypes, such as neurodegenerative disease, enables the SNPs of the present invention to be used to develop superior diagnostic tests capable of identifying individuals who express a detectable trait, such as neurodegenerative disease, as the result of a specific genotype, or individuals whose genotype places them at an increased or decreased risk of developing a detectable trait at a subsequent time as compared to individuals who do not have that genotype. As described herein, diagnostics may be based on a single SNP or a group of SNPs. Combined detection of a plurality of SNPs (for example, 2, 3, 4, 5, 6, 7, 8, 9, 10, 11, 12, 13, 14, 15, 16, 17, 18, 19, 20, 24, 25, 30, 32, 48, 50, 64, 96, 100, or any other number in-between, or more, of the SNPs provided in Table 1) typically increases the probability of an accurate diagnosis. For example, the presence of a single SNP known to correlate with neurodegenerative disease might indicate a probability of 20% that an individual has or is at risk of developing neurodegenerative disease, whereas detection of five SNPs, each of which correlates with neurodegenerative disease, might indicate a probability of 80% that an individual has or is at risk of developing neurodegenerative disease. To further increase the accuracy of diagnosis or predisposition screening, analysis of the SNPs of the present invention can be combined with that of other polymorphisms or other risk factors of neurodegenerative disease, such as disease symptoms, pathological characteristics, family history, diet, environmental factors or lifestyle factors.

It will, of course, be understood by practitioners skilled in the treatment or diagnosis of neurodegenerative disease that the present invention generally does not intend to provide an absolute identification of individuals who are at risk (or less at risk) of developing neurodegenerative disease, and/or pathologies related to neurodegenerative disease, but rather to indicate a certain increased (or decreased) degree or likelihood of developing the disease based on statistically significant association results. However, this information is extremely valuable as it can be used to, for example, initiate preventive treatments or to allow an individual carrying one or more significant SNPs or SNP haplotypes to foresee warning signs such as minor clinical symptoms, or to have regularly scheduled physical exams to monitor for appearance of a condition in order to identify and begin treatment of the condition at an early stage. Particularly with diseases that are extremely debilitating or fatal if not treated on time, the knowledge of a potential predisposition, even if this predisposition is not absolute, would likely contribute in a very significant manner to treatment efficacy.

The diagnostic techniques of the present invention may employ a variety of methodologies to determine whether a test subject has a SNP or a SNP pattern associated with an increased or decreased risk of developing a detectable trait or whether the individual suffers from a detectable trait as a result of a particular polymorphism/mutation, including, for example, methods which enable the analysis of individual chromosomes for haplotyping, family studies, single sperm DNA analysis, or somatic hybrids. The trait analyzed using the diagnostics of the invention may be any detectable trait that is commonly observed in pathologies and disorders related to neurodegenerative disease.

Another aspect of the present invention relates to a method of determining whether an individual is at risk (or less at risk) of developing one or more traits or whether an individual expresses one or more traits as a consequence of possessing a particular trait-causing or trait-influencing allele. These methods generally involve obtaining a nucleic acid sample from an individual and assaying the nucleic acid sample to determine which nucleotide(s) is/are present at one or more SNP positions, wherein the assayed nucleotide(s) is/are indicative of an increased or decreased risk of developing the trait or indicative that the individual expresses the trait as a result of possessing a particular trait-causing or trait-influencing allele.

In another embodiment, the SNP detection reagents of the present invention are used to determine whether an individual has one or more SNP allele(s) affecting the level (e.g., the concentration of mRNA or protein in a sample, etc.) or pattern (e.g., the kinetics of expression, rate of decomposition, stability profile, Km, Vmax, etc.) of gene expression (collectively, the "gene response" of a cell or bodily fluid). Such a determination can be accomplished by screening for mRNA or protein expression (e.g., by using nucleic acid arrays, RT-PCR, TaqMan assays, or mass spectrometry), identifying genes having altered expression in an individual, genotyping SNPs disclosed in Table 1 that could affect the expression of the genes having altered expression (e.g., SNPs that are in and/or around the gene(s) having altered expression, SNPs in regulatory/control regions, SNPs in and/or around other genes that are involved in pathways that could affect the expression of the gene(s) having altered expression, or all SNPs could be genotyped), and correlating SNP genotypes with altered gene expression. In this manner, specific SNP alleles at particular SNP sites can be identified that affect gene expression.

Pharmacogenomics and Therapeutics/Drug Development

The present invention provides methods for assessing the pharmacogenomics of a subject harboring particular SNP alleles or haplotypes to a particular therapeutic agent or pharmaceutical compound, or to a class of such compounds. Pharmacogenomics deals with the roles which clinically significant hereditary variations (e.g., SNPs) play in the response to drugs due to altered drug disposition and/or abnormal action in affected persons. See, e.g., Roses, *Nature* 405, 857-865 (2000); Gould Rothberg, *Nature Biotechnology* 19, 209-211 (2001); Eichelbaum, *Clin. Exp. Pharmacol. Physiol.* 23 (10-11):983-985 (1996); and Linder, *Clin. Chem.* 43(2):254-266 (1997). The clinical outcomes of these variations can result in severe toxicity of therapeutic drugs in certain individuals or therapeutic failure of drugs in certain individuals as a result of individual variation in metabolism. Thus, the SNP genotype of an individual can determine the way a therapeutic compound acts on the body or the way the body metabolizes the compound. For example, SNPs in drug metabolizing enzymes can affect the activity of these enzymes, which in turn can affect both the intensity and duration of drug action, as well as drug metabolism and clearance.

The discovery of SNPs in drug metabolizing enzymes, drug transporters, proteins for pharmaceutical agents, and other drug targets has explained why some patients do not obtain the expected drug effects, show an exaggerated drug effect, or experience serious toxicity from standard drug dosages. SNPs can be expressed in the phenotype of the extensive metabolizer and in the phenotype of the poor metabolizer. Accordingly, SNPs may lead to allelic variants of a protein in which one or more of the protein functions in one population are different from those in another population. SNPs and the encoded variant peptides thus provide targets to ascertain a genetic predisposition that can affect treatment modality. For example, in a ligand-based treatment, SNPs may give rise to amino terminal extracellular domains and/or other ligand-binding regions of a receptor that are more or less active in ligand binding, thereby affecting subsequent protein activation. Accordingly, ligand dosage would necessarily be modified to maximize the therapeutic effect within a given population containing particular SNP alleles or haplotypes.

As an alternative to genotyping, specific variant proteins containing variant amino acid sequences encoded by alternative SNP alleles could be identified. Thus, pharmacogenomic characterization of an individual permits the selection of effective compounds and effective dosages of such compounds for prophylactic or therapeutic uses based on the individual's SNP genotype, thereby enhancing and optimizing the effectiveness of the therapy. Furthermore, the production of recombinant cells and transgenic animals containing particular SNPs/haplotypes allow effective clinical design and testing of treatment compounds and dosage regimens. For example, transgenic animals can be produced that differ only in specific SNP alleles in a gene that is orthologous to a human disease susceptibility gene.

Pharmacogenomic uses of the SNPs of the present invention provide several significant advantages for patient care, particularly in treating neurodegenerative disease. Pharmacogenomic characterization of an individual, based on an individual's SNP genotype, can identify those individuals unlikely to respond to treatment with a particular medication and thereby allows physicians to avoid prescribing the ineffective medication to those individuals. On the other hand, SNP genotyping of an individual may enable physicians to select the appropriate medication and dosage regimen that will be most effective based on an individual's SNP genotype. This information increases a physician's confidence in prescribing medications and motivates patients to comply with their drug regimens. Furthermore, pharmacogenomics may identify patients predisposed to toxicity and adverse reactions to particular drugs or drug dosages. Adverse drug reactions lead to more than 100,000 avoidable deaths per year in the United States alone and therefore represent a significant cause of hospitalization and death, as well as a significant economic burden on the healthcare system (Pfost et. al., *Trends in Biotechnology* [August 2000]). Thus, pharmacogenomics based on the SNPs disclosed herein has the potential to both save lives and reduce healthcare costs substantially.

Pharmacogenomics in general is discussed further in Rose et al., "Pharmacogenetic analysis of clinically relevant genetic polymorphisms," *Methods Mol. Med.* 85:225-37 (2003). Pharmacogenomics as it relates to AD and other neurodegenerative disorders is discussed in Cacabelos, "Pharmacogenomics for the treatment of dementia," *Ann. Med.* 34(5):357-79 (2002); Maimone et al., "Pharmacogenomics of neurodegenerative diseases," *Eur. J. Pharmacol.* 9, 413(1):11-29 (February 2001), and Poirier, "Apolipoprotein E: a pharmacogenetic target for the treatment of Alzheimer's Disease," *Mol. Diagn.* 4(4):335-41 (December 1999). Pharmacogenomics as it relates to cardiovascular disorders is discussed in Siest et al., "Pharmacogenomics of drugs affecting the cardiovascular system," *Clin. Chem. Lab Med.* 41(4): 590-9 (April 2003); Mukherjee et al., "Pharmacogenomics in cardiovascular diseases," *Prog. Cardiovasc. Dis.* 44(6):479-98 (May-June 2002); and Mooser et al., "Cardiovascular pharmacogenetics in the SNP era," *J. Thromb. Haemost.* 1(7): 1398-402 (July 2003). Pharmacogenomics as it relates to cancer is discussed in McLeod et al., "Cancer pharmacogenomics: SNPs, chips, and the individual patient," *Cancer Invest.* 21(4):630-40 (2003) and Watters et al., "Cancer pharmacogenomics: current and future applications," *Biochim. Biophys. Acta.* 17; 1603(2):99-111 (March 2003).

The SNPs of the present invention also can be used to identify novel therapeutic targets for neurodegenerative disease. For example, genes containing the disease-associated variants ("variant genes") or their products, as well as genes or their products that are directly or indirectly regulated by or interacting with these variant genes or their products, can be targeted by therapeutic agents in order to, for example, treat, prevent, or delay onset of neurodegenerative disease. In certain exemplary embodiments, the genes or gene products that are directly or indirectly regulated by or interacting with NEDD9, and that are targeted by therapeutic agents for treating, preventing, or delaying onset of neurodegenerative disease, are selected from the group consisting of the NEDD9-binding proteins disclosed in Table 7, and the targets for the inhibitors disclosed in Table 8 (e.g., $\alpha 2\beta 1$ and $\alpha V\beta 1$ integrins), Table 9 (e.g., FAK kinase), and Table 10 (e.g., Fyn, Src, and Lyn kinases). The therapeutics may be composed of, for example, small molecules, proteins, protein fragments or peptides, antibodies, nucleic acids, or their derivatives or mimetics which modulate the functions or levels of the target genes or gene products.

The SNP-containing nucleic acid molecules disclosed herein, and their complementary nucleic acid molecules, may be used as antisense constructs to control gene expression in cells, tissues, and organisms. Antisense technology is well established in the art and extensively reviewed in *Antisense Drug Technology: Principles, Strategies, and Applications*, ed. Crooke, Marcel Dekker, Inc., New York (2001). An antisense nucleic acid molecule is generally designed to be complementary to a region of mRNA expressed by a gene so that the antisense molecule hybridizes to the mRNA and thereby blocks translation of mRNA into protein. Various classes of antisense oligonucleotides are used in the art, two of which are cleavers and blockers. Cleavers, by binding to target RNAs, activate intracellular nucleases (e.g., RNaseH or RNase L) that cleave the target RNA. Blockers, which also bind to target RNAs, inhibit protein translation through steric hindrance of ribosomes. Exemplary blockers include peptide nucleic acids, morpholinos, locked nucleic acids, and methylphosphonates (see, e.g., Thompson, *Drug Discovery Today,* 7 [17]: 912-917 [2002]). Antisense oligonucleotides are directly useful as therapeutic agents, and are also useful for determining and validating gene function (e.g., in gene knock-out or knock-down experiments).

Antisense technology is further reviewed in: Layery et al., "Antisense and RNAi: powerful tools in drug target discovery and validation," *Curr. Opin. Drug Discov. Devel.* 6(4):561-9 (July 2003); Stephens et al., "Antisense oligonucleotide therapy in cancer," *Curr. Opin. Mol. Ther.* 5(2):118-22 (April 2003); Kurreck, "Antisense technologies. Improvement through novel chemical modifications," *Eur. J. Biochem.* 270 (8):1628-44 (April 2003); Dias et al., "Antisense oligonucleotides: basic concepts and mechanisms," *Mol. Cancer. Ther.* 1(5):347-55 (March 2002); Chen, "Clinical development of antisense oligonucleotides as anti-cancer therapeutics," *Methods Mol. Med.* 75:621-36 (2003); Wang et al., "Antisense anticancer oligonucleotide therapeutics," *Curr. Cancer Drug Targets* 1(3):177-96 (November 2001); and Bennett, "Efficiency of antisense oligonucleotide drug discovery," *Antisense Nucleic Acid Drug. Dev.* 12(3):215-24 (June 2002).

The SNPs of the present invention are particularly useful for designing antisense reagents that are specific for particular nucleic acid variants. Based on the SNP information disclosed herein, antisense oligonucleotides can be produced that specifically target mRNA molecules that contain one or more particular SNP nucleotides. In this manner, expression of mRNA molecules that contain one or more undesired polymorphisms (e.g., SNP nucleotides that lead to a defective protein such as an amino acid substitution in a catalytic domain) can be inhibited or completely blocked. Thus, antisense oligonucleotides can be used to specifically bind a particular polymorphic form (e.g., a SNP allele that encodes a defective protein), thereby inhibiting translation of this form, but which do not bind an alternative polymorphic form (e.g., an alternative SNP nucleotide that encodes a protein having normal function).

Antisense molecules can be used to inactivate mRNA in order to inhibit gene expression and production of defective proteins. Accordingly, these molecules can be used to treat a disorder, such as neurodegenerative disease, characterized by abnormal or undesired gene expression or expression of certain defective proteins. This technique can involve cleavage by means of ribozymes containing nucleotide sequences complementary to one or more regions in the mRNA that attenuate the ability of the mRNA to be translated. Possible mRNA regions include, for example, protein-coding regions and particularly protein-coding regions corresponding to catalytic activities, substrate/ligand binding, or other functional activities of a protein.

The SNPs of the present invention are also useful for designing RNA interference reagents that specifically target nucleic acid molecules having particular SNP variants. RNA interference (RNAi), also referred to as gene silencing, is based on using double-stranded RNA (dsRNA) molecules to turn genes off. When introduced into a cell, dsRNAs are processed by the cell into short fragments (generally about 21, 22, or 23 nucleotides in length) known as small interfering RNAs (siRNAs) which the cell uses in a sequence-specific manner to recognize and destroy complementary RNAs (Thompson, *Drug Discovery Today,* 7 [17]: 912-917 [2002]). Accordingly, an aspect of the present invention specifically contemplates isolated nucleic acid molecules that are about 18-26 nucleotides in length, or 19-25 nucleotides in length, or 20, 21, 22, or 23 nucleotides in length, and the use of these nucleic acid molecules for RNAi. Because RNAi molecules, including siRNAs, act in a sequence-specific manner, the SNPs of the present invention can be used to design RNAi reagents that recognize and destroy nucleic acid molecules having specific SNP alleles/nucleotides (such as deleterious alleles that lead to the production of defective proteins), while not affecting nucleic acid molecules having alternative SNP alleles (such as alleles that encode proteins having normal function). As with antisense reagents, RNAi reagents may be directly useful as therapeutic agents (e.g., for turning off defective, disease-causing genes), and are also useful for characterizing and validating gene function (e.g., in gene knock-out or knock-down experiments).

The following references provide a further review of RNAi: Reynolds et al., "Rational siRNA design for RNA interference," *Nat. Biotechnol.* 22(3):326-30 (March 2004); Epub Feb. 1, 2004; Chi et al., "Genomewide view of gene silencing by small interfering RNAs," *PNAS*100(11):6343-6346 (2003); Vickers et al., "Efficient Reduction of Target RNAs by Small Interfering RNA and RNase H-dependent Antisense Agents," *J. Biol. Chem.* 278: 7108-7118 (2003); Agami, "RNAi and related mechanisms and their potential use for therapy," *Curr. Opin. Chem. Biol.* 6(6):829-34 (December 2002); Layery et al., "Antisense and RNAi: powerful tools in drug target discovery and validation," *Curr. Opin. Drug Discov. Devel.* 6(4):561-9 (July 2003); Shi, "Mammalian RNAi for the masses," *Trends Genet.* 19(1):9-12 (January 2003); Shuey et al., "RNAi: gene-silencing in therapeutic intervention," *Drug Discovery Today* 7(20):1040-1046 (October 2002); McManus et al., *Nat. Rev. Genet.* 3(10):737-47 (October 2002); Xia et al., *Nat. Biotechnol.* 20(10):1006-10 (October 2002); Plasterk et al., *Curr. Opin. Genet. Dev.* 10(5): 562-7 (October 2000); Bosher et al., *Nat. Cell Biol.* 2(2): E31-6 (February 2000); and Hunter, *Curr. Biol.* 9(12):R440-2 (Jun. 17, 1999).

A subject suffering from a pathological condition, such as neurodegenerative disease, ascribed to a SNP may be treated so as to correct the genetic defect (see Kren et al., *Proc. Natl. Acad. Sci. USA* 96:10349-10354 [1999]). Such a subject can be identified by any method that can detect the polymorphism in a biological sample drawn from the subject. Such a genetic defect may be permanently corrected by administering to such a subject a nucleic acid fragment incorporating a repair sequence that supplies the normal/wild-type nucleotide at the position of the SNP. This site-specific repair sequence can encompass an RNA/DNA oligonucleotide that operates to promote endogenous repair of a subject's genomic DNA. The site-specific repair sequence is administered in an appropriate vehicle, such as a complex with polyethylenimine, encapsulated in anionic liposomes, a viral vector such as an adenovirus, or other pharmaceutical composition that promotes intracellular uptake of the administered nucleic acid. A genetic defect leading to an inborn pathology may then be overcome, as the chimeric oligonucleotides induce incorporation of the normal sequence into the subject's genome. Upon incorporation, the normal gene product is expressed, and the replacement is propagated, thereby engendering a permanent repair and therapeutic enhancement of the clinical condition of the subject.

In cases in which a cSNP results in a variant protein that is ascribed to be the cause of, or a contributing factor to, a pathological condition, a method of treating such a condition can include administering to a subject experiencing the pathology the wild-type/normal cognate of the variant protein. Once administered in an effective dosing regimen, the wild-type cognate provides complementation or remediation of the pathological condition.

The invention further provides a method for identifying a compound or agent that can be used to treat neurodegenerative disease. The SNPs disclosed herein are useful as targets for the identification and/or development of therapeutic agents. A method for identifying a therapeutic agent or compound typically includes assaying the ability of the agent or compound to modulate the activity and/or expression of a SNP-containing nucleic acid or the encoded product and thus identifying an agent or a compound that can be used to treat a disorder characterized by undesired activity or expression of the SNP-containing nucleic acid or the encoded product. The assays can be performed in cell-based and cell-free systems. Cell-based assays can include cells naturally expressing the nucleic acid molecules of interest or recombinant cells genetically engineered to express certain nucleic acid molecules.

Variant gene expression in a neurodegenerative disease patient can include, for example, either expression of a SNP-containing nucleic acid sequence (for instance, a gene that contains a SNP can be transcribed into an mRNA transcript molecule containing the SNP, which can in turn be translated into a variant protein) or altered expression of a normal/wild-type nucleic acid sequence due to one or more SNPs (for instance, a regulatory/control region can contain a SNP that affects the level or pattern of expression of a normal transcript).

Assays for variant gene expression can involve direct assays of nucleic acid levels (e.g., mRNA levels), expressed protein levels, or of collateral compounds involved in a signal pathway. Further, the expression of genes that are up- or down-regulated in response to the signal pathway can also be assayed. In this embodiment, the regulatory regions of these genes can be operably linked to a reporter gene such as luciferase.

Modulators of variant gene expression can be identified in a method wherein, for example, a cell is contacted with a candidate compound/agent and the expression of mRNA determined. The level of expression of mRNA in the presence of the candidate compound is compared to the level of expression of mRNA in the absence of the candidate compound. The candidate compound can then be identified as a modulator of variant gene expression based on this comparison and be used to treat a disorder such as neurodegenerative disease that is characterized by variant gene expression (e.g., either expression of a SNP-containing nucleic acid or altered expression of a normal/wild-type nucleic acid molecule due to one or more SNPs that affect expression of the nucleic acid molecule) due to one or more SNPs of the present invention. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the SNP or associated nucleic acid domain (e.g., catalytic domain, ligand/substrate-binding domain, regulatory/control region, etc.) or gene, or the encoded mRNA transcript, as a target, using a compound identified through drug screening as a gene modulator to modulate variant nucleic acid expression. Modulation can include either up-regulation (i.e., activation or agonization) or down-regulation (i.e., suppression or antagonization) of nucleic acid expression.

Expression of mRNA transcripts and encoded proteins, either wild type or variant, may be altered in individuals with a particular SNP allele in a regulatory/control element, such as a promoter or transcription factor binding domain, that regulates expression. In this situation, methods of treatment and compounds can be identified, as discussed herein, that regulate or overcome the variant regulatory/control element, thereby generating normal, or healthy, expression levels of either the wild type or variant protein.

The SNP-containing nucleic acid molecules of the present invention are also useful for monitoring the effectiveness of modulating compounds on the expression or activity of a variant gene, or encoded product, in clinical trials or in a treatment regimen. Thus, the gene expression pattern can serve as an indicator for the continuing effectiveness of treatment with the compound, particularly with compounds to which a patient can develop resistance, as well as an indicator for toxicities. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

In another aspect of the present invention, there is provided a pharmaceutical pack comprising a therapeutic agent (e.g., a small molecule drug, antibody, peptide, antisense or RNAi nucleic acid molecule, etc.) and a set of instructions for administration of the therapeutic agent to humans diagnostically tested for one or more SNPs or SNP haplotypes provided by the present invention.

The SNPs/haplotypes of the present invention are also useful for improving many different aspects of the drug development process. For instance, an aspect of the present invention includes selecting individuals for clinical trials (e.g., to gather data for an FDA submission, such as that needed for FDA approval of an agent) based on their SNP genotype. For example, individuals with SNP genotypes that indicate that they are likely to positively respond to a drug can be included in the trials, whereas those individuals whose SNP genotypes indicate that they are less likely to or would not respond to the drug, or who are at risk for suffering toxic effects or other adverse reactions, can be excluded from the clinical trials. This not only can improve the safety of clinical trials, but also can enhance the chances that the trial will demonstrate statistically significant efficacy.

In certain exemplary embodiments, individuals having a 'G' nucleotide (based on the sequence orientation of SEQ ID NOS:2 and 24), or the complement thereof, at SNP rs760678 are selected for inclusion in a clinical trial of a drug, or selected for inclusion in a particular arm of a clinical trial, such as a clinical trial for neurodegenerative disease. In certain exemplary embodiments, individuals having a 'C' nucleotide (based on the sequence orientation of SEQ ID NOS:2 and 24), or the complement thereof, at SNP rs760678 are selected for inclusion in a clinical trial of a drug, or selected for inclusion in a particular arm of a clinical trial, such as a clinical trial for neurodegenerative disease. In certain exemplary embodiments, individuals having a 'GG' genotype (based on the sequence orientation of SEQ ID NOS:2 and 24), or the complement thereof, at SNP rs760678 are selected for inclusion in a clinical trial of a drug, or selected for inclusion in a particular arm of a clinical trial, such as a clinical trial for neurodegenerative disease. In certain exemplary embodiments, individuals having a 'CC' genotype (based on the sequence orientation of SEQ ID NOS:2 and 24), or the complement thereof, at SNP rs760678 are selected for inclusion in a clinical trial of a drug, or selected for inclusion in a particular arm of a clinical trial, such as a clinical trial for neurodegenerative disease. In certain exemplary embodiments, individuals having a 'GC' genotype (based on the sequence orientation of SEQ ID NOS:2 and 24), or the complement thereof, at SNP rs760678 are selected for inclusion in a clinical trial of a drug, or selected for inclusion in a particular arm of a clinical trial, such as a clinical trial for neurodegenerative disease.

Furthermore, the SNPs of the present invention may explain why certain previously developed drugs performed poorly in clinical trials and may help identify a subset of the population that would benefit from a drug that had previously performed poorly in clinical trials, thereby "rescuing" previously developed drugs, and enabling the drug to be made available to a particular neurodegenerative disease patient population that can benefit from it.

SNPs have many important uses in drug discovery, screening, and development. A high probability exists that, for any gene/protein selected as a potential drug target, variants of that gene/protein will exist in a patient population. Thus, determining the impact of gene/protein variants on the selection and delivery of a therapeutic agent should be an integral aspect of the drug discovery and development process. (Jazwinska, *A Trends Guide to Genetic Variation and Genomic Medicine* S30-S36 [March 2002]).

Knowledge of variants (e.g., SNPs and any corresponding amino acid polymorphisms) of a particular therapeutic target (e.g., a gene, mRNA transcript, or protein) enables parallel screening of the variants in order to identify therapeutic candidates (e.g., small molecule compounds, antibodies, antisense or RNAI nucleic acid compounds, etc.) that demonstrate efficacy across variants (Rothberg, *Nat. Biotechnol.* 19[3]:209-11 [March 2001]). Such therapeutic candidates would be expected to show equal efficacy across a larger segment of the patient population, thereby leading to a larger potential market for the therapeutic candidate.

Furthermore, identifying variants of a potential therapeutic target enables the most common form of the target to be used for selection of therapeutic candidates, thereby helping to ensure that the experimental activity that is observed for the selected candidates reflects the real activity expected in the largest proportion of a patient population (Jazwinska, *A Trends Guide to Genetic Variation and Genomic Medicine* S30-S36 [March 2002]).

Additionally, screening therapeutic candidates against all known variants of a target can enable the early identification of potential toxicities and adverse reactions relating to particular variants. For example, variability in drug absorption, distribution, metabolism and excretion (ADME) caused by, for example, SNPs in therapeutic targets or drug metabolizing genes, can be identified, and this information can be utilized during the drug development process to minimize variability in drug disposition and develop therapeutic agents that are safer across a wider range of a patient population. The SNPs of the present invention are useful in conjunction with a variety of toxicology methods established in the art, such as those set forth in *Current Protocols in Toxicology*, John Wiley & Sons, Inc., New York.

Furthermore, therapeutic agents that target any art-known nucleic acid molecules (either RNA or DNA) may cross-react with polymorphic forms of the nucleic acid molecules disclosed in Table 1, thereby significantly affecting the pharmacokinetic properties of the drug. Consequently, the SNP-containing nucleic acid molecules disclosed in Table 1 are useful in developing, screening, and evaluating therapeutic agents that target corresponding art-known nucleic acid molecules. Additionally, as discussed above, knowledge of all polymorphic forms of a particular drug target enables the design of therapeutic agents that are effective against most or all such polymorphic forms of the drug target.

Pharmaceutical Compositions and Administration Thereof

Any of the neurodegenerative disease-associated proteins, and encoding nucleic acid molecules, disclosed herein can be used as therapeutic targets (or directly used themselves as therapeutic compounds) for treating neurodegenerative disease and related pathologies, and the present disclosure enables therapeutic compounds (e.g., small molecules, antibodies, therapeutic proteins, RNAi and antisense molecules, etc.) to be developed that target (or are comprised of) any of these therapeutic targets.

In exemplary methods of the invention, an agent that targets NEDD9, or an agent provided in any of Tables 8-10, or an agent that targets a NEDD9-binding protein in Table 7, is used to treat neurodegenerative diseases (e.g., AD or PD). In exemplary embodiments, an agent that targets NEDD9, or an agent provided in any of Tables 8-10, or an agent that targets a NEDD9-binding protein in Table 7, is administered in a therapeutically effective amount to an individual having neurodegenerative disease. In certain exemplary embodiments, these compounds are administered to an individual having a 'G' nucleotide (based on the sequence orientation of SEQ ID NOS:2 and 24), or the complement thereof, at SNP rs760678. In other exemplary embodiments, these compounds are administered to an individual having a 'C' nucleotide (based on the sequence orientation of SEQ ID NOS:2 and 24), or the complement thereof, at SNP rs760678. In yet other exemplary embodiments, these compounds are administered to an individual having a 'GG' genotype (based on the sequence orientation of SEQ ID NOS:2 and 24), or the complement thereof, at SNP rs760678. In further exemplary embodiments, these compounds are administered to an individual having a 'CC' genotype (based on the sequence orientation of SEQ ID NOS:2 and 24), or the complement thereof, at SNP rs760678. In further exemplary embodiments, these compounds are administered to an individual having a 'GC' genotype (based on the sequence orientation of SEQ ID NOS:2 and 24), or the complement thereof, at SNP rs760678.

In general, a therapeutic compound will be administered in a therapeutically effective amount by any of the accepted modes of administration for agents that serve similar utilities. The actual amount of the therapeutic compound of this invention, i.e., the active ingredient, will depend upon numerous factors such as the severity of the disease to be treated, the age and relative health of the subject, the potency of the compound used, the route and form of administration, and other factors.

Therapeutically effective amounts of therapeutic compounds may range from, for example, approximately 0.01-50 mg per kilogram body weight of the recipient per day; for example, about 0.1-20 mg/kg/day. Thus, as an example, for administration to a 70 kg person, the dosage range can be about 7 mg to 1.4 g per day.

In general, therapeutic compounds can be administered as pharmaceutical compositions by any one of the following routes: oral, systemic (e.g., transdermal, intranasal, or by suppository), or parenteral (e.g., intramuscular, intravenous, or subcutaneous) administration. An exemplary manner of administration is oral or parenteral using a convenient daily dosage regimen, which can be adjusted according to the degree of affliction. Oral compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills, or capsules can be used) and the bioavailability of the drug substance. Recently, pharmaceutical formulations have been developed especially for drugs that show poor bioavailability based upon the principle that bioavailability can be increased by increasing the surface area, i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Pharmaceutical compositions are comprised of, in general, a therapeutic compound in combination with at least one pharmaceutically acceptable excipient. Acceptable excipients are non-toxic, aid administration, and do not adversely affect the therapeutic benefit of the therapeutic compound. Such excipients may be any solid, liquid, semi-solid or, in the case of an aerosol composition, gaseous excipient that is generally available to one skilled in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Exemplary liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences* 18th edition, ed. E. W. Martin (Mack Publishing Company [1990]).

The amount of the therapeutic compound in a formulation can vary within the full range employed by those skilled in the art. Typically, the formulation will contain, on a weight percent (wt %) basis, from about 0.01-99.99 wt % of the therapeutic compound based on the total formulation, with the balance being one or more suitable pharmaceutical excipients. For example, the compound may be present at a level of about 1-80 wt %.

Therapeutic compounds can be administered alone or in combination with other therapeutic compounds or in combination with one or more other active ingredient(s). For example, an inhibitor or stimulator of a neurodegenerative disease-associated protein can be administered in combination with another agent that inhibits or stimulates the activity of the same or a different neurodegenerative disease-associated protein to thereby counteract the affects of neurodegenerative disease.

For further information regarding pharmacology, see *Current Protocols in Pharmacology*, John Wiley & Sons, Inc., New York.

Human Identification Applications

In addition to their diagnostic and therapeutic uses in neurodegenerative disease and related pathologies, the SNPs provided by the present invention are also useful as human identification markers for such applications as forensics, paternity testing, and biometrics (see, e.g., Gill, "An assessment of the utility of single nucleotide polymorphisms (SNPs) for forensic purposes," *Int. J. Legal Med.* 114-[4-5]:204-10 [2001]). Genetic variations in the nucleic acid sequences between individuals can be used as genetic markers to identify individuals and to associate a biological sample with an individual. Determination of which nucleotides occupy a set of SNP positions in an individual identifies a set of SNP markers that distinguishes the individual. The more SNP positions that are analyzed, the lower the probability that the set of SNPs in one individual is the same as that in an unrelated individual. Preferably, if multiple sites are analyzed, the sites are unlinked (i.e., inherited independently). Thus, preferred sets of SNPs can be selected from among the SNPs disclosed herein, which may include SNPs on different chromosomes, SNPs on different chromosome arms, and/or SNPs that are dispersed over substantial distances along the same chromosome arm.

Furthermore, among the SNPs disclosed herein, preferred SNPs for use in certain forensic/human identification applications include SNPs located at degenerate codon positions (i.e., the third position in certain codons which can be one of two or more alternative nucleotides and still encode the same amino acid), since these SNPs do not affect the encoded protein. SNPs that do not affect the encoded protein are expected to be under less selective pressure and are therefore expected to be more polymorphic in a population, which is typically an advantage for forensic/human identification applications. However, for certain forensics/human identification applications, such as predicting phenotypic characteristics (e.g., inferring ancestry or inferring one or more physical characteristics of an individual) from a DNA sample, it may be desirable to utilize SNPs that affect the encoded protein.

For many of the SNPs disclosed in Table 1 (which are identified as "Applera" SNP source), Table 1 provides SNP allele frequencies obtained by re-sequencing the DNA from 39 individuals (Table 1 also provides allele frequency information for "Celera" source SNPs and, where available, public SNPs from dbEST, HGBASE, and/or HGMD). The allele frequencies provided in Table 1 enable these SNPs to be readily used for human identification applications. Although any SNP disclosed in Table 1 could be used for human identification, the closer that the frequency of the minor allele at a particular SNP site is to 50%, the greater the ability of that SNP to discriminate between different individuals in a population since it becomes increasingly likely that two randomly selected individuals would have different alleles at that SNP site. Using the SNP allele frequencies provided in Table 1, one of ordinary skill in the art could readily select a subset of SNPs for which the frequency of the minor allele is, for example, at least 1%, 2%, 5%, 10%, 20%, 25%, 30%, 40%, 45%, or 50%, or any other frequency in-between. Thus, since Table 1 provides allele frequencies based on the re-sequencing of the chromosomes from 39 individuals, a subset of SNPs could readily be selected for human identification in which the total allele count of the minor allele at a particular SNP site is, for example, at least 1, 2, 4, 8, 10, 16, 20, 24, 30, 32, 36, 38, 39, 40, or any other number in-between.

Furthermore, Table 1 also provides population group (interchangeably referred to herein as ethnic or racial groups) information coupled with the extensive allele frequency information. For example, the group of 39 individuals whose DNA was re-sequenced was made-up of 20 Caucasians and 19 African-Americans. This population group information enables further refinement of SNP selection for human identification. For example, preferred SNPs for human identification can be selected from Table 1 that have similar allele frequencies in both the Caucasian and African-American populations; thus, for example, SNPs can be selected that have equally high discriminatory power in both populations. Alternatively, SNPs can be selected for which there is a statistically significant difference in allele frequencies between the Caucasian and African-American populations (as an extreme example, a particular allele may be observed only in either the Caucasian or the African-American population group but not observed in the other population group); such SNPs are useful, for example, for predicting the race/ethnicity of an unknown perpetrator from a biological sample such as a hair or blood stain recovered at a crime scene. For a discussion of using SNPs to predict ancestry from a DNA sample, including statistical methods, see Frudakis et al., "A Classifier for the SNP-Based Inference of Ancestry," *Journal of Forensic Sciences* 48[4]:771-782 [2003]).

SNPs have numerous advantages over other types of polymorphic markers, such as short tandem repeats (STRs). For example, SNPs can be easily scored and are amenable to automation, making SNPs the markers of choice for large-scale forensic databases. SNPs are found in much greater abundance throughout the genome than repeat polymorphisms. Population frequencies of two polymorphic forms can usually be determined with greater accuracy than those of multiple polymorphic forms at multi-allelic loci. SNPs are mutationaly more stable than repeat polymorphisms. SNPs are not susceptible to artifacts such as stutter bands that can hinder analysis. Stutter bands are frequently encountered when analyzing repeat polymorphisms, and are particularly troublesome when analyzing samples such as crime scene samples that may contain mixtures of DNA from multiple sources. Another significant advantage of SNP markers over STR markers is the much shorter length of nucleic acid needed to score a SNP. For example, STR markers are generally several hundred base pairs in length. A SNP, on the other hand, comprises a single nucleotide, and generally a short conserved region on either side of the SNP position for primer and/or probe binding. This makes SNPs more amenable to typing in highly degraded or aged biological samples that are frequently encountered in forensic casework in which DNA may be fragmented into short pieces.

SNPs also are not subject to microvariant and "off-ladder" alleles frequently encountered when analyzing STR loci. Microvariants are deletions or insertions within a repeat unit that change the size of the amplified DNA product so that the amplified product does not migrate at the same rate as reference alleles with normal sized repeat units. When separated by size, such as by electrophoresis on a polyacrylamide gel, microvariants do not align with a reference allelic ladder of standard sized repeat units, but rather migrate between the reference alleles. The reference allelic ladder is used for precise sizing of alleles for allele classification; therefore alleles that do not align with the reference allelic ladder lead to substantial analysis problems. Furthermore, when analyzing multi-allelic repeat polymorphisms, occasionally an allele is found that consists of more or less repeat units than has been previously seen in the population, or more or less repeat alleles than are included in a reference allelic ladder. These alleles will migrate outside the size range of known alleles in a reference allelic ladder, and therefore are referred to as "off-ladder" alleles. In extreme cases, the allele may contain so few or so many repeats that it migrates well out of the range of the reference allelic ladder. In this situation, the allele may not even be observed, or, with multiplex analysis, it may migrate within or close to the size range for another locus, further confounding analysis.

SNP analysis avoids the problems of microvariants and off-ladder alleles encountered in STR analysis. Importantly, microvariants and off-ladder alleles may provide significant problems, and may be completely missed, when using analysis methods such as oligonucleotide hybridization arrays, which utilize oligonucleotide probes specific for certain known alleles. Furthermore, off-ladder alleles and microvariants encountered with STR analysis, even when correctly typed, may lead to improper statistical analysis, since their frequencies in the population are generally unknown or poorly characterized, and therefore the statistical significance of a matching genotype may be questionable. All these advantages of SNP analysis are considerable in light of the consequences of most DNA identification cases, which may lead to life imprisonment for an individual, or re-association of remains to the family of a deceased individual.

DNA can be isolated from biological samples such as blood, bone, hair, saliva, or semen, and compared with the DNA from a reference source at particular SNP positions. Multiple SNP markers can be assayed simultaneously in order to increase the power of discrimination and the statistical significance of a matching genotype. For example, oligonucleotide arrays can be used to genotype a large number of SNPs simultaneously. The SNPs provided by the present invention can be assayed in combination with other polymorphic genetic markers, such as other SNPs known in the art or STRs, in order to identify an individual or to associate an individual with a particular biological sample.

Furthermore, the SNPs provided by the present invention can be genotyped for inclusion in a database of DNA genotypes, for example, a criminal DNA databank such as the FBI's Combined DNA Index System (CODIS) database. A genotype obtained from a biological sample of unknown source can then be queried against the database to find a matching genotype, with the SNPs of the present invention providing nucleotide positions at which to compare the known and unknown DNA sequences for identity. Accordingly, the present invention provides a database comprising novel SNPs or SNP alleles of the present invention (e.g., the database can comprise information indicating which alleles are possessed by individual members of a population at one or more novel SNP sites of the present invention), such as for use in forensics, biometrics, or other human identification applications. Such a database typically comprises a computer-based system in which the SNPs or SNP alleles of the present invention are recorded on a computer readable medium.

The SNPs of the present invention can also be assayed for use in paternity testing. The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child, with the SNPs of the present invention providing nucleotide positions at which to compare the putative father's and child's DNA sequences for identity. If the set of polymorphisms in the child attributable to the father does not match the set of polymorphisms of the putative father, it can be concluded, barring experimental error, that the putative father is not the father of the child. If the set of polymorphisms in the child attributable to the father match the set of polymorphisms of the putative father, a statistical calculation can be performed to determine the probability of coincidental match, and a conclusion drawn as to the likelihood that the putative father is the true biological-father of the child.

In addition to paternity testing, SNPs are also useful for other types of kinship testing, such as for verifying familial relationships for immigration purposes, or for cases in which an individual alleges to be related to a deceased individual in order to claim an inheritance from the deceased individual, etc. For further information regarding the utility of SNPs for paternity testing and other types of kinship testing, including methods for statistical analysis, see Krawczak, "Informativity assessment for biallelic single nucleotide polymorphisms," *Electrophoresis* 20(8):1676-81 (June 1999).

The use of the SNPs of the present invention for human identification further extends to various authentication systems, commonly referred to as biometric systems, which typically convert physical characteristics of humans (or other organisms) into digital data. Biometric systems include various technological devices that measure such unique anatomical or physiological characteristics as finger, thumb, or palm prints; hand geometry; vein patterning on the back of the hand; blood vessel patterning of the retina and color and texture of the iris; facial characteristics; voice patterns; signature and typing dynamics; and DNA. Such physiological measurements can be used to verify identity and, for example, restrict or allow access based on the identification. Examples of applications for biometrics include physical area security, computer and network security, aircraft passenger check-in and boarding, financial transactions, medical records access, government benefit distribution, voting, law enforcement, passports, visas and immigration, prisons, various military applications, and for restricting access to expensive or dangerous items, such as automobiles or guns (see, for example, O'Connor, *Stanford Technology Law Review* and U.S. Pat. No. 6,119,096).

Groups of SNPs, particularly the SNPs provided by the present invention, can be typed to uniquely identify an individual for biometric applications such as those described above. Such SNP typing can readily be accomplished using, for example, DNA chips/arrays. Preferably, a minimally invasive means for obtaining a DNA sample is utilized. For example, PCR amplification enables sufficient quantities of DNA for analysis to be obtained from buccal swabs or fingerprints, which contain DNA-containing skin cells and oils that are naturally transferred during contact.

Further information regarding techniques for using SNPs in forensic/human identification applications can be found in, for example, *Current Protocols in Human Genetics* 14.1-14.7, John Wiley & Sons, New York (2002).

Variant Proteins, Antibodies, Vectors & Host Cells, & Uses Thereof

Variant Proteins Encoded by SNP-Containing Nucleic Acid Molecules

The present invention provides SNP-containing nucleic acid molecules. Certain SNP-containing nucleic acid molecules may encode proteins having variant amino acid sequences as compared to the art-known (i.e., wild-type) proteins. These variants will generally be referred to herein as variant proteins/peptides/polypeptides, or polymorphic proteins/peptides/polypeptides. The terms "protein," "peptide," and "polypeptide" are used herein interchangeably.

A variant protein may be encoded by, for example, a nonsynonymous nucleotide substitution at a cSNP position. In addition, variant proteins may also include proteins whose expression, structure, and/or function is altered by a SNP, such as a SNP that creates or destroys a stop codon, a SNP that affects splicing, and a SNP in control/regulatory elements, e.g. promoters, enhancers, or transcription factor binding domains.

As used herein, a protein or peptide is said to be "isolated" or "purified" when it is substantially free of cellular material or chemical precursors or other chemicals. Variant proteins can be purified to homogeneity or other lower degrees of purity. The level of purification will be based on the intended use. The key feature is that the preparation allows for the desired function of the variant protein, even if in the presence of considerable amounts of other components.

As used herein, "substantially free of cellular material" includes preparations of the variant protein having less than about 30% (by dry weight) other proteins (i.e., contaminating protein), less than about 20% other proteins, less than about 10% other proteins, or less than about 5% other proteins. When the variant protein is recombinantly produced, it can also be substantially free of culture medium, i.e., culture medium represents less than about 20% of the volume of the protein preparation.

The language "substantially free of chemical precursors or other chemicals" includes preparations of the variant protein in which it is separated from chemical precursors or other chemicals that are involved in its synthesis. In one embodiment, the language "substantially free of chemical precursors or other chemicals" includes preparations of the variant protein having less than about 30% (by dry weight) chemical precursors or other chemicals, less than about 20% chemical precursors or other chemicals, less than about 10% chemical precursors or other chemicals, or less than about 5% chemical precursors or other chemicals.

An isolated variant protein may be purified from cells that naturally express it, purified from cells that have been altered to express it (recombinant host cells), or synthesized using known protein synthesis methods. For example, a nucleic acid molecule containing SNP(s) encoding the variant protein can be cloned into an expression vector, the expression vector introduced into a host cell, and the variant protein expressed in the host cell. The variant protein can then be isolated from the cells by any appropriate purification scheme using standard protein purification techniques. Examples of these techniques are described in detail below (Sambrook and Russell, *Molecular Cloning: A Laboratory Manual*, Cold Spring Harbor Laboratory Press, Cold Spring Harbor, N.Y. [2000]).

Variant proteins can comprise, consist of, or consist essentially of amino acid sequences that contain one or more variant amino acids encoded by one or more codons which contain a SNP.

Accordingly, variant proteins can consist of amino acid sequences that contain one or more amino acid polymorphisms (or truncations or extensions due to creation or destruction of a stop codon, respectively) encoded by a SNP. A protein consists of an amino acid sequence when the amino acid sequence is the entire amino acid sequence of the protein.

Further, variant proteins can consist essentially of amino acid sequences that contain one or more amino acid polymorphisms (or truncations or extensions due to creation or destruction of a stop codon, respectively) encoded by a SNP. A protein consists essentially of an amino acid sequence when such an amino acid sequence is present with only a few additional amino acid residues in the final protein.

Further, variant proteins can comprise amino acid sequences that contain one or more amino acid polymorphisms (or truncations or extensions due to creation or destruction of a stop codon, respectively) encoded by a SNP. A protein comprises an amino acid sequence when the amino acid sequence is at least part of the final amino acid sequence of the protein. In such a fashion, the protein may contain only the variant amino acid sequence or have additional amino acid residues, such as a contiguous encoded sequence that is naturally associated with it or heterologous amino acid residues. Such a protein can have a few additional amino acid residues or can comprise many more additional amino acids. A brief description of how various types of these proteins can be made and isolated is provided below.

The variant proteins can be attached to heterologous sequences to form chimeric or fusion proteins. Such chimeric and fusion proteins comprise a variant protein operatively linked to a heterologous protein having an amino acid sequence not substantially homologous to the variant protein. "Operatively linked" indicates that the coding sequences for the variant protein and the heterologous protein are ligated in-frame. The heterologous protein can be fused to the N-terminus or C-terminus of the variant protein. In another embodiment, the fusion protein is encoded by a fusion polynucleotide that is synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology [*1992]). Moreover, many expression vectors are commercially available that already encode a fusion moiety (e.g., a GST protein). A variant protein-encoding nucleic acid can be cloned into such an expression vector such that the fusion moiety is linked in-frame to the variant protein.

In many uses, the fusion protein does not affect the activity of the variant protein. The fusion protein can include, but is not limited to, enzymatic fusion proteins, for example, beta-galactosidase fusions, yeast two-hybrid GAL fusions, poly-His fusions, MYC-tagged, HI-tagged and Ig fusions. Such fusion proteins, particularly poly-His fusions, can facilitate their purification following recombinant expression. In certain host cells (e.g., mammalian host cells), expression and/or secretion of a protein can be increased by using a heterologous signal sequence. Fusion proteins are further described in, for example, Terpe, "Overview of tag protein fusions: from molecular and biochemical fundamentals to commercial systems," *Appl. Microbiol. Biotechnol.* 60(5):523-33 (January 2003); Epub Nov. 7, 2002; Graddis et al., "Designing proteins that work using recombinant technologies," *Curr. Pharm. Biotechnol.* 3(4):285-97 (December 2002); and Nilsson et al., "Affinity fusion strategies for detection, purification, and immobilization of recombinant proteins," *Protein Expr. Purif.* 11(1):1-16 (October 1997).

Variant proteins include, but are not limited to, proteins containing deletions, additions and substitutions in the amino acid sequence caused by a SNP. One class of substitutions is conserved amino acid substitutions in which a given amino acid in a polypeptide is substituted for another amino acid of like characteristics. Typical conservative substitutions are replacements, one for another, among the aliphatic amino acids Ala, Val, Leu, and Ele; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in, for example, Bowie et al., *Science* 247: 1306-1310 (1990).

Variant proteins can be fully functional or can lack function in one or more activities, e.g. ability to bind another molecule, ability to catalyze a substrate, ability to mediate signaling, etc. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, truncations or extensions, or a substitution, insertion, inversion, or deletion of a critical residue or in a critical region.

Amino acids that are essential for function of a protein can be identified by methods known in the art, such as site-directed mutagenesis or alanine-scanning mutagenesis (Cunningham et al., *Science* 244:1081-1085 [1989]). The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899-904 [1992]; de Vos et al., *Science* 255:306-312 [1992]).

Polypeptides can contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Accordingly, variant proteins can also encompass derivatives or analogs in which a substituted amino acid residue is not one encoded by the genetic code, in which a substituent group is included, in which the mature polypeptide is fused with another compound, such as a compound to increase the half-life of the polypeptide (e.g., polyethylene glycol), or in which additional amino acids are fused to the mature polypeptide, such as a leader or secretory sequence or a sequence for purification of the mature polypeptide or a pro-protein sequence.

Known protein modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such protein modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W.H. Freeman and Company, New York (1993); F. Wold, *Posttranslational Covalent Modification of Proteins* 1-12, ed. B. C. Johnson, Academic Press, New York (1983); Seifter et al., *Meth. Enzymol.* 182: 626-646 (1990); and Rattan et al., *Ann. N.Y. Acad. Sci.* 663:48-62 (1992).

Variant proteins can also include fragments of variant proteins in which the fragments contain one or more amino acid sequence variations (e.g., substitutions, or truncations or extensions due to creation or destruction of a stop codon) encoded by a SNP. As used herein, a fragment may comprise at least about 4, 8, 10, 12, 14, 16, 18, 20, 25, 30, 50, 100 (or any other number in-between) or more contiguous amino acid residues from a variant protein, wherein at least one amino acid residue is affected by a SNP, e.g., a variant amino acid residue encoded by a nonsynonymous nucleotide substitution at a cSNP position. The variant amino acid encoded by a cSNP may occupy any residue position along the sequence of the fragment. Such fragments can be chosen based on the ability to retain one or more of the biological activities of the variant protein or the ability to perform a function, e.g., act as an immunogen. Particularly important fragments are biologically active fragments. Such fragments will typically comprise a domain or motif of a variant protein, e.g., active site, transmembrane domain, or ligand/substrate binding domain. Other fragments include, but are not limited to, domain or motif-containing fragments, soluble peptide fragments, and fragments containing immunogenic structures. Predicted domains and functional sites are readily identifiable by computer programs well known to those of skill in the art (e.g., PROSITE analysis) (*Current Protocols in Protein Science*, John Wiley & Sons, New York [2002]).

Uses of Variant Proteins

Variant proteins can be used in a variety of ways, including but not limited to, in assays to determine the biological activity of a variant protein, such as in a panel of multiple proteins for high-throughput screening; to raise antibodies or to elicit another type of immune response; as a reagent (including the labeled reagent) in assays designed to quantitatively determine levels of the variant protein (or its binding partner) in biological fluids; as a marker for cells or tissues in which it is preferentially expressed (either constitutively or at a particular stage of tissue differentiation or development or in a disease state); as a target for screening for a therapeutic agent; and as a direct therapeutic agent to be administered into a human subject. Any of the variant proteins may be developed into reagent grade or kit format for commercialization as research products. Methods for performing the uses listed above are well known to those skilled in the art (see, e.g., *Molecular Cloning: A Laboratory Manual*, Sambrook and Russell, Cold Spring Harbor Laboratory Press, New York [2000], and *Methods in Enzymology: Guide to Molecular Cloning Techniques*, eds. S. L. Berger and A. R. Kimmel, Academic Press [1987]).

Detection of variant proteins can be accomplished using, for example, antibodies, small molecule compounds, aptamers, ligands/substrates, other proteins or protein fragments, or other protein-binding agents. Preferably, protein detection agents are specific for a variant protein and can therefore discriminate between a variant protein and the wild-type protein or another variant form. This can generally be accomplished by, for example, selecting or designing detection agents that bind to the region of a protein that differs between the variant and wild-type protein, such as a region of a protein that contains one or more amino acid substitutions that is/are encoded by a non-synonymous cSNP, or a region of a protein that follows a nonsense mutation-type SNP that creates a stop codon thereby leading to a shorter polypeptide, or a region of a protein that follows a read-through mutation-type SNP that destroys a stop codon thereby leading to a longer polypeptide in which a portion of the polypeptide is present in one version of the polypeptide but not the other.

Variant proteins can be used as targets for diagnosing neurodegenerative disease or for determining predisposition to neurodegenerative disease in a human. Accordingly, methods are provided for detecting the presence of, or levels of, one or more variant proteins in a cell, tissue, or organism. Such methods typically involve contacting a test sample with an agent (e.g., an antibody, small molecule compound, or peptide) capable of interacting with the variant protein such that specific binding of the agent to the variant protein can be detected. Such an assay can be provided in a single detection format or a multi-detection format such as an array, for example, an antibody or aptamer array (arrays for protein detection may also be referred to as "protein chips"). The variant protein of interest can be isolated from a test sample and assayed for the presence of a variant amino acid sequence encoded by one or more SNPs. The SNPs may cause changes to the protein and the corresponding protein function/activity, such as through non-synonymous substitutions in protein coding regions that can lead to amino acid substitutions, deletions, insertions, and/or rearrangements; formation or destruction of stop codons; or alteration of control elements such as promoters. SNPs may also cause inappropriate post-translational modifications.

One preferred agent for detecting a variant protein in a sample is an antibody capable of selectively binding to a variant form of the protein (antibodies are described in greater detail in the next section). Such samples include, for example, tissues, cells, and biological fluids isolated from a subject, as well as tissues, cells and fluids present within a subject.

In vitro methods for detection of the variant proteins associated with neurodegenerative disease and fragments thereof include, but are not limited to, enzyme linked immunosorbent assays (ELISAs), radioimmunoassays (RIA), Western blots, immunoprecipitations, immunofluorescence, and protein arrays/chips (e.g., arrays of antibodies or aptamers). For further information regarding immunoassays and related protein detection methods, see *Current Protocols in Immunology*, John Wiley & Sons, New York, and Hage, "Immunoassays," *Anal. Chem.* 71(12):294R-304R (Jun. 15, 1999).

Additional analytic methods of detecting amino acid variants include, but are not limited to, altered electrophoretic mobility, altered tryptic peptide digest, altered protein activity in cell-based or cell-free assay, alteration in ligand or antibody-binding pattern, altered isoelectric point, and direct amino acid sequencing.

Alternatively, variant proteins can be detected in vivo in a subject by introducing into the subject a labeled antibody (or other type of detection reagent) specific for a variant protein. For example, the antibody can be labeled with a radioactive marker whose presence and location in a subject can be detected by standard imaging techniques.

Other uses of variant proteins are based on the class or action of the protein. For example, proteins isolated from humans and their mammalian orthologs serve as targets for identifying agents (e.g., small molecule drugs or antibodies) for use in therapeutic applications, particularly for modulating a biological or pathological response in a cell or tissue that expresses the protein. Pharmaceutical agents can be developed that modulate protein activity.

As an alternative to modulating gene expression, therapeutic compounds can be developed that modulate protein function. For example, certain SNPs affect the amino acid sequence of the encoded protein (e.g., non-synonymous cSNPs and nonsense mutation-type SNPs). Such alterations in the encoded amino acid sequence may affect protein function, particularly if such amino acid sequence variations occur in functional protein domains, such as catalytic domains, ATP-binding domains, or ligand/substrate binding domains. It is well established in the art that variant proteins having amino acid sequence variations in functional domains can cause or influence pathological conditions. In such instances, compounds (e.g., small molecule drugs or antibodies) can be developed that target the variant protein and modulate (e.g., up- or down-regulate) protein function/activity.

Therapeutic methods may include methods that target one or more variant proteins. Variant proteins can be targeted using, for example, small molecule compounds, antibodies, aptamers, ligands/substrates, other proteins, or other protein-binding agents. Additionally, the skilled artisan will recognize that novel protein variants (and polymorphic nucleic acid molecules) may themselves be directly used as therapeutic agents by acting as competitive inhibitors of corresponding art-known proteins (or nucleic acid molecules such as mRNA molecules).

Variant proteins are particularly useful in drug screening assays, in cell-based or cell-free systems. Cell-based systems can utilize cells that naturally express the protein, a biopsy specimen, or cell cultures. In one embodiment, cell-based assays involve recombinant host cells expressing the variant protein. Cell-free assays can be used to detect the ability of a compound to directly bind to a variant protein or to the corresponding SNP-containing nucleic acid fragment that encodes the variant protein.

A variant protein, as well as appropriate fragments thereof, can be used in high-throughput screening assays to test candidate compounds for the ability to bind and/or modulate the activity of the variant protein. These candidate compounds can be further screened against a protein having normal function (e.g., a wild-type/non-variant protein) to further determine the effect of the compound on the protein activity. Furthermore, these compounds can be tested in animal or invertebrate systems to determine in vivo activity/effectiveness. Compounds can be identified that activate (agonists) or inactivate (antagonists) the variant protein, and different compounds can be identified that cause various degrees of activation or inactivation of the variant protein.

Further, the variant proteins can be used to screen a compound for the ability to stimulate or inhibit interaction between the variant protein and a target molecule that normally interacts with the protein. The target can be a ligand, a substrate or a binding partner that the protein normally interacts with (for example, epinephrine or norepinephrine). Such assays typically include the steps of combining the variant protein with a candidate compound under conditions that allow the variant protein, or fragment thereof, to interact with the target molecule, and to detect the formation of a complex between the protein and the target or to detect the biochemical consequence of the interaction with the variant protein and the target, such as any of the associated effects of signal transduction.

Candidate compounds include, for example, 1) peptides such as soluble peptides, including Ig-tailed fusion peptides and members of random peptide libraries (see, e.g., Lam et al., *Nature* 354:82-84 [1991]; Houghten et al., *Nature* 354:84-86 [1991]) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767-778 [1993]); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the variant protein that competes for ligand binding. Other candidate compounds include mutant proteins or appropriate fragments containing mutations that affect variant protein function and thus compete for ligand. Examples include a fragment that competes for ligand, for example with a higher affinity, or a fragment that binds ligand but does not allow release.

Various other end point assays can be used to identify compounds that modulate (stimulate or inhibit) variant protein activity. The assays typically involve an assay of events in the signal transduction pathway that indicate protein activity. Thus, the expression of genes that are up or down-regulated in response to the variant protein dependent signal cascade can be assayed. The regulatory region of such genes can be operably linked to a marker that is easily detectable, such as luciferase. Alternatively, phosphorylation of the variant protein, or a variant protein target, could also be measured. Any of the biological or biochemical functions mediated by the variant protein can be used as an endpoint assay. These include all of the biochemical or biological events described herein, in the references cited herein, incorporated by reference for these endpoint assay targets, and other functions known to those of ordinary skill in the art.

Binding and/or activating compounds can also be screened by using chimeric variant proteins in which an amino terminal extracellular domain or parts thereof, an entire transmembrane domain or subregions, and/or the carboxyl terminal intracellular domain or parts thereof, can be replaced by heterologous domains or subregions. For example, a substrate-binding region can be used that interacts with a different substrate than that which is normally recognized by a variant protein. Accordingly, a different set of signal transduction components is available as an end-point assay for activation. This allows for assays to be performed in other than the specific host cell from which the variant protein is derived.

The variant proteins are also useful in competition binding assays in methods designed to discover compounds that interact with the variant protein. Thus, a compound can be exposed to a variant protein under conditions that allow the compound to bind or to otherwise interact with the variant protein. A binding partner, such as ligand, that normally interacts with the variant protein is also added to the mixture. If the test compound interacts with the variant protein or its binding partner, it decreases the amount of complex formed or activity from the variant protein. This type of assay is particularly useful in screening for compounds that interact with specific regions of the variant protein (Hodgson, *Bio/technology,* 10[9], 973-80 [September 1992]).

To perform cell-free drug screening assays, it is sometimes desirable to immobilize either the variant protein or a fragment thereof, or its target molecule, to facilitate separation of complexes from uncomplexed forms of one or both of the proteins, as well as to accommodate automation of the assay. Any method for immobilizing proteins on matrices can be used in drug screening assays. In one embodiment, a fusion protein containing an added domain allows the protein to be bound to a matrix. For example, glutathione-S-transferase/$^{125}$I fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and a candidate compound, such as a drug candidate, and the mixture incubated under conditions conducive to complex formation (e.g., at physiological conditions for salt and pH). Following incubation, the beads can be washed to remove any unbound label, and the matrix immobilized and radiolabel determined directly, or in the supernatant after the complexes are dissociated. Alternatively, the complexes can be dissociated from the matrix, separated by SDS-PAGE, and the level of bound material found in the bead fraction quantitated from the gel using standard electrophoretic techniques.

Either the variant protein or its target molecule can be immobilized utilizing conjugation of biotin and streptavidin. Alternatively, antibodies reactive with the variant protein but which do not interfere with binding of the variant protein to its target molecule can be derivatized to the wells of the plate, and the variant protein trapped in the wells by antibody conjugation. Preparations of the target molecule and a candidate compound are incubated in the variant protein-presenting wells and the amount of complex trapped in the well can be quantitated. Methods for detecting such complexes, in addition to those described above for the GST-immobilized complexes, include immunodetection of complexes using antibodies reactive with the protein target molecule, or which are reactive with variant protein and compete with the target molecule, and enzyme-linked assays that rely on detecting an enzymatic activity associated with the target molecule.

Modulators of variant protein activity identified according to these drug screening assays can be used to treat a subject with a disorder mediated by the protein pathway, such as neurodegenerative disease. These methods of treatment typically include the steps of administering the modulators of protein activity in a pharmaceutical composition to a subject in need of such treatment.

The variant proteins, or fragments thereof, can themselves be directly used to treat a disorder characterized by an absence of, inappropriate, or unwanted expression or activity of the variant protein. Accordingly, methods for treatment include the use of a variant protein or fragments thereof.

Variant proteins can be used as "bait proteins" in a two-hybrid assay or three-hybrid assay (see, e.g., U.S. Pat. No. 5,283,317; Zervos et al., Cell 72:223-232 [1993]; Madura et al., *J. Biol. Chem.* 268:12046-12054 [1993]; Bartel et al., *Biotechniques* 14:920-924 [1993]; Iwabuchi et al., *Oncogene* 8:1693-1696 [1993]; and Brent WO94/10300) to identify other proteins that bind to or interact with the variant protein and are involved in variant protein activity. Such variant protein-binding proteins are also likely to be involved in the propagation of signals by the variant proteins or variant protein targets as, for example, elements of a protein-mediated signaling pathway. Alternatively, such variant protein-binding proteins are inhibitors of the variant protein.

The two-hybrid system is based on the modular nature of most transcription factors, which typically consist of separable DNA-binding and activation domains. Briefly, the assay typically utilizes two different DNA constructs. In one construct, the gene that codes for a variant protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a variant protein-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected, and cell colonies containing the functional transcription factor can be isolated and used to obtain the cloned gene that encodes the protein that interacts with the variant protein.

Antibodies Directed to Variant Proteins

Antibodies can be produced that selectively bind to variant proteins and fragments thereof. Such antibodies may be used to quantitatively or qualitatively detect variant proteins. As used herein, an antibody selectively binds a target variant protein when it binds the variant protein and does not significantly bind to non-variant proteins, i.e., the antibody does not significantly bind to normal, wild-type, or art-known proteins that do not contain a variant amino acid sequence created by one or more SNPs (variant amino acid sequences may be due to, for example, nonsynonymous cSNPs, nonsense SNPs that create a stop codon, thereby causing a truncation of a polypeptide or SNPs that cause read-through mutations resulting in an extension of a polypeptide).

As used herein, an antibody is defined in terms consistent with that recognized in the art: they are multi-subunit proteins produced by an organism in response to an antigen challenge. Antibodies include both monoclonal antibodies and polyclonal antibodies, as well as antigen-reactive proteolytic fragments of such antibodies, such as Fab, $F(ab)'_2$, and Fv fragments. In addition, an antibody further includes any of a variety of engineered antigen-binding molecules such as a chimeric antibody (U.S. Pat. Nos. 4,816,567 and 4,816,397; Morrison et al., *Proc. Natl. Acad. Sci. USA,* 81:6851 [1984]; Neuberger et al., *Nature* 312:604 [1984]), a humanized antibody (U.S. Pat. Nos. 5,693,762; 5,585,089; and 5,565,332), a single-chain Fv (U.S. Pat. No. 4,946,778; Ward et al., *Nature* 334:544 [1989]), a bispecific antibody with two binding specificities (Segal et al., *J. Immunol. Methods* 248:1 [2001]; Carter, *J. Immunol. Methods* 248:7 [2001]), a diabody, a triabody, and a tetrabody (Todorovska et al., *J. Immunol. Methods,* 248:47 [2001]), as well as a Fab conjugate (dimer or trimer), and a minibody.

Many methods are known in the art for generating and/or identifying antibodies to a given target antigen (Harlow, *Antibodies*, Cold Spring Harbor Press, New York [1989]). In general, an isolated peptide (e.g., a variant protein) is used as an immunogen and is administered to a mammalian organism, such as a rat, rabbit, hamster or mouse. Either a full-length protein, an antigenic peptide fragment (e.g., a peptide fragment containing a region that varies between a variant protein and a corresponding wild-type protein), or a fusion protein can be used. A protein used as an immunogen may be naturally-occurring, synthetic or recombinantly produced, and may be administered in combination with an adjuvant, including but not limited to, Freund's (complete and incomplete), mineral gels such as aluminum hydroxide, surface active substance such as lysolecithin, pluronic polyols, polyanions, peptides, oil emulsions, keyhole limpet hemocyanin, dinitrophenol, and the like.

Monoclonal antibodies can be produced by hybridoma technology (Kohler and Milstein, *Nature,* 256:495 [1975]), which immortalizes cells secreting a specific monoclonal antibody. The immortalized cell lines can be created in vitro by fusing two different cell types, typically lymphocytes, and tumor cells. The hybridoma cells may be cultivated in vitro or in vivo. Additionally, fully human antibodies can be generated by transgenic animals (He et al., *J. Immunol.,* 169:595 [2002]). Fd phage and Fd phagemid technologies may be used to generate and select recombinant antibodies in vitro (Hoogenboom and Chames, *Immunol. Today* 21:371 [2000]; Liu et al., *J. Mol. Biol.* 315:1063 [2002]). The complementarity-determining regions of an antibody can be identified, and synthetic peptides corresponding to such regions may be used to mediate antigen binding (U.S. Pat. No. 5,637,677).

Antibodies are preferably prepared against regions or discrete fragments of a variant protein containing a variant amino acid sequence as compared to the corresponding wild-type protein (e.g., a region of a variant protein that includes an amino acid encoded by a nonsynonymous cSNP, a region affected by truncation caused by a nonsense SNP that creates a stop codon, or a region resulting from the destruction of a stop codon due to read-through mutation caused by a SNP). Furthermore, preferred regions will include those involved in function/activity and/or protein/binding partner interaction. Such fragments can be selected on a physical property, such as fragments corresponding to regions that are located on the surface of the protein, e.g., hydrophilic regions, or can be selected based on sequence uniqueness, or based on the position of the variant amino acid residue(s) encoded by the SNPs. An antigenic fragment will typically comprise at least about 8-10 contiguous amino acid residues in which at least one of the amino acid residues is an amino acid affected by a SNP. The antigenic peptide can comprise, however, at least 12, 14, 16, 20, 25, 50, 100 (or any other number in-between) or more amino acid residues, provided that at least one amino acid is affected by a SNP.

Detection of an antibody can be facilitated by coupling (i.e., physically linking) the antibody or an antigen-reactive fragment thereof to a detectable substance. Detectable substances include, but are not limited to, various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies, particularly the use of antibodies as therapeutic agents, are reviewed in: Morgan, "Antibody therapy for Alzheimer's Disease," *Expert Rev. Vaccines.* 2(1):53-9 (February 2003); Ross et al., "Anticancer antibodies," *Am. J. Clin. Pathol.* 119(4):472-85 (April 2003); Goldenberg, "Advancing role of radiolabeled antibodies in the therapy of cancer", *Cancer Immunol. Immunother.* 52(5):281-96 (May 2003); Epub Mar. 11, 2003; Ross et al., "Antibody-based therapeutics in oncology," *Expert Rev. Anticancer Ther.* 3(1):107-21 (February 2003); Cao et al., "Bispecific antibody conjugates in therapeutics," *Adv. Drug Deliv. Rev.* 55(2):171-97 (Feb. 10, 2003); von Mehren et al., "Monoclonal antibody therapy for cancer," *Annu. Rev. Med.* 54:343-69 (2003); Epub Dec. 3, 2001; Hudson et al., "Engineered antibodies," *Nat. Med.* 9(1): 129-34 (January 2003); Brekke et al., "Therapeutic antibodies for human diseases at the dawn of the twenty-first century," *Nat. Rev. Drug Discov.* 2(1):52-62 (January 2003) (Erratum in: *Nat. Rev. Drug Discov.* 2[3]:240 [March 2003]); Houdebine, "Antibody manufacture in transgenic animals and comparisons with other systems," *Curr. Opin. Biotechnol.* 13(6):625-9 (December 2002); Andreakos et al., "Monoclonal antibodies in immune and inflammatory diseases," *Curr. Opin. Biotechnol.* 13(6):615-20 (December 2002); Kellermann et al., "Antibody discovery: the use of transgenic mice to generate human monoclonal antibodies for therapeutics," *Curr. Opin. Biotechnol.* 13(6):593-7 (December 2002); Pini et al., "Phage display and colony filter screening for high-throughput selection of antibody libraries," *Comb. Chem. High Throughput Screen* 5(7):503-10 (November 2002); Batra et al., "Pharmacokinetics and biodistribution of genetically engineered antibodies," *Curr. Opin. Biotechnol.* 13(6):603-8 (December 2002); and Tangri et al., "Rationally engineered proteins or antibodies with absent or reduced immunogenicity," *Curr. Med. Chem.* 9(24):2191-9 (December 2002).

Uses of Antibodies

Antibodies can be used to isolate variant proteins from a natural cell source or from recombinant host cells by standard techniques, such as affinity chromatography or immunoprecipitation. In addition, antibodies are useful for detecting the presence of a variant protein in cells or tissues to determine the pattern of expression of the variant protein among various tissues in an organism and over the course of normal development or disease progression. Further, antibodies can be used to detect variant protein in situ, in vitro, in a bodily fluid, or in a cell lysate or supernatant in order to evaluate the amount and pattern of expression. Also, antibodies can be used to assess abnormal tissue distribution, abnormal expression during development, or expression in an abnormal condition, such as neurodegenerative disease. Additionally, antibody detection of circulating fragments of the full-length variant protein can be used to identify turnover.

Antibodies to variant proteins are also useful in pharmacogenomic analysis. Thus, antibodies against variant proteins encoded by alternative SNP alleles can be used to identify individuals that require modified treatment modalities.

Further, antibodies can be used to assess expression of the variant protein in disease states such as in active stages of the disease or in an individual with a predisposition to a disease related to the protein's function, particularly neurodegenerative disease. Antibodies specific for a variant protein encoded by a SNP-containing nucleic acid molecule can be used to assay for the presence of the variant protein, such as to screen for predisposition to neurodegenerative disease as indicated by the presence of the variant protein.

Antibodies are also useful as diagnostic tools for evaluating the variant proteins in conjunction with analysis by electrophoretic mobility, isoelectric point, tryptic peptide digest, and other physical assays well known in the art.

Antibodies can also be used to assess aberrant subcellular localization of a variant protein in cells in various tissues. The diagnostic uses can be applied, not only in genetic testing, but also in monitoring a treatment modality. Accordingly, where treatment is ultimately aimed at correcting the expression level or the presence of variant protein or aberrant tissue distribution or developmental expression of a variant protein, antibodies directed against the variant protein or relevant fragments can be used to monitor therapeutic efficacy.

The antibodies are also useful for inhibiting variant protein function, for example, by blocking the binding of a variant protein to a binding partner. These uses can also be applied in a therapeutic context in which treatment involves inhibiting a variant protein's function. An antibody can be used, for example, to block or competitively inhibit binding, thus modulating (agonizing or antagonizing) the activity of a variant protein. Antibodies can be prepared against specific variant protein fragments containing sites required for function or against an intact variant protein that is associated with a cell or cell membrane. For in vivo administration, an antibody may be linked with an additional therapeutic payload such as a radionuclide, an enzyme, an immunogenic epitope, or a cytotoxic agent. Suitable cytotoxic agents include, but are not limited to, bacterial toxin such as diphtheria, and plant toxin such as ricin. The in vivo half-life of an antibody or a fragment thereof may be lengthened by pegylation through conjugation to polyethylene glycol (Leong et al., *Cytokine* 16:106 [2001]).

Also provided are kits for using antibodies, such as kits for detecting the presence of a variant protein in a test sample. An exemplary kit can comprise antibodies such as a labeled or labelable antibody and a compound or agent for detecting variant proteins in a biological sample; means for determining the amount, or presence/absence of variant protein in the sample; means for comparing the amount of variant protein in the sample with a standard; and instructions for use.

Vectors and Host Cells

The present invention also provides vectors containing the SNP-containing nucleic acid molecules described herein. The term "vector" refers to a vehicle, preferably a nucleic acid molecule, which can transport a SNP-containing nucleic acid molecule. When the vector is a nucleic acid molecule, the SNP-containing nucleic acid molecule can be covalently linked to the vector nucleic acid. Such vectors include, but are not limited to, a plasmid, single or double stranded phage, a single or double stranded RNA or DNA viral vector, or artificial chromosome, such as a BAC, PAC, YAC, or MAC.

A vector can be maintained in a host cell as an extrachromosomal element where it replicates and produces additional copies of the SNP-containing nucleic acid molecules. Alternatively, the vector may integrate into the host cell genome and produce additional copies of the SNP-containing nucleic acid molecules when the host cell replicates.

The invention provides vectors for the maintenance (cloning vectors) or vectors for expression (expression vectors) of the SNP-containing nucleic acid molecules. The vectors can function in prokaryotic or eukaryotic cells or in both (shuttle vectors).

Expression vectors typically contain cis-acting regulatory regions that are operably linked in the vector to the SNP-containing nucleic acid molecules such that transcription of the SNP-containing nucleic acid molecules is allowed in a host cell. The SNP-containing nucleic acid molecules can also be introduced into the host cell with a separate nucleic acid molecule capable of affecting transcription. Thus, the second nucleic acid molecule may provide a trans-acting factor interacting with the cis-regulatory control region to allow transcription of the SNP-containing nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequences to which the SNP-containing nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region, a ribosome-binding site for translation. Other regulatory control elements for expression include initiation and termination codons as well as polyadenylation signals. A person of ordinary skill in the art would be aware of the numerous regulatory sequences that are useful in expression vectors (see, e.g., Sambrook and Russell, *Molecular Cloning: A Laboratory Manual*, Cold Spring Harbor Laboratory Press, Cold Spring Harbor, N.Y. [2000]).

A variety of expression vectors can be used to express a SNP-containing nucleic acid molecule. Such vectors include chromosomal, episomal, and virus-derived vectors, for example, vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors can also be derived from combinations of these sources such as those derived from plasmid and bacteriophage genetic elements, e.g., cosmids and phagemids. Appropriate cloning and expression vectors for prokaryotic and eukaryotic hosts are described in Sambrook and Russell, *Molecular Cloning: A Laboratory Manual*, Cold Spring Harbor Laboratory Press, Cold Spring Harbor, N.Y. (2000).

The regulatory sequence in a vector may provide constitutive expression in one or more host cells (e.g., tissue specific expression) or may provide for inducible expression in one or more cell types such as by temperature, nutrient additive, or exogenous factor, e.g., a hormone or other ligand. A variety of vectors that provide constitutive or inducible expression of a nucleic acid sequence in prokaryotic and eukaryotic host cells are well known to those of ordinary skill in the art.

A SNP-containing nucleic acid molecule can be inserted into the vector by methodology well-known in the art. Generally, the SNP-containing nucleic acid molecule that will ultimately be expressed is joined to an expression vector by cleaving the SNP-containing nucleic acid molecule and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial host cells include, but are not limited to, *E. coli, Streptomyces*, and *Salmonella typhimurium*. Eukaryotic host cells include, but are not limited to, yeast, insect cells such as *Drosophila*, animal cells such as COS and CHO cells, and plant cells.

As described herein, it may be desirable to express the variant peptide as a fusion protein. Accordingly, the invention provides fusion vectors that allow for the production of the variant peptides. Fusion vectors can, for example, increase the expression of a recombinant protein, increase the solubility of the recombinant protein, and aid in the purification of the protein by acting, for example, as a ligand for affinity purification. A proteolytic cleavage site may be introduced at the junction of the fusion moiety so that the desired variant peptide can ultimately be separated from the fusion moiety. Proteolytic enzymes suitable for such use include, but are not limited to, factor Xa, thrombin, and enterokinase. Typical fusion expression vectors include pGEX (Smith et al., *Gene* 67:31-40 [1988]), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301-315 [1988]) and pET 11d (Studier et al., *Gene Expression Technology: Methods in Enzymology* 185:60-89 [1990]).

Recombinant protein expression can be maximized in a bacterial host by providing a genetic background wherein the host cell has an impaired capacity to proteolytically cleave the recombinant protein (S. Gottesman, *Gene Expression Technology: Methods in Enzymology* 185 119-128, Academic Press, San Diego, Calif. [1990]). Alternatively, the sequence of the SNP-containing nucleic acid molecule of interest can be altered to provide preferential codon usage for a specific host cell, for example, *E. coli* (Wada et al., *Nucleic Acids Res.* 20:2111-2118 [1992]).

The SNP-containing nucleic acid molecules can also be expressed by expression vectors that are operative in yeast. Examples of vectors for expression in yeast (e.g., *S. cerevisiae*) include pYepSec1 (Baldari, et al., *EMBO J.* 6:229-234 [1987]), pMFa (Kurjan et al., *Cell* 30:933-943 [1982]), pJRY88 (Schultz et al., *Gene* 54:113-123 [1987]), and pYES2 (Invitrogen Corporation, San Diego, Calif.).

The SNP-containing nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell. Biol.* 3:2156-2165 [1983]) and the pVL series (Lucklow et al., *Virology* 170:31-39 [1989]).

In certain embodiments of the invention, the SNP-containing nucleic acid molecules described herein are expressed in mammalian cells using mammalian expression vectors. Examples of mammalian expression vectors include pCDM8 (B. Seed, *Nature* 329:840 [1987]) and pMT2PC (Kaufman et al., *EMBO J.* 6:187-195 [1987]).

The invention also encompasses vectors in which the SNP-containing nucleic acid molecules described herein are cloned into the vector in reverse orientation, but operably linked to a regulatory sequence that permits transcription of antisense RNA. Thus, an antisense transcript can be produced to the SNP-containing nucleic acid sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include, for example, prokaryotic cells, lower eukaryotic cells such as yeast, other eukaryotic cells such as insect cells, and higher eukaryotic cells such as mammalian cells.

The recombinant host cells can be prepared by introducing the vector constructs described herein into the cells by techniques readily available to persons of ordinary skill in the art. These include, but are not limited to, calcium phosphate transfection, DEAE-dextran-mediated transfection, cationic lipid-mediated transfection, electroporation, transduction, infection, lipofection, and other techniques such as those described in Sambrook and Russell, *Molecular Cloning: A Laboratory Manual*, Cold Spring Harbor Laboratory Press, Cold Spring Harbor, N.Y. (2000).

Host cells can contain more than one vector. Thus, different SNP-containing nucleotide sequences can be introduced in different vectors into the same cell. Similarly, the SNP-containing nucleic acid molecules can be introduced either alone or with other nucleic acid molecules that are not related to the SNP-containing nucleic acid molecules, such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication can occur in host cells that provide functions that complement the defects.

Vectors generally include selectable markers that enable the selection of the subpopulation of cells that contain the recombinant vector constructs. The marker can be inserted in the same vector that contains the SNP-containing nucleic acid molecules described herein or may be in a separate vector. Markers include, for example, tetracycline or ampicillin-resistance genes for prokaryotic host cells, and dihydrofolate reductase or neomycin resistance genes for eukaryotic host cells. However, any marker that provides selection for a phenotypic trait can be effective.

While the mature variant proteins can be produced in bacteria, yeast, mammalian cells, and other cells under the control of the appropriate regulatory sequences, cell-free transcription and translation systems can also be used to produce these variant proteins using RNA derived from the DNA constructs described herein.

Where secretion of the variant protein is desired, which is difficult to achieve with multi-transmembrane domain containing proteins such as G-protein-coupled receptors (GPCRs), appropriate secretion signals can be incorporated into the vector. The signal sequence can be endogenous to the peptides or heterologous to these peptides.

Where the variant protein is not secreted into the medium, the protein can be isolated from the host cell by standard disruption procedures, including freeze/thaw, sonication, mechanical disruption, use of lysing agents, and the like. The variant protein can then be recovered and purified by well-known purification methods including, for example, ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that, depending upon the host cell in which recombinant production of the variant proteins described herein occurs, they can have various glycosylation patterns, or may be non-glycosylated, as when produced in bacteria. In addition, the variant proteins may include an initial modified methionine in some cases as a result of a host-mediated process.

For further information regarding vectors and host cells, see *Current Protocols in Molecular Biology*, John Wiley & Sons, New York.

Uses of Vectors and Host Cells, and Transgenic Animals

Recombinant host cells that express the variant proteins described herein have a variety of uses. For example, the cells are useful for producing a variant protein that can be further purified into a preparation of desired amounts of the variant protein or fragments thereof. Thus, host cells containing expression vectors are useful for variant protein production.

Host cells are also useful for conducting cell-based assays involving the variant protein or variant protein fragments, such as those described above as well as other formats known in the art. Thus, a recombinant host cell expressing a variant protein is useful for assaying compounds that stimulate or inhibit variant protein function. Such an ability of a compound to modulate variant protein function may not be apparent from assays of the compound on the native/wild-type protein, or from cell-free assays of the compound. Recombinant host cells are also useful for assaying functional alterations in the variant proteins as compared with a known function.

Genetically-engineered host cells can be further used to produce non-human transgenic animals. A transgenic animal is preferably a non-human mammal, for example, a rodent, such as a rat or mouse, in which one or more of the cells of the animal include a transgene. A transgene is exogenous DNA containing a SNP of the present invention which is integrated into the genome of a cell from which a transgenic animal develops and which remains in the genome of the mature animal in one or more of its cell types or tissues. Such animals are useful for studying the function of a variant protein in vivo, and identifying and evaluating modulators of variant protein activity. Other examples of transgenic animals include, but are not limited to, non-human primates, sheep, dogs, cows, goats, chickens, and amphibians. Transgenic non-human mammals such as cows and goats can be used to produce variant proteins which can be secreted in the animal's milk and then recovered.

A transgenic animal can be produced by introducing a SNP-containing nucleic acid molecule into the male pronuclei of a fertilized oocyte, e.g., by microinjection or retroviral infection, and allowing the oocyte to develop in a pseudopregnant female foster animal. Any nucleic acid molecules that contain one or more SNPs of the present invention can potentially be introduced as a transgene into the genome of a non-human animal.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the variant protein in particular cells or tissues.

Methods for generating transgenic animals via embryo manipulation and microinjection, particularly animals such as mice, have become conventional in the art and are described in, for example, U.S. Pat. Nos. 4,736,866 and 4,870,009, both by Leder et al., U.S. Pat. No. 4,873,191 by Wagner et al., and in B. Hogan, *Manipulating the Mouse Embryo*, Cold Spring Harbor Laboratory Press, Cold Spring Harbor, N.Y. (1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes a non-human animal in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1 (Lakso et al. *PNAS* 89:6232-6236 [1992]). Another example of a recombinase system is the FLP recombinase system of *S. cerevisiae* (O'Gorman et al., *Science* 251:1351-1355 [1991]). If a cre/loxP recombinase system is used to regulate expression of the transgene, animals containing transgenes encoding both the Cre recombinase and a selected protein are generally needed. Such animals can be provided through the construction of "double" transgenic animals, e.g., by mating two transgenic animals, one containing a transgene encoding a selected variant protein and the other containing a transgene encoding a recombinase.

Clones of the non-human transgenic animals described herein can also be produced according to the methods described in, for example, I. Wilmut et al., *Nature* 385:810-813 (1997) and PCT International Publication Nos. WO 97/07668 and WO 97/07669. In brief, a cell (e.g., a somatic cell) from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell (e.g., a somatic cell) is isolated.

Transgenic animals containing recombinant cells that express the variant proteins described herein are useful for conducting the assays described herein in an in vivo context. Accordingly, the various physiological factors that are present in vivo and that could influence ligand or substrate binding, variant protein activation, signal transduction, or other processes or interactions, may not be evident from in vitro cell-free or cell-based assays. Thus, non-human transgenic animals of the present invention may be used to assay in vivo variant protein function as well as the activities of a therapeutic agent or compound that modulates variant protein function/activity or expression. Such animals are also suitable for assessing the effects of null mutations (i.e., mutations that substantially or completely eliminate one or more variant protein functions).

For further information regarding transgenic animals, see Houdebine, "Antibody manufacture in transgenic animals and comparisons with other systems," *Curr. Opin. Biotechnol.* 13(6):625-9 (December 2002); Petters et al., "Transgenic animals as models for human disease," *Transgenic Res.* 9(4-5):347-51 (2000); discussion 345-6; Wolf et al., "Use of transgenic animals in understanding molecular mechanisms of toxicity," *J. Pharm. Pharmacol.* 50(6):567-74 (June 1998); Echelard, "Recombinant protein production in transgenic animals," *Curr. Opin. Biotechnol.* 7(5):536-40 (October 1996); Houdebine, "Transgenic animal bioreactors," *Transgenic Res.* 9(4-5):305-20 (2000); Pirity et al., "Embryonic stem cells, creating transgenic animals," *Methods Cell Biol.* 57:279-93 (1998); and Robl et al., "Artificial chromosome vectors and expression of complex proteins in transgenic animals," *Theriogenology* 59(1):107-13 (Jan. 1, 2003).

EXAMPLES

Statistical Analysis of SNPs Associated with Neurodegenerative Disease

The following examples are offered to illustrate, but not limit, the claimed invention.

Example One

Statistical Analysis of SNPs Associated with Neurodegenerative Disease

Overview

Several SNPs were found to be significantly associated with neurodegenerative diseases, such as AD and PD. For example, one SNP was identified that is significantly associated with disease risk in multiple AD ($P<10^{-5}$) and multiple PD ($P<0.05$) sample sets. This SNP, which is located within a putative transcription factor binding site in the NEDD9 gene, has the publicly known reference identification number rs760678 (this SNP is also interchangeably referred to herein as hCV10039123, which is an internal identification number). In determining a potential mechanism for the observed association, it was found that expression of NEDD9 and APOE show a strong inverse correlation in the hippocampus of AD cases. These data indicate that NEDD9 is a novel susceptibility gene for AD and PD. Thus, SNPs in NEDD9 may be used, either alone or in combination with other biomarkers (e.g., APOE), as a predictor of risk for neurodegenerative disease, particularly for AD and PD.

Materials and Methods

Clinical Samples

All samples used in the studies described in this Example were collected or acquired with informed consent from the participating individuals and approvals from the participating institutions. For late-onset Alzheimer's disease (LOAD), a total of 5 case-control sample sets were used that were collected by Cardiff University and King's College London (UK1, UK2), University of Cambridge (UK3), Washington University in St. Louis (WU), and the University of California, San Diego (SD). Cases had a minimum age at disease onset (AAO) of 60 years and a diagnosis of probable or definite AD (NINCDS-ADRDA), while controls were ascertained at the age of 65 years or older and screened for evidence of dementia (MMSE≧28, Clinical Dementia Rating=0, or full neurological exam). All individuals were of Caucasian descent. All sample sets show the expected APOE ϵ4 distribution in cases and controls. Detailed information can be found in the following studies: (Li et al., *Proc Natl Acad Sci USA* 101, 15688 (2004); Li et al., *Hum Mutat* 25, 270 (2005); Li et al., *Hum Mol Genet* 15, 2560 (2006); Grupe et al., *Am J Hum Genet* 78, 78 (2006)).

For PD, one case-control series (Celera) was constructed from PD cases and matched population/convenience controls that are available through the NINDS Human Genetics Resources at the Coriell Institute. Cases had a minimum AAO of 50 years and met UK Brain Bank criteria for idiopathic PD (Hughes et al., *J Neurol Neurosurg Psychiatry* 55, 181 (1992)). Controls were neurologically normal. All individuals were of Caucasian descent. Detailed information can be found in the following studies (Li et al., *Am J Hum Genet* 78, 1090 (2006); Li et al., *Hum Mutat* 27, 1017 (2006)). A second case-control series, consisting of 358 cases (218 males and 140 females) and 486 controls (178 males, 301 females, and 7 unknown genders), was obtained from the Washington University at St. Louis (WU). Cases met diagnostic criteria of the British Brain Bank for idiopathic PD as implemented by Racette et al. (Racette et al., *Am J Med Genet* 88, 539 (1999)). Cases had an AAO ranging from 40 to 85 years (mean [±SD] 60.56±10.48 years) and were sampled at the age of 41 to 90 years (mean [±SD] 66.96±10.4 years) (1 sample without age data). Controls were sampled at the age of 41 to 105 years (mean [±SD] 72.36±11.49 years) (36 samples without age data).

SNP Genotyping

A total of 17,343 SNPs were tested for association with LOAD in a previous genome-wide association study, and a total of 4,692 SNPs were tested in the present study. The majority of these SNPs are putative functional variants. Genotyping of SNPs was performed by allele-specific real-time PCR using primers designed and validated in-house (Germer et al., *Genome Res* 10, 258 (2000)). Genotyping of SNP rs760678 in 80 HapMap CEPH samples gave results that are 100% concordant with the HapMap genotypes. Significant markers from a pooled DNA study were followed up by individual genotyping of the UK1 and WU sample sets. Genotyping of SNP rs760678 in the UK3 and WU Parkinson's disease case-control samples was done on the Sequenom (San Diego, Calif.) platform.

Statistical Methods

Exact tests were used to compare genotype frequencies with those expected under Hardy-Weinberg equilibrium as described by Weir ("Genetic Data Analysis II", Sinauer Associates, Sunderland M A 1996, $2^{nd}$ Edition). A chi-square test P-value <0.01 was used to exclude assays with inconsistent allele frequencies across triplicates of identical DNA sample pools. Initial testing of SNPs for association with AD in pooled and individually genotyped sample sets was performed using Pearson's chi-square test. Logistic regression models were used to estimate odds ratios and a Wald test was used to assess statistical significance of replicated SNPs. A multiplicative risk model was assumed to assess allelic odds ratios. Sample set was entered as a covariate in models containing subjects from more than one study. Tests for heterogeneity of allele or genotype frequencies across sample sets were performed using Pearson's chi-square test. Gene-gene interaction was assessed by testing for significance of the cross-product term of the two SNPs in a logistic regression model. Stepwise regression models were performed using a P-value criterion of 0.05 or less for including and retaining variables in the model. Differences in median age of onset by genotype subgroups were evaluated using the Wilcoxon rank sum test.

Expression Analysis

Microarray expression data (Affymetrix HG133 A and B chips) on 79 individuals (Huntington's disease (HD) cases and age-matched controls) was accessed. Correlations were calculated between four probes mapping to NEDD9 and a total of 32 probes mapping to the following genes involved in the γ-secretase and β-amyloid degrading pathways: APH1A, APH1B, PEN2, NCSTN, PSEN1, PSEN2, APP, BACE1, BACE2, ECE1, ECE2, NEP, IDE, and APOE. Three brain regions were analyzed: cerebellum (70 individuals), cortex (67 individuals), and caudate nucleus (controls only; 33 individuals).

For more details of the samples and procedures used to generate the expression data (including quality control) see the following references: Hodges et al., *Hum Mol Genet* 15, 965 (2006) and Jones et al., *BMC Bioinformatics* 7, 211 (2006). Expression correlations were also investigated in a sample of 22 AD hippocampi from cases of varying severity (Blalock et al., *Proc Natl Acad Sci USA* 101, 2173 (2004)). For these, data were only available on the A chip.

Pearson correlations between the NEDD9 probes and those from other genes, together with their p-values, were generated. "Gene-wise" p-values, correcting for multiple probe-probe comparisons within genes, were obtained by randomly permuting the expression values for all probes within a gene simultaneously among individuals (performing a separate permutation for each gene), repeating the correlation analysis, and comparing the resulting correlations to those in the actual data. A similar procedure was used to obtain "experiment-wise" p-values, correcting not only for multiple probe comparisons within genes, but also for multiple gene-gene comparisons.

NEDD9 Immunohistochemistry

After death, the consent of the next-of-kin was obtained for brain removal, following approved Local Ethics Committee procedures in accordance with state law. Brain tissues from clinically and neuropathologically characterized cases of AD, PD, and normal aged controls were obtained from the Washington University Alzheimer's Disease Research Center (WUADRC). Cases with AD or PD displayed the characteristic pathological features of these diseases, as previously described (*Neurobiol Aging* 18, S1 (1997); Braak et al., *Acta Neuropathol* (*Berl*) 112, 389 (2006); Braak et al., *Cell Tissue Res* 318, 121 (2004); Mirra et al., *Neurology* 41, 479 (1991)).

Brain tissue was preserved in buffered 10% formal saline for up to 3 weeks. Antigen retrieval was performed by microwaving tissue sections in a solution of 0.1 M citrate buffer, pH 6.0 at 100° C. for 10 minutes. Immunohistochemistry was undertaken on 5 μm thick sections prepared from formalin-fixed, paraffin wax-embedded tissue blocks using anti-NEDD9 antibodies (1:5000 mouse monoclonal, Abnova Corporation, Taipei City, Taiwan) and the avidin-biotin complex detection system (Vector Laboratories, Burlingham, Calif.) and the chromogen 3,3'-diaminobenzidine (DAB), and sections were counterstained with hematoxylin.

Results and Discussion

Strong genetic contributions to LOAD have long been documented (Gatz et al., *Arch Gen Psychiatry* 63, 168 (2006)), but the apolipoprotein E (APOE) ϵ4 genotype is so far the only undisputed genetic risk factor (Strittmatter et al., *Proc Natl Acad Sci USA* 90, 1977 (1993)). However, many LOAD patients do not carry an APOE ϵ4 allele. Extensive searches over the past decade have suggested numerous other putative associated genes, but none has unequivocal statistical support.

In an attempt to search for LOAD risk factors, a large-scale, genome-wide, gene-centric association study of 17,343 SNPs, located in 11,221 unique genes in multiple case-control series from the United Kingdom (UK) and the United States (US) was carried out. To increase the number of interrogated genes and variants, an additional set of 4,692 putative functional SNPs in 3,664 unique genes were also tested. 80% of these markers are either missense variants or occur within predicted transcription factor binding sites, and these markers are distributed across all autosomes and cover a wide range of allele frequencies. To identify markers that show the strongest and most consistent association, a multi-stage approach was used to test up to 5 LOAD case-control sample sets.

Specifically, in the hypothesis generation phase, allele frequencies of 4,930 SNPs in DNA pools from the UK1 sample set were determined (DNA pools were constructed with 380 cases and 396 controls, respectively). After excluding markers of low frequency (minor allele frequency of <2% in both cases and controls) and inconsistent allele frequencies among the triplicate pools of identical composition, 4,692 SNPs were tested for association with disease risk. 304 SNPs had an allelic P<0.05 and odds ratio (OR)>1.25 or <0.8. 285 of these SNPs were then assayed in pooled cases and controls in the Washington University (WU) sample set (pools were constructed with 376 cases and 344 controls, respectively). Association testing revealed that 19 of the 285 SNPs had an allelic P<0.05 (1-sided, based on the OR direction in the UK1 pooled samples). To eliminate false positives derived from fluctuations in frequency estimates from DNA pools, 19 of these SNPs were genotyped in individual samples of the UK1 and WU sample sets. To increase the power of the analysis, the association of these markers with disease risk was tested in the combined sample sets. This identified 13 SNPs that had allelic P<0.05.

To validate these 13 lead SNPs, each of these SNPs was individually genotyped in two independent case-control sample sets (the UK2 and SD sample sets). Association tests were performed in the combined UK2 and SD sample sets.

A SNP that met the replication criteria (P<0.05, 1-sided, based on the OR direction in the UK1 and WU sample sets combined) was rs760678 in NEDD9 on chromosome 6 (P=0.0015 [UK1+WU], P=0.0051 [UK2+SD]) (Tables 3 and 4). The comparison of the allelic and the genotypic models of rs760678 indicates a recessive mode of inheritance for the major allele in each of the 4 sample sets (recessive genotypic $P_{meta}=9.13\times10^{-7}$ and $OR_{meta}=1.50$ [95% CI: 1.28, 1.77] vs allelic $P_{meta}=2.36\times10^{-5}$ and $OR_{meta}=1.27$ [95% CI: 1.14, 1.43]). This marker was then tested in a fifth LOAD case-control sample set (UK3), which revealed that both the allelic OR and genotypic OR are in the same direction as in the other four sample sets (Table 3). The frequency of the risk allele, 'G' (based on the sequence orientation of SEQ ID NOS:2 and 24), is consistent across all 5 sample sets as demonstrated by a test for heterogeneity within cases (P=0.86) and within controls (P=0.12), but the UK3 control genotype frequency is significantly different from other sample sets (P=0.033, heterogeneity test of GG genotype within cases of the 5 sample sets). In the combined analysis of the 5 sample sets, rs760678 remained highly significantly associated with risk of LOAD (Table 3). The relatively common risk allele homozygote (0.396 in cases vs. 0.323 in controls) has a modest effect size, as expected from the common disease-common variant hypothesis.

To further identify SNPs that are associated with AD, additional SNPs in linkage disequilibrium (LD) with SNP rs760678 were tested. These candidate SNPs were selected based on their LD profile in the HapMap dataset, and they were located on each side of rs760678 over a 500 kbp region. 7 SNPs (rs6940151, rs2064112, rs2179179, rs12154199, rs2950, rs6905278, and rs3823017), which are located over a distance of 20.7 kbp, share $r^2$>0.1 with rs760678. Furthermore, 3 SNPs (rs2950, rs2064112, and rs6940151) were significantly associated with LOAD at the allelic level in the UK1 sample set (Table 5). All 3 were significant under a recessive genotypic model, and the $r^2$ of markers rs2950, rs2064112, and rs6940151 with marker rs760678 among the UK1 controls is 0.309, 0.433, and 0.932, respectively (Table 5). The $r^2$ of markers rs2179179, rs12154199, rs6905278, and rs3823017 with marker rs760678 is 0.139, 0.166, 0.146, and 0.131, respectively. Furthermore, in the UK2 sample set, rs6940151 was significant under the allelic model (P=0.038) and showed a trend for significance assuming a recessive model (P=0.10).

Expression of NEDD9 in brains of LOAD patients and normal controls was confirmed by in situ hybridization. As a member of the Cas family of adhesion docking proteins, NEDD9 is involved in the formation of neurite-like membrane extensions and neurite outgrowth (Sasaki et al., *Stroke* 36, 2457 (2005), Bargon et al., *Biochim Biophys Acta* 1746, 143 (2005)). NEDD9 is up-regulated after transient global ischemia in rats, while a splice variant (Cas-L) that lacks the first two exons is not (Sasaki et al., *Stroke* 36, 2457 (2005)). Expression of NEDD9 is also up-regulated in human stem cells exposed to hypoxia (Martin-Rendon et al., *Stem Cells* (2006)). rs760678 is located in a region containing clusters of TATA- and GATA-binding motifs (FIG. 1). GATA-binding proteins play an important role in regulating neuron-specific gene expression, and rs760678 is within the region that surrounds the core consensus sequence to which TF binding extends (Lawson et al., *Mol Cell Biol* 16, 3596 (1996)). Thus, rs760678 may play a role in the differential regulation of NEDD9 and the Cas-L transcript. rs760678 may affect the number of neuronal cells/synapses in the brain such that risk genotype carriers have a significantly smaller reservoir of cells/synapses to withstand the gradual loss of neurons caused by other factors. Risk genotype carriers may be less capable of neuronal regeneration under stressful conditions. Such scenarios indicate that SNPs in NEDD9, particularly rs760678, may influence susceptibility to other neurodegenerative diseases besides LOAD.

To test this hypothesis, the role of NEDD9, particularly rs760678, in risk for late-onset PD was examined. rs760678 was genotyped in a late-onset PD case-control series (Celera) (Li et al., *Hum Mutat* 27, 1017 (2006); Li et al., *Am J Hum Genet* 78, 1090 (2006)) and results similar to those found in LOAD were obtained; rs760678 showed a significant association with PD under the allelic and recessive models, and the risk allele and risk genotype frequencies in cases and controls were comparable to those observed in the LOAD sample sets (Table 3). To further validate the association in PD, rs760678 was tested in a second, independently collected PD case-control series (WU). A significant association of rs760678 with PD was observed at the allelic level, and the risk genotype frequencies are in the same direction as in the other PD sample set (Table 3). Meta-analysis of the two PD case-control sample sets showed that rs760678 is significant at both the allelic and recessive level and the ORs are comparable to the LOAD study.

A potential mechanism for the observed genetic association was then explored. Gene expression correlations, using Affymetrix (Santa Clara, Calif.) microarray data, were calculated between probes in NEDD9 and probes from the following genes that are relevant to AD: APH1A, APH1B, PEN2, NCSTN, PSEN1, PSEN2, APP, BACE1, BACE2, ECE1, ECE2, NEP, IDE, and APOE. 4 datasets were analyzed: data from 3 brain regions (cortex, cerebellum, caudate nucleus) on 79 Huntington's disease cases and matched controls (Hodges et al., *Hum Mol Genet* 15, 965 (2006)), and data from a sample of 22 AD cases of varying severity (Blalock et al., *Proc Natl Acad Sci USA* 101, 2173 (2004)). The correlation between NEDD9 and APOE was the strongest observed across all genes examined (r=−0.76) and was specific to the Blalock LOAD cases (data not shown). Other AD pathway genes showed consistent significant correlations with NEDD9 across all four datasets, most notably PSEN1, BACE1, BACE2 and ECE1. These results provide independent evidence linking NEDD9 to biological pathways connected to AD pathology.

Taken together, the above evidence provides strong statistical support that NEDD9 modulates LOAD risk and also indicates that NEDD9 is involved in PD. Genetic studies indicate the existence of risk factors common to AD and PD (Li et al., *Am J Hum Genet* 70, 985 (2002)); and cellular and molecular studies have revealed pathways shared by both (Selkoe, *Nat Cell Biol* 6, 1054 (2004)). The role of NEDD9 in neuronal growth and differentiation makes it a strong candidate for both diseases; similar to NEDD9, APOE ϵ4 and APOE ϵ3 also have differential effects on neurite outgrowth (Nathan et al., *Science* 264, 850 (1994)).

Example Two

Additional LD SNPs Associated with Neurodegenerative Disease

Another investigation was conducted to identify SNPs in linkage disequilibrium (LD) with certain "interrogated SNPs" which have been found to be associated with neurodegenerative disease as shown in Tables 3-5. These interrogated SNPs were SNP rs760678, as well as SNPs rs2950, rs6940151, and rs2064112 shown in Table 5. The methodology is described earlier in the instant application. To summarize briefly, the power threshold (T) was set at an appropriate level, such as 51% or 70%, for detecting disease association using LD markers. This power threshold is based on equation (31) above, which incorporates allele frequency data from previous disease association studies, the predicted error rate for not detecting truly disease-associated markers, and a significance level of 0.05. Using this power calculation and the sample size (1652 cases and 1869 controls), for each interrogated SNP a threshold level of LD, or $r^2$ value, was derived ($r_T^2$, equations (32) and (33) above). The threshold value $r_T^2$ is the minimum value of linkage disequilibrium between the interrogated SNP and its LD SNPs possible such that the non-interrogated SNP still retains a power greater than or equal to T for detecting disease-association. The threshold value $r_T^2$ can be set such that one of ordinary skill in the art would consider that any two SNPs meeting such a $r_T^2$ value would be in LD with each other.

Based on the above methodology, LD SNPs were found for the interrogated SNPs (the interrogated SNPs were rs760678, rs2950, rs6940151, and rs2064112). Several sample LD SNPs for the interrogated SNPs are listed in Table 6. Also shown are the public SNP IDs (rs numbers) for the interrogated and LD SNPs, when available, and the threshold $r^2$ value and the power used to determine this, and the $r^2$ value of linkage disequilibrium between the interrogated SNP and its matching LD SNP. As an example in Table 6, the interrogated, neurodegenerative disease-associated SNP rs760678 (hCV10039123) was calculated to be in LD with rs2064112 (hCV11967348) at a $r^2$ value of 0.43933, based on a 51% power calculation, thus establishing the latter SNP as a marker associated with neurodegenerative diseases as well. This approach of calculating LD SNPs and determining that the resulting LD SNPs are also associated with risk of developing neurodegenerative diseases is validated by the fact that three of the calculated LD SNPs in Table 6, rs2064112, rs2950, rs6940151, were also assayed and determined to be associated with AD (Table 5).

Using another exemplary methodology to calculate LD, based upon the requencing genotypes, additional sample LD SNPs were identified that have 80% power at a significance level of 0.05 to replicate the association of SNP rs760678 with neurodegenerative diseases, particularly AD. The LD threshold was set at $r^2$>0.447, which was based on the meta-analysis result in Table 3 ("All AD" sample set). However, other threshold $r_T^2$ values could be implemented since the threshold $r_T^2$ value can be set such that one of ordinary skill in the art would consider that any two SNPs meeting such a $r_T^2$ value would be in LD with each other. This analysis demonstrated that 6 additional SNPs are in LD with rs760678, which are shown in the section of Table 6 labeled "Additional LD SNPs (based on resequencing genotypes)". Therefore, these 6 SNPs are also associated with one's altered risk of developing neurodegenerative diseases, particularly AD. Of these 6 SNPs, the LD values for the following 4 SNPs were calculated based on sequencing data from 200 DNA samples: hCV2476872, hCV11967343, hCV27968956, and hCV29058750. The LD values for the following two SNPs were calculated based on sequencing data from 100 DNA samples: hCV2476868 and hCV30529212.

Genetic association of the SNPs with neurodegenerative disease, particularly AD and PD, observed in these studies specifically indicates that the genes and regions of the chromosome in which these SNPs reside are potential contributors to disease susceptibility. Novel medicines including, but not limited to, small molecules, proteins, protein fragments or peptides, antibodies, or nucleic acids, may be designed to target NEDD9 for the treatment of neurodegenerative disease and other neurological pathologies. Furthermore, a genotyping kit for the detection of various SNPs including those in NEDD9 may be designed for the diagnosis of neurodegenerative disease and treatment response in the management of neurodegenerative disease and other neurological pathologies.

All publications and patents cited in this specification are herein incorporated by reference in their entirety. Various modifications and variations of the described compositions, methods and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments. Indeed, various modifications of the above-described modes for carrying out the invention that are obvious to those skilled in the field of molecular biology, genetics and related fields are intended to be within the scope of the following claims.

TABLE 1

```
Gene Number:                1
Celera Gene:                hCG36758 - 83000098845313
Gene Symbol:                NEDD9
Protein Name:               neural precursor cell expressed, developmentally down-regulated 9
Celera Genomic Axis:        GA_x5YUV32VT9V (10797246 . . . 11016295)
Chromosome:                 6
OMIM NUMBER:                602265
OMIM Information:
Genomic Sequence (SEQ ID NO:
1):
SNP Information
Context (SEQ ID NO: 2):
CCAAAATTTTTTACAGTGAGTATGTATTATCTTTTGTCATCTGAAAAATAACACAAATAAATAAGTTAAAATAGAATTAACTGAATTTGTACA
AATCGGG
S
AAGATAAGGGTGCCCCTGTTTTCTCTATTCATGCCACCGCTACCACTGTTTAGACTATTGGTCATAATTTTTTTCTCACCTGCAAATATCTCC
TTGCCTG

Celera SNP ID:              hCV10039123
Public SNP ID:              rs760678
SNP in Genomic Sequence:    SEQ ID NO: 1
SNP Position Genomic:       161133
SNP Source:                 dbSNP; HapMap; ABI_Val; HGBASE
Population (Allele, Count): caucasian (G, 56|C, 64)
SNP Type:                   TRANSCRIPTION FACTOR BINDING SITE; INTRON
Context (SEQ ID NO: 3):
ATACTCTTTTTCTACTTGAGGTAGTTAGATATGCCTCAACCTCTATGAAAACCTACTTTTCTCATGTTTTATACAGGTGTGGCCAAAGTGGAG
CAGCTTA
Y
GTCTGTTGTGCAACTGGTGCATCCTGCCCCACCAGATCATATTTCACCAAGTTTTTCTCCTCTGATGAGCTATGCTAAAAATGATCAATTGGA
CACATGT

Celera SNP ID:              hCV11967348
Public SNP ID:              rs2064112
SNP in Genomic Sequence:    SEQ ID NO: 1
SNP Position Genomic:       166247
```

TABLE 1-continued

```
SNP Source:                 dbSNP; Celera; HapMap; ABI_Val
Population (Allele, Count): caucasian (T, 77|C, 43)
SNP Type:                   INTRON
Context (SEQ ID NO: 4):
AAAATAATCCTTGGCCTATCTAGCTTAGAGAGGCTCTTAGTTTGAAAGAGACAATGGATGGTGTGCAAATTGAAGGTCACATTATCCTTCTAG
GCTGAGA
Y
GTTCATAGTTCACAGTTCTTCAGGAGCTGGCCTGGGCAATACAGTTTGATCTAATACACAATAAACTAATTGACAATTGGCTGTTAATGGCCA
AAGAGTG

Celera SNP ID:              hCV11967349
Public SNP ID:              rs2950
SNP in Genomic Sequence:    SEQ ID NO: 1
SNP Position Genomic:       176744
SNP Source:                 dbSNP; HapMap; ABI_Val; HGBASE
Population (Allele, Count): caucasian (T, 85|C, 35)
SNP Type:                   INTRON
Context (SEQ ID NO: 5):
GGTGGTGTTGTCTTTTCTTATTCCACACAACAACAATGAACCATTTCTTGATCGGATTGTGACATGCAATGAAAAGTGGATTTTATACAACAA
CGAGTGA
Y
GACCAGGTGAGTGGTTGGACCGAGAAGAAGCTCCAAAGCACTTTCCAAAGCCAAACTTGCACCAAAATATGGTCATGGTCACTGTTTGGTAGT
CTGCTGC

Celera SNP ID:              hCV29058753
Public SNP ID:              rs6940151
SNP in Genomic Sequence:    SEQ ID NO: 1
SNP Position Genomic:       161956
SNP Source:                 dbSNP; HapMap
Population (Allele, Count): caucasian (C, 57|T, 63)
SNP Type:                   INTRON; REPEATS
Context (SEQ ID NO: 6):
AAAATGCTTTCCAAGTGTTCATTGAATCCCAAAGCACAGACCTTTATGCTACAGGAATAAACAAACTTATTTCTCATTGGCAAAAATGTGTTG
ATAGTAA
W
TGTTCCTATTTGAATTAATAAAGATGTGTTTGAGTCTAGTTATAAGGATCTAAAATTCACAGTCCCAAACCACAATTCCTTTTGCACCAATCT
AATATAT

Celera SNP ID:              hCV2476868
Public SNP ID:              rs34350240
SNP in Genomic Sequence:    SEQ ID NO: 1
SNP Position Genomic:       162463
Related Interrogated SNP:   hCV10039123 (Power = .8)
SNP Source:                 Celera
Population (Allele, Count): no_pop (A, -|T, -)
SNP Type:                   INTRON; REPEATS
Context (SEQ ID NO: 7):
TACATGCCTTCTCTACAAAACCATCCTAAGCAGCTCTTGAATTAGATGCTCCTTTGCACTCTGTGCTTAACTTGTTTACAGCACACGTCGTGT
TCTATTT
R
AGTGACCTCCCAACTAACCTGTGAGATTCCAGAAGCTGGGTGAGTGTGCTCTGGAACTGATTCTTCTGCTAGATGCTGAGAACATGTGGGCAA
TGGCACG

Celera SNP ID:              hCV2476872
Public SNP ID:              rs2223292
SNP in Genomic Sequence:    SEQ ID NO: 1
SNP Position Genomic:       159376
Related Interrogated SNP:   hCV10039123 (Power = .9)
SNP Source:                 Celera; HGBASE; dbSNP
Population (Allele, Count): no_pop (A, -|G, -)
SNP Type:                   INTRON
Context (SEQ ID NO: 8):
AGGTAGATCTGTGCTTGATGATTGAATGGATGAGTTTCAGTGAACTGTGAATGATGGGGAGCTTTTCAACAAAGCCACACTCCATGTTTTCTC
TTCAGCA
R
AATAAATGCTGCATAGAAGCGGTTAATAGTCCCCCTTATGTCAGCTCAGCACATAGATATATGAGGAGTCCCACGGTTTCCCATAAGCCAAAT
AAGACAA

Celera SNP ID:              hCV11967343
Public SNP ID:              rs1883237
SNP in Genomic Sequence:    SEQ ID NO: 1
SNP Position Genomic:       159617
Related Interrogated SNP:   hCV10039123 (Power = .9)
SNP Source:                 dbSNP
Population (Allele, Count): no_pop (A, -|G, -)
SNP Type:                   INTRON
Context (SEQ ID NO: 9):
AATGAAAGCCTGGGTCAATTAGTCAGTTTCTTTCCCAATATCTGCCCTAACATTGTCTTCTAAGTTTTTGGAAATGAATACGCTTTATTATTC
ACCTCAG
```

TABLE 1-continued

Y
TGGATTTATTGTGCCTCACAGGTATTGACTCCTCTTGCTCTTCCTCCTCTCGCTATGGAAAGACTGAGCAGAGGAAGTGCTCGGACAGGCATG
CCCTCCC

Celera SNP ID: hCV27968956
Public SNP ID: rs4713432
SNP in Genomic Sequence: SEQ ID NO: 1
SNP Position Genomic: 160163
Related Interrogated SNP: hCV10039123 (Power = .9)
SNP Source: HGBASE; dbSNP
Population (Allele, Count): no_pop (C, -|T, -)
SNP Type: INTRON
Context (SEQ ID NO: 10):
AATATTAGGTTGGAGCAAACGTTAATTGCATTTTTGCATTGTTGGAATTTGCTGTTTGATATTGGAATACATTCTTAAATAAATGTGGTTATG
TTATACA
W
CATTTTAATGGGCATTTCTCGCTTTATGTTTTTTTGCTAATGACTTACTACTTGCTGTTTATTTTATGTTTATTTTAGACTATGGAAATGATG
TTAAACA Celera SNP ID: hCV29058750
Public SNP ID: rs2003664
SNP in Genomic Sequence: SEQ ID NO: 1
SNP Position Genomic: 161379
Related Interrogated SNP: hCV 10039123 (Power = .8)
SNP Source: dbSNP
Population (Allele, Count): no_pop (A, -|T, -)
SNP Type: INTRON; REPEATS
Context (SEQ ID NO: 11):
GACATGCCCCAGGACTCCCTTTTCCCTAGTCACCTCCTCCTGCCCTCACCTCCCTCAGAGTCAGCCTTTCACAGTCATCTCTTATGACACTTC
TCATAGG
S
CACCTTCCTTGGCATCGCCAAGTGGAGTTAACGGTTTTCTTTCTGCCTTGGTCATGGCTCTACATTTACTATACTATAGTGATATAATTATAG
CCATGTG Celera SNP ID: hCV30529212
Public SNP ID: rs6457330
SNP in Genomic Sequence: SEQ ID NO: 1
SNP Position Genomic: 162854
Related Interrogated SNP: hCV10039123 (Power = .9)
SNP Source: dbSNP
Population (Allele, Count): no_pop (C, -|G, -)
SNP Type: INTRON

TABLE 2

| Marker | Alleles | Primer 1 (Allele-Specific Primer) | Primer 2 (Allele-Specific Primer) | Common Primer |
|---|---|---|---|---|
| hCV10039123 (rs760678) | C/G | GGGGCACCCTTATCTTG (SEQ ID NO: 12) | AGGGGCACCCTTATCTTC (SEQ ID NO: 13) | CCAAAATTTTTTACAGTGAGTATGT (SEQ ID NO: 14) |
| hCV11967348 (rs2064112) | C/T | CCAGTTGCACAACAGACG (SEQ ID NO: 15) | CCAGTTGCACAACAGACA (SEQ ID NO: 16) | CTTTCCACTGCTCTCTCCCTCATTA (SEQ ID NO: 17) |
| hCV11967349 (rs2950) | C/T | ACATTATCCTTCTAGGCTGAGAC (SEQ ID NO: 18) | ACATTATCCTTCTAGGCTGAGAT (SEQ ID NO: 19) | AACAGCCAATTGTCAATTAGTTTA (SEQ ID NO: 20) |
| hCV29058753 (rs6940151) | C/T | GGATTTTATACAACAACGAGTGAC (SEQ ID NO: 21) | TGGATTTTATACAACAACGAGTGAT (SEQ ID NO: 22) | GGCAGCAGACTACCAAACAGT (SEQ ID NO: 23) |

TABLE 3

Allelic and Genotypic tests of rs760678 (hCV10039123)

| | | Allelic Test | | | | | | Genotypic Test | | | | |
|---|---|---|---|---|---|---|---|---|---|---|---|---|
| | Sample | Sample No. | | Risk Allele Freq. | | | | Risk Genotype Freq. | | | | |
| Disease | Set | Case | Control | Case | Control | P | OR [95% CI] | Case | Control | $P_{2df}$ | $P_{recessive}$. | OR [95% CI] |
| AD | All AD | 1652 | 1869 | 0.623 | 0.574 | 2.94E−05 | 1.23 [1.11, 1.35] | 0.396 | 0.323 | 2.86E−05 | 5.38E−06 | 1.38 [1.20, 1.59] |
| AD | UK1 | 345 | 350 | 0.610 | 0.545 | 0.018 | 1.29 [1.05, 1.59] | 0.401 | 0.289 | 0.0079 | 0.0021 | 1.64 [1.20, 2.26] |

TABLE 3-continued

Allelic and Genotypic tests of rs760678 (hCV10039123)

| | | Allelic Test | | | | | | Genotypic Test | | | | |
|---|---|---|---|---|---|---|---|---|---|---|---|---|
| | Sample | Sample No. | | Risk Allele Freq. | | | | Risk Genotype Freq. | | | | |
| Disease | Set | Case | Control | Case | Control | P | OR [95% CI] | Case | Control | $P_{2df}$ | $P_{recessive}$. | OR [95% CI] |
| AD | WU | 396 | 367 | 0.636 | 0.583 | 0.035 | 1.25 [1.02, 1.53] | 0.424 | 0.327 | 0.018 | 0.0057 | 1.52 [1.13, 2.04] |
| AD | UK2 | 282 | 318 | 0.615 | 0.550 | 0.022 | 1.32 [1.04, 1.67] | 0.367 | 0.299 | 0.07 | 0.08 | 1.36 [0.96, 1.92] |
| AD | SD | 235 | 322 | 0.621 | 0.575 | 0.098 | 1.24 [0.96, 1.61] | 0.379 | 0.292 | 0.092 | 0.032 | 1.48 [1.04, 2.11] |
| AD | UK3 | 401 | 523 | 0.626 | 0.601 | 0.29 | 1.11 [0.92, 1.33] | 0.397 | 0.375 | 0.51 | 0.5 | 1.10 [0.84, 1.43] |
| PD | All PD | 668 | 796 | 0.633 | 0.579 | 0.0032 | 1.26 [1.08, 1.46] | 0.395 | 0.333 | 0.013 | 0.015 | 1.31 [1.05, 1.62] |
| PD | Celera | 310 | 310 | 0.640 | 0.584 | 0.039 | 1.28 [1.01, 1.62] | 0.410 | 0.326 | 0.09 | 0.031 | 1.44 [1.03, 1.99] |
| PD | WU | 358 | 486 | 0.627 | 0.576 | 0.035 | 1.24 [1.02, 1.51] | 0.383 | 0.337 | 0.071 | 0.18 | 1.22 [0.92, 1.62] |

TABLE 4

Allelic and Genotypic tests of rs760678 (hCV10039123)

| | | Case Count and HWE Test | | | | | Control Count and HWE Test | | | | |
|---|---|---|---|---|---|---|---|---|---|---|---|
| Disease | Sample Set | CC | GC | GG | Sum | HWE P-Value | CC | GC | GG | Sum | HWE P-Value |
| AD | UK1 | 62 | 143 | 137 | 342 | 0.031 | 69 | 177 | 100 | 346 | 0.59 |
| AD | WU | 60 | 168 | 168 | 396 | 0.100 | 59 | 188 | 120 | 367 | 0.330 |
| AD | UK2 | 38 | 138 | 102 | 278 | 0.45 | 62 | 156 | 93 | 311 | 0.91 |
| AD | SD | 32 | 114 | 89 | 235 | 0.680 | 46 | 182 | 94 | 322 | 0.006 |
| AD | UK3 | 58 | 184 | 159 | 401 | 0.671 | 90 | 237 | 196 | 523 | 0.203 |
| PD | Celera | 40 | 143 | 127 | 310 | 1.000 | 49 | 160 | 101 | 310 | 0.300 |
| PD | WU | 46 | 175 | 137 | 358 | 0.430 | 90 | 232 | 164 | 486 | 0.640 |

(Genotypes indicated above for rs760678 are based on the sequence orientation of SEQ ID NOS: 2 and 24.)

TABLE 5

Association of SNPs with Alzheimer's disease (UK1 sample set).

| Marker (rs) | Risk Allele | Marker (hCV) | Genomic Position* | Distance** | $r^2$*** | D'*** | OR [95% CI] | RAF**** | Allelic P Value | Recessive Genotypic P Value***** |
|---|---|---|---|---|---|---|---|---|---|---|
| rs6940151 | T | hCV29058753 | 11,443,464 | 824 | 0.932 | 0.994 | 1.32 [1.00, 1.74] | 0.468 | 0.015 | 0.0024 |
| rs2064112 | G | hCV11967348 | 11,447,755 | 5,115 | 0.433 | 0.989 | 1.35 [1.02, 1.79] | 0.653 | 0.0023 | 0.0055 |
| rs2950 | G | hCV11967349 | 11,458,251 | 15,611 | 0.309 | 1 | 1.34 [0.99, 180] | 0.730 | 0.0036 | 0.0015 |

*based on internal "build 36" genome assembly, in bp

**distance from rs760678 in bp

***based on the UK1 control samples

****RAF: risk allele freqency in UK1 controls

*****based on the risk genotype

TABLE 6

| Interrogated SNP | Interrogated rs | LD SNP | LD SNP rs | Power | Threshold $r_T^2$ | $r^2$ |
|---|---|---|---|---|---|---|
| LD SNPs (based on HapMap genotypes) | | | | | | |
| hCV10039123 | rs760678 | hCV11967348 | rs2064112 | 0.51 | 0.224 | 0.43933 |
| hCV10039123 | rs760678 | hCV11967349 | rs2950 | 0.51 | 0.224 | 0.31473 |
| hCV10039123 | rs760678 | hCV29058753 | rs6940151 | 0.51 | 0.224 | 0.96711 |
| hCV11967348 | rs2064112 | hCV10039123 | rs760678 | 0.51 | 0.418 | 0.43933 |
| hCV11967348 | rs2064112 | hCV11967349 | rs2950 | 0.51 | 0.418 | 0.73735 |
| hCV11967348 | rs2064112 | hCV29058753 | rs6940151 | 0.51 | 0.418 | 0.45526 |
| hCV11967349 | rs2950 | hCV11967348 | rs2064112 | 0.51 | 0.536 | 0.73735 |

TABLE 6-continued

| Interrogated SNP | Interrogated rs | LD SNP | LD SNP rs | Power | Threshold $r_T^2$ | $r^2$ |
|---|---|---|---|---|---|---|
| hCV29058753 | rs6940151 | hCV10039123 | rs760678 | 0.51 | 0.392 | 0.96711 |
| hCV29058753 | rs6940151 | hCV11967348 | rs2064112 | 0.51 | 0.392 | 0.45526 |
| Additional LD SNPs (based on resequencing genotypes) | | | | | | |
| hCV10039123 | rs760678 | hCV11967343 | rs1883237 | 0.51 | 0.224 | 0.908 |
| hCV10039123 | rs760678 | hCV2476868 | rs34350240 | 0.51 | 0.224 | 0.448 |
| hCV10039123 | rs760678 | hCV2476872 | rs2223292 | 0.51 | 0.224 | 0.95 |
| hCV10039123 | rs760678 | hCV27968956 | rs4713432 | 0.51 | 0.224 | 0.99 |
| hCV10039123 | rs760678 | hCV29058750 | rs2003664 | 0.51 | 0.224 | 0.486 |
| hCV10039123 | rs760678 | hCV30529212 | rs6457330 | 0.51 | 0.224 | 0.88 |

What is claimed is:

1. A method for determining that a human has an increased risk for developing late-onset Alzheimer's disease, comprising testing nucleic acid from said human to determine the nucleotide content at polymorphism rs760678, wherein the presence of a G/G genotype at said polymorphism rs760678 based on the sequence orientation of SEQ ID NO:2 is detected and indicates that said human has an increased risk for developing late-onset Alzheimer's disease.

2. A method for determining that a human has a decreased risk for developing late-onset Alzheimer's disease, comprising testing nucleic acid from said human to determine the nucleotide content at polymorphism rs760678, wherein the presence of a C/C genotype or a heterozygous G/C genotype at said polymorphism rs760678 based on the sequence orientation of SEQ ID NO:2 is detected and indicates that said human has a decreased risk for developing late-onset Alzheimer's disease relative to having a G/G genotype at said polymorphism rs760678 based on the sequence orientation of SEQ ID NO:2.

3. The method of claim 1, wherein the presence of said G/G genotype at said polymorphism rs760678 further indicates that said human is in need of receiving treatment for said late-onset Alzheimer's disease.

4. The method of either claim 1 or 2, further comprising providing a report of said human's risk for said late-onset Alzheimer's disease based on which genotype is present at said polymorphism rs760678.

5. The method of claim 4, further comprising transmitting the report to said human or to a medical practitioner.

6. A method of determining that a human has an increased risk for developing late-onset Alzheimer's disease, comprising testing nucleic acid from said human to determine the nucleotide content at a polymorphism in gene "neural precursor cell expressed, developmentally down-regulated 9" (NEDD9) as represented by position 101 of SEQ ID NO: 2 or the complement of SEQ ID NO: 2 wherein the presence of a G/G genotype at position 101 of SEQ ID NO: 2 or a C/C genotype at position 101 or the complement of SEQ ID NO: 2 is detected and indicates that said human has an increased risk for developing late-onset Alzheimer's disease.

7. The method of claim 6, wherein said nucleic acid is a nucleic acid extract from a biological sample from said human.

8. The method of claim 7, wherein said biological sample is blood, saliva, or buccal cells.

9. The method of claim 7, further comprising preparing said nucleic acid extract from said biological sample prior to said testing step.

10. The method of claim 9, further comprising obtaining said biological sample from said human prior to said preparing step.

11. The method of claim 6, wherein said testing step comprises nucleic acid amplification.

12. The method of claim 11, wherein said nucleic acid amplification is carried out by polymerase chain reaction.

13. The method of claim 6, further comprising correlating the presence of said G/G genotype or said C/C genotype with an increased risk for developing late-onset Alzheimer's disease.

14. The method of claim 13, wherein said correlating step is performed by computer software.

15. The method of any one of claims 6 to 14, wherein said testing is performed using sequencing, 5' nuclease digestion, molecular beacon assay, oligonucleotide ligation assay, size analysis, single-stranded conformation polymorphism analysis, or denaturing gradient gel electrophoresis (DGGE).

16. The method of any one of claims 6 to 14, wherein said testing is performed using an allele-specific method.

17. The method of claim 16, wherein said allele-specific method is allele-specific probe hybridization, allele-specific primer extension, or allele-specific amplification.

18. The method of claim 16, wherein said allele-specific method detects a G allele of said G/G genotype or a C allele of said C/C genotype.

19. The method of any one of claims 6 to 9 and 11 to 14 which is an automated method.

20. A method of determining that a human has a decreased risk for developing late-onset Alzheimer's disease, comprising testing nucleic acid from said human to determine the nucleotide content at a polymorphism in gene "neural precursor cell expressed, developmentally down-regulated 9" (NEDD9) as represented by position 101 of SEQ ID NO:2 or the complement of SEQ ID NO: 2 wherein the presence of any of the following genotypes is detected and indicates that said human has a decreased risk for developing late-onset Alzheimer's disease relative to having a G/G genotype at position 101 of SEQ ID NO:2:

a C/C genotype at position 101 of SEQ ID NO:2, a G/G genotype at position 101 or the complement of SEQ ID NO: 2, or a heterozygous G/C genotype at position 101 of SEQ ID NO:2 or the complement of SEQ ID NO: 2.

21. The method of claim 20, wherein said nucleic acid is a nucleic acid extract from a biological sample from said human.

22. The method of claim 21, wherein said biological sample is blood, saliva, or buccal cells.

23. The method of claim 21, further comprising preparing said nucleic acid extract from said biological sample prior to said testing step.

24. The method of claim 23, further comprising obtaining said biological sample from said human prior to said preparing step.

25. The method of claim 20, wherein said testing step comprises nucleic acid amplification.

26. The method of claim 25, wherein said nucleic acid amplification is carried out by polymerase chain reaction.

27. The method of claim 20, further comprising correlating the presence of any of said C/C genotype, said G/G genotype, or said heterozygous G/C genotype with a decreased risk for developing late-onset Alzheimer's disease.

28. The method of claim 27, wherein said correlating step is performed by computer software.

29. The method of claim 20, wherein said testing is performed using sequencing, 5' nuclease digestion, molecular beacon assay, oligonucleotide ligation assay, size analysis, single-stranded conformation polymorphism analysis, or denaturing gradient gel electrophoresis (DGGE).

30. The method of claim 20, wherein said testing is performed using an allele-specific method.

31. The method of claim 30, wherein said allele-specific method is allele-specific probe hybridization, allele-specific primer extension, or allele-specific amplification.

32. The method of claim 30, wherein said allele-specific method detects a C allele or a G allele.

* * * * *

SEQUENCE LISTING

```
<160> NUMBER OF SEQ ID NOS: 24

<210> SEQ ID NO 1
<211> LENGTH: 219050
<212> TYPE: DNA
<213> ORGANISM: Homo sapiens

<400> SEQUENCE: 1

tcttggagac ttcaacttct ttaataggaa tttaagtcac aaagggccca gatggttctg      60

aaaaaaaaac ccgttaggct gcctgggtca taaagaaggc tcataaactg cgcttggatg     120

atgactgggt gaggggctgt gtgggggata gacaatgtct ggtgtctggt ggtctcctga     180

ctgccaggca ggccagagaa aattaggggt atgttttcat ttaacatcat tccctgctga     240

ctcttgtctc tctggaaaat tgacagttag gagacaaagt aaggtgccct ttctgttaac     300

tcagttttct taattatagt tgttgggaga tgacttaaat catgctgtga ggtatggtgg     360

tggttcctgc ccctcaatgc cccctcccag gctgcagagg aatttgcttt agagattggt     420

aatagttgag tctgagatga aggtcagtca gtgtgctgaa gcttttcagt tgcccttgta     480

gaggtttctc cccctgcagg ctggcctcta ctcattaaaa ccttttcttt ctttctttgt     540

ttctttcctt ccttctttct tttccttttt ctttctttct ttctttcttt tctttctctc     600

tttttttctt tcttttcttc tttccttcgt tcgttcgttc cttttttttt ttttttttt      660

tttctgagtc tcactctgtt gcccaggctg gagtgcagtg gtgcgatctt ggctcactgc     720

aaccttcgtc tcccaggttc aagcgatcct cctgcctcag cctcctgagt agctgggact     780

acaagctccc gccaccatgc ctggctaatt tttgtatttt tagtagagac agatttcact     840

atgttagcca ggctggtctt gaactcctga cctcatgatc cccccgcctt ggcctcccaa     900

agtgctggga ttataggcgt gagccaccgt gcctggccta gaactatttc aaggctgttt     960

ttctcttttc ttttccttct tttttcccaa ccataaaata agcatgtgcc tacacatcca    1020

cgccctagga ggaagtaaag tgggcttaac ttagcctcct ccagataaga gtctggaggt    1080

tcttgcccaa tgttgctcct ccctcatgcg ctttgctcag tgccagggag ggggagtgca    1140

gtaagtgtgg attgcacccc aggctggttc catggagatg gaaatagcgt tggcacatcc    1200

tagctcatga atggatccac atccatccag atgcccagcc aagaagccct tccccgggct    1260

cctcatcatc atgcaccagg tgctgttcat cacttttcct acggacttgc cctcccacgt    1320

ccctggaacc tatctgcatc tccccatctc cactcctcca ttctaatcca acgtatcttc    1380

actgcttctc ctagaactga ttcaatgccc tcctaactga actgccagga tccacatggc    1440

ccctcttcac cactctccac actgcagcca gggagctatt ttcagagcaa aaatatgatg    1500
```

-continued

```
gtgtcatata gctgtttaaa attctttaat taggccaggt gcagtggctc acacttataa   1560
gcccaacatt ttgggaggct gagggtggag gatctctcaa agctaggagt ttgagacaag   1620
cctgggcaac acagatatct gtctctccaa aaaaaaaaaa aaaaaaaaaa aaaattagct   1680
gggcatagtg tcatacacct gtaatcctag ctacttggga ggctgagatg ggaggattgc   1740
ttgagcccag gagttcaggc tgctgtgaac tagggtcttg ccattgcact tcagcctggg   1800
caatagagca agacttgtct cttaaagaat aaaaataggg ccaggcgtgc tggctcacgc   1860
ctgtaatccc agcactttgg gaggctgaga tggcggatca caaggtcagg agttcaagac   1920
cagcctggcc aacatggtga aaccccatct ctactaaaaa cagaaaaatt agccgggcgt   1980
ggtggtgtag gcctgtggtc gcagctactc gggaggctga ggcaggagaa tcacttgagc   2040
ctgggaggtg gaggttgcag tgagccaaga tcacaccact gcactccagc ctgggtgaca   2100
gagcttttgt ctcaaaataa ataaataaat aaataaataa ataaataatc tttcaatcat   2160
ttaatgtggc cttgaaggcc ttgcatggcc aggtacctgc cacttcttca gcctcatttc   2220
tcaccattct cccacttctc tgctgtgcgc caggcacact ggactcttcc tggtcctaga   2280
acacagcagg atcctggggt tctcagggcc tttgtcctta ctcctacttc tgcttggaat   2340
gtcctttccc agctttgctt agataaagtc cattcactca tcagatctca catcaaacat   2400
cttttccaga agaaagccat ccctgctccc cacactactt taggatgcgc caatattccc   2460
tcttatggag ctatgtatct tgacttcata gtgtttcata gagttgcgct tttcttttct   2520
tttttgacaa aaccaacatt tttttttcac tcaccagatt ggaagtttca taaagcaagg   2580
gatgtattaa atttttattg cttcccttgt accctcagtg ccaggtacat aataggtgtt   2640
caataaatat ttgcagaaca aatgaatgat tgaagttgta ttgatagtag tgcaaacttg   2700
gaggagaggc taataaagcc tgtccaaaat ataccaccca ccaggtgtgt ataacttact   2760
ctctgccttt cctgacttgt attttgaatg tcagagatga aggtgaataa caatgagtaa   2820
ataggatgaa agaacagaaa aatcaaagat actcaggaat gactgagtgg cccagagagg   2880
ctgttcagga gaattcatga aaggatatag taggaaatga gagtgaaaga gccatttggg   2940
gttagatcat gatgggcctt aaaagccaca tcatatactt taaagtgtta gactttagag   3000
aaagaataat agcacataag tgatgctgta ctagaaacaa gctgtggtct cactatattt   3060
actgtaaaga tgatatgtca tgatgctgta tgatttactg tgttatataa cccgttatga   3120
agaccctggt gagaaatctc tctgaggtcc cagtatggga aacagtgggc ttgatttcat   3180
tttatggata cttataaatc atataacgga tttcattttc cttccttcct tccttctttc   3240
tttctttttc tttttctttt ttgagatgga gccttgctta gtcgcccagg ctggagtgca   3300
gtggcgtgat cttggcttac tacaacctcc gcctcccagg ttcaagcaat tctcctgcct   3360
cagcctcccg agagtagctg ggattacagg ctcccaccac cacgcccagc taatttttgt   3420
attttttagt agagatgggg tttcaccatg ttggccagtc tggtcgtgaa ctcctgacct   3480
caggtgatct gcccaccttg gcctcccaaa gtgttgggat tacaggcgtg agccaccgca   3540
cccggccgga tctcattttc tttatctcat gggctgtcca gaaaactcaa ggccaaagtt   3600
cacaggcctt tgcaacatgc attttgtgta tgaactatgt taacagctac gtcttatttt   3660
ttttaccttt attttctttt tattcagttg tcttcttcta aaacgaaaat attgtatgca   3720
ccttagtctt tgtggggaga aagagactag ttatatgaat taataaataa tgtgagtatt   3780
ttactattag gaaaattaat tgcaaagagg accatattca aaatcacata caaatgtcat   3840
```

-continued

```
aatatttaaa attgcacgcg aatatctttt gtccatgcct cttacctgat ttggggtaaa   3900
gctaccagct aaaccctgct caggtcatga ctgtaatgca attacccaga gaatatcctt   3960
tgtacacttt tctacctgca gctcccagag tgcttgtgtg gtatagggaa agggctactt   4020
ccattttcca gccttgaaac ttgggccaag ttgtttaatt cccttctagc ttcagcctcc   4080
tcctctgtaa agtgaaaata agaactatct ataagaggtt tgctatgagg gcaaagataa   4140
tgtgcttgat gtagtgtctg ctgactcaaa ctagacacca ataaatggtg gcgattgatg   4200
tcatttatac actagcacat ctattgatct tatgccttaa catagccagg gtttaaccac   4260
ttaaatcata tttttcaaa gtatgtattt gtccttatca ttcttgccac cttcaaaagc   4320
ctttccatgc atcaagcacc tcttcttaga ttaaatttct agatgggcca gacaatgtgt   4380
ctctgactct atttatcttc ccatttgtat gtattttatt tttctttcac ttttttggtt   4440
ctcttctgag agatattttt attttaaaat tcttcatata aaattgggct ttccaaagca   4500
tttctacaaa aaaatcctgg tcccaaggag ttgatgattt gggaaagctc atccaaatta   4560
attattggtt tgtttcctcc atgtttattc taagacaaat attcagataa tcagaaatga   4620
atgggggaaa taataaagta tcttcacata cttatttaga agctttgtac agattcaggg   4680
tgagtatggg tgctaaagat cagaacaggt gctgccccgt agcctattgg ttctaaaaga   4740
ctgttaaaga cagaggactt gaccttgatg aatgtagtcg agaacaataa tgattctgtg   4800
agctgagtca cattggcggg cctcaccctt ttgttggggg aggaaaacga aaactatctg   4860
aatatcctag accaggtttt tataaatgtt aagagagaaa acagctttta gggtcaaaat   4920
aattttgtga agtagtagac aaggcaagtt tttatattgt aagacttctt ggagcccttt   4980
tttttctttt ttcttttttt tttttttgag acagagtctc actctgttgc ccaggctgga   5040
atgcagtggc gtgatctcag ctcactgcaa cttccgcctc ccgggttcaa gtgattctcc   5100
tgtctcagtc ttccgagtag ccggaattac aggcgcccgc caccaagcct ggctaatttt   5160
tgtattttta gtagatatga ggttttgcca tgttggccag gctggtcttg aactcctgac   5220
ctcaggtgat ccacccacct cagcctccca aagtgctggg attacaggcg tgagccacca   5280
aacccggcct agagcctttt acatgctcac gagtattaag tctctccaag agactgatat   5340
acgatgttgt atttttcaaa atgacaatgc agccctgttt tcaagtaata tgtactgact   5400
gtttgtttct gactatatct tgagaaccta gatgacctaa gaacatagca ttttgcttta   5460
gcatatactg tgtatctctt gcagtctgtt acttgtttca ctgactcttt tctaatcacc   5520
ctgtgtcagg gtctttcttg cttcttctct ctgtctctct cctctgctct ttcctctcct   5580
ctgctctcca tcccctccct tttatccttt catagtcttc actatctgta tcatctttgt   5640
ctcatccagg ctccccatcc tgctttctct cctttctctt ctttgaaagg atatgatgcc   5700
atctaatgcc cagtttcatt aggccaacga atatttggta tgtctattct gaatgaattc   5760
tctgaaggta caaaatgcaa agccaaagtc gctgcagtgt gattctagag agcccctcat   5820
cacctaaact ctccactgca tctctgcagc acgccgtcct ggccaccagc ctttgccagg   5880
ctttcctgtg ccgtccagtt agcctttctg gtatagtctg aatgtatctc ccaaaaagcg   5940
tgtgttggaa acgtaatccc ccttgcaaca gcatttggag gtggggccta atgggaagta   6000
tggagagctc caccctcatg catggttaat ggggattata aaattttggg cttgaggctg   6060
ccggttcaat cccttgctct ctcatgctct cttgcctttc taccttccat catgggatga   6120
tgcagcaaga aggccctcac tggatgtgag ccctcaacct tgaacttctc aggttccaga   6180
actgtgagaa atacatttct gttctttata cattacccag tgtttggtat tctgtgatag   6240
```

```
cagcacagta cagacaaaga cacctttctt tatgatcaac ctcttcaacc ccaccccttgg   6300
caaaaagctc tttctcacca gctagatcac tttgattttt ctcattctct ctactttaaa   6360
gtctttgcct gtaaattact taaacatttg tctataatct gccttcaatt gtttaaagga   6420
catgtttact ttttatttca aacaaaggga ggcagaatcc acgtctccct tcttctcctg   6480
tccctttggt ccacagcacg ttgctgagca cacagagaca ctggctgtga ggtggggcca   6540
gctcctctgg cggagacagc tggggttcta ttgatacgca gggcagattt gcctgctctg   6600
gccggccagg caggaaatgt tcaatgaata agtgaatcct tgttgttttt tatgttcttt   6660
ggtgaatgac aatatttctt ttgtcataat ccctcaaaaa tataaagaat gtagatgtgg   6720
tttatgggga agcatctaaa acccagacag gcttttacca actcagggtt aggaagccac   6780
atttgtcttc ctggtgggac atgaacgagc tcagtatcat tgactctaaa gcagtagcct   6840
gctatggatt tagaagcttg gctttccggt ttgttctctt tctatggaac cgccaatgtt   6900
tctgtgaact gctgataata ttgacttgaa aaattggagc attagagtta gttgggaaat   6960
gctttgcctc tttttaaaat caactttatt caggtaaggc ttatatacaa taaaatgcac   7020
ctatttttag tgtattttat aataagtttt gacaaattta tccatgcaca caattactgc   7080
aacaatcaag atatagatac cgtgctgtcc agtagaatag ccactaaaca catgtggcta   7140
tttcaagtct aatgagctaa aattaaaatg aaaaacgtcc tcagttgtac taggtatgtt   7200
tcaaatcctc agtagccata tgtgactgtt attcagcata ttagacagtg caaatggaag   7260
acatttttac cattgcagaa agttctgcag tgttggacag tgatgatata aaacatatcc   7320
atcctaccaa aaggctcctt cgtgctcttt cccaaataat cgccaacccc taccccctggc   7380
cttaggaaat cacaggtcta atttttgtca ctacagatta gattcctgcc ttctggagct   7440
tcatacagaa ttcctcttta tttgcctggc tttcattcag catgtttctg aggttgatct   7500
gctcatgttg ttacatgtct aatttgttca ctccttttca ttgctcaata gtattccatt   7560
gtatatatag accacaattt acttatctac tcacctgttg atgacatttg ggttgtttct   7620
atttggcaca attatgaata aagaaattag cttttcatat ggatatatgt tttcattttt   7680
tggggggtaa atatctatga ttgggattgc tgggttatgt tgaaagcata tgtttaactt   7740
tattagaggt taccaaacca ttttctaaaa cgattgtacc attttacact cctatcagca   7800
acggaagaga gttccattct taccaattat tactggtttt attttgtttt gtttgcttgt   7860
tctattaatt actgagagac aagtattgaa atctctacct atcattatag attttctatt   7920
tgtcctttca gttatatcag tttcagcttc atgtattttg agacttcgtg attggtacat   7980
acacatttag gaatgttttg tctttttat gaattaatcc ctttatcatg aaatgcctct   8040
ctttgccctt gttctgaatt ctactctgtc tgttaataat atagctgctc cggcttttta   8100
agaaaaaaat agaatgcaca tggtacatct ctttctatcc ccttgttttt aatttatctg   8160
tgtattttta tttcaagcga gcatctttta aatagcatat agttggtctt gcattttaaa   8220
atccaggctg agaatctcta acttttaatg ggagtgccta gaccatttac tttgaaaaaa   8280
ttaacaaaga ataaactgta catatttaaa gtgtacaatc tgaagaggtt tggcatgcat   8340
acatctgtga aaccatcacc acaatcaaga caatggacac tgctttcatt cccaagtttc   8400
catggacttc tttggaatcc attccttcca ccatttctct ctaggcaacc acttatgtgc   8460
tttctgtccc tataggttag tttgaatttt ctaaaatttt gtataaatgg aaacatagca   8520
tatgtattct ttttgtcttg cttcttttt gcgtcataat gattttgaag ttcattcatg   8580
```

-continued

```
ttggctattt gttgcaatat ttttcctttt gatttctgtg tagtattcca ttgtgtggat    8640
ataccgcagt gattttattc attcatatag atgaacaaac atctgggttc tttctagctt    8700
ttgctattac aaatagagct gctataaata tttttatgta agtctttgta tggacatatg    8760
cttttatttc ttctgggtaa atacctagaa gagaaattgc taggtcatag ggtagacata    8820
ggtttaactt tttaggaaat cgccaatctg ttttccatag tgtttgtact gtttaacatt    8880
cttaccagtg atatacaaga gcaatgtttg ctcccctttc ttgcaccaac acagggtatc    8940
atttgtcttt ttaattttag tgattctatt tggtgtggtg tttatttact ttttccattt    9000
acctacataa gtcttctttt atgaagtttc ttctccaaat ttttgccgag ttaaaaaaat    9060
ttagtttttt gtctcctaag tctgatgtaa gtccttggct gatagatgtg atgtattttc    9120
tcccattttc tggcttgact tttggttttt taatggtatc ctcagaagaa taagagtttt    9180
taatgttgac aaagtccaat aaatcatttt ttttctgagt taagttttta aagtgtttca    9240
aatatggaaa ttttgtctac ctaagataac aaagattttc tcctgtgttt tcttctagga    9300
gttttaagtt ttacatttag gtctatgatc catttgggtt aatctttggg tagaacgtaa    9360
ggtacacatt cattttattt catagatcta gttgttcccg caccactttt tttttcggaa    9420
gagttttcat tccctccttg aagtgccttg acattttgtc aaaaaataagt taatgcttat    9480
atgtgtgggc aaaatggtac atgatacatt taaataattt gtctgtaaat ctcagtggga    9540
tacctgaata aaagagtggg ccaaccatta aaaatgataa ttacatgatt acaaatctct    9600
tattttcatt aaatatagtt tgctttaaat tatttcttta tgactattcc aaaacaaata    9660
gaaaaatttt ctttgattct aaaaaccaca tgactggtaa catccatatt atgaaaacaa    9720
atcatcctat atgttactga gtgtatgggt tttttggtga acacaagtct tgttccagat    9780
atttgaattt gataatgttc acagattcta gaattttctt tgaatgcaaa tacacttgga    9840
agtgacacat atacagaaaa aaccaaaccc tcaattttcc taaaaaaatc cagacctata    9900
gcattgctaa aataatcata atttaacttt ttatattagg agtaccaaag taagccaata    9960
tttaattctg tgacagagga gtatgaaaaa gaaaacccag tggctatgaa aacagagatc   10020
taaaaattta atgatttaaa aatagcctct acatacaaga cggcaaagag taatacagat   10080
tgaacatttg gttttaaaaa tgtgaaatgt ctccacttag cgtagatcaa tcaagtcagc   10140
catctcctaa gaaatacaca ttatacaatg aaatctacaa agacacactt tttaacttca   10200
agcgttgttg attttcagca accctcttcc cacatgaaca tttccttgta atgtaatgta   10260
tgacttttaa tcttcttttg gcagagtagg actttgagaa ttataatagc agttgttttg   10320
aaaagcacct tctatgatca tttatttcca ctgatttttt tttaatcacg ctgagatcat   10380
gcattcttgt tttttaaatc cttttctgtt ccaatgattt ggttgtttaa aacaagcaag   10440
cttaattcag tcaggcatat attgcaaata aaaacatgtt tccaagtagg ctggaataaa   10500
aatgctaaat aagaactggg ccaaaagatc atagataatg tgcttcttct cttggtaata   10560
tgtaaataca tttacccatg gggtagaagt atttcacctg ccccatgaag aacctgatgg   10620
cttgtggtgt ctgtgctgtg tcaatactaa cagatgtgag gagacagact atggaatgga   10680
cgctgtgact atctgtgaga tagtggaagg ggttatacac actggccaca ggaagttgca   10740
aaaattagat ggactctgtg tagctagcca ctcttgagtg tcaggtctgc atatgtgagt   10800
tttaaagaag gtgcaagata gcaataaatt cccttagaga gcaggatatg tcctggtagc   10860
tctatagttc catgatcaag gacctggcca gtttccctca ggtaatgggg gtagtagcac   10920
caaagtgaat attaagagtc agaaaggcct ctacttgcaa ctggcggatc aaaccattcc   10980
```

-continued

```
cctattttgg tgaacaatca tagtctgata cgcctttgta aatctttgct gcaaatatgg  11040
tttttacaac tctaaaaaca tcttttggaa aacctcatga ctgaaccact cacaaatgca  11100
gaagattgaa cagccccagg gaggcaattg ctctcctttt attgtagctg tctctcagta  11160
ttgaaacaac ccaatcctaa ctgtggtcct ggcctctaaa cacacaggtc tctcttccct  11220
ccagcacctg aactatcaga gcttggatcc acatatatat tctgaaattt gctccgcaag  11280
agggcttttg ggcacttggc catcatgtgt ttaagatggt cagttttgaa aagagttttc  11340
aaaacaagaa taagtcatgc tatgcctcat gatttggaag gtgaacactt gcaaataaac  11400
tatgcttccc agatttggga gtgccaggct cagaatcatc acaaggacgt ggagaacaat  11460
attataacca gctggtatgt ttttaacaac aacaaaaaaa atgcagcatt agaaggtgct  11520
tactaaggtg cttcgtaatt catggttttt tttttaatga aatgcatcag acaaacatct  11580
acaaacaaac atgaatacat gggcatacaa aagcacgtgg acaagttttc tgtacagttt  11640
atgtctcaga tacttctatg tatacataag aaccactcag ggggaaaaaa aaagatttcc  11700
ctctccagct ccctgaattt ctgaaagttg tctgacccat aaaatgttaa aatatttcat  11760
ttttatataa aatatctaca aaaatagata acatttacaa aaaccagaca gtatttccag  11820
ttttccttag taaccgttaa cgcagtcccc ttcctctttt ttttcttctc agaacgttgc  11880
catctccagc aaagagcgct tgaacagctg ggcatttcta gaaaggtctg tcacttggtg  11940
caccatttcc tgcagggccg tggtgctggg gtaatggagg gcggccatct tggttgccat  12000
gactatggtc ttgagctgct cgcagagctg gttgctggag ttcatgactt tgttgcgaat  12060
gtcctgggca gtcacctgcc gtgtcagcgt gtctccaatg aacaccagtt tgtgtgcact  12120
gaggatgaca aacttgctgt gtgccacgaa gattcgcggg ggctgggctg agctgacaca  12180
actgaagagt gcgtcaatgg cgttgagaag ggaaatgaaa tgggtctcac attggtcata  12240
gtagaagcac agcaactgcc gatcctgagc actcacgcca ctgtttgtgg tgggtaggct  12300
ctgagagggc ttccacttcg agatgtcatt ctccacgggc tttgtaatct cttgttccaa  12360
cagctggaac tggctcagct gcaaggaaga cgaaagcaga tctcattaga gcaagggagt  12420
gtgttgcaat ggaaattcac taggccttgg agttaaaaga cagggatttt agtcgctagt  12480
aactgtcaga tgcatgtgag ctgtaaagcc tgggtcaagc tgccttgctt tcctaaattg  12540
taaaatgtag acgttgggaa agatgatcct caagctcaga ccttctatga ttggactact  12600
ggtcacttgt accctctggc tagaaggtag catagtgttt aaaccgcagc cctgttacct  12660
acacctttat ggaggttaaa tgagttaacg tttataaagt gcttataata gtttggtatg  12720
tagtaggctc tatgtaaatg tttattaatg ttgaggggtg gcaagggaaa accaaatgta  12780
gtgacctcct tgtcaagtaa gtcactgaca gtttgctcct tctcggagaa agcctcgact  12840
atctcaggat gctcagatga aatgaccatt catgacccct ttctgtttat cctactcttt  12900
ctgtcaagat tgatagacat gttatgatcc agcactacag gaagattaat gcatataaat  12960
atatgagcac ttaaggaaaa aaagtttcta aggcagtctg aatgggaatt gtgcatcata  13020
atatttagtc ccccagagct gttaaaagaa gggggtttta cccagagtca gatgcatcag  13080
gtgctggctt tcttccttct ttcctcattg ctaccaaatg gtgtattatt taaattgcaa  13140
ttataataat ttctagggat tccactaaga ctcaagagag acctctcttc tgcagataag  13200
gactatctgt gacctgagct tcagactcag ttaatctccc acctggacgt agggatgagc  13260
tggagcagtg atcacctcac ccagcttccc cagcttctct gagagatgca cagccagctt  13320
```

-continued

```
tactttactt ttcttttttt ttgagacaga gtcttgctct gtcacccagg ctggagtgca  13380
gtggcacgat ctcggctcac tgcaagctcc gcctcccagg ttcacaccat tctcctgcct  13440
cagcctccca agtagctggg actacaggcg cccgccacca tgcctggcta atttttttgta  13500
tttttagtga gacggggttt cattgtgtta gccaggatgg tctcgatctc ctgacctcat  13560
gatccgcccg tctcggcctc ccaaagtgct gggattacag gtgtgagcca ccgtgcccag  13620
ccttcaacag ctttactttt ctagaatctg ttttcttctt agcgattgct atggtttcta  13680
caagttcccc aaagccctgc agtcttacct tgccagatgc caaggcaaac ataaataggt  13740
acaaggtgat attccaaggt atttaatcat aatggattat attttatata tcttaggctt  13800
tatgcaaata tgttcatcaa tatatcatgt cattagatgg ggggggtact ttcccatttt  13860
atagggaagt aactgaagct cggggaggtt acctgacttg acatagttgg ttggccagaa  13920
aggattagaa ctcagatttc ctaaatatag catgccattt catgtcatta catgccattt  13980
cacttcattt catcttaaaa ggcttgtaaa taaatcctca atccatctct ctttatttgt  14040
atgcccttgt tctagcaata gtcgtcatta tctcccctac tcatacccag cttttgaatg  14100
aacatgccct gcccaaagtc ctcagtagat aggcctggat atatgttgaa aacattgaat  14160
tctgctctcc tacctttaga ttggaccaag gccaggcaaa ccataggctt gtgttgctgg  14220
cgaaagagag acaaatagcg aggtagagac agaaagagag agagagagag agaaagagaa  14280
atggcccaat caacgtggcc caatcagact ctttcttggg aatctgatga acaagagaag  14340
ggagctaacc atcggaagag gaagccgaga tgaaaagcca tctatagaag ttctgagtgg  14400
ccatttatgg gttctgcaaa gttacagggg agccaaatga gtagataatt agagaaaacc  14460
agaaaatagg ggagagtgaa gtagattgat agaaagaagc aaaggaacta caagaaggag  14520
agataattta cagttctagt tctccccaga cctggctcta tcttcacttt ctgttactga  14580
attcccctac tgtggcttta ctataaacct gcttgcttag gctagcttga atgggtcttg  14640
tttcttgaga ccaaatgcct taacccaaat agtcctcata tgttagatat gcaggtttag  14700
cctttaaaaa aattgccgtt tagatggaac ccaggtacac ccagttgaac taacaaggtc  14760
ataaaccttc tctttgcttt taaaccccat tccgtgcttt ggagctgatt cctgccagtg  14820
agctggaaga atcaaaatca taatctcttg aagtgatacc tttccttagt gctaggtggg  14880
aaatctttcc aatgccaagc agtttttgct ctgattgaac ttacctgatg atgttccagc  14940
tgcatcttgt tctgtttcat gatattctct ttttccaata gctctttctg ttgcctctca  15000
aactcctcct taccctgtta attttcaaca taaagaacat attatgtcat cactgtgatt  15060
cacttatgct aacaatttca ttgacggatg agtaaatact ctttattttc cactgccttg  15120
gcaacatctc aaatgcccag tgaggcactg tgaaccctag acgacagggg tggcagaaaa  15180
ataaagccca ttgccatata gggtgccagc tttctggggc accttaaaat tttcggagag  15240
ctactcatga ttcccttcaa atctcatata taaatgttct ttttatagtc tctgggttct  15300
tttctcatag attatatgtg aacctgtaaa cccccaaatg caggtctaaa tgtggtccac  15360
ctctcacttc tagttccctc aaatcatcta tagatttctg ctccaaggca gtatttccca  15420
ctgtgcaggg tcagacaacc agtaagatga atgttcaatg cctccatcct ctctctctcc  15480
acttccttcc tcagcatcag gtggggctca gttctccttg ccacactttc ttgcgcttga  15540
gggaatttgg cataaatagtt acgtagttct cagtataatc tgtgactctc agtcaaatta  15600
aaagaatggc agaataagat agtaagccta gtcctaaaca atggatcttg gtagattttt  15660
tttttttttt ttctgagaca gagtctcgct ctgtcgccca ggctggagtc cagtggcacg  15720
```

-continued

```
atcttagctc actgcaacct ccgcctccca ggttcaagtg attcttctgc ctcggcctcc  15780
caagtagctg ggactacagg cgtgcatcac catgcctggc taattttcgt acttttagta  15840
gagatggggt ttcaccatat tggccaggct ggtcttgaac tcctgacctt gtgatccacc  15900
tgcttcagcc tcccaaagtg ctgggattac aggcgtgagc cactgcgccc agccagtaga  15960
atgttttaat ccctcaaagt ggaagggaaa gctgtcggaa tcccaggtca acttggagct  16020
tggtagaatt cccaattgta ggaggccaac tgtgactatc caatgtccca tacacagatt  16080
aagctcctag gacaactagc taatgcccag tggtcctcta ggtaagtctg agatggggct  16140
aagttttaaa gcaattatac acacacatac acagagtagg gctagcaggg gccttagaaa  16200
ttctctggtg caaaggtctt ctattctttt tcttaatgac gaaaactttt ttttcaaata  16260
aaatattgca tggaactata cataaaacac aaatagaagt ggagctggta ttattattag  16320
agggcctatt atcctacttg gtgagtctcc tcttacctga ggtatatcaa cgggatctaa  16380
tccaacccct taccccattc attttgcaaa tgaggaaatt aaggcccaag gaggttgaat  16440
aagttggtca cacagtaaac gtcagagaaa gggctagatc tgagtgagta ctcaggactc  16500
tcagcccagc gttcttacta ctctacgaca ctccctccaa tttgtgaacc atgtagatta  16560
acattaatta tgttctctcc tttggcagtc caacccgaca tccttatagg catctttctc  16620
aggctccctg catgtgagtg agtgtaggtg ttttatgagt tccgctgttt tacctgtagg  16680
tggacgtaat cgtagtcatc catccagctc ctctcagaac catcactgct gctacagtca  16740
ggggcctgct ccttgctcag gcctgggggc agtgccttgt tgtgggcctg ggccttgtgg  16800
tcaccaggat gcagcagctg tccctgggag ccaccgtgtg ggtactccgt tgagttcatg  16860
atgctctccg gcccattctt cagatgcaag ctgccagggc cgggtctgaa gagggcctct  16920
gcgttggtgt tgatggttgt ggtgagctgc ttggcgtcat cgggcaccgt ctttgccacc  16980
atcacaaacc ggtccagatc gtcacacttg ttctggggct tgttgatggc caagatattc  17040
agggaccagc tgcactcatt taagtcatgg ctggtttgac tcaggatctg gtgggagtct  17100
tcgactcgtt gcagctcccg cttcatcttg ttgtggagga tgagttccgg gaggcaggca  17160
gcatttgcaa cagctccctt gacaaagtgg aggtactcct tcaggaacag ctccaccttg  17220
tccactgctg tgcgtatttc attgatgtgt ctttccatat atccgtaaca ccgccagtcg  17280
gtagtgacca gtgccattag gctggagaca cccatctcaa gggcctgctg gagccgctga  17340
agtctctcaa tagctgtgtc tggatccagg aagagccttt tgtcctgagc tggggaggct  17400
gacagtgagg actccttgga ggaggtggaa gacgtggaca tgttactccg ggtgctgcct  17460
gtactggaga aagacaatcg gttgatccca tccaccaagt cccgagagcc tttagcatct  17520
ggcgggttat gcagagggac atcataaaca ccatcccttt cctgggggtt tgctttctca  17580
ctggtttctg ctggtggctc aagaaactga acgcctcggg ggacatcata tgcgtcgttc  17640
tgagagccca ctgactgtcc gagttgcggg ggtgggtgat tcggggacag gctctggtgc  17700
cttcgagcca ccggttctgc agctcctgga atgtcacagt tgtattttac atgaaggtcc  17760
ttccctgctg gcttggtgca ggttggagga atgtcataaa ccccctccgg tctgaggtcc  17820
ggccttccag cttgtctcat gggagggggg aagtcatagt ctttttccct aagccctgct  17880
tcatcccggc aagcagaggg cggaatggca tatacctgca aagcaagtag aaagcgaaat  17940
gctatttatt gagttggctc atgggaacct gtggtcccat gtgctcagtc ctatttgctg  18000
gcactttttc ggtcgccctc ccccgcccca atgttaggca cttccaaggt tccccgttat  18060
```

```
tctgctgtca cttcccttgt cctttgccaa gtgtgtccaa ccccacgttc ttggtgcaga  18120
ctcgtatgtg caaccctcct ggctaaattg ctcaccctgt gtttccagtc ctgtgtttct  18180
gaccacctcc tgggtatcct ttctctgctg atctgtgccg agaggcagag taagaccaga  18240
gttctccccc ggtcttttcg gttatcacac cagctgtgtg atgctgaatg agctgcatag  18300
gcgtctgaaa cacagtcccc ttgtctgtaa agtagggatt actgtgcctc ctgtgcaggc  18360
ataccccata gggtaacaga gtgagtcaaa cgagttcact caaacataca cactgaggaa  18420
actgtcaaac cctctacagg ccaggcgcgg ctcagcctgt aatctcagca ctttgggagg  18480
ccaaggtagt aggatcattt aagcccatat gttcaaaaca agcctgggca acatagggag  18540
acaccgtctc tacaaaaaat aaaatttatc cagtcatggt ggcgtgcacc tgtggtccca  18600
gctacttggg agcctgaggt gggaggattg cttgagcctg ggaagtaaag actgcaatga  18660
gctgtggttg cgccactgca ctccagcctg ggtgacagag cgagaccctg tctcaaacaa  18720
aatgtaacaa aacaaaacaa accctctaca aatatatatt agtacttgcc aaactgaact  18780
aattatcttc cctgccaaag ggttatcctt attggccacc tagtgttttt tagttggggc  18840
ttctcaatat gaaatcccta gagctatctt taattagtgc ctttcctttt ttgcttcctt  18900
cctttactct caccaagact acattttccc cttttgggtt tgcctttctt gttttattcg  18960
agtgaactac ttacccaccc tcccaaccct gcacccccct gacacacaga cacacacaca  19020
cactcctttt tgctgctttg tagtcactca cttacccctt ttgtaggcgg gatgtcatac  19080
accccttgag gttttatctc tcccactgga actgaaaaca cagggccttt tgctgatgag  19140
ggagggatgt cgtatacctg aagagaaacc cgtgagttac ccagaatgga aatgtcttat  19200
acttggtcat tttttatgct cctaagcact taattatgga tttatttacc aggttatgta  19260
caagcttgat ctttggcagt gctccatgtt ataacagatt tattgccttt ttttttttta  19320
atacatttta tggtttttaa cttacattta atataaaaat gattttggcc aggcacggtg  19380
gctcacgcct gtaatcccag cactttggga ggctgaggtg ggcagatcac aaggtcaaga  19440
aatcgagacc atcctggcca acatggtaaa accccatctc tactaaaaat acaaaaatta  19500
gctgggtgtg gtggtgcaca cctgtagtcc cagctacttg ggaggctgag acaggagaat  19560
cgcctgaacc cgggaggcag aggttgcagt gagctgagat cgtgccactg cactcccagc  19620
ctggtgacag aacaagactc tgtctcaaaa aaaaaaaaaa aaaaaaaaaa aaagatctta  19680
tgtgaaatat ctacgctgtc tgtactttaa agtgtagttt aaattttcta ctttccagct  19740
gggggccgtg gctcacacct gtaatcccag cactttggaa ggccgaggtg ggcagaccac  19800
ttgcagttag gagttcaaaa ccagcctggc caccatggca aaagcctgtc cctacaaaat  19860
acaaaaatta gtcaggtatg gtggtgtgtg tgcctgtagt cccagctact tgggaagctg  19920
aggcaggggc aggagagttg cttgagcctg ggaggtggag gttgcagtga gctgagatag  19980
agccactgca ctccagcctg ggcaacaaag tgagattctg tcttaaaaaa aaaaaaaaga  20040
aaaaagaaaa atctactttc tgaagcaaaa ttgtagaaga acataagctc tcttgggtga  20100
aatactagga tttcctgata aagcaaatcc agaaaacata atttaaatag cattggctaa  20160
agtggctact gggtagacaa cctaaacaaa gcttcatatg acatatatta atgcataatt  20220
tgtgaactcc cttttctcta cagccctgaa ggaatgctac ccttagaagc gcttctcctc  20280
ttgtgaccat gttctggtac gcaccccttg agtggtatga gaaggaggga tatcatagac  20340
gtccttttgg tatctggatg ggtactcgta tacgtagcca tggcctgtcc tcacgggggt  20400
tatcacctgt gggagagaag gcacagaggt gtaaatttcc aagcctgagt ccttgaatct  20460
```

-continued

```
ccttgcctcc taactaagca ctcatccctc aactctccct cataaaaaga tagaaagaaa  20520
ccaaagaaag aagacataac aggaaggaga caagtagaca ccacgttagt aaactttttt  20580
tttttttttt gaaatggagt tttgctcttg ctccccaggc tggagtacag tggcacaatc  20640
tcagcttaca gcaacctctg cctcccgggt tcaagtgatt ttcctgcctc agcctcctga  20700
gtagttgaga ttacaggtgc acgccaccat gcccagctaa tttttgtat ttttagtaga  20760
gacagggttt catcatgttg gctggtctca aactcctgac ctcaggtgat ccacccacct  20820
cagcccccaa aagtgcaggg attacaggtg tgagccactg catctggccc aggttagtaa  20880
acttttaaat ccctcttgaa tcccaatgag aaaaaaaatc cctaaaatat ctctatcacc  20940
cttaattgtg atcatctcaa agttcatcag atagagttga tgcactgcaa gtatatttct  21000
gaaatatact ttaagggata cttgtgtgta acttatgaaa gtcctagagg agcattttgc  21060
atctaaagta ccgcatactg aaatttgctt taaggctctg aaacaatttg taaaatgaat  21120
aatgcaaata gagtttagcc acttaaaatt cctctcatgc cttcctcagt atgcctcttc  21180
attggacatt attatgatga ttataactgt aattccacag gtcaccagag tacttttaca  21240
aagccaatgc tcaaactgtg ctgtccttag aaacctctgg gagctttcat tctaacgtat  21300
caaacaaaca aaatactgag tcagggaggc accaggaaca gaattcaggt ctcctgacct  21360
ctggtctcta atcattttcc catttccacc aggaaagaaa acatccccaa cagtacctac  21420
gtcaagggat atcagaagtc aaatagcgtt catcacgatg ctggcatctg gaaccagtgc  21480
caataaaatg aatcttacct agcagcctcc tgttttcata tctacatact tcattggtgt  21540
gctaagcacc agcaaaaaat tatttgaact taactcattt tgaaatatat gtaatcgtcc  21600
aagggcttct aaatgcccag ggtcttgttt ctgcctaacc cccacccttt gagtcattga  21660
gtgcccatct caagcgttgc ccacgacatc tttgaggaga acagacattg caaatgagga  21720
agagttggtt gttccctaag aaaccgtcaa cttttatcct ttctctgaag tgaaaactct  21780
ggcgtcaggc tgcctacaga actatgtgaa aaatgctcca cgtccatctt atgctgaaat  21840
gggtggaact cagccaaatg caccaatgcc ttctccccag gcgctctcaa aatgcctgag  21900
ttcaatttgg cttttaatcc ctagtgctta caactgattg tttcttgcaa cgaagtaaaa  21960
gagattagta tgcactcaaa atttccatca agtctctcca ctgtcttggg tttaaaaaag  22020
gaacctattg ctttgaggtc tgttggcatg gagcatacgg aaccacttta tagaatggcc  22080
actgtattgt gcatagcaaa ccttcctttt caaagcagga tgccctttgc taaagaaaaa  22140
cacaatgtgt tcctaatgcc cttatatgat tgtttttttt tttttactcg ctattgtcca  22200
ggagagaaat gaagatctcc ccttagtcta tttcatcagc ccctctactt agagcgctgt  22260
cttggcttta tcatagcacc tgctcatagt gcagcttttg ttcagcttaa aagtttccaa  22320
gagtggattt tatccaaggt tgccaactta gcaataatgc taatggaaaa ccaaggctaa  22380
gtccagctta actgttcatc tttcgtttaa aaaacagaag cgggcatgtc gggcgcagtg  22440
gctcatgcct gtaatcccag cactttggga ggccaaggcg ggagaatcac ctaaggtcag  22500
gagttggaga ccagcctggc caacatggtg aaactccgtc tttactaaaa atataaaatt  22560
agccgggtgt ggtgacatgt gcctgtaatc ccagctactc gggaggctga ggcaggagaa  22620
tcacttgaat tcgagaggcg gaggttgcag tgggctgaga tcttgccact gcactccagc  22680
ctaggcaaaa agagtgaaac tccgtctcaa aaaacaaaca aacaatcaaa caaacaggct  22740
gggcgtggtg gctcacgctt gtaatcccag cgctttggga gggcaaggat cgcggatcac  22800
```

-continued

```
gaggtcagga gatcgagacc atcctggcta acacagtgaa accccatctc tactaaaaat  22860
acacaaaatt agccaggtgt ggtggtgggc gcctgtagtc ccagctactt gggaggctga  22920
ggcaggagaa tggcgtgaac ctgggaggag gagcttgcag tgagccaaga tcgttccact  22980
gcactccagc ctgggtgaca gagagagact ctgtctcaaa acaaaacaaa acaaacaaac  23040
aaacaaaaaa cccagaaggg gattgggagc tagagtgggt ggcgttggtg tctgaaaata  23100
gcactaggtg acatataaac acatagcacg acctcagaaa aggaaggcag gttcaccgct  23160
aaagtgtttc cttgcctttg tggatcttcc ctggcagaaa gcgctaatgc ttcccggtat  23220
ttaacatttc acttcctgac aaatgtcaca gaaccccaac ttgctctctc tttctcattt  23280
agaggatgcc tgtggtcatc tggtttttta aaactctgca ttccaaacca gtcattttcc  23340
ttgtttatgc attcaaagaa acagatggtg aaaaccacag gggggaaacg ccaaccgaat  23400
acagcacccc ccgcccgcca ccaccgattc cagccttcct gacattacca tctaattcac  23460
gttggtccac aaatggcatt taaatgggac caggatgcaa aatgctggtc ccatttaaat  23520
gccaagtcca gtgcagcaat ccgcattgtg acgtgtggaa gatcagggag ctcgaagtct  23580
tctacttttg gacattctct gcctcgacct gttgcttggg tcactttcat gccaattgtg  23640
tgtcctctcc tcggaggaaa agtgctgact gagctgtacc ttacaaagtc tccagttttg  23700
tggttcatta aggctttttc ttgctgcgtg acataagtac acaaaaacct tccaacgatc  23760
tctcctcatt ccacctccca gaactgctga atttcagctg aagacgcaca ccaaggtctg  23820
gttaagggga cctcaagttt ggaagaattc tcctaggcat ttgttcggtg aggcattaaa  23880
ggaattgcta cacaaaggac atttttaaac taattttctc aatgaaatca agtcaggttt  23940
ttcatttcct ttccccctct gtttgctttt ttttttttct acattccttt cattctgtgc  24000
atttatttat agttacaaag gcttagcctt tggaattacc aaactgacct cttaattcat  24060
tagtgttgcc aggaaggggg ctgaattgtg aggtctcctg gggctctatg atccaatgct  24120
actgcaactg ctttcgtgat tacccggcac aggatttgca ctttccatat gtggattttc  24180
tgtccctagg aggaatccaa cctttctcag atgttagtat accattctca gtaactaacg  24240
ggagggtcca agacagagac tttgagaaga gctatgaagc cgagaagggc agattcttcc  24300
atttagaaaa ggaagaatcc atttaataca tctccaagtc tgggtcctgg caggatagga  24360
tcaaaagccc aaagactggc gttatgttag ttctctaatt aatctgctta cataaaaaca  24420
aggaaacaaa ctcgaattgc ccccaccccac actttgatgg tgtttgatcc acactgtttt  24480
gagtctcaga tcctggcggc atgagtttct ggagatgctt ttgacacttt catgcctcat  24540
aattttgaaa gccatgtatg ctgaaatttt aaagaggagg gtctgtgttt ggatagcaga  24600
gagagatagg gaggtctgag aaccagcatg atgacagtca gcaagttgga tgagaggccc  24660
ttgggactct ttctgatgtt tctgcatctg tgttccctga gctggtaccc atagcagagc  24720
aagggtccta tactcagatg ctcacggacc gagcaagcag ggtgtaggga agaaacaagc  24780
caggctttgg tgccggggag acagaactcc ttctaccgaa agagggaaga cattgcgccc  24840
tgtgttgcca gatctttcac gttttcagaa gccagaaatt tggaatttta tgtgaaacct  24900
ggttttcaaa attgacttaa attttaaaaa cagtgtcttg gccaaactaa acgcgtcttt  24960
ggcctccggg ctgccagtct ttgccttcat ctgtgtattt ttgccctcct tcctcttgga  25020
aatcttctga aggcagggcc cccaggctct gcaccaactc cctccctcgg cgagaactga  25080
gctgtccatt tccacagatg ccctgcacgc ccatacctct gtgccttcat ccatgccatg  25140
tccttgtctg agatgctctt ctttctttcc tcatattcaa actttaattg attttcaagg  25200
```

-continued

```
cccggctgaa tgcctttccc ccaccaagcc cttcccaaac agataatatg tctctatcct  25260
tggaactccc tgagccagtg atccacacat ctctaacagc acttatcact tgtggtttga  25320
cggtcttgat gcatctcatc tcttcttcca gcattttaaa gtcagagatc attccctctt  25380
catttaaata taaaccacag ggcctagtac agtgcctagc agagtaggtc ttgcataatc  25440
tattgagtga tacattaatc aactaaagga aaactgaagg ctattaagca agatggcgtg  25500
aggtctgcca ctacagaata agcttggttt ccaggtaagc cagctctggg ttaagtagaa  25560
cccatgggat atggggcaga acagtgccct atcagccatg catggtagtg ttgggcaaga  25620
gagggatcca agaaggcaag ggaatgttag gtgaagttga gaaatcagaa actgtagaag  25680
aatgcacccc aagttgggtg aagccactat tggcaggcaa ggagggctgc tggatggttt  25740
ccttttcccc agttgagctc gtatgtgaca tgaacacctg ggttcttctt aaccacaagc  25800
cagaaacatg tgggggagtg ttttggaaaa gggaaaccaa aacaaaccct gctttttacc  25860
tcaacatcag aaggaacata cgattgcttt agttctgggg atgtgtgata ggctcgttta  25920
tgagaagctg tgtgccagag gccatggccc cactgggtct ttttctgttg cttattggaa  25980
gaattaggtc tgaagaggga agtaattgac aaacagaagc tggactcagg cagagctgga  26040
tctaaatccc ggttctacca ctcacaagct atgagaacaa aggttccatt ctaagcctgt  26100
tttctcatag gtaaaatgga aattatactt ccctcatagg ctatatgagt attaaatgag  26160
atcaagtgca taaagtacct ggcataaagc cataataagc cttagctatt gttattgtta  26220
ttgtaattgt cacctaggct atatagattt taccttttga ctttgacttc cagaaatcat  26280
ggactaggta attgagatta accatcttgc tgaagacaac ttaaaaaaat gaagaaaagc  26340
taggaaagat cttttttttt tttttttttt tttttttttt tttttttgag acagagtctt  26400
actctgtcgc ccaggctgga gtgcagtggt gagatctcgg ctcaccgcaa gctccgcctc  26460
ctgagttcac gccattctcc tgcctcagcc ttccgagtag ctgggactac aggcacccgc  26520
ccactgcgcc cgccaccgtg cccagctaat tttttgtatt tttagtagag acggggtttt  26580
accgtgttag ccaggacgat ctcgatctcc tgacctcgtg atccgcccgc ctcggcctcc  26640
gaaagtgctg ggattacagg cgtgagccac tgcgcccagc cgaaaagatc ttcttaatag  26700
tgtcaagagt tcaaggataa taaagaatta ctaggtcaaa ctttgggaga agagttaata  26760
gaggtgagat tgcttttcaa gcctgggggc atttgctatt ttttgctgat ctgaaactgg  26820
tgcctgggag gctgtgctgg gttttctaca gcttctttgg gtaaggggga acattggact  26880
atagggctca ccaaggtagg gaccccaaac cacccccgac tttgggttgg aaccctaagg  26940
actgtatcca aaataaggat taactggaag taaacccacc cttgcacagg ctgaagacat  27000
cagggttgcc agaacagctc aaagcatgga atcagatgta tgcttgccta tgaggctggc  27060
agaaggaaac aaaattctct ctggaggcag agaacatctt tataggcttc acattatttc  27120
tacaaatgta ctgaaaatac aatgtcccac atacaatcaa agataaacag gaattcaggg  27180
gacaagacaa caggaacaag acaagcaaca gtcaattctt gctttctaat gtgataagaa  27240
tgttatgtat gtcttagtaa tcacagatct caaggctgtt tcctttcaaa atgttttagg  27300
atcaaatcat gggagaaatg aagatttaat cattcctaaa tttaagtcag atagaaagaa  27360
atcaatcttt aggaatgtat agtgctcaaa atgagatcta cgaggcagtg agaatttcaa  27420
accaaagcag caaatggtaa gagacagtgg tccttgatga tcatctgtag agttcttggg  27480
gttactgttt tctgctgttc gtatcagtat tggcattatt acggttatca ccagagcagc  27540
```

-continued

```
tcaagacacg ccaatgggaa accccaggag aaaatgtgtt tttccaagtc taggagatga  27600
agatatttat ccaagagaaa gacggcaagc ctccaaactc aggacacttt attaaaatgc  27660
tcatcagatg agatcttttc agtggaggtt cacaagctgg tttgtttaga ggctctcact  27720
aagaaatagg acacttgccc atctctctgg aacacctaga gacaaagcat tttctgtcaa  27780
gacaagttct gctcacattg tgtcacttgt tcaaggtctc agcaagtctc cttgggggca  27840
cttctttcct tgggcatcca cttcacctcc ttaatgcaga gctggctagg tgcctgggat  27900
ggggcagagc agtggcagca gaggccatgt ggtcagaact tcaacttctc agctgcatgc  27960
tgctagctca atggagcact aagggaagcg ggaagggagc agacggctgc cactcacaaa  28020
ggccaatccc cctccccaca gcaagcctca tatccatcat gttttgctat gtttccttct  28080
gatgccagcc ctgtgggtca cccacccacc tacttatcat gacttctcat ctctcccctc  28140
acaacactgt cttgttttga ctacttccct ccttccatgt gcttccagca accctaagta  28200
agaacaaagc agtaaaaaaa cgaagcagaa aaatcctact ctttgaaagg aagagttggg  28260
tagagtggat gggagacaga gagatgggat ggagaggaga ctgggtaact tcactagtta  28320
gtcatgctct agtgacttat tattatttat acttctacat tatctatcta tctatgtcta  28380
tctttgtatg catcaaaatt ttaaaaatta caaatatata tatattttgt cattttaaca  28440
agattttaaa agataataag aaatattact tgaaaggttt tcttttaaga gaatgatggg  28500
acacagacct gttctagatt ctatgtcccg tgattcctct gagtctaagt ctctacaatc  28560
caaagcaaca ttacaaatag cctgaattgt gcaatccttt gcctccaata tagagatagt  28620
gacttgatta ttgaccagtg gagtttaccc atgaatttag tagagtacta atgtgtggag  28680
tcagcttctt gtgtccttcc ctaatgccta gtcaggagct aggtaaccca ggatgtgctc  28740
aggaaataac aatgggtaat tgatgagaag ttaaaaagtg tccccgtgct gtaatgatta  28800
cagatttata acctcaccat tcatagtacc tacgattctc tgaatttaaa agtaggtttt  28860
actaagtaac agccatgtat ttgcactttt cttggcatat gtgggaagta aaatttgact  28920
gcttcctgtc tatctctaat tcctccccag cccctgattt atttatatta tctctctttg  28980
cgtttcatga attaacaaga gtgtttagct ttccaaaact gcctgttgga aagggcttct  29040
ttcacttaaa tgcccttgaa aagcattaac agagctacca cagtatttat tagactttat  29100
aataacctct ttgtcttaaa tgaactattt gatcccttcc ctttaaagaa aaccttagga  29160
aaagaaacat taccattatc actgcctgcc cattagaact gggatccaat tttcagaaac  29220
tgtaaagcta cagaggtttg cctgcttaaa atccaagagt actagttgct tctctatgac  29280
cagaagaaaa gccacatgtt gcctaccctg gatttattaa ttctctgtaa attcattctg  29340
cccagcttgg gtgtagcagt gagctcattt atttacttgc atagcaacaa tataatgaaa  29400
actgagtctg gccttaaaaa tacaccctcg taagccatgt ccaaggttaa ctcttccaaa  29460
tgcttctctg gtgctcatga agttttttcc ccatgtattt ctgaaggtga attactttct  29520
ttcaaagtcg ttctgatgcc tgattttatg ccagaactaa accttttgct agccacatct  29580
aaatcacagc cagcttcttt ccccagtgag gaaaaagtca caagtggaag ctcagaagtg  29640
gagcagtggt gctcctgggt cactttcatt tgacacagcg ttgggcagca aacccgctca  29700
atggaaacag tgcccctatt gttaagcccc tagcatgtcc cccctgctgc tttcaggaag  29760
ctctttgtgt agccagtgct aaagcaatat ttagttatag agtgaccaag caccagccag  29820
cagctagaag catttaacat gaaagaacac gacgggaaat gacgtctggg tttcacgagt  29880
ggttgaggtc tttctcagaa caatgccaaa tacaagcctg tgacaagttg gatacagcaa  29940
```

-continued

```
agccattttt tttctgtctc atggactgaa atgttctttg aaagaaaact ataaaaaagc  30000
acaagtattg tggctctttt gatgtccaaa taaattcaac aggactctga gcgctacatc  30060
tagattggga aatggatttt agagagatgc ccacagactg ccctaagggg aaagggactg  30120
tgaagaggag gtgagagatg agaattttgg gacccaaatg ccgattggta tcatttcttc  30180
ctaaagagga gaacgctcag gtttagttgg aagaagggat gcagtggctg atggggcaaa  30240
ccactcacaa ggcagaactc ggtgccagct ctgaaggtgg ttgtcgtgtc cagagacaac  30300
aggcctaaaa cgtctgcaaa atccaagagg attacatagg ggaaaatggg cagaaaacaa  30360
tgagttccag gatgaagtgc tgtcttagct cttggtaaca aaacagggat gagagtgctc  30420
cttaatgggg aactctggaa gtttttttgg gtacaggacc caggtctgtc aaacactgat  30480
tctcactggc tcagcacact ccagtccctg cctccttgtg tccctgcctg ctcctgctgt  30540
cttttggcat agctctgtct tccaaagggc actgtggttc tggatgggat ggtgggctgg  30600
atcctaaagg aagagtagga aagatttgca aaaacttaag ggtcaagttg aaatttataa  30660
tcaatgcttg agtatctttt ctttaaaaaa aaaaaaactc ttgatgtcag gccgttttta  30720
ttaaactgtt aaagtgattc tgagaaagaa tcagataagg atatctggat cataaaattt  30780
tagcaaagat cattagagat aatctagcat cacttgccat ttcacagttg agggaactaa  30840
agtggagtta gttactcagg ctattaatga caaagaagtg aaggagaccc ttggttagct  30900
gggccagcag tgcagcggta tacgtttctc aatgccctgc ggcctacgct agcaatacat  30960
gttagacatt ttccagaaat ttactacttt tctaatttca caagtaaata ctctcaaaga  31020
aagttacttc cttatatgag agccacaact tgaaagctgg gtaacttgtg ttttgggagg  31080
tgcccccacc tggttaaatg aagttaccca tttgaaggaa tttgaagtca tttggaaaga  31140
cagtcttagg ccaggcgtgg tggctcacgc ctataatccc agcactttgg gaggccgagg  31200
tgggcagatc acgaggtcag gagttcgaga ccagccttgc caacgtagtg aaactttgtc  31260
tctactaaaa atacaaaaat tagccaggca tggtagtgcg cacccatagt cccagctact  31320
cgggaggcta aggcaggaga atcacttgaa cccaggaggc ggaggttgtg gtgagccgag  31380
attgtgccac tgcactccag cctggtcaac agagggaggg tccgtctcaa aaaaaaaaaa  31440
aaaaaagaaa gaaagaaaga aaagaaaagg aaagaaaaga cttttctgtg tggcagagaa  31500
agccaacata gcaacattct cagtggtact ggagtctaga catcacccta ctgacctggt  31560
caggactcct ggatcagccc actctgaaac tgcccactac agctaggtgg ggggaacttc  31620
caagctcctt aattcagatt ccctcagtat tgaggctact ccctggacct gaggtgggag  31680
ccctgggcag caactttaat tcttcctggc caacagggta tgatttagcg cccaaattgc  31740
taatgaggtg tccaaatatg ccttcttctt taagggcttg gcaatatcat ccttcagccg  31800
ggatgtaaaa atcattagca ttggagtcag acagacgtgg gctcaaatat caatcctgcc  31860
tctcactgga ggcagcaagt taacttcagc aagtgaattt ccttctcaga cctcagttcc  31920
ctcctctgaa cagcaaatgc tgtgaggtgc acctcacgag gctgtggaga ggatcaggtg  31980
gtagtacctc tatgggatcc ctaacatgga gccaaggctc aaggcgcctt ggggtcaccc  32040
ccactttagt tctaacacta tcttgcaaaa tgagacggaa gcatggggta atgacaccag  32100
tgaaggctgc acattcaatt ggtagtgact ttgaaaacaa aaactattcc aataaataac  32160
tggtttaagt gtgccatgct ttaagaaaac caagtattac aaaaattaat caaataaatc  32220
agaggcgatt gtggcattgc taaaggcttc tttgcttcaa aaaactgata tactgtagga  32280
```

-continued

```
tccctttaaa gagaggactc cttggcactc ttcaaatgtt actggagtta catcctactt  32340
ttttttttt ttgagacaga gttttgctct tgttgcccag gctggagtgc aatggcgtga  32400
tctcagctca ctgcaacctc tgcctcccag gtacaagcga ttctcctgtc tcagcctccg  32460
aagtaactcg gattaacagg catgcaccac catgcctggc taattttttt gtatttagtg  32520
gagacggggt ttcatggtat cagtcagact ggttgcaaac tcctgacctc aggtgatcta  32580
cccacttcgg ccttccaaag tgctggaatt acaggcatgc gccactgcgc ccgacctaca  32640
tccgactttt gaggaacaca cattgtccta tgtgagtggc actgacacac tttaaacagg  32700
agcagcacat ctctctagaa gttatcttga caacgtttaa ggcacagcta gttagaatga  32760
agtgcttttg attgctgaca gtttctagtt ctgcattttg cacaatgtag tcaagcaagt  32820
cttttttaa agatttgtac aaccaggccg ggcgtgatgg ctcatgtctg taatcccagc  32880
actttgggag gccgaggtgg gcagatcacc tgagatcagg agtttgagac cagcctgacc  32940
aatatgatga aaccccgtct ctactaaaaa tacaaaaatt agccgggcaa ggtggtgggc  33000
acctgtaatc ccagctactt gggaggcgga gacaggagaa tcgcttgaac ctgggaggcg  33060
gaggttgcag tgagccaaga ttgcgccatt gcattccagc ctggacaaca agagtgaaac  33120
tccatctcaa aaataaaaaa aaagatgtgt tcaacgaata ttgtttatca tgaaattaaa  33180
taaataaatt tattctgttt tctctctctc acagtgttct cctacttagc cagacatcat  33240
attaaagcag tctcttacct cttcactctg ataagcacag tcatttagca tgaaatcatt  33300
gaaaaaggag ggttaacctc tgtttgcttt ggtgtgggtt tataagaagt tactaatgca  33360
ctcttagaaa tatgcattat ctataaaatt tagaacgaag tgcaactgag tttgaaggct  33420
ttggcactgg ccaaacaaaa aggacctttg ttaattttta aggaggggtg ttagagtttg  33480
ctcattgctt tggctcgggt gacttgtctg agaaaagata cttctcattt tcaaagtgag  33540
ctcataaagt cctgcccttc aagagctgaa tgacctccag ttttgtgtaa tattaaaatg  33600
tatcttgaaa cttcaggggt gacattttag atggcaagta cagttctctg catagcccca  33660
aaacccatgt atcgaggcaa acaattcata tacattagga ttatctttat gtagaaatgt  33720
acaattctgg aacatagttg tactttattg atttataaat gaggaaaccg aagtaccctc  33780
tgccctagga gtatttttg ggtgtgtacg tattttgtgt gtgtataggc aaggaacagg  33840
agaaagtgag gtgaagtcag aatttaactt ttctggaagc tttcatttcc tctaaaccta  33900
tttttgctt gttgttagac aagtcatgct gctaatatat agcacttagt tggctagtat  33960
ctgagtgtcg ctctgggcaa ccagattgca caatgcctca aattccaata agggaagtcc  34020
ttgttcctta gccaacagct tatgggtgtc tgtgtgtgtg tatgtgtatg tgtatgtacg  34080
tgtatgtgtg taatttgtga tgactcagtg tctaggaagg tacaaacatt gtagctaatc  34140
tatttctgtt tcttacatta cctttcagga atgggcctgg aagacctggc taaaaccttt  34200
gaatcatttc ctgccaacat ttggccgtga cccatttttgg aaggtagaaa atggtcctta  34260
aagatgatgt cataggatct tggtaaatct gaatattact tcagttttcc aagtgccacc  34320
tcaaagcaat acttacccca gtccagacca tcacacacat tgcaatggca gaccattcca  34380
tttttaagaa gcccttgaga tcaatggaat atacaacaca ttctgggacc atagggaagg  34440
gagaaactgc tgggttgcag agaggaagct tcatgagggg gatgaacctt ggagtgggtt  34500
ttaaagaatg gataggagtt cacagggaaa atagaaggga aaggcattct aggtaaatca  34560
taacatatgc aaaggaagtt ctgcccctca gtagaaaaag ttaggccagg cgcagtggct  34620
catgcctatt atcccagcac tttgggaacc tgaagcgggc atatcacctg aggccaggag  34680
```

-continued

```
ttcaagacca gcctggccaa catggcaaaa ccccgtctct actaaaagca caaaaattag  34740
ccaggcttgg tagcgcatgc ctatagtccc agctactggg caggctgagg aatgagaatc  34800
gcttgaaccc aggagccaga agttgcagtg acccgagatg gcaccaccgc acttcagcat  34860
gggtgacaga gcgagaccct gactcaaaaa aaaaaaaaaa aagcctagtt ttcctcctta  34920
ggtgaccaca gaggagttaa ctaatcttgt ctaaattggg caaaatgcac agaagttaaa  34980
ctctcagata agcccttctt tacatcactc atgctttgca tcaaggtgct cattgattgt  35040
atatgaatag ttacccttac aggacacagg cagtgacatt ctggaaggtc cttcagcgag  35100
ggaaatgact gtatataatc tgacacctct cataccagat ggtaatgagc tgaaccatgg  35160
gattcgagca gcagcgtgtg agggtggatg tgtgataaga tcagaaccac ctttcagtta  35220
attaaaggtt aactctcatt taacactttg attcttgctt ccacctgttc attggttcac  35280
tgggctgcta tctgtgggct gatgctctac caagtgctca gcctacagca gtcaggaggc  35340
agccatggcc cctgcgctga tggagcttgt aatttagccc caaactgatc ttcagaaaga  35400
ggtacaacaa atagttccag cagttagaat aaaagcgaca catccaaaga aaaatcagag  35460
aagcacatat aatttcccat gcagatcaac tgtgaaatgg atgaactcag gtagcaattt  35520
cactgatctt tgaagcagag aaatgagact attttagatc tttttaggct tttggttttg  35580
aacatttgta gatttcattt accccaaacc ataatcccat attaagtaga atttttgctg  35640
ttaaaaattg aaaacttttt ttcttccttt ataattcagt ttttcaaatt attcgactat  35700
gagtaactta tttaatttag gattgcctgt gggttcttgg caaccatgat gcatatttag  35760
aaatctttgc aaagtgagaa aaatataacc tacatactgt tttctaatat gatgaaatag  35820
ttataagccc taaataaaac aattaatggg gcagacatga tatggtttcc tagacattga  35880
cctaaatgtt tattaatttc tattttgcag tttttgtgtt tcatattttg gagtcaaaag  35940
atcttttatt cagctcccaa acattcttat aggcactggg catattgcct acaacgccta  36000
atggataaaa cggccctgtg cacaaaacac agagtgaaaa agaccaatga aattaagtaa  36060
aggtgtcagc gtatatggtt ttcagataac ttggagagtt tttttccacc ctttgcagaa  36120
ttcttgcaga accaaagaga aagccacaca ctcaaaaaac acagcatatg tgttagcaag  36180
aaagcacttg taccttcggt gtgtcgtaag aaacacaaca gggctgatgt agtaggaaat  36240
aaactctgag aaaggaaacg caaggtgaga ggaatgcatt cttttaagcc cctgccatgc  36300
taagcactga gccagggact ttctatgtat gcttctgttt aattctcacg acagcctatg  36360
aagtagttag tatcattccc attaaacaga tgaagaaacc aaggcgtaga gatggtcagt  36420
aacttaccaa aggatataca gctatggaga aacaacccag catcagctga accctgaagg  36480
ccttactctc tccacaattc tcacactgtc tgcttgtttc ctaaaagggt ggggatttta  36540
tgactatatt tctttctcta aatgctgatt taatatgtga tgaatgtcag ttagtgtgga  36600
ggggatgcaa gagggtgggt agaggttgga gtttccaaga gagcaaagtt gaagtgatag  36660
aaggcagaat tcactgtctt tttttttttt tttttttttt ccttaagtga ttcattagta  36720
gaaaaaagca gtgctgggta aaacttcgga agcccacagt ctgtagcaat atcaagggaa  36780
ttttgaacta tggaaagtcc caaatcataa tcagattgga acatgtccca gccccttcat  36840
ggtcccttta cagtgtttct caaagtctag tcctaggcca ccacccacaa aactatgcaa  36900
ggagctcaat aagatgcaga ttcctgggcc cccaaccaga cctactggat taatttctct  36960
gagggaaaga cctgggaatc tgcatttaaa ctcactgccc tacctctctg ggtgattcta  37020
```

-continued

```
tgcccattaa catttttaaa ccccaccccg gtggctcaga ataagattcc actgcctcct  37080
tattttctta ttcaagagct tttaaagacc atagcttaaa ctaccaggca tatctagttc  37140
tgggctcata ttatcttaca gatgaaaaat ttaaagagaa aatgagcaaa ttgctttatt  37200
aagccagtca gtaaaactac taaaatgcaa actcagaaaa atgaaaaagc cacgcctgat  37260
ccccagtgtg ctgggattat ctcttagggc ctaggcttaa gtcattagaa tgattcccac  37320
ccactgagaa tatcctatac ccaggaagat gttgacagat gtttttttaaa gcagttgcaa  37380
ttgcctggaa ggctaaaatc acctcctagc agctaagcca tctccactat gaaagaaagg  37440
aaggaaggga ggaagggagg gagagggaag gagggaggga tggggggaga gagagagaga  37500
gagagagaga gagagataga aaagagaagt gaggaaggga gtgaaaagaa aggaagaggc  37560
aaccacactc ccatggatgt gaaccactgc tctggggtac atggagagag gcagcctaga  37620
gacccaggat caggatactg tggagaagcc cttggtattt ggcagggaag gtgccagggc  37680
caccctcttg ccctccccat cctggccatg tcactacccc agaccctgac tgtgtgatgc  37740
tttaggcacg gcctactctt cagccctggc tgcaactcct ggaagggctg gcacaggtca  37800
ttttcagaag ttgatttcct cctgcaggac tcatctacct tttgctaaac agaaaatgtt  37860
ctactgagtg tagacttaaa aaaagcaaaa caaaacatgg aatgtgagtg cccgagggtc  37920
accccagcac cccagccctt tgacatcaat ccaagggaag atgagtccgt atctctgccc  37980
tctggaagga cggggagcca tggggaaagc ctgcagggca gtcccagcag atacaagggg  38040
aagaagtctg aaggcttagg cttctctgac ttggagctga aaaggttggg tctaaaaagg  38100
aaaacacgct accttcctgc caaagtcaac tgtgatgaaa gtttagagcc caccacctcc  38160
cagccaagca tttcctgctc tggcctcccc ttctgcctca cactggctca gatgtgggag  38220
agctattttt aaggtgcaaa caaccaggac taagaatgag tgaagttact tatttatagt  38280
tacacctttc aactgttatt tttcccctct ggagatagaa gccaggtttt gttttccctt  38340
tgaatctaca attcctagga caaggaagac tgaaaagcca caagtcagtt tatcacctct  38400
aggcagcatc gttgtcgtgg gcagtacaag tctaaaagct gtgcaccacc cttgaggaat  38460
ccctcttaac gaacctacgc tcagttcatg ccacacgcgt gctcttgaga agtattttgt  38520
aaaacatact ttttatatca aaggtgattt aaaaatgcat tagtgctttg ttgtttaaag  38580
gaatctaccc acacagggtc agggtctggg gtggtgacat ggccaggatg gggagggcag  38640
gagggtggcc ctggcacctc cccagccaaa cactaagggc tctccacagg gtctctaggc  38700
tgcctctttc catgtaccca aaaatgcatt agtgctttca ttgtttaaag gaatcctttg  38760
ttttttcaac agaggattct aatacatcaa atagatattc cctaatttac agaggtttgt  38820
aaaatcagac ttcatattag atttacttgg ggcaggacac atctatagtt agtgttctaa  38880
gggtcaacaa gctctttctg gtatgtaatt gcatctttcc tcttgtaatt cagggatatc  38940
ttcttatcca gttaaatttg ttcattccta ataccaaacc ttgtaggacc cattggaatt  39000
tgccagcaaa tgaaagagaa aatccctcct ttgtgatgct cacataagca tcaccttggt  39060
tgtgggtgtt acccccgatc agtccactga cattattttc ctgataacac gtgtccctac  39120
ctagcattct cttggttgct tctgtctccc ccacggcaat gtaagcatca ccagggcttt  39180
gtttatcttt aattaatcac tgtatcacaa gcatcaaaaa tatattagat gctcaacatt  39240
cattgttcaa ttagtgaatt tctattgacc tcaaattgct aaagtatttg ggattacaca  39300
gggtgttgca gagctcccca cactgtattt ttaaattaat tccttcctaa atatccaagc  39360
tccactgttt tcacccactg cctcaggcat tattataaga atgacttgaa ggacaggagg  39420
```

-continued

```
atggcttcat tccaattcca ctagtatctg tgcattttta aatgagtcaa actaagctga  39480
taactctata gaacgagttg gtcagcatga catactccca gcttcctcac tctcgctact  39540
ttgggtgggt tccttgtcca gccaggccac tgaggtcatg attcagcttt tggccaaggg  39600
aggatccttg ttgcatcatc aggcttgtac gagatttggt gtttgttcca ctcaatgaag  39660
aaacagaaaa gataggaaac gatctgagca cagagtgaag gcttagaagc tgatatatga  39720
gaaagatgga gagaaacagt ttaataaccc atgtaaccca ggatgacaca ggaacttagg  39780
agggctggaa atcaactgta ctcagcacat ggtagttcaa agaagttttg ctgaatgatg  39840
gatgaatggc aaaatcatgc aaacatgatg cctgagctaa ggtattggtt atatctactt  39900
cttggcagct tcaagttatt aatttgggaa catttccaaa tgctccaagt gtaatgggaa  39960
aaaaaaataa gtaggaacaa aaatttagtt agtcatttac tcaccttttt acccacgtgg  40020
ggcccactgg ttcccccaat gcttctctgc actgatggtg gcacctgata tacctcttgt  40080
tcttgggtgc cgtggccagt ggggacttgg taaattccct gattttggta ggaaggtggc  40140
acttggtaga tggtgtctcg gggagcagcc tgtgggtttg gcacttgata gagcttctgt  40200
tggccaaagg tctgctgcat cagtccagag gcaggctgct cgtgactgga ggcagtctcc  40260
tgcatgggac caatcagaag cttcacccgg ttgcctggga caatgccttg ccgaccgtgt  40320
aatgagcaca gccaccatcc ttccagtccc cctgtgttct gctctatgac ggtcaggatg  40380
tctcccttgc gaaaggccag ttcctcggca cactctggga cattgtcata taaggccctt  40440
gccataagat tctaggaggg aaggaagaga aggaaaccgt gttagaatat tgggtcggtc  40500
cctttatcac ctaaggcccg tgctcttatg gaaaggcaca cttcctggaa agagagaagc  40560
ataaatctga acaatagact gtaaggagaa aaacagatgg tgcagacaaa agacagatac  40620
atatacactg catctgccac cagtgacatc agactgcctc cttggaaaag ctcaaaacac  40680
cagaagagtt ctttcctcta gcaggagatg ccgtgccaag gaattatgag tagcagtgtt  40740
acagagttag agcatggttc actatacaaa acatttttct tcctttttca aagtgagctt  40800
aaggaaaaaa aaatcccgag atattcagat gttcgacaat gaacatttct caatattgtt  40860
ctatattgga ggtgaaaaga gtaaaagaaa aatcccaaat aacacacagt acaaatagca  40920
tttatatttg gagttgaaaa gccaatagaa gtacacatat atatgccttg gcagggctta  40980
gaaattcttg ttctcagatg acaggagcct tggatccaga gagaatccac aagcaaggca  41040
tgtagacatg ccatcaagcg tggagcatag gccagcagcc atatacatct ccagctttga  41100
caacaaattt attaacacat aggtggatgc caactcttct ctctcggtct tttatgcata  41160
cctttcctga gggcccctcc tcgccctccc ctttcatcac ctacttcttg aatctcacca  41220
ttcacatcag aaaagctgtg ccttcccctt tcatgggccc aacacactct ccgtctttgt  41280
atgaaggcct gtctggcaca ttcagtacta agcagacagc caaagtaggc attcagcaga  41340
gagtgggcag gcagtacgtg ctgacattct tggaggcctt tcaaaggctc ggaagatttc  41400
atttcttggc attagtaaag tttcccagca cgcgggcagc cattcccgca tgtctgcccc  41460
cttcccagag cacagcgaag tcggggacgt tgttgattca gcacaagccc tcggaacact  41520
aaaagtgaac tctaatgctt tgttaagatg tttggatgca cttaatgtca ttgaggtggg  41580
gctcatttat ggaagaaagg attacggatt ggatggggca ggttcatgac tttattttat  41640
accatgacat attcgtggga ttttcggctg tcattgtctg agcttttgct gtctattttc  41700
ttctctagca acgtggactt gatcattcag cctcgtgctt ttcatttctt tgcagctgac  41760
```

-continued

```
ttgcactact cgcgtcccct tgtgctagcc ccattgccac gggtcctgtg tgttttccgc  41820
tctggagggc tgtgcaatgg aagggatctg ccctctattc agtagttggg acgggtccag  41880
ttctgctgct gtgagccagg ttcctcttag ccagggcaat taaaagagat aaagccatag  41940
aggacagtcc tcaggaagct ttgtgatact cttcaagaat aaggttgaag tcctttttct  42000
tgacagttat gagatccagg aagtgtgaga cacagagagg tgagcggcca gggaagctaa  42060
agggaaactg aggagtgcat atttcagggg aaggtttcac tgggtagtta atattccagg  42120
aggcgctggg tttcatctaa caatgaaaag ttcacataca taaagaaaaa atcaggcagc  42180
agtttcccct gttcatggaa ccatttaagg atggtgtcat aatcctaaaa ttgtctctgt  42240
ttctcttctc ccatcttttg ggtattctgt attttacaag agaagtcata gagttacaga  42300
ggacaagatt ctggtccttt tactaaaatg acctccagga aatgactcca ccagagctgt  42360
actgagatta ttaagtgagg agatagctga ccactctggc ctctgtctgt ccctttcttc  42420
tgggcccatt cagcaatcgg gaagccccca catgaaatca gaagcaacag agtcgggcta  42480
gttgtatggg agctgagggt tggtagctgt gcaattatac tggctacaaa gaagggaaag  42540
aagagaaaca gaaaacagta gaaaggcaaa gggctacaga tctaatcagc ataaatcagc  42600
tcaaggcatt cggaattggg ccacttccaa ctccaagagc accatgaggc actgaagtgg  42660
agcaccggag catgcttgat cagaggcaga tagaaatccc cgtgcgagag tcgtcctggg  42720
cgttctttgt ctcctgcccc agtaaccttc ttaccacctg gtgagcagcc ggctaatgtt  42780
tctacactgg cctgtgagct gcttcttggg ggaaactctc agagccccac agtctgggct  42840
aatgtgggca ccgcaggtga gtcctcctga ctggttgtca ggacttccca gcagtcctcc  42900
tcagtgccca tagagattag gtttcaggca cagcttgaca gtgctgttag tagccaggac  42960
cccggcacca gcctattcac acaccgatac atattctcag ccttggccga acaggagtat  43020
gagttattta atatctgcgc aagctacaga gagccaatgt ctacatccag ccactctcct  43080
aaaccgaagc ttacggctcc agggaccttt agagatcacc tggacacaat gcccttgtgt  43140
cacagatgag gaaatagatt tgaagtttat catttgccca agaccacact attggcagcg  43200
atggaaagag aattgcgttc tttcagttta atcctctttc cagaacttta agctacctta  43260
gctcagccac gcagcatcct tgttactggg ctcagttcca ttatatgata aagttctgaa  43320
gaggagcggt tcttcttttt gtgtctatgg aataaattgg atatttgcgg tcttaggttc  43380
tagctgtgtt actttgccag gcaacagcat ccctttgggc cttagtttcc cggtctttgg  43440
taagctatgg tgatgtttta tttaatttgc tagatggccc ttgggcttca ggctccctcc  43500
ccgccttgcc tcctttccat ttgcagtcca ggcttggtcc tattccaatg atgctattat  43560
atatgttttg tacctatctg atatttatct tgctcaggat tacatttcag aagaactgtt  43620
atcttaaagc agtatatttc tgaattatga atgagttctt gtcactgcaa cctcttgttg  43680
agtatctgcc tacaaacagc aatagtgaaa ccattggttg cattcaaggg aacttctgag  43740
acaacatatt aataatgata ctacttgata aattatggat aaatgtcatc agattccaac  43800
acagataata catcagcagg taggaaaagg catgaggcag gagttggact ttcgaaaaga  43860
tttggtgttg gtgcaaggtt tcagtaagac cataacagcc aaatgaattt cagctggacc  43920
ataaaccatc tcattcaaaa gtgcacatca gtcgtaatag gaaaatcaag aatgaattct  43980
tctggcaagg aagtggaggg atcctctcct tcagtgcaaa ggtgtgattc cttgagccac  44040
aaagtcagaa gctgatgatc tgctatctta gaaaaacccc agagaggcag tttaatctac  44100
tcaagatgta ctctttctcc tgcccactca ccccccttgga tatttatctc cagggtaggg  44160
```

-continued

```
aaggtcaaca cagaaacaaa tcaaggagag ataagagagc tatgtaactc tatattcagt  44220
tggatggtta gtctccaaag gctggcagtt agcagtgcag ctagagcttg gcaaaacacc  44280
aaaacagtta gggcacagaa cttgaaagcc agaaggaact ttaaacaatt accgtccaac  44340
cctttcactt tacaaaagaa aaaaatgagc ctcaagaagt taatgatttg ccagctcacc  44400
tggcaagaaa gtcttagagc tgagacagga attcaggcct cttgtcttca ggtctagaat  44460
taggacagaa tttagtcaag tgaaatacag gtgcaacaca agctgtggct ctaatcagga  44520
ttgcaaatca gcatttagga tcatgagccc tatctgaggg aaccctgatt gcagcagcct  44580
ctagccttga tccccagccc aagcttcctt gaaactgtct tcttctggcc tccacgatac  44640
cactttttcg ttctctgtct tctcttgacc actctcatcc ttattctcca ctggagacta  44700
aatctttttc ccatccctaa agtgatcatg ttccaaagag atttgtcctt tgcactttcc  44760
tcttctcagc tatgtgctta cgctctacag gaggatggca tctgaacaca cagataattc  44820
ctaaagccat agtcttcgct ggatatttct tctgcattcc agtcccttat atccagtcta  44880
atgggcatct tcctctctaa aagcaagtgc aaacaccttt ttctcctgct ttgctttgct  44940
tggttaacag catgcacaca gctgtgcagt aagagccgca gaggtttgct gtgtctcttc  45000
atgacctgca acccatctgg ggccctgctt ttcacctcac tgccaccctt cattcaggtc  45060
ttcagcaact tttttttttt ttttttctgt agcacagaaa ttgcttccca attggctttc  45120
ctgcattaaa ttccttcctc cctcgaaacc catcttccat ttaaccagaa tgggtatcta  45180
ttcaaaggct gtttcctttc ccagttctcg atcatactat ttctttacag tacaacttgg  45240
attgccctgt tcaagactgt gaactcctta agttcagaga tgcaaattcc ttttgcattt  45300
ccagaacttt accccagtat ccgaaacaaa atatagactc agtaaatgtt tgctaagttg  45360
aaatggattc tggactctga tttcctcatt gtctgcaggg agggtgaaat tgttgtactt  45420
agagaattca gcaagacatt tggttagaat tttcagatgg aagtggggaa aatgaatgaa  45480
ccagaaagag aaatgtcatg tccaagtcac tcaagcctca cagccagaga ctatgggaga  45540
cagacagcag gaaagggcct gcccctccct atttaaacag gataatgacg cagatcggga  45600
gcctgacccc cctgaaacta gtgttcgcaa ctacggagca aacaggaagg ccaagaggaa  45660
ctgaccatcc cagtgagatt aaacacaatg gtctctttta agagcctttc tcccttcagt  45720
gtagcaatct gcttttggca ctaggtgaca gagcaccatt caaacacttt gccagaccac  45780
ttgggttctg ctgttcctgg ttcccaagct atgcctgagg agtgggaaga aaatactgta  45840
cagttgacca gaacgctggt acagagagct ctaggacaca tgacggcttc taccccctcac  45900
cccacctcca actcctccct gccttttttc ccttccctca ctgctatcaa aatgtcaaga  45960
aagcttatta ctcctatgtc agagaaacga tctgcttttc caaatacgga gaggtgtgac  46020
ttgtagtttc catgaccact catgcggtcg tttgaagaga aatgagacag aatgtctggt  46080
gtatcacccc actaagactg atagcatcat caatggcccg gcttcctctg attattttta  46140
cttcattcta tatttgtcat gcaggggatc ctgccatggc ctcagggttg ccccattctc  46200
aatgacatga ttttcctgta cccaatcccc caaaacttta gcctggactc ttgtgggttt  46260
gcatgcctgc atgcgcaaat gcatgcatgc agaggacaga ccctgagaaa cagacacatt  46320
caaggaaatg gccatcatca aggaagtcag tcctaaggca ggcagctgag ggatgaacat  46380
tgtcaaggtc agtctcaggg cacaacaggg aagagaaaga aaggctcacg tgcttttgtg  46440
catactgacg aaaaccggct ttggtctgag aactgcaaac cattttggct acatttctcc  46500
```

-continued

```
tttccttccc accatcacct ttgggataga gggggatgtg ggctttcccc agagaaggaa  46560
acagccatag tcagaaaaca tggatatctg taagtgtcag gattttaatt ctcagaatac  46620
ttggtttaca cttaggttct tgcatctgaa gatctggaat gttgaatttt ttgagttggt  46680
tcctcttgag attatgaagt cacaggcatg aagctttcaa tacaggagac agaagatatg  46740
ataagttatg atataatata agatatgcta atttttcccc agtactattt gtcgactgtg  46800
ttctgacaca cttttcacta ggtgagctga atggagctca cagaaaggca aaagcaggac  46860
cccactttgt cccactaatc cctggcatcc ttctgcccac tgctgagggg tgttcaacat  46920
ttcccacaag gcctcctgtg gcacccagac tgcatttcag gcagtaattt ttattttctg  46980
ggaagtgctt cttctagacc cctatgacag ttacaaagct tataggagta tcttggaccc  47040
ccccgccgaa tcttgacgtc attcactttg ccccgagtcc tcaagttttc ttagattttc  47100
cagctttgtg aactttagct atagcattct cttttgagca tgtctgagtg ggagaaggtt  47160
tgagaaatgt gacattaaat acttgcctcc cgaaggtact ctttgacatg gcaagagaag  47220
ctgttaatac tccctggatg tgctgtgggg cagcgccctg tgtgtggttg tagatccagg  47280
gcttggaatc ttaacatctc ttccacactg gccaatcctg tctgatgaag gatcatttgg  47340
aacccagcac tattttggtg gctcatatac caaagtgaag ttactttttg aggactggtg  47400
aaaagatctg atgctcactg caaatttgga tatttggatc tcagaaagaa atctctctct  47460
gaccagattt ggtaacatga tatggacagc atagctgtgc aattacaaag gggttcctca  47520
aaagctgggt tcctctcctt ccccatactt gaatgaatgc catctattct tgcttgattt  47580
agggttcgtg ctggacagac acattcatat gctaggattt gtttactatg taaccaacaa  47640
aatcttaggg caaagagtta gtaggcagat ttgcatatat gtgtgtatac gtgcaatgtc  47700
acagtcaact tctattattt cctggcccac ggtggaagat gaatttgact gctgagttct  47760
ttttcactca tctgtggtct ttgggtttac cgaagcaact cctgagaatc ttaaagaagg  47820
tggaggccgc gcacggtggc tcacacctgt aatcccagca ctttgggagg ctgaggtggg  47880
cagattgcct gagctcagga gtttgcgacc agcctgggca acatggtgaa accccgtctc  47940
tactaaaata caaaaaatta gccaggcatg gaggtgtgca cctgcagttt cagttactcg  48000
ggaggctgag gcaggagaat tgcttgaacc tgggaggcgg aggttgcagt gagctgagat  48060
cacgccattg cactccagcc tgggtgacag agcgagactc tgtcataaaa aaaaaaaaaa  48120
gaaaaagaaa aagaaaaaaa gaagggggaa gaacacctag gtttttttata ggtattagaa  48180
ccagaagtca cccatacctt gaccagagtt gattagagta gaatttcaga gtaagaagga  48240
accattctaa cccaatctcc ttattttaca gcccagaggg tctcagatta gcggcagagc  48300
cagagctagc atctggttca cctcttaatc tagaattttt ccccaccgga caaggatgcc  48360
cttcctgaga atcttctcca tcttagaagt cagcactgtt gctattaagc cttggaatct  48420
cgaagcattt gtcccaggtt gcctgatttt gatagatttc agtacagtat cttggcaagg  48480
ggtcaaaaat gcggggcagg cacaagctgt tttcagggtt ctgtctgtag ataaatctga  48540
caggcaccat ataatgatga aggcctgaca cccacccacc cacaagatag attttattaa  48600
caataaaaca accatctgga tttcagccag cattacagtg ttggcactgg atcatatcta  48660
tctgcctgtc tagacaaatc cctctaacat ccaggtactc agggaagaga aataagaatt  48720
aagttttaat ggagtaggag accccaatct actatattac aatatacttc caaaaatgat  48780
gtcatttctc aaagtcaaaa tgcacaagtt ataacatctg ataaggtgtt tgaaagaaga  48840
aaaagaggtt cctatttttc cattcctgtc tatcttatct tccttcacca agctatgcag  48900
```

-continued

```
cccaaggtta tatctaaacc caccaataca aatgcataca catcctggca actgttgtcc  48960
atctcccagc cagaaccgag ttgatgtaaa taggatgcaa ccctccctgg aactctttta  49020
gatgtcactt gacctggatt tggtgcctga ttggtattat ctacttcact tgtgaggtcc  49080
tcagagagtt ttagaaaaca gattcacaca cttggctgag aggtgtttac agtcatacac  49140
tgtcagcaat gcagccacta agctgtctca aggaagagtt tttgaagctg cagcttctta  49200
gttagaagac agggaaaagg tggcaggagc aaagggaaca aaaaaccttc attgtgaaat  49260
tgttcagtgc cgaggtggag agacaagctc ttacacgcac atgttataca ccagtttatg  49320
agaataaaat agctttctta aagacccagc tctaaatgca tgttccatga tgaggtacat  49380
attgtagaga gagaagccag agaaatactt taaagttgcc ttagagatgg tttgatgggt  49440
tttacatttg acttgaatga aactctgcgc ttcttagtat tttgtggtat tcactgaaac  49500
aaactggggc taggcctgta agaggaagtt gctttttggt taggacctgt tacattaagc  49560
tcaatatcag taatgataaa attatggcag tcagttctat gggggtattt ttgagtaggg  49620
cagttatttt taaggagaag gagtagaaga gattagacca ctgcttctca actaggagga  49680
tttttgtccc ctctgggtac gggcaatgtt tagtggcatt ttttggttgt cactgtgtgt  49740
gtgtgtgcat gtgcacatgc atgcacacgt gtgttactgg catctagtgg gtagagtggc  49800
cagggatgtt gctaaacatc ctacagtgta caggacagcc cccaccacaa agaatgacct  49860
ggccctaagt gtcagtagtg ccaaggttga gaaaccctgg atagaggaat ggacaccaga  49920
ctgaattagg agggtctagc ttcagacttc acatttgaag actaatgacc atcaaatctc  49980
tgccttttgt gcctctgttt ccctgtctgc aaaataaata ttaatagaca tgttcttctt  50040
tataaaaata tgaggaatca tgagattatt tactccaaat gctctgattt cttcaggaaa  50100
aagagtctct ataaaatcaa agcacagtta ttattactgc gccaagatga gctcatgaaa  50160
ttgtgtctta agaactgtac tcctcccctt ggaaaaaaaa acttcctcta ggaaaaaaaa  50220
aaccaacaaa acaaaaaacc cagaaatgat ctcatcatga ttacacctgc cacaccaaaa  50280
aacagacaca cttcagagaa atgaaattct ttcccttcag caatgaacta agctgagtct  50340
gtaattaaga tcttaataag ggaggcagga ggcttgattc aggtgctgcg ggctatgagg  50400
cgagagcgcc catgccaggt ttaaagcaag aacaattgga tgcaaatccc ccgcactgct  50460
taacactctc aggtgttcca aacaagttct tatttcaaaa tgggcatggc tttatttcta  50520
aagatgccta tttctgcaaa gaaaaggaaa gagagcacct tgttatttac aagtaaatga  50580
aaaaaaaagc acaacatctt agatagtttc ctgcaaaagg ctgctgtaag ggagatggga  50640
taatgccttc gacagtggat taatctcagg agcagccctt gatgacagtc tctagagtga  50700
ccatgtgctt ccggactctc ccaggcagtc cccaggttca aatatccttc cctttgtcag  50760
accatatgtc ccattttttt ggtttgtaaa acatggatac atactcacaa aaaagaaata  50820
tttttgaaac caacaacaaa ggatgggaat gtaagtatat ttcttgatta tggatctgcc  50880
atggctgaat ttcggatttg ggagaaaaag agctaggcac tgataagaat cttaaattca  50940
atcaacgtta tgtgttctct aattgacaag gtgatgtctg taaggaaatg agatcgattc  51000
cagtgcctct gggcctctgt gagatagcct agaagtccag ctccacagtg acaggggtta  51060
tcaagagaaa ggaggctgtc gggctgcgtt catttctgct attcccttcc ttgaacccat  51120
ttaaaggtgt gcttgtcatg ctgggctctg agtggagagg gtcagggaag cggagatagc  51180
actggacttc tgccccaggg gagcacgcaa gggaaagagg gctcaacatt ttgctaggcc  51240
```

-continued

```
catgctgctg tggtagtgcg actgtaccac aggtccacga acccatttcc tgccaaactc  51300
tcagtcatgc cacagtgact agtaacaaga acgaaagaac aaaaggaaaa gaaaaaaaaa  51360
atctcatcga cagatgactg atgtgtcctg acactgaaga ctcagaagta gctggagtgt  51420
ctagaagtcc acttactgcc attttctgtg tgctggcttt gcctgttatg gttattttgg  51480
gaggcggagg gtgttggggg gcagataagc ccagctcatt cttaaagagt cctctagatg  51540
agtcctcagt tagcctcatc tcctgtggga gtgaggcatt aaattaagga aaacaagtgg  51600
actgtcatga atcactgaga ttaaggctaa ctcatagtta ccaagagata gcacagtgtt  51660
tctgcctgac caataaaacc taggaaaaac atgaatgaca tatactatct aaatgcacaa  51720
tgccttaaga agtagacagg agatctggtt caaatctgaa ctttacacgt gttttggtta  51780
ctgcaacttt ctactgggtt tcacagataa ttaatccatc caccgccccc ctgcccccca  51840
accacacata cacacagtaa aaaaaggaat tcaaattaat ttcaaaaggg ctatcaaata  51900
tttttgttgc ttgaaatggt ttcactttta catatttgtt gctaaatctt tgtttcctgt  51960
gggcataaac ataacatttc atgtgaggga catttttagt aacatcatat aactattacc  52020
ttgatatgtt agacatatca gggggaattc taattcgcaa gactgagatt tgcaaagaaa  52080
catgacactt acaaatcact ggatccagcc tttgaataag gatcatgaac tacctactta  52140
gacaccgtgt aagcaccaga agcactagta gtggttagtg aggggattag ggagaaagag  52200
actagctgtt ttgtttgttt gtttatttgt ttgtttgttt tgtttttgag acagtctcac  52260
tctgtcgccc aggctggagt gcagtggtgc aatctcggct cactgcaagc tccgcctccc  52320
gggttcaagc cattctcctg ccttagcctc ccaagtagct gggattacag gtgaccacca  52380
ccatgcccag ctaatttttt gtatttttag tagagacggg gtttcaccgt gttagccatg  52440
atggtctcga tctcctgacc tcgtgatccg cctgcctcgg cctcccaaag tgctgggatt  52500
acaggtgtga gccaccgcgc ccggcctttt tttttttttt ttttaaagaa taactgggat  52560
ttaatagtcc attgtggggc ccaggaatat gtattggaaa acattccact ggcaacttta  52620
atatctccat gacagctgcc tccactccct acgtcaacca tgaaaaactg ctgtcagctc  52680
caccactatc catatttctg gagtgcccgt tctatcttcc tcaaattcac ctagatctca  52740
ttgtttggtc aaactgtctt caaagagagt caccctttcc aatgaagggt acaaaaggtt  52800
accaacaagg tgacttatct taaaatgcag attgttcagg aaaataatcc tttgcaggct  52860
gtcatgttcc ctagctgtgt ggaatcctca ttagccagca ggaattactg cagagagatg  52920
gctggaatgt tcaaagtaaa taagatggag gggggtgttg ttggcaaagt ataaacaggg  52980
tttttttttg tgtgtgtgtg tcccctttc atgcccgtac tctttgcaac catctatcac  53040
ctaggaaacc gtcagttact ctctggcatt ttaagttaga aatatagtat ttcttcccaa  53100
tggccctgtt tcatttgtct tggcgagaag tcctggtaat tcagcctata tgttcttgca  53160
gagtattgcc ttggtcctag tggttggcat ttcaaaccaa tttgttcaga tttctttctg  53220
accctaaaat gatctaaaca tagacaacca agacctctta ctttacattt atgtcattct  53280
aattgactgc aattggataa gagagttcac cctgaacttc tcatgtactc ccaacttaca  53340
ttctttggat tttatctttg gttttttgaa ttgacgactt tctcttcctc actgatattt  53400
ctgttatggg taaacaattc tagtgaatgt ctcctttaaa cacttttatc tatataaaaa  53460
ttccatatct atatatctgt atatctttgt gggtatgtgt atataacatc atataatagc  53520
tgccatttat taaatgccta atatctgcta gaaaggacaa ttgtcatata ttatatccta  53580
taactatctg acaagacagg tattattctc atttgataaa tgaggaaaag aaggtttaaa  53640
```

-continued

```
gtagctagca taaaattata ctgttagaaa gtaacaaaag tgggatctga aacaaagccc  53700
atgttttttg ttgttgttgt tgttttttta ctatgccata tagtattaag atcctcttaa  53760
atggctattt gtgtatacat tttgtcttct atgagcaaag tcttgtaatt tcaggaatac  53820
tgagtccaat gaacaataat gaaggaatca agtcattagt atattagcaa gtggggccat  53880
atgctgttag ggccctatgc ttacaataca catccaggcc cacagaatac tcaacaatat  53940
tcaaccatct caacctagta actgggattt tgacataatt ctgtcaccaa gtcttgagta  54000
cataccatcc tttcaacatc tattgagcat ctaccataca aagagagctg gagccagctt  54060
gcattgtctg cttactatat gccaagagcc atagtaagta cttcattcat atattatccc  54120
aggtcttcga atagtatgag gcagttattc ttatccctat tttacagaca atgctgtaaa  54180
atgaggctta gagagcttaa cttgcctaag gtccagagct ataagccata aggaacagaa  54240
atgcctttct tcaaagccca tgctctatca tgtctctaac acaagagcat aaaacaccaa  54300
gtcttggccc cctcaaaact tcacagaccc tagatcatgt tttttattca aggacttttc  54360
gatcaatctg cctctacata caaatagagg gtgggtctct catattcagt ggggtttact  54420
taaaactaaa caggcccagt aggcaaccta tctgagttac gggtatcctt tagataacga  54480
tttgattgaa agaggtcaat aagtaaggta gtgctaacag agtagggcag aggtgaaaag  54540
cataacagcc tattttaggg attataggat ggtccaggag acacaggttt cagagtttga  54600
ttgtttaaac agagtggatg gatgaggaga ctttactagc gggactgaca ggccgctcaa  54660
gtcatgtaaa cgcaaacaga gaggcagatg aatgggggca gtgagggacc aagatttccc  54720
atagcagagt ctaaggagaa ggaaaaatga gggctacaga atgtgcatta aaagtgtcac  54780
atctgtgtgt cgggggcaag ggggcggcag tagataggtg cgggtggggg gctggggagt  54840
agggggttgg aagtaagatc tacggaagtc agtattaaag aagcgtaagg aaagcctgaa  54900
aagaagaaga agaagataaa aggagaacca atgaggtcat aaaagcacga aagtgggaga  54960
gaatttgcaa aaaggccggg tgcggtggct cacacctgta atcccagcac tttgggaggc  55020
tgaggcaggt ggatcacctg aggtcaagag ttcgagacca gcctgaccaa cacagtgaaa  55080
cccatctcta ctaaaaatac aaaacttatc caggcatggt ggtgggcacc tgtaatccca  55140
gctactccgg aggctgagac aggagaatca cttgaaccca ggaggcagag gtcgcagtga  55200
gctgaggtgg caccactgca ctccagcctg ggcgacagag tgagacttga tctcaaaaaa  55260
agaaaaaaag aaaagtggag aggaaggtgt tttttttca gaagactgga gtgaagggag  55320
agacagggaa ccactgaatt ctgagaacag gactgacgtg tatcccagca aggaaaggat  55380
gctaaaggaa tccttggcat gttacgcact gtacaacttg ctaaatttgg tattatcagg  55440
caccttcagt actctaaagg cttttatctc tgtgtaggta agccatttag ctctgcaaat  55500
gggtttacta aataaataaa taaatgcata aatacataaa taaccaagtt gatatttttc  55560
aaagcatgtt ttagtgattt taaatccata gatctcatac aaggtttaaa aaggaaaagg  55620
acaggagtcc tacatttgga ttggttgcaa aaatcataca gagaaaaata aagcatttta  55680
aaccaaaata tcaaagcaag gaaataattg ggaatttaat agcttatgca tgaccatatt  55740
gactaaatta aagatcctct gtcattattt tcctcggtct tgcttgagga aatacgaata  55800
ctttcaaagt cctttccaaa gcgtttcacg gcacacaggt tctcctttcc ctgacctacc  55860
ccattcaacc agaacacagg actctgactt tcagaatgca cctttcttaa tggcattgta  55920
agttccgtct gtaatttttc ttcagtcaaa acgttaaaga atgaatttgt tgcatggtag  55980
```

-continued

```
acgagataaa taatttagaa ttttaatgta ggcacgtaag ggctcagaaa tttggcaaag  56040
ccacaaaagc gtctctgctc agccattagc agccaggcca aggggccgct gagcccccgc  56100
ccgggctggg cctgaggtgg gcggggcctc gggcctggca ggcacaaacg gggtggggtc  56160
tcgggggctt ctgctcaaac acagctgcgc agagaccctt ccatcaccct cctgggaaac  56220
agcacaacca tacacctcca gaccctcagg agggagcctt cactgggtaa gcaaaccaag  56280
gccatcgagg caatcaccta accccgccag cccccgccca attaagaaca tgctctgtat  56340
atgaagggga ttttgtagaa aattcttaat aaatgaagcc cccgtaattt actatcacat  56400
aaccacagac tgaatccctt ctaagagaaa tggaaaatta agtacgtatg acagtgactg  56460
caaccttcct gtggacaaat aaaaacatac agggaaataa agacagatta gataagtgct  56520
aaccagaaat gtctgtccgg agtaatagct tacattccac agttctcagg attactgcaa  56580
gtaccttgct gcctggcctg aagctatgta tattaagtgc aaaataagtg aaggtttgtt  56640
gttccgtagt tgtgatccct ggggcagcca aaccagataa tcaggttaac aacgacaatc  56700
ttatagggcc tgattcataa gtctttcagt aaacatttta aggtttgtgc taaatttaca  56760
gtgcatagag caacgtagta ttttagagat aattcctgtc tctgggattt taccatctaa  56820
taattatctg gttttactac ctaagtggct cgaattaaac aaataactgc caaacatgca  56880
cttcattttg ctttatagag ttactatctt aaaaagaaat tatcctgcag gaatacttgg  56940
gatgaaatag tcttaaactt tctgggagaa gaaaacactg gccatatttt agagaggtca  57000
acgatagctc tttctctttc tcttaatagt ggttaaagtc atgagttctg gagccagatc  57060
gccttagttc taatcccagc tcaccacttt ctagctgtgt ggcattagat aaattactta  57120
gcctctctgt gtcatttgaa attgagtata aaaataatac ccaccttgta gagctattgg  57180
gagagttgaa tatgacaatc ttgtgttgtc acagtaagtc tcaattaatg ttacttcatt  57240
acttttgtgt ctctcctcta cttacaataa caaaatcctt tcctgaagta aagttgttca  57300
ttattaacta gagagaaaga aaactttata aaaaaggaaa gtggatttct tcagctattg  57360
gttgatttaa tagtcatcat agggcataag tcatgtgttc ggtcggagaa gttagctttt  57420
ttgctggtga aggtgcctac aaggtaataa aaatcatgta tttacatcat ttggcaaggt  57480
gttcaacacc agtaaggccc agtggagaag caggtttctc catgaatgcc aatcgcagtt  57540
tacgctgtca gtcactttat cagttgcctt tagattttct ttccataaag agtaaagcta  57600
accacgatga gatcattgaa taaaagtgac ttgagacttt gtcgctttcg tcactttcta  57660
gattatagca ctcaatgtta atttcagcca tttatacttt ccaataatag acatatgaac  57720
atactttctc ttttttctgc aagccagttc ttattcaaca acagggaaag gaggagcaaa  57780
aaagtcactc caggctgagt aatatctggt cctatcattg ttctaaataa ggaaatatgg  57840
ggtgagccac tttaaggaag ataactttcc tgccaagtag agggatttgt ttctggttgc  57900
atcctaaagt caaatattaa tagtcttcag gatgaccctt tcctctgatc ttccctactg  57960
atgaagataa tagaaagctg atgaaacaga aatagctgat acctgtgtct tcagacagtg  58020
gtaacgtagg cattactata aagacttttg acatttagac ttaaagcttt tgaataagat  58080
tcatagtttt tgaacaaaag ctttattact gaggctagtc agtggctatc agttagacca  58140
agtatttaca accttacatc aaaaaaggat ggaccagaaa aatttagaaa aaaagcgaag  58200
tagcttccag ctagtgtaca gttaatataa attgtcaatc cacaagccta gcacccttgc  58260
ccaaatccat cttaataata acacttttgt ttaaaatagc ataaaataaa atagtagcac  58320
tagcactcat gtctattcat cattcaagaa aaattcatgt ccaattcatt gcagtctgct  58380
```

-continued

```
ttctttgtgt cccctggaag ctgcttgcct ccttagatgg gagtgactta aaagaaaaag  58440
gggagggggg aatatacgga gcaagtcaaa aatccttttg gcaagaaaaa tccacaaaca  58500
atggtgtaaa atgcattgga aaataatgct gctgaagtac tatgactatg acactctgta  58560
agctttcagg cacaatgagc cagcctgagc cttcgcactc tcaccccatt caaactccaa  58620
taaaaatgtt ttcaagaaat ggctcatact tatttattcc tacatccaat ataacataag  58680
gatgtcaaaa ttttccatcc tcagctgtgt aatctgggct tttaatttct cccaccaaaa  58740
gtgcatatgg catactcctt ccgagaccaa acgattaaag caaagtctgg aaaactttgc  58800
actaagagcc agtctgagac agactatgca gtcctcattc ctctcattac agttccccag  58860
ggcagtggaa gccaggcctg gggaagccaa ggagacttga gccaatgcct gccgcgattc  58920
aagtcagaca ccctctgatc tccagtggct gctgtgaagc ggctccaagt cttaacttct  58980
caccgaggta tttccccggc aactttcaga gcagatggac tcgggtgtac tgtgaacccc  59040
tggagtgggt ctcaaagacc gggtctctgc ttgcttgtct gcttgcatgt caacctcagt  59100
gaccgagact catcttagaa ctctccggga cacacaaggg actgacagta aggaacacgc  59160
atacacaagc acacacccgc aggcacagct ttcagcttgc aaggtaacct gtaaaaggca  59220
ctctcttacc ttatacttca tttcggcagc ggtgggttga gccgttttcc tacactagtt  59280
aagacagcat taagcactgc ggtgcccgcc cctccattga gtgcagcgct agatgaaagc  59340
gagaaggtcc cgggcagagc cgcttgtcag tcgcagcgcc tccctcaagt ctctgagctc  59400
actgttgtga ctgaggcagg ctgatcgcgg acctcatttg catgccgccc cgccattggc  59460
tagtgggaca aggtaatgct caggccctgc ccacccctaa ttctgaaaaa ctgacaaaga  59520
acttgtaatg tgatcgcttc tttttgcttt atcagacggt ggaaaataaa acagaaagtg  59580
gggaaccgtc ctgaacctta ctctgtcctc ccgcccccgc caaaaaagaa gacagaaaga  59640
gaaagaacag gaaaaggaga tacattcttt ttaagattaa cccaaatttt aaagaaactg  59700
aattcacaaa agcagtctga cagtcgcgct tcctgtgacc tagcaactcc ttcataaacc  59760
catttcgttt caaagccatt cacctcacaa tctctacatg aaacgaactc cgggaacaaa  59820
aggttttctg tctccgggcc ccttttttact aaccacccct gctgatacct ctctctctct  59880
ctgtcccttt ttctttcccc ctcctcccgc ctacttttttg tgtgtgtgtg actgtttgct  59940
ttttttgttc ttttcaacgt tcaaagtact ttgcgatgtc agtctgcaag gagctggaag  60000
acaattctcc cttagtgaaa aggaaccctc tagcacacgc accagcgttt tcctggacag  60060
cttctcacca gggcctcaga gttgcgggtc acacatattg agcgaccttc agtggctttg  60120
ctgaggataa aggttagatg tgacctctcg gatggggttg gccagtgcac gccctataca  60180
tcatcaccgt ccactgagtt ctgtgttctt tgacggctgg catttctagc tccagctttg  60240
aacactgcag tgtttttcct tctgacctct gtcctgagga tgacccatta acccaccaac  60300
acttattatc caggagaacg aaaatgccca ctgtttgatg agcctggtta aaaagaccag  60360
tctctctcca gcgaagcaca gaacataatt tctataaagg ttccatttta ggatttctat  60420
agagaaagag aatcacccag aaaacagaaa tggtcacctt ctgcaactct tctcacggac  60480
agagcagtga ggcgaaaaat tcctttttcc cgggcaagac tgagactcgg tgaatccaga  60540
caatagctgt ccctgagtgg gatgcactcc aaccagacta catgacttgg atggaaaaat  60600
cagcccttat tttttttttt cctgaccaag ttggatcaga atctgattcc cttcgcgtct  60660
aacacacaaa ttcccaatgg atgaaaactc tacttttatg atctaagcaa aaggaatgag  60720
```

-continued

```
agaacagctg tcctacaaaa gtggtttcca gatacagggt tggcaggtta gtttgcagtt  60780
cagtgtggca ctgattccag ggacatgacc ccccaggcca tcctaatgag gttgacatac  60840
ctgttccagc ctgtattagg ccttgcttct cctcatttgt ccttagagca aaaataagcc  60900
tgagtgattg tgcaaggcct ttctgaacac aaattaagca cgcagcatat tgcattgtaa  60960
cgatctcctt aagaatcctg cagactgacc ggagagtcgt tagtttgcag gaaattgttt  61020
ttggtgtcta cctggataaa ggaggacaat gattcaaagc ccttcccatc tgtaagatga  61080
gtcttgcggc ctccaagaga tctagataac attcctttgg cttcctaagt ggtcaagctg  61140
aatccttttt ctgttttgtt tgatgaatat cattgagtaa gtgagtgctg tcccatccta  61200
ttttaatgtt ttcaaacagt ttcctaaagt ttgtgctggg gttttttttgt aatttcattc  61260
tctagctagt ggccctcctg ctttcctgtt tctgtcctgt aaggtaagta agacacatgt  61320
aatctacccg aagttcattt caagaaggct tgggtcagta tatagttagc tgcctaaagg  61380
aaagcacaag ggtgttggaa tcaggtaaac ctgtgctgga acctcaaaac atttttaatt  61440
tttttttttt tttttttga gacaaagttt cattcttgtt gcccaggctg gagtgcagtg  61500
gtgcaatatc ggctcactgc aatccccgca tctctggttc aagcaattcc ctcagcctcc  61560
cgagtagctg ggattacatg tgtctgccac catacctggc taattttttg tatttttagt  61620
agagacgggg tttcaccaga ttggccaggc tggtctcgaa ctcctgacct caggtgatct  61680
acctgcttca gtctcccaaa gtgctgggat tacaggcgtg ggccactgtg cctggccagt  61740
tgaacttctt aattttgatg tccttcagta tgaaatagag aaaataataa tacctgctag  61800
cctcataatg aggattaaat aagataatgt ggatagaatt taatagtact tgttacattg  61860
taagacctta aatggttgct tgttcttatt actgttgtta ttagttatta ttttaattaa  61920
tatcagattt atgatatttt gttaatattt tatgacatta ttgctatatt ctatagatta  61980
ttatttaatt attgtattaa ttataactag tattaatatt agactactgt tgataagtgt  62040
ggtaggcatt cagaagaagt tggaggaacc ccttctctgt gtgccattct ttcataaggc  62100
agctttctca ctgaactgtt atcactagag cacctagcat gtgccaggta cctttctagg  62160
aggggaggat acagtagtag cccagacaaa gttcccatct tcatggagct tacagtctag  62220
tgagagttga ggaaaaataat taaatgaatg tataaatatga tttgcagtga taaatgctat  62280
gaagaaaaat taagcaggga aaattgctgg aggaaaacag accagggtgg gacaggaggt  62340
gtattatttt agataaagtg gtcagggaag ctcctctgag gagatgatat ttaagcagaa  62400
atctgaatag tttcagggat ccagccactc agagatctag gggatgagca ttccggacag  62460
aagtgaccca ggggaagggc ccgcagtagg cacgagctta gtgtgtctaa gcgcagcaag  62520
ctgtctagtg tgcttagcgt ggggtacaca gggctggatg gagaggatga gctcagagag  62580
gtaggtggta gggagcttgg attttttttcc tgagtgtgac atgaagcctc tgcagtgttt  62640
tgaccaggga gtaatctgtt tctctccggt ttgttaaaca ctcaaggaca gcaggctact  62700
agttaaaata ttgagctctg gtcttaatgc agcttaaata atgcagatag ttgttacttt  62760
attagtgtca tttagtatgt tgcccttaaa actcttcagg gaaacacaaa ttgtctcagt  62820
gaatacagaa acaattccct tcctcattta ttactatcag atgcaaaaat gatgtttaaa  62880
ctgggctatg taattgattt atgcagcagc cctaggattc ccatagagac cctcctgaaa  62940
ttggctagaa ctctgggcct ccggttccac ttcctgcact tgccagcact ccggtgggca  63000
tcccctcctg tcatccttgc cgcctgcctg ctcttcaacc aagcactctt ccttccagat  63060
gcttgtgcag gcaggagtga gggaaatggc accggatgcc attctaatga ttttccagct  63120
```

```
gcaactgggc actggcataa atacagcaaa aaatcaagag gaggctagaa agaagaaata  63180
cttctgttga caacttggaa tgaacccacg tgactgctct ctaagagtga agggcaaaga  63240
gtgaagagca tgtgagggca ggaaatgact ttggaaatca cctaatccag ccactcatag  63300
agagggcaga gctgtctgtc gctcagagag attgagtgcc tcacacaggg ccccaccagt  63360
ttgagttata acagcaattg gtggtgaggt caggcccctg aatctcttgg tctggtctat  63420
tctaatgatt tctttttagt ttctttgcct aactctctca ctgctgtcat ctatcttcca  63480
cgttgctcac tacgtgttta attcctggaa tacagagtcg atcacattac taccgtgttt  63540
aaaaacctct agtgacactt caatggctta acaagcaaaa tctggacact ttggcatgga  63600
ccaccatctg aacccaccct ttctttctcc ctctaccgcc gacccccatc ccaccctcta  63660
gccatacttg ggagtgtggg gttgccggga acttactgat tccaagacgg acttgcacct  63720
tcctgacttg cacaggcagg ccccttttgct gagaatgacc ccccttcact cttctgctgt  63780
caagtttggc ctcaacacta acccttttgt gtatccttgt ctacaacccc caccctgccc  63840
acctcgccct ttcagaacta attcctccct cccttcacta tgccccccatt gtactggaac  63900
acggccctat tataagggct ttccacgttg tctcataatg atttgttgat gtctgtttcc  63960
ccagctccga tgtgtgttct tggggaacag ggtggtatct tgttcatctg tgtcccctgt  64020
cctgttgtat accttagagg tgcctaaatg cttgcagcat caatgagtaa gaagataaat  64080
gtaacttcaa agaacgtatg tttatcatga ggttctgttt ggtgcccagg aagggaacag  64140
ggaagacata ttcccccgtg tgtttgagtt tagcagtgag ttttccattt atttaaaatg  64200
gtgttaggat gcacctttttc agaaccaact caaggcctgt tgctagttct gcatctatga  64260
gccaagaata gcttttacat ttttaagtgg ttgggaaaaa aaccaaagat gagacatgaa  64320
aatgatgtga aattcaaatt tcgatgtcta taaataaaat tttattggaa cacagccatc  64380
cctattcatg tagggatgtc ttttgagctg taatggcaga ctctgagcac atgccacaga  64440
gatggcaaag cccccaaagc cgaagaagaa aaagtattat ttggttgtct ctagaagttt  64500
gccgacccac actctagatt agtgcaaggt acatctatgc ctgagttcag aataaagtat  64560
agatctttcc acatctacag gggaacaatc tggaagctga gtgagtgcta gaccagagga  64620
acaagcccag tcctaaaaag gaaccattct agggccatgt tttatcattt ctagtttgac  64680
attagttttt aaaaacaatc tacatatacc aagcttattt caaaaataat tggaggcagc  64740
aactttttcca gtcttttaca agtctccaga aacctcctca aagaccagcc attgagagtt  64800
ttctccttca atacaactga ctcttggttc attcagcctt caccgaaacc ctccgaggtg  64860
ccaggccctg tgccagatgt ttacaagcag gagtccattt aatattcatc tcacgtaaca  64920
gccctgtgag gtagcttgta ttgttcttac tttacacttc acaaaaccaa gactggagaa  64980
gttctacagc atgcgccaac ttacagggtg atggcccatt ttgtttatga acccaggctt  65040
tctggtttct gagtctgtgt ggccctgacc atggagctat attgctgcca ttctcttcat  65100
atgaatgaat gaattaatgc acttcgttat ctgagcacat gtttgtccgc tcaataaggt  65160
cgagtctcca ccctcgtggg actaagctca actgagaaac aggtattgtt cttgagttgt  65220
gaggagggct gatgcagccg tgtaaataca aatgcacaca ccccttactc acgtgcacgt  65280
tggagcctgt gcgtatgtag ttcttctttc atcactctgc cccacttcgt ggctctgctt  65340
acctacatcc tatcgtgcct cccgcttgta ccccatcttc tttataaaac ctttcctaga  65400
aaaatctctc cattgttgct ctcctccctc caatcttcct ctgtatctct ggactcccgt  65460
```

-continued

```
cacctgtggc ctaagtctat gcttcccaaa tccaatttcc cttaagaaac aattagaaat  65520
gcttaggcct ctctccttta agtatgagcc gcagtaggct tagtatgagg ctatggaatc  65580
tacccgttta aagtgatctt catggctgtg tgcggtagct cacacttgta atcctagcac  65640
tttggttggc caaggcagga ggattgcttg agcccaggag tttgagacca gcctgggcaa  65700
tatagcaaga ctccaactct acaaaaaataa aaattaaaaa aaattaacca ggtgtggtgg  65760
tgcatgccta tagtctcagt tacttaggag gctgaggggg gaggatcact tgagcccagg  65820
aggtcaacgc tgcagtgtgc catgtttgtg ccactgcact gcagcctggg agacagagtg  65880
agaccctgtc tctaaaaaaa taaaaataaa aaaaatctgc atatgctctc tagtcagttt  65940
tatgtatata acacaccatt tagtgcttgg tattccctta catggtttct tttgtgagag  66000
tttcttttcc gcaatgagat tttgagcaat ttatagaaga gggttctgtc ttttcttttg  66060
ttgtagccca ttttgcactt atgtaggtga ctgaacccca tcttttgtcc tctcaaagcc  66120
tgtgtcttgt ctgtgcacac tgccttcact gaattcaaca gggggacaaa taagccactt  66180
ctcagaaggc aagggaatga gctcctctca cttcaaggca ataaacctct tttatctgtt  66240
gaactggtca agctcttgga atgaatgaaa gtctattatt agagaaaagc ccaaaagagt  66300
tttaatgctt gattctttat atactgtgaa atagggcttt cattcacttt ccctccacta  66360
atattttggc acaagagacc tcatgaaggc tacccgacct taccccgaac tacctcgtta  66420
gcaacagtgt cctaggaata cattctattt tctgaaagac ttgttaagtt cgtattaaaa  66480
aaaataatag gccaggcacg gtggctcaca cctgtaatcc cagcactttg ggaggctgag  66540
gcaggtggat catgaggtaa ggagattgag accatcctgg ccaacatggt gaaaccccat  66600
ctctactaaa aatacaaaaa ttagctgggc atggtggtgc acacctgtag tcctagctac  66660
ttgggacgat gagacaggag aatcgcttga acccgggagg cggagatttc agtgagccaa  66720
gatcgagcca ctgcactcca gcctggggac agagcgagac ttcatctcaa aaaaaaaaaa  66780
aaaaaaaaag aaatttgttt ctgcagatgg aggtggaggg tagtgtcttc taaaaaagct  66840
ccttgactcg tgatccctga atttcttctc atttggttcc ctcctaactc atttcgctct  66900
caaggacaag ctgcctgggg tgggtggggc gctaggcagc agagaatgga agcagtttct  66960
ctagatcttc taggttacag cgacgcggtg ggtctccaca ctgtgaagac ttgacgagga  67020
cctggtgcct cttaccactt agctgagctt gagcaggctg tcactgtaca gcccccttaca  67080
accaccactc ctactgagcc ctcttcctgc ttccttccat ctctttgagg tggcttttaa  67140
ttatcccaag ggtgaagcgc taaaatggga tgtcttaggc ccctcttagt tcttgataaa  67200
ccatgaaata gaacacgtaa aaccgtgtca ctaccgtgct actaaaaacc tagccagacc  67260
accttaagtg gagtgactat ggctaatatc ttgacttgat gtttaaaaaa ctgtgcgatt  67320
gtgaagtttt gatgtttagt gttattataa ctttggaata cttaattact accttttttt  67380
cttcaaagaa ttgaaaaacg ttgacagatt aaattaggtg ttaaataaat tcactcgact  67440
ctagtgaaat gtgacaagca attgtgacgc tccattttag cattttcttt acatgaaaga  67500
cttggatgaa ttaacttaaa ggtgaagtga taagaaaaat tagaaatgca taaagattta  67560
ggcttatctc cataattgtg caaggttcac atttctacta tttatgtgtc cccagctagg  67620
taaaggcata gagttcagtg gaacaaaagg agtttaatag taaaattgtg caggctgcct  67680
ggcaaagcct ctctctcctg ttttctctag ccgtgaggtg ttctgttatt acatgcttta  67740
gtttgtccaa ataaacaact tgttatatga aactgtcatg gaaatctttt ctgctgatag  67800
aaacttcaca ctgtggattt ttacaaaggt tgaagtgatc tgccaacatc aaataaacag  67860
```

-continued

```
gaatggactc tcatggctga aatgagagtg gccgtctcct ctttccggag gcactgccca  67920
aacacaatca tcttggtgca tactacctat taaatgaagg ggagcaaagg catcaggtct  67980
tcttcttgct aacctttgtg cttcctctat atgttcttac atttgaaaag tcttcctgac  68040
ttctctggca tacactttct atgtgatgtc atgtggtata agacatgatc tttcctactt  68100
gccatggcat gacatcatgt gatatgatgc gactttgtag ccctcttccc ctctccacgt  68160
cttgctattg tctagttgga ctaagcagaa aaggcttatg gattgtgtgc cctagcttcc  68220
tagatgggct ggattttctg tttccaatct acttccgagc tttgccattc tccagcgcac  68280
actggcctcc ggaagccatc ttccacacca gccatccagc atagctccgg gggcggaggt  68340
agggacagta cacaatgggg gagaagggag tgttttaaac accaaatggc cactagtaat  68400
gcccagggta cctcatttct tcaggggttg gagatgcatt ttctcccccct cgtgccttaa  68460
aagagcccag ctgacccagc cctccaagaa ggcctccctc ccgtgccccg ctgccctcat  68520
cagctgaggc cggccaatgt ccagcaggcc ccgggcccag agcctctggc ctgtccggcc  68580
agcccaagca gccgccagct ggcgctcgtg agcgcatgaa aggaatccgg ataatacaag  68640
gcctggtgga gaggcgggtg agaggaatgt ggcgggaaca cagcacaccc tgcacggttc  68700
aagccaagct tttgaagagt ttgactcgtt ttagaaagca aacaaagtgc tccagctatc  68760
agcaatcttt tattttgtct gctagaggaa tgccttgcca gtgtgggccg aggactgggt  68820
ggtgataaag acaccagtgt ccacccttga cttgccgaac ggagtatgga cggagcattc  68880
ctttctgccc actgagcccg gaaataaaga gcagctctct tctttataca aaaagccaaa  68940
gggggtctgg caatgagcat gcacaagact tgaagtctcg ctcactggta cccctgagct  69000
ttacaggcac taagtataag ttctcttaac ttgctgaagg cctggcaccc tgtgatttca  69060
gacttgacga tgtagacaag ggagtgttgc aagggtgttc ttgaacccag ggcatgcagt  69120
tctcctgatt catgctctaa cctgcttttg gagcttctgg tcttaggagg ggtggagagt  69180
agtgacaaga agaaaggctg tgccctcctg gccctagctg atagaggcca tgtcttcccc  69240
cagttttcat tttgccatct taaaatcact ctacattttc aaaagtcatc acctgtgcag  69300
ttctggtcac caggcaaaaa aaaaaaactg tctttccttt ttatccagac agctctgtgc  69360
attttttttc tctcctctca agcccactct gggactcagc tccctaacca tcccctctct  69420
gatgtgcccc ctaatctttc ccaccctgct ctctgcaagt aagttctggc cttcctcacc  69480
ctaaaaacag attcacagtt ccttgttcaa aaacctggag gccagatgag cttgtggaat  69540
tcagaatatt tcagatttta gaaagagatt tagagcatat accacatatt acaagacact  69600
cccagtgaaa tccatggctg tgtcccatga gcaaaggcat gcatgtttca gcaattgaat  69660
ctacaaagag tcatgccaag tgggtaaaag aatacatatc actcaggcca actccaatca  69720
ggctgtgctg ctgagtgagc tatcaaaata ctccagattt ttacattttg ttactgtgga  69780
tgagcaaata tgagccacaa acaacattct ctgggtcttc aggatcttcc ctttgccacc  69840
tctccttccc caacactgac caagtgccct ctatctttca cttgccatga ccagagagtg  69900
ggtggtccag catcctggcc tcctgctcag tcctccaggc atctgcttct gacccctgtt  69960
ccatcaataa ccatcaaagc cattgatgca tagaatagga gtagtgttga aattactaga  70020
aaaaagaaat gaaaaagact ggcaaaatac aagccttgat gatgatgatg atgatcatga  70080
tgataattga attcagctga taaaaaatca ctcttgtcta atggctgtca gagcttctaa  70140
gcactagctc tcaatttctg cacctacctg ttggtgggcc tgtccagtgt gtggcctggt  70200
```

-continued

```
gcaggtctgc agaacacatt ttgaggagtc ctgctccagg ggaaccccca gcctccattg  70260
tccaagccgg ggactcttct ctgcctgcca actctatgat ctcccctcaa ctcctgaaac  70320
tccttgttat ttcccctgtt atgaaatcaa ctccttcggt ttccaaagca gtgggctctt  70380
ctgattcttc tacttctctt gccaatgtgt ttcagtcttc ttttcaggag cctttcttca  70440
aggttccatt ctcagctcct tttccttgtg tatttttctcc cttatctatc tcatgctctc  70500
caatgacgtc tactctgatg acaatcacat ctcccaacct gtgttctgag ttccaagccc  70560
tcattttcta ctgcacctaa atattccaga ggcatgtcat aagctcctta tagtcaaata  70620
ttgggatgat taattttatg tgtcaacctg gataggccat gcatgctacc cagatatttg  70680
atcaaacact agtctagacg ttgctgtgaa ggtgttttaa agaggagata acatttaaat  70740
cagtagactt tgagtaaagt agataccctc caccatgtgg gtgggcctca tctaatcaga  70800
tgaaggcctt cagggaaaag agactgaggt tccctgaaga agagggaatt ctgttccacc  70860
agccttcaga ctcaagctgc aacatcagct cttcccaggg tccacatgct gtgggtctac  70920
cctgcagatt ttggacttgg agacaactcc ttgaaaacaa accaatcttt tactctcttt  70980
ctctttacac acacacacac acgtgtgtgc acgcacacac acacatagat acacacatgt  71040
cctggagaac cctgattaat acacctatga atgataaatt ccctttaaaa cagtgtctgt  71100
tttaaaccat tctctttcta tttatgtccc taccagtcac ctagaatcaa aacctcagac  71160
tgatctttta tttctttctc ccacctactt cccacatcca atcagctgcc aaggcacatc  71220
aatatttaaa tatcaatatt taagacataa atcgcctcct tttcattcat ccacaaaggg  71280
agagtcccaa ccaccactca ggcctgattg gtcatagaat acatcctctt ttctacagta  71340
attaatctga gaacttgaca tgtaactcag agtcaatcca agatcttttt gagatttgta  71400
tatgaagcct gggagagaga caacttctct gtctttggat catagactgt aaatgtttgc  71460
tcggtggtga atatgttttt ctccttgtag agagagtcaa tagcaagaga gaatgagtcc  71520
atgtgcaaaa agaagcaaag gcatttagag tggagagatg gagagaaccc taatcctgtt  71580
gtctgtgcct ctggatctag ccatgcctga agtctactct tagacaactc agttcagaag  71640
gccataaata caccttcctg actaacctag tataagttag atttctttta catgcaatga  71700
cagtgtgctg actaaccctc tactggaaag tattttccta gaaggcaaag actatacctt  71760
attcctttgc accccctgtg gcagcacata cagggtcttg gagattatag gcactcagtc  71820
aatatgctgt gttgaactcc cagcttatct ttaaggtatt agctacattg tgaacttgtg  71880
tgtgggagga gagggagaca tgaccaaaag gagcattttc tgtggctgct atgatggcag  71940
aaatagaaat gagacttatg tattaggaac attccagggt gatggtggtt tgaagcatgg  72000
tgacccaaag gcgaagcaga tccacccttt tatttcaggt tcattgattt taatccacag  72060
ctttaacaat gaaaggaaaa gcaacccata ttttcactat tatgtgtgtg atagcggcag  72120
tgttttgtct acctgtagat ctgtataaat atttatatta catttccttg ccagttaact  72180
agtacttgtt aatccctgct gagatttcat tcacccatcc accaatactt actaattgcc  72240
caatataatg ctaggcacct tgggagctac aaagatgaat aatacctaga ggctgcccta  72300
cttcttaaat acctattaca gtagcagcca acgcggctgc aggaagataa acttgcgttg  72360
ggggaaaaaa atcacaccgt aaagttatgt aagtttctat tttaaaatca tctggttcta  72420
atttactaaa tttaatgctt tagagccaat gccaaagtgc tacatttgat ttgtggaaat  72480
actttagcac atttttccat cgtgctcttg tacaatatat ttaccaccct tttgttatgg  72540
ttagaaagat tatggacctt aaaaaaagcc ctctttatga gcttgctgat attttgtcat  72600
```

```
aaaatgccat aagatggaat aagtctagta aacaataata ttcacttagg agcattccac  72660
atggtttagt tttttttttt ctttttaaat ttaacaagga tatccatctg gaaaatggat  72720
gtttaaaaac tttcactatg ccaaaccact tcttttcagt gcagacagta tttttttcgg  72780
gtgggggagc gggcagggat ggggatggat gtttaaatag cagtcatact gagctatact  72840
gctaacacaa tgataatgtt aatagcaaag gataaaagaa tgtcatggac ccagaattcc  72900
aagagggagc ttacagaaca ttccagcaaa atggactgaa tgtaagatat caacctaagt  72960
gccatttctg tactggctcg gggcctggca cagggcagcc gggaagaggc acaacttgcc  73020
tcaggttgag agagttcctg ggctgcttcc atctctctca tcctccctga caggctcagt  73080
ccactgctgt catgggttcc agtgacaggc aaaggcagat ggatcccagg gcccaggaat  73140
gaaccatcac gacgtggtcc cccaggcccc gggccccacc agttacctgg cagggcagta  73200
cggccactgt cctgtggcct atcatagaag aatcaagatc tcatgccagc atttttgctg  73260
aagcctccct gacaggctgc ggtttaacca atgaagcctg cctcgaattt tcacagtggc  73320
atttgaagct cgagtgtgga ctgattttgc tcctgctttt gggctttgct cagcttacca  73380
aaaatgagag gtttttcact tcccacccac agaaaacaag atggcagccc gggaaactct  73440
ccctctccct tgcagtattc tatttcttta aaacaaagaa acctcatttc tttcaaacag  73500
agcttagaca tctcttacaa aggaaaggct gcaaaggctg ggccagtcga catgtttcct  73560
atccaacagg ctctcgttgc ctccagttac gtgacttagg atgcaggagt tcagacgcat  73620
cagaatgaac gacatgtgac tgttcatggc tccagggctt cagacgactg ccctgcaacc  73680
tcccacatca agataaaggc tgcttgtgaa gggacactct aatgtggctc ttccctgccc  73740
agccaaacaa gatttgtgct cccaactccc ttgcctagaa gtccaatctt cccatctccc  73800
cttgaaaaca ctgccacatg aaatgaaagt ttaaaacagt aaccaagtaa agagagcatc  73860
atgatctctc cctccttctg aattcctctt tggaatgtct tttactttgc tcttccagtc  73920
cattctttcc tccctgcata ctcagctcaa gtctgtcctc ctaaaattga cgccagcctc  73980
tctagatgag tcctttttcc tgaatttgta ctatgctcaa agtcagttct gctagttcaa  74040
cacggagtcc tggtgccatt gtctgccatg tatgaatccc taatgctgcc ccgcctttca  74100
taacacttga ccttagaagt aggcgatcca ctatttgacc caagcgatag aaatttgttt  74160
ttattgggac ataattcacc tacataaaat tcacaatttt aaagtgtact cttcggtgtt  74220
ttataggata gtcacagagc tatagcaaca tcatcactat ctaattccag aactttttca  74280
tcactccaga aagaaacacc atgcccatca gccatcactc cccatttccc cccaggcccc  74340
agacctctgg caaatactca tctcatttct gtttggcaat agcaatttat aactgacttc  74400
atgcattttt attttcagcc tgatttcaaa ggctaacaca aacacgagat tggctattta  74460
catttttgta tgtatttcaa aagatgactt cagtcgcatg aacacatgta tacatttaac  74520
acatgcaagg gaacatggag tgataacagc caaaaaatgg taataaaata gaaaagaaaa  74580
gcaaaatttg gggtgtgttg gtgatgcttt agaaggcttt tagaaagaaa ggagaaagaa  74640
ggtcccatga agatgggaga ttattccttt gtaggctttc cactgggaca catctatttt  74700
tcagattatt ttgatttagg ccaggtatat tatcttcatt tttaagggtt tttttaaaac  74760
tcataaagag ttaaaaaaag ctcttcattt taaagagttt tttaactctt gaaagacaat  74820
ttttgggata tagagctgaa agtttcaggg tgccattttt ctataagatc ttcccaaaag  74880
aaacatttaa aaagatgaca tatataccac tgcttactta aaaaaaataa aaacaataga  74940
```

-continued

```
tttgagaagg aaaaaaaaaa gaaagaaaga aaggaaagcc tttaccatgt agaagtcatg  75000
tgccagatac agctaagtgc gccatctctt ctccgtaatg gtgaatcagg gaggggttag  75060
taatcctaca tatggaacct gatgctcagg gagtgactgc cttgctcagg atcacagcaa  75120
ggatctaacc aaggcccacc tggcttcaaa cctcatgctt ataaccttgt tactgccttt  75180
gaacaaaatt gcagttctat atattctcaa actggttccc caaaagtatc ctaataagaa  75240
aattgatgtt gtacagaaaa cggcaatagg cattacatct tctggtcttg gagaacagct  75300
ggacagggaa ggggcttggc tgttctgctg gctgctcagg gtcctggctt ctgtggccct  75360
ccattcttca ttgtagaagg catcggagcc tttggcctga cacgtcccca aggccaggcc  75420
catccagaat ggtcaagcac tgattggcac taagccccca gcacaccagt gctaccctga  75480
tctcacttgg ttctggaaac ttgctcgatg ggaaactgag gccccacctt ggccctggga  75540
tggctctgct acctgcacac ggctctccct acagtactgg tatctgagga cttgatgaag  75600
tgtcagctgt ctcctttgcc agctacctgc cctctcctcc atctgatcat tgaatagtga  75660
tgttccttag gccctgcctt ctccttctct tctctctccc cagagtccac agtcatgcca  75720
gctattcata tgccagtgac tcaccagttt tcatccccat gatgggtaat ttcatatgtc  75780
aacgtgactg ggctgcaatg cccacgtatt tggtcagaca ttattttgga tgtttctgcg  75840
agggtttttt gggaggagac ttacatttaa accaatggac tttgagtaaa gcagattgcc  75900
cttcataatg ttggtgggcc tcatccaatc agttgaaggc ctaaataaaa caaatatata  75960
ttgagtccaa tagggttaag tttgactgtg agtaacagaa aaaccctaga tgaatgagtt  76020
taaaaagaag ttaattttct tcttatttgt tagaattcct gggttggttc agggctctat  76080
aaagtctgta gagacccagg tttctcctct cttgtgcttt gaaatcctca gtacaaggtc  76140
caaggtggct caaattctag acatcacttc taaataacat cttccagcca gcaggaaaga  76200
agaattaggt gaaaaaagtg cctcctccct gaaaggtgct cctagaacct ccattctcat  76260
cccattagcc agatcttggt cacatggtca cagctagctg caagggatgc tgggaggtgt  76320
agtctctatt ctaggtggtc atttcatgac taaggaagag gagaatgggt attagaggat  76380
gactgctagt gttggccaca agtacctact aggtaaatat gtacagtaga tgctccataa  76440
ctgtttgata aatgtacatg tgccaggttt tttctgcctg tttggataga cctctgctca  76500
tggtaggtag tcatgctagg gtactgggca atagagtgca tttccctctt cctgcccaga  76560
ggttatgttc tgttggctcg cgtgggcttc cttctggctc ctgtgtctgg atctgccctc  76620
ctggtacaca cgtggtgagt gtggagatca tggtcaaggg gcccagagat tcctgccaca  76680
ggcaggtcct ttccagcttt ctccagccca cagcagtgcc tggaccatgg ctgtctgggt  76740
cctgaagtgg gcggtgagct cccccactgc ctgtcactcc acaggaacag atgtgcaaat  76800
ggctggctgt ggccaaagac acagtcagac atccacctca ggagcacaag ttccagaaag  76860
agggagggag agagacgttg agactagagg aggaatgagc ctctgctggt ctttctcccc  76920
actggccctt gtccttggag gtcaaagtca gtgtaaagtc ataaaatttt gtgagatgct  76980
ggccctgggt gagagttaga gcccccatga caagcacagt agccaaaacc taaatctaat  77040
ttgacatacc atgaaaatga ggcaattgta tgttggcctt gctggaatcc ccatgtcacc  77100
ctccattaat ttctttgtca aggtagtttc caaaatctct tttcctcagc atcataaatg  77160
ctaagggaaa acatcctcaa gtgttcttaa cacacagcag gggagagagg ctgctaactg  77220
cccagaatca tgtcctgaat ctaccgaagc agtcttgctg cccgtcctac gaccagagag  77280
ttctctggtg tccctttgcc ggcataccat tctctgctga cattcaccca gtgggaatcg  77340
```

```
ctcctcccca ggtccccagg agacacctgt aagctgagtc cagacctggc ttttgagctt  77400
gacaatgact gttcctttgg gataaaggag ctggaaatgt actgtggctt aggcgcagag  77460
ccccacatcc cgtctctcat tcctttacac ttggccactc caggatgttt caaagttccc  77520
atttgcaaat caatttaaca aggtcccagg ctgaaccact gattaacaac attaaaatga  77580
ttctttttac tgacttcggg ataaaactac acacctgcaa attccttact acctttaatt  77640
atgaactttg agccaatgtt ccatatttta atttctctag gtactgggcc tggattttcc  77700
acctttgaaa atgtctccag aatttttctg ctgtaaggag acttaaagag atgatggggt  77760
ataggataag tggctgttta atttgagctt taaagaaata taacctacaa tggaaagaat  77820
acaaaaatgt tgttgtataa aaactggctg gctgttagtt cattctcttg accttaattc  77880
tctcaacatg gaaaagtcaa ttcaaatgta accaataggg tcaaccccat actaacattt  77940
caggaaagat agtggttcta ggaatcagta aatgtgtttt gctgtcgggg tggtggctgt  78000
tttgattaaa tcacctttgt ctcttgtcct ctactaatga gatacctatg gtggagacat  78060
ttcagagagc ttaatattaa acagataggg atactggagt ccaggctggt taggtgagga  78120
gcataaatcc atactgcaga ggaaattgac aacctcccct gtgcagaagt tatgtcctga  78180
ggcatcttcc tcggtcacgg tcatggtttt ctctctcctc tctaaggtga gcgggactca  78240
catcaggatc tcagttttgg ttgtgagaaa gctgaggccc actcattacc tgtaggagtg  78300
atttgccaag gcggcagggc aggtcagacc cgattccagc tttccacgtt ccagtccagt  78360
tcctccccct cactaggctc ttttctagtg acccacgaaa gcttctggcc tcagacacag  78420
tgttcaacca cttcagggat ttagaatcag agctacaaga ggaaaacaaa gcaaaacaag  78480
gagctggcaa ggtttagctg gagaatattg tcctttttct ggtgtttcta aaaacaaatg  78540
acccttgtg ctctagctgc cctcagagcc tttgactaat ttctctgtgg ctcagtgcca  78600
gggatggctg aatgctgggg attctgtgct gcttcatgct ttggcatgac tctatgtatg  78660
tgtgtgtggg gggggatggt gagtgatggg caaaattctc ccctcacctt ctgcttgcac  78720
ttcccatcaa tgcaaaagca tatctgggtg ctttcgctcc acctcagggt tgaaggctgt  78780
gtcgattcct gtcacacaca gattatattt tgctgtccca tgtgaatcag agcttgtgtt  78840
aatatcttct agctgggcgc tgtagtgctc tctcagccag atcttcattt catgtctgtc  78900
ctggggctct tagctatgcc agcagagccc tctggagagc tgactggtat tctcattttc  78960
taccagcctg agcatgtcat gaactttctg gctcactggg agctgagaat acagatgaac  79020
ataaaaattg agaagagtta ttggagggtc taagaggatg ccagtcaagc aaaagaatag  79080
tagtttccta ttgcaatatc ggaaccagct ctcacgtccc gatttcacag taactcatgt  79140
attatctctg cttattttga atgcttcagc aagatctatg ttaatagaat tctctatggc  79200
tctccatcct ttaaacaaat taacacagcc cacagctacc tcccatgcct cctggaagca  79260
ccccttcca tggtcaaaga aaccctgtag agagcagaaa ggagctggta ggaaatagac  79320
atcttaggtc catgtcactt acactattta gttatataga gccttctgca caagcaaagc  79380
attattatcc taatcaaagt tgaaaatgac aaatagagga cagaaatgaa ttcctagcct  79440
gcagtttcat tttcccagaa aaaaaaaaca actctgtctc ttaaatatag ggtttgtttg  79500
tgagtaaatt ggttgtatgc cccagggcct aactattcta agaaaataca tactttacat  79560
attctaaaaa taaataaata aaaattagac acagaaatgg aagtgatagg aatgtatttt  79620
ttttttctcc taaacttcaa acaagaaatc attcttttgg gaaaattggg cttgtgctag  79680
```

-continued

```
atgtttttaa tgctttcctg gcagttgcct aagaacaaaa cattatcttg tgggagagga  79740
gtaggggcac gagaatgttt aaatatgtct taatgatcta ggggtcttac aaacatctga  79800
gtcataaaaa agtcaggtca tagtttttta agaacatcta gacaaggatc agggtacggt  79860
caaaagaaaa cgcttggatt ttagtcctaa caggttccca tctctttggc actttcatga  79920
atgtgcgcag tcgttgaact tacaacccat gttgataaaa aagagaaagt atcactttgc  79980
aggattgcaa aggaggaaaa gatataatga aatcagacaa ggcctccccg cttgtaggaa  80040
tctggcctcc tccattgagg ttgcggggag taagtgtact gtagcagtta atatttctga  80100
aggtaaaatt tgatcgggga tatgtctcat tcttcacttt tatttcctct tgcttgaaaa  80160
gtcatacatc tccaggaaaa ttgctggaga atatttgcct tttctttccc tgcacaaccc  80220
cgtgccccag gacaaactca caccgcatgg gaatgaaaac ctgaactttt atgttaactt  80280
atttcaaatg ttcaaaacta gtttccacgt ttaaatttta tggtgttttt tgaaatgtaa  80340
aattttaagt gtgggaaact atggtatcat tttggaattt aaatcttctg tgggaacatt  80400
ataaaaacta ttaccaaagt ccattccttc ttctggacat cacaggcagc aagacaaata  80460
tactttaagt gcatatgtga atgcaacatc aggattctat aaaaagaata aaatagatcc  80520
agcacccacc ctctaagaca ataatgactc aggcagtgat attatagaca ggcagacaaa  80580
caaggataca gtgagaagga gttgcacacg tctggtcatt ttgtactggt attttttttt  80640
aaatgaattt tcatttggag ccaccaatta atattatggc atcttcaagc ttatgctaaa  80700
agcatgaaat tacagataaa atacacgatg gccaattaca tttgaatttc agataaacta  80760
tgagcaactt tttagtagaa gtacatgcca tgaaatattt gggttatatt tgtgcaaaaa  80820
tgtatttgtt gtttatctga aacttttctt tctttttttt ttctgagatg gagtctcgct  80880
ctgtcaccca ggctggagta cagtggcatg atctcagctc actgcaatct ctgcctcctg  80940
ggctcaagca attcttctgc ctcaaactcc tgagtagctg ggattacagg tgtgtgccac  81000
catgcccggc taatttttgt atttttagta gagatggggt ttcgccatat tggccaggct  81060
ggtcttgaac tcccaacctc atgatctgcc cacctcagcc tcccgggatt acaggtgtga  81120
gccaccaagc ctggctgttt ttctgaagct gaagcttaaa tataactggg agccctgtat  81180
ttttaaaaat taaatatttc tatttttaaa cttttatttc aataattttt ggggaacagg  81240
tagtttttgg ttacataaat acattctttg gtggtgattt ctgagatttt gctgcacctg  81300
tcacccaaac agtgtaaact gtacctaaaa ccctgtattt ttatttgcta aatctgacca  81360
tcttacatgc agagaaatag ttactgccat gacagccatc tggagcaaga ggagaaatcc  81420
cactgggccc caaaggtggt ggtaacttac tgctaattag aaaactctca cagcatttct  81480
agctgctctc tccccatgga gagagaccct cttcccagct acattctaca tcctctctta  81540
gaagtcggag tgggtggaat gaaagtggca ttggtgtttt ggtgtgatct taaagttgcc  81600
acctgcgatt attcctatca cctgagcttt cacaagtggt atttcagttc aacaaatatt  81660
tattaagtac atgctgcttt gcagaacaat atgttgggtt gagtctcttt tctcaaggag  81720
ttcagagccc caaagggaag actagcatgt ctacagctga tgctattcaa ggcaaagtgt  81780
ggaaaaatag agaaaatgca acaggattca tagagtgaga caaataagtt ctgtgaggag  81840
taggagatga gagaagggtt catggagaaa tgagtggatg aatgggattg gccagaaagg  81900
aagaatctta tgggcagaga tacaaatcaa cagctaacca tgctgagagg acagaaccac  81960
caaagagatg gaagtaagaa tgtgtggtcg gagggattct ctgttccacc ccagaagggg  82020
gtgattcatt cattcatttg tttattcagt agatatttat tgaattccaa tgcataaatt  82080
```

-continued

```
aatgtaaaac tgcaattttg taaagaacta cgtaaaagaa attcgcgttg ccatgatagg  82140
tggtgtatga ggcatgatct ggtgagggag gttggccagg gccttgtgag agaggtaagg  82200
actgaggaga atagaattag tctggtgaca agaggtggtg ggggcctggg aggagaagat  82260
ctaaggtagc tgaaacagca tgtgtgaagg ccccgtggca gaaggaagct tggggcatcc  82320
aaggaaatga aagcaagctt ggcgcatggt gggatgttag gcttgagagg cagaaaattc  82380
cttaacagac cccaaaaggc cttgcatgga tccacatagc cgctggagcc atgcgaggcc  82440
ttttgagatc tgttaaggat ttttccctta atccctgagc actatggaat cactttatgt  82500
atttaagcag gagtgtaaca aattagcttt cagtgtgaag gaatccctct ggctgcatag  82560
gaggggagag attggaaggg aaccagagag ctataaggaa actggttagg aggctactgc  82620
agaaatttgg gcagaagttg aagggacgct gtattctcct gatctccctg tatctctcct  82680
aatactattt ttttgctacg gaggaataca ggagtaacac cactaggccc ccatcagcat  82740
gcccacagag catctgggtc ttggcccagc aaagtgaaaa gaatttccca agtcactatg  82800
catggttttt gctagaggct ggtagggcat ggggcatcat aactgaacaa cagcaactct  82860
ctggagccct gaggggatat ttcaagcctc agagagttag gggaatgtag gcagattcac  82920
aagccacctg ccttggtgct tcagaaccac ctttcccatg ccaagcacct gccaaggcag  82980
ggccccccatc tggctggaat cttcccggcg agaccttctc ccattggttc ctctcctgcc  83040
aggtgtatgt gcagcaggag ggcaggatat ttctgtaata tttggcaaac ttgtggaaac  83100
actccagccc actctaacac cacagaggcg cctctgctct tgttggctgt attcaccaaa  83160
caattaccaa gaagcgtagg tggtatctct ttcacagaat ttattagtat ttaattttta  83220
tttatttatt tttttgagac aggtctcact ctgtcaccca ggctagagtg tggaccttcc  83280
ggctcaagtg atcctcccac ctcagcctcc tgagtagctg ggactacagg tgcgtgccac  83340
cgtgcttggc taattcttat atttgttttt gtagagacag ggtttcgcca tgttgcccag  83400
gttggtctca aactcctggc ctcaagcgat tctcctgctt tgacctccca aagtgctggg  83460
attacaggtg tgagccaccc tgcccggtcg aattctgata tacttattac aaaccctgga  83520
ttcaatagag cctttgcagt aggctgtttg tatcagtaga tgtgaattga tttaggtgac  83580
attctgtcct ttgtgcaaac tcagagcagc cccatgtgga tggcatattt gtaggctgac  83640
ccactctcac tcacctttca acttgactgc aggccaagcc tctcttagag aatcattttt  83700
caacctccaa tgctcatgaa tgccagaaaa cagggtaaca tttataagga ttgtaggtca  83760
ctttggcact caggccctgg aaaaatgtaa agtatggcca ttggactctt ggtcccagac  83820
caatactctt ctgggggacc atcgatcacc tgcatcagat ccttcaaatg gtggagccag  83880
ggttcctcaa ctttggcatg attgacattc tgggctggat aattctttgc tgttggagag  83940
tatcctgtgc atttcaggat gtttcacaac agccgtggcc tgcacacatt agatgccagt  84000
agcacccacc accttcagtt ttgacagcca aaaatatctc tacacattgg caaataaccc  84060
ctgggaggca aaattgcccc tagttgggtg tccctggtgt agtcctccat cctcattgat  84120
ctaatgggaa gacaaggatc tggagaggga agagagggaa gagtgccttc tgagggcccg  84180
tgagtacatg gaggcaaccc tggaattagc ctagtccagg tctgtctaac agccccccaa  84240
atagaccatg tgttctgact ttgcttcttt ttgtcagtgt tcccattcta gacactgctc  84300
cttacttgtt cctttttgtt ctaatttttt ctggggtccc ctttctcccg aggtcaacct  84360
ggaaacactg agatttgcaa agttgaattc caatgcagca gaagagcctg gcccaggcaa  84420
```

-continued

```
aactctaaac aagatgaggg ccgaggcttc tcatttctgc cttccagcag ccccgcagag  84480
tgacagaaac aatgtagatt ctgtgtgtgt gtgtgtgtgt gtgtgtgtgt gtgtgtgcag  84540
tacggcatca aggttatctt tgtctcatat cttgtctctt tttatttctt gtctctagtt  84600
atttgtcccc tactcataag cacatgtcct tatgtccatc tcttgttttt tgaaactgac  84660
tctgaagttt tcatttacag tcaaatataa ataactgatc ataatcgcaa atgatcacct  84720
tccacagagt tggaatatcc ccaaagaggc aaaggccaga agaaagagga ctctattctg  84780
ttacagccat ggaattgcac tcttgaagca cacaattatg gactcttttc taaatgaacc  84840
aaagtgcaaa cagaaggtag agaaactcaa attttatcac agcatcccat agcatactta  84900
agagttgatt tcccattgta actgcatttt tacagggctc agagcattca gttatggatg  84960
ttctgagcct gccatgtgct taccagggag gctcaggggc tgaaccaggc caccaaggct  85020
tttacatcaa catttttctc aagagctgag ccccagcacc ctggctggct ggctcttcta  85080
tcaaaggtgt gaatgctctt ctctgaattt tgcttagatt aaggttcact taatgctgta  85140
acatgtttgg tatcaagaat tttaaaggaa gtggttttgt gggttttaat gcatttttttg  85200
catttaaatt tcaggtcact cagctattgg tctgaagaag ccttttttttt ttctatttgg  85260
ccttctttgg aagccaattt atcgtctgag ttcttctcct gtaatctgaa ctacaggttg  85320
caggttctga actacctgaa gccatgcaag tcataacaca tcattactga cttctagctc  85380
tttccttcaa gtgagtgtga agctgagagg ggtcattaaa ctccccccaga gggtaatgtc  85440
cattgggttg aaggacacaa agccataaac ttgtcagaac tgattgcacc tcaaagcaag  85500
gtaatgcttg tcaagagctg gggggaaaggt tgtttattac ttcacaggtc tctggcattg  85560
cagatgttat ttctgtccta agaagagcaa gaggagctgc aatatgaaac cagaaaacag  85620
acacacttca tttctctctg ctgttggtgt tttctgggga gaccagtgga gtcactctgg  85680
gcaggactga gggggacctg ggtatatgac caagccctgg acagttcatg tgaaggagca  85740
ggacccagct tccaggtcag gagggaaaca tgcctgacct ttgtgctgct ctgccaggtg  85800
aggtgtcctt tcctctcctc acccaatggc tgcaggcagg ctgagaagcc ttgcaaaaca  85860
agaccttctg gcagcaggag ggctctttct actgcctttt cgctgataac cttgcaggga  85920
gtgttgtttt ggcaagtgaa ggtatcttgg agtgtaccct ccacctggag cctgcttact  85980
cagaaatatt ctccagttta cttaagctta aagacctttc gcttccaaag gccaacctgg  86040
aagggggcag caagggctaa tctcaagttt ttaacacagc aaatgatttc ggattcctgt  86100
aaattaagca ttggattgta tccttggaaa cagcaggacc ctgcaaaggc ttgaagtaat  86160
agggttgact ttgaagatgg gttctatcct gttccctaat accaacatta ccaaggagta  86220
ctactgtgaa taattttatt agtatgtgta ataatttaat ctgagtgctc taggcatgtg  86280
ttattattac caaaattgac tgcttataca gtggaatttt gtttgtatgc tctcaatttg  86340
aagcaaaaga aaaaaccacc ttacaaaaac aaataataca cagacaagta tagtctgaaa  86400
catattcatt cacttccctt ggagttagag aaacaaattg tatctttagg aacaatagat  86460
ataatttcta attttcctat taacagaggt aggtattgtt ttaagataaa gcaaccaaat  86520
actaatatta attagcaatt ttaacgtgta ggatgaggat attgagaatg atgccaatac  86580
tgtcaaacct tttgagagat cagattagat ggttgtctgc atggtatggt acgagtagtg  86640
cagtgcttga ctgcgccctt aacacacaca cacacacaca cacacagaca cacaccccac  86700
cacagaaaca aagatccttc tccatctgct agtctcagtg tcagaaatcg taccattagg  86760
gattcattca cttggcttat agcatatagc ctttctttta aaatacaaat aacccaaaaa  86820
```

-continued

```
acggaaatta aataactggt agtcacttac attatagaaa taattgtttt taatattctt  86880
ccaggcctag catcattggc catatataaa aaagggttca aaaatatatg ttggtataca  86940
gacaaaaata aacagagtag agaatgtaca ttgagaagct cccggaaggc cttgcaaacc  87000
tctgtcctag cacaccaaag atttcctgtg attaagaaca ctcagcatta cagtgaggtg  87060
gttaaaaaca tggtctttag aatcaggtgg aattggtttc aaatccagag tctgtcacat  87120
tagggtgtgt gcctttggga aaattaatca ttctgagtct cgacttgccc atctgcaaaa  87180
tggggttaat agtatatatt tcataagatg ttgtcacaat agacagagat gatgaatgta  87240
aagctacaga gtaagtgttc atgaaatgat gaagatcaca aagatggtga tgaagaaggt  87300
gatgacttct catcccaccc gttgtcactc cagttctggg cattgagtga atgggcttga  87360
attaaatgac ttacagaagt ggtagaagtt tagcaacatg tatgctgggt cctaagtaac  87420
ttgaagatcc tggacatctg gggtaaggat ggtattgaag aggaagatga tataaaaagt  87480
gtgttagtca cagaaatagt cacacactat ttctcagttt tctgtgggtg agtcttcaca  87540
cctactatta accattctca gtgctgaaag gatgtgtgat attgtgtgtg agcatgtatg  87600
tgtgagcacg tgtgtgagcc tgtgtgtgtg tgtgtgtgtg tgtgtgttgt aaaagaattc  87660
ttcctgggat tcatgctcca taattctcca catttgatca tgtcctggtt ggctcactag  87720
ggacaaagaa tgacaggttt tgagttgtgt tttaatgact ataaaaacga agccattttg  87780
gaaagtaagc tcacatgtgg cacaagatgt tttgtggctc ccagcagttt tctttttgca  87840
agatttgaga ggactgagca tccctgagta ccagagccgt gatgattggt aataataacg  87900
ataatgatga aaatgtacat tggtacgcat cttttccgat tatcaagcgt tttcacattc  87960
agtgtctcag gtggtttaca taacaactcc ataacataag ctaagtcagg gaagttatta  88020
actccatttt ctatatggca aaactgagtc tttggaggat aagtaacttt ctccctggta  88080
ttctgcagaa ccacaattag aacctatgtc tttgcattct tagtgtatgt taaaatcagt  88140
catagaggta aaacaataat gcttaataca ataactatcc tcccatattt ctgttgattt  88200
tcattagcat atttatgttt caattcattc attcaacata aattgagctc tttgtcatgt  88260
gcaagtcatt agaaacacga agataaatat ggcacaatca ttgctctcaa agaacaatag  88320
agttgtgtct tacctgttat aaactatacc aagtttatgc ttttaacttt tctaattcta  88380
gtgagtatga ctacctttat gggaacaatc agagagatta tatggatgcg gatcatggaa  88440
aatccagaat atatggctgt tgtgacaact tgaaccttgt ttttacctta ttttctctct  88500
tccccttgtt tttgctctgc taaaattccc aaacaactaa aagtctgtgt gcagtgaaag  88560
agcacttcgg cccagcggtg aagcttgcag accaccagac agtcattatt gctatgatgt  88620
gttagattct cgtcttaccc tgaggatgtc aaatttggaa ctcagctcct tggaataatt  88680
attcctagtg gaaacctcca ccttaaacac ctttcaaatt ccttaacttt atctgacttt  88740
ggagaatttc ttttaaagaa acagaaaaat tgagagcctt atgtattttg gaatatgccc  88800
cagtgtagaa aattgatgcc aaacatgtgc ccggacctga cttgcaaagg gctgtggttt  88860
aatgagaccc tttgctttgc agcctgctgg cccagcttct atttgctgag agttgatggt  88920
acaaaagctc tagctctcag atcgccaggg aagcagagga ggaaattagc aagaaacttc  88980
caaaaagaag gcacaaagag cctttgcttt aaagacttac tttctcggca atgtgaaaat  89040
tttggcagct gcgttagtga cagattggtg gcaacattct actggcctag ctgaacattt  89100
gctctcctta ccaccccata ccctcccaga ctgtgcaatc aagagcatgc ggtctaaatt  89160
```

-continued

```
ccccttcctgt cctaaggtgc caacacacaa cccacacttt ggagagtaga agagggaaaa  89220
cataggcttt gttcacttcc cagattctct gtgtgaagca agtttaggaa tttatgtgtg  89280
gttggaacgg ggaaatatga ctattctgga agctgtatat cagtgtggct ccacatttcc  89340
aatttggctt ccctatccca gaatagggtt cttagagaaa agcatttcca tcctcacatc  89400
tcagaaagcc aaaatagaaa agtctgagtt aaacacagta tacattcatt aaaagaataa  89460
aataagttaa agctcagtta aatacatgga aaatgggtat gtggatgaac agagctattc  89520
atggaattca ggtaaattat gacatctgct taatgtgaaa atcacaaata aaatcagatg  89580
acatttaaaa tgcaaaatca tacattaaag tgtaaattct gggccaaatt ctcacccaat  89640
acaatttgat ggaaattgtc ttatagaaaa tgagttattc aattttttc ccatttcctg  89700
atggtgaaaa tctggggtaa ccagtgtttt aacaggaaat ctaaaggaaa tgaacaatat  89760
gaccttggct aatttttaat tctgatgatt tcatgacatg catagtaatt gcatttttgg  89820
ttttgtttga ctttatttca aagctattaa atatacgttc gatgcagggg atatgttcca  89880
gataaaccat tgtttgaatg ttaaaattca tttaaatcag ataaccaggc aggattttgt  89940
agcttttttg tgtgtgtaag ggggaggatt ctgattaaat gtgaaacaac tcaaagaggt  90000
tcaagagtct ggccttcatg attaatagtc tgcagtagat attagaaatc cagacagact  90060
gaaggcaaaa tgccttctct tggtagacag actgtattct aacctccaag gactctgcat  90120
atttagccac tctcaattca actgcctttg ccagcccagg cttcattgga ttagaaagta  90180
gtggaaaaaa accctcccag gagtgatcgt ctagaattcc tttagtgttt aatctgtctg  90240
gcgcatggat ggccctcttg aactgcaggg agcacatggc agagagaaac gtcttgggct  90300
ggctggcttg tgcttggaaa gtgaaagcaa gctgttattt tcgccttccc aattcacatt  90360
cctggccttt gacatcatga ggtcattgtt tggttggctg gaagggtgtc acacgtggat  90420
aggtgccatg aggtcacatg tgcataggtg ccatttttgt ctgggacatt tacacagggt  90480
acttataacc tcttttggta gactgagccc tgttgctctc aagaaaggaa gtttgttctt  90540
agtcctaacc caaattttaa tgtatgcttc tgtaagccta catccttgca aaccttagtc  90600
aagatagaga ccatttctct cacaataatc catgtagata tcagagcatc tcttagtctt  90660
cttaggttca agtctagact tgagcttatt agctatctga acacgggcat attccttaat  90720
tcctctatgt ctcagtgtcc tcatctttaa aatagggaca gtggtagagc ctccttcatg  90780
gaagaaggga aacggcaacc atcagagttc cccggatgtg gaaggcaggt ctggggcaag  90840
gaaggagggt cagcctctgc tgccattctt gtagatggag aaggggcttt gcaaccggct  90900
acctccccac tggaaatgca gattgagccc aggggctggg cagtggcgag agggggccca  90960
acaaaagctg gactcccatc acctcctcga ggtgacagga gcatgcccag gctgcagtct  91020
gagtgagatg gcgcccccag aggaagaatc agggctctgt gaggaaccac atgccccagc  91080
atcccgcgct catagtcac tgcttgggga accaccaggg atagtggagt ggtgtctata  91140
aagattgagc aagagaaggg gtccccaaga attcaatctc tagcccagtt gttccttgag  91200
taagaaagca ggaggcagat atttaggaac gaatcaaacc tcaaggaaca cagcatccat  91260
gggttctttt tgcaaataaa aagtgtgtct tgaaaaccaa tccagccaaa taaaaaatga  91320
atcaaaataa agaactcaga aactgagagg ctgtggattc gtttaaaaca gaactgagac  91380
caaacaattt ggggagtaag gctgaaaaaa agaatttaaa ggtcacaagt aagtatttta  91440
atataactaa tcatactggt aagagaagaa aagaggttga aaaaaatatg ttaactgact  91500
tcctcatctt tcctgtcaag gagtcaacag tgaaaagcac agtttaaaaa taacaataac  91560
```

-continued

```
ttcagctctt ttaagttttt ctgtttgttt gtttgtttct tttttaagag atgggggtct  91620
tactgtattg cccaggctgg tctcaaactc ctaggctcaa gtgatcctct agccttgcct  91680
tcccaaagtg ctggggttac aggcgtaagc cactgctccc agccagctct ataggttttg  91740
cacattttct taaattatag ggacctttta agaactaata tctctagcag tgaagaaatg  91800
tccaaagttc atcagattct tcagttttca gattttttaa tctgttaatt caaggaaaat  91860
taaatcaaat acttcaagtt taaaattgca tgagtatcct ctcattattc taaatgtcaa  91920
tatgaaacta cgggataatg aatcctgggt tatttcacag aagaacttct ttgtgtctac  91980
caggctttat atctgttata tggacaagga gagataagtg gaaaaacgct caccaaatat  92040
cagcaatggt tatttctgtg tggtttcagg tgaagatttc agatgagttt taaattttca  92100
tttttttctg gttttctcga tgacttgaat attgctacag tattttctgg actttaactt  92160
attttgttct ttcaataaat ctatgcttaa agttttccag catgtatgga tggaagcact  92220
tttctctatc ctgaaagaac aattggatca attaatgtat tgtccttatg actagtaata  92280
ttggcagaaa aattgttcaa actaagactg gtcacctttt tacagaagaa aaggcaattc  92340
ttttggaggc aattcttttg gaaggaagta cttttggaga gcaaggaatc aggggagagg  92400
tgtcattggt acagatgaaa tgtgtttatt aaataatgcc ctaaagataa ctgtatttac  92460
atgtttatca cagcactatt cacaataaga aggatatgtg ataaacttaa gtgtctatca  92520
atggaggatt aggtaaagaa aatgtggtat ataaatgcaa tggaatactc ttcagccata  92580
aaaaagaata aaatcatgtc ttttgcagca aaatggatgg aactgaggcc attatcttaa  92640
gtgaaacaag ccagacacag agagtcaaat accacatgtt ctcactcata agtgggagct  92700
aaaaaaacca tgtatgcatg gacatagaga gtagaatgat tgacaatgga gacttggaag  92760
ggagaggggg tgggaaggga ggggaccaag agaaattact taatgggtac aatgtatatt  92820
attcaagtga tggataggct aaagccctga cttgtcctca gtgcaatcta tgcatgtaac  92880
aaatttgctc ttggacccca tacatttata caattaataa acaaataatg ccctaaagca  92940
gtggttctca cctgtgggtg attttgcacc cctcccccct cacttactcc agggaacatt  93000
tttccatatc tggagacatt ttggattgtc aaacttgggt ggattcgggg gagggggaga  93060
catagtgcta ttggcatcta gtagcatctg gggatgctgc caaacgtatt acaatgcaca  93120
gggcaactcc acaataaata attatttgtc cccaggtgtt aatagtgctg atgctgagaa  93180
accctgcccc aaactctgga aaaagaagcc attatataca caattccctt acaagagtga  93240
gcctggaagc agatcctatt ttagcaacga aagctaagat gctaaattta ttccttctgg  93300
ccactggaat ttttagccag gtgtatttat tattattaaa aaaaactttt ctgcttttta  93360
ttggtcctta gtcttcaact actgtatggg tttatatttg tcacctagga atgggaagtt  93420
gtaaccagtg gtctgagtct aagccaggat agttgtagtt tccaatggta ccttcagtga  93480
ccttgatgta ggggtctctg atctcaaccc tactggctga acaagccaag tcaggctatt  93540
tgaagtctct ggaaaaccag ccaatggtcc ggatcaattg cattcagcaa gaagttaatg  93600
caagaagact gggctcatct tggtgtgtgt gtagggaatg aattaccctc ctctcattca  93660
ctttaaggac catttattgc tgtgaatcag gagcaaagta tcaatagatg ggagtgagga  93720
ttgcttctgt caggtagaga ttttgctttt agcccaagag tttttatagc accatgtcaa  93780
agagaatctg cacatgctgg aattacctgc tggcttatga ttacaaacat ccctcatatg  93840
aaaatctcag catttctggc tgctgccttc aatcgctttt tctgaaatag gtatcccttg  93900
```

-continued

```
atgtcgacta tttgatttca gccagtcgtt tctctctggc agtgctccct gcaaatgtgt  93960
cctttcaaga aaacaaaacc tgcaagtggc ttgtaatgta ccatgacctt atcatgtgaa  94020
ggacaaatgg ctcttgtgct tattagatag cagatgaact gatgaactga attcttggtc  94080
tgaagctttg ataaggtcag atgtctttga aaaaaaaaaa aaaaccacca cttccttggc  94140
tgcagggatg tagttcccaa gtatcttttc ataatgcctt aagatttgta cttagacttt  94200
attttacatg gcttaagaaa tggtttatta gtaaaataga atattttgat attagaagag  94260
aaagctgggc ttttaaggct gttggagaca ttggttttca actaaataca tatgctgatt  94320
gctgcatata ttttcaacaa caatcctagg gaacaagggt atgggcaatt cattagacat  94380
agcactaatc agctagtaag aaaaaaaaat taggaagcta ttgtcaatgc ctgtggagat  94440
acgggtcttg tctgggggag aaaaatggcc tttctccagt tctccaataa actgtttaaa  94500
aaatggcctt tctccagttc tccaataaac taattacctt tgaatattat atctaaggct  94560
tataatagaa agtttatttc taagtattat gccgtaagaa tagattgaat ttaagtagag  94620
aaaagtaaaa gggggcacca aactgaccct caggcttcac cctacaacag atttagacca  94680
cagcagagtt gggcctcagc tttgctggct ctgaaactgg atgtcagtga gtcaaggtaa  94740
aaacggcatc tataatatac ttttattttg tttcagacag ggccccactc tgtcgcccca  94800
ggctggagtg cagtggcgcg atctcggctt gctgcagcct caactgccca ggctcaggcg  94860
attctccctc cttactctcc ctagtagctg ggactacagg catgcgccac cgagactgca  94920
taacttttgt attgcttttt aatagagtcg ggtttcgcc atgttaccta ggctggtctc  94980
aaattcctgg gctcaagtga tcttgtcttg gcctcccaaa gtgctgggat tacaggcggg  95040
agccaccact cctggctgaa gtcagtatac ttatagaagc attcattgaa atacaagaag  95100
aatgaaagaa cagatatata gaataagact gagtcaaaat tgttggcttt taatgataat  95160
aaagaattta ccagctgggt gcagtggctc gtgcctgtaa tcccagcact ttgggaggcc  95220
gaagcgggca gatcacctga ggtcaggagt ttgagaccag cctggccacc atggtgaaac  95280
cctgtctcta ctaaaaatac aaaaattagc ctggcgtgat ggcaggcacc tgtaatccca  95340
gctacttggg aggctgaggc aggagaatca cttgaaccca ggaggcggag gttgcagtga  95400
gccgagattg ggccactgca ctccagcctg ggcaacaaga acgaagctcc atcacacaca  95460
cacacacaca cagacacaca cacacacaca cacacacaac caatatttgg ggaaaaaggg  95520
ctaaatttat atttatttca actggcccaa atgggagaac tatatcatat cctaggtttt  95580
aacctggttt cagaggtatt taaatcagct tgaaattagg aagagggatt ttacttctct  95640
gtaagaaatt tcagtaaaaa tgaaaattaa aatgggaatt tgtgaactta gagaggtcaa  95700
gtatctgaaa tttcttatta cgtaaaagtg ctattttcct ctcgtcttaa aacatttaac  95760
aaaaaaccca aacgtttgag gttaactgca attcagtgaa gttaagccat tcactacaaa  95820
caaagtacct gttaaaggtt ttgggctgga agtgagtgat ggcagtgcaa ggtaaacctt  95880
ctaagaactt ctgctccttc agttctgctc tggactttgt ctggttaggt gacaggtcat  95940
tctagctgct gtgacaataa atttctgact ttctctggtg tcttaggcta tttagggagc  96000
tgcagagaat ttggggatga ggattgagag aactatagct atgctatttg ttttggtttt  96060
cttttgtaga gcgtggaaaa cctttatttt acaacattat taccagattt atagtcaatc  96120
tagtttatgg actatttcat tcactaaaca ctaatatcta agttgagatt ggcagagggg  96180
atatcacaga cctccttggg tatctgaata aagtatgact tttctttcca gaaaatgcat  96240
acacaaaatt gcatacaaac ttaaatacag gtttccaatt gcccttatgg ggccatgcac  96300
```

-continued

```
tcaattaaat aactcttttt ttttctttct ggtgatttct ttccttttta attcatacaa  96360
aatagatata tgtagtttct gggttgtttc ggtctgtcat tatttccaaa gataaattta  96420
gtttgtaata gtaaaatgga tcacttatta attgagttgt gccaggttaa atacccaagg  96480
gtgttctgca gaataatctc ttacttcctc tgaattaaac ctagagtaaa ccattaaaaa  96540
acaaacaaac aaacaaacaa acaaacactc ttgggcggat gcggtggctc atgcctgaat  96600
cctagcactt tggaaggcca aggcgggtgg atcacctgag gtcaggagtt gtagcacagc  96660
ctggccaaca tggagaaacc ctgactctgc taaaagtaca aaaattagcc gggtgtggtg  96720
gtgcgtgcct ataatctctc agctattctg gaggctgagg cagaagaatt gcttgaaccc  96780
aggaggcaga ggttgcagtg agccgagatc gcatcactgc actccagtct gggcaacaga  96840
gtgtgactcc ttaaaataaa caaacaaaaa atccactctc ttgttgataa acaaagataa  96900
aacactctcc tgatgaaagg ggtttgccat agggcgcttt ctcgcattct gtcaacttca  96960
attagcaagc aaagctacag tgttcattac cttagattac aaaatagtaa gtagtgatta  97020
actgtaatta aagggagcta gaattacagt atcaccaaat gcaggctatg tggtttctct  97080
ccctcccctc aacctttttt tttttttttt ttaaatgttc cagggatctc aatatatctt  97140
cacagagtga tttcttgccc ccggcttttc ctaccatccc aggaataata gcaacactta  97200
tctacctaaa ataaacaagc agacactttt atgacagctg gagaccttga acacacttgg  97260
ccatggctta tcagcctcca atgacgtagt cgtgaagcaa agaacctctt ggacccttaa  97320
ctttatcact aatagcaaca tccccagcag cctcacgtcc gcatacagga gctggcaaaa  97380
ccctagaaag cagctgctct aatgctctca tctggttcag tgaagttact taacacagca  97440
cttagaaggg tctgtttctt tccatgcaga taccctcatt agttatttac gttcagtcta  97500
gcaggacaga caaacccaaa gagacagttg aggctccaaa gagggaagtc aaagaaagag  97560
aactgcttga ggatttcagg gaaggcttct aggaggaggt aatgccttag ctgagtattg  97620
gaggaagcag aggagttaga tgactggaga agggaattgg gggtgggaaa tgcagaattc  97680
caatcccagg tgacggcaca ggcaaagagg aaccgcagtc aagtatcact ctttttggc   97740
ccattcttca agttcagatt cctttattta cttttttga gacagggtct cactctatct  97800
tccaggctgg aatacagtgg tgctatcata gctcactcca gcctccatct cctgggctca  97860
agtgatcctc ccgatttagt gtctcaagag ttggcaccac agttgccacc acacctgatt  97920
aatttttttt aaccttattg ttttgtagaa atgcggtctc attttgttgc ccaggctggt  97980
cttgaactcc tggcctcaag tgatcctccc accttggcct ctcaaagtgc tgaggttaga  98040
gaaatgagcc actgcgcctg gcccagatcc ctttgctgat ccattttccc tgcttcagct  98100
gcctttggca gaacagaaag gtctgctcag gcagtgtgaa gctggccttg ttgcagaaag  98160
atctggtagc ctggccaagt ctggtcttaa cagttagcag gtgcaatctg agctcttgca  98220
cttcttggag ggcaactttc cagcaagaga agggccagta ggttcagtct aagcagctac  98280
aagggcccag tgtggggagg gagtaaacat atccaaggaa ttgaagaaat caagataaag  98340
tcttgggcct caatggcttc atcttcatag tcctgcatta agtttacccc atacttctgt  98400
gtttggaagg aaaaatgcag tcttgacatg gcgacatcaa ctacatgtgg ctgaatctgc  98460
agcttcattc attggggaag tggtatgtca tccattccaa ggttttgact tcctctctac  98520
ctctgctccc tcctctccaa tctcagccat tttctccagc tgttgttggt aaagaaatga  98580
taaacacgca catagctgaa gtatgacaat attatacaga gctgcatttg ggcccctgct  98640
```

-continued

```
atgtaaacta ggctcatgta ttgaaaaacc acaataagca acaagacaca tcccttctct  98700
gaaagcatgt ttccgtctag ttctcctatc aagatatttt cccaagcact tcttaggtgg  98760
ccccaccaca gaagagagct gtcatatcaa aggacagccc ggtgcagaac tcgtgtgcca  98820
actcagagga ctctctccct ctgctccttt ccatgggtgc tgagcctggg gacttggttt  98880
accttttctc tcgtgctgca gatgaggatc tctgtgtctg aaggattact cattatgtgc  98940
agaaaacaaa tcaggtcttg tcactccctc cacctgcaaa tctgtcttcg tctatcacaa  99000
atggtagttc ctcttgcttt ctaatgttcc atagaagaga ggggcgactc agtacaagat  99060
gtagaattca cagtcagtac ctgacagatg ttatactttt taaaaaattc aaacaaaaca  99120
aaatgatcac cttctacttt taaggtttct ggctacatgc acatttgaac gcagcttggt  99180
ctagatttgc tttttacatt tctctttcat tgcaatgttt caaattaagg taggatgtgt  99240
gagcaaaaga aggggcaaaa gaagaaggag aacgctatca tctgatgaat ttatttcaag  99300
atcggtaact gggaaaattc tcgttttgca ctaatagtag aaggtgtgtt tcctttcccc  99360
cacctaacct cagattgctc agttccttgc ctccccttcc acctgccttg gtgtgcacag  99420
accctggagg tgtgggatga gaatggagct gcagaggagt ctccaaggtg cagaaagaaa  99480
agccatgcct gggagccgca gttggaagca tcatttcttt gttttcggct tcatcctggt  99540
cacacttcat tgcattctcc agtgtgcaaa cggagcgttg tttacccata cagatattgg  99600
gtggttgttg tttttatatg ttcttcatag ctgtttgctg gattttcctc tgtcttcttc  99660
ccagtttgat taatcacttc cctcttgacc ctgaaatcat cagcctgtct gtgccaaaac  99720
accgcctccc acagagatag ggtctggtga atatatccgt cacatagctc tgcttgtttt  99780
ccagtcttcg tgattaacag ggacaagtgg ctctgtgctg gcatctgaaa aaaagacact  99840
cctattgctt aaccgttgcc cagtttaact cacttgagga agtgatttct tgggaattgg  99900
ctaggtgaag gtttattgaa aggagtgtcc aagattatga tattgggaat taaatagcca  99960
ggcaattaac catctacttt tccttatgtg agtgtacttt acctaataga tatattcttg 100020
aaaatgtgta tccaagttga gattaaaaaa attataacta gcacagaggt atcagttact 100080
taagactctg gttaaaatga acaatttgtt tgtaaatgaa taatccctct ctaatttagt 100140
ttctataaaa acaagcattc aaaagggttg aatttgctga aagcaagggc aacctgaatc 100200
atgacaagtg ccaccgatgc tgaggtgcga acggccgggg actgcgccta tctgtgtgcg 100260
ttcacctgtg ttgccctcca cacagtcccc gcctgtggtc tagccttcta ctccctttcc 100320
ggccggcaga ttccgtcttg ccagtggctt gatatgactt catttatttg aggttgtgag 100380
tcaatgttat caagatccga attaccctgg gcattgttca tacaatggaa ggccgaaatg 100440
gacacccatg acatgtaggg caaccgtgag tagagcctca ctcaatatga gattgttccc 100500
tggaaaattc ctgtgttcac ccgacagcaa gtgattcaga tgtcaagatt aaggaaaacg 100560
actatggggg tggacaggta ctttgacgta ctctgacctc tttttatagg attggtttct 100620
tcttcattag cattttccca agtcgagcaa agaaatgttg cctacctgaa tgtcacgtca 100680
acatccaaat gtgcttttcc tctttctaat gaaagaattc agccaaaggc tgcaatgaac 100740
atgctacgag atactgtttc caggcaaaat ccaaaagttg ttttgagacc aaatcctttt 100800
tccactctct ctccctctct atgtcaagcc caagaaccag atgagaattg gagttagtat 100860
ttgttaggag ctttttggaa catacoctca tttgcacata tctcaatttc caagttttac 100920
ggaagtaata atagagtatt ttgttataaa ggggtatggg atagggctaa atgacctggg 100980
ctgtccctgt gatcagggag tgtccatgtc ttatgttctg aagggtgatg tgggccccac 101040
```

tcttcagatt cttccctgga cctggaaggg gtacccagtc acatctcact cacctggccc 101100
tcagtgcaga cagggctaca gctggtgcca cactctgggc ccctttcacc aggctgtgaa 101160
tgctgtagat caaccttggt ttctcacaag caccccctagg tctatccttg ctctctggga 101220
gtattaatgc tttccttatt tcccactaat cagttattca atcaactcgt taatccactt 101280
ctgggcctgc tgggcacaga gcactgtact ctctgttggg aactgtactc tctgctgtac 101340
tcactgtacc aagctgaata atacctactg catcacaata atatatgacc tcagacctgt 101400
tagaattgct attaccaaaa aataaagcat gaaaaaacca atgatgtgtg ttggtgaaga 101460
tgtgaataaa agaaccctta cacacggctg ggaaaaatgt acactagtac agtccttatg 101520
aaaaacagta gggaaattcc tcaaaaaatt aaaaatagga ctaccatatg acccagcaat 101580
tccattctgg tctagatata tacacacttc taggtacaaa tctaaagaaa tgaaatcagt 101640
gtgtcaaaga gctctctgca cccccatatt cattgtagca gcattgacaa gagccaagtt 101700
atggaatcaa cctaagtgtc caatggataa atgaataaat gtagatgaat aaagaaaacg 101760
caggacatat agatagtaga atactacata tcctcaaaaa aggccatctt ggcatttgtg 101820
acaacatggg tgaacctgga ggacattttg ctcaggggaa taaaccagac acagaaagac 101880
aaatacaaca cgatctcact tacttgcagg ctgtaaaaaa gtggaactca tagaagtaga 101940
gagtagaaag gtggttatga gaggctaagg ttggggagag gaggtacagg gattgaggaa 102000
atgttagtaa aaggatacaa aatttcagtt aggaggagta agttcagaga atctattgtg 102060
tgtcatggtg actatagtta atagtaaagt attgcatact cgaaaattgc taagagagtg 102120
gattttaaat atttttaccc taaaaaaatg atatatgtca gctaatgcat atgttaatta 102180
gcttgattta gccattgcac aaacattcaa aagatcatgc tgtacatcat aaaatatacg 102240
catttcttat ttgtcaatta aaatacatac atacacacac acacacacac acatatatat 102300
atatacaaaa tttttttaa aagacctcct gcatgttctc agctagtgaa tggtctagca 102360
aggaggccga catgcccaca ggcagcaagc tcagcacttt gtcaagggtg ctaggataga 102420
aacaagcaca gagcaaacag agcaggtgtg actgatgagt taatggttta cttgtattaa 102480
tgctcgttca gtataagctg caagctggga aattcttcca agccactcaa atcactcagc 102540
attggacttt tgcttttctg gtgacacatc tactcaaact gggggaggat gttcttgtag 102600
ttattggctt tgctaaagca gcacccacat taaaaaaaat gagaaccgaa gataggaagc 102660
acatgtttca acctcctcaa acgggaagtt agattctact ttagataatc actactttaa 102720
agtgttttaa tcataagaaa tcatctcaag acatcattag atactgatgg atcaatctat 102780
agtaaatttg tggagatgtc ataaattcaa aatttcaaac aatacgctag atttggaagt 102840
gggagacatc tttcagttgt gcaaacagaa acagagatag attaagaaat ctaattaaaa 102900
cctccaccaa taccaattaa aatggaaatt acctgggaga aaatgagtct tgattaagag 102960
aaatgcctgt gttacagatt tttaaatgca agttaattat tattatttag ctactactta 103020
attggcattc attctatgct agcctgcatt attggctctg tgtgtgtgtg catgtatgtg 103080
tgcatgcgtg tgtgtgcacc tgtgcacgtg tgtgtgtgcg tgcatgtgtg tgtgcacgtg 103140
tgtgtgcgca cgcgcacaca tgctgagtct tctctcctta tctaaaatgt aagttccttg 103200
agggtaggga ttgatggaat tcctagggcc tagaacaggg gtttgcaggg agtgggtaca 103260
cagagggtgc tgctgttgct gctactcacg cttttggccc acctgaaccc aaatcagtgc 103320
ttaaaattct gccaagtcaa acctcattag gatttttttt aacttcaaac ccagctcttt 103380

-continued ctggaggtcc tggttccctg attctgatgc ttttgcagaa gggcatctga gtaccagagg 103440
ggaacaggat tggttccacc ttctctcttt actcaggaga gcacagtagt aacatgtgcc 103500
aggcttccaa gggaaaacag agccaaatag tggccattat tatagcataa tgcatatgtg 103560
atgggaaaga gggattcaaa ggaatttgga aggaacataa tggaggaaca aggatgaata 103620
gttcaattag atcctggcaa aggaatagct ctttggttac aggatctgga aacaaacaaa 103680
caaacaaaca aacaaactag tgatggaaat gaaaatagag tcactgcaga gtttccaagg 103740
cagcgaagca agtgtaccag cacagtacaa gagggctctg atgcccgggg ggtgcatctg 103800
gaagtgacta attttcattt gtaatatggt gcagtggcaa agcatggggc ggaactatca 103860
cgctgcaaag acatccactg ggaaagccac cagccactct gagcaatgtc tcttgtcctt 103920
acacttaaaa tggaagctgc tggaagaaaa gggtttctgc ctctacttac accactgagt 103980
acttgatagg tagtgagact atggttttgg agagcaaatg taaacacagc caagaatggc 104040
tacttaagtc aatagtggga ggttggaaga atgaagcttt tattagacaa aaggtcaaca 104100
ttcatgagtg agaagagaga ggtggcgttt gggggtgggg aagtggtgga ggaagaaatt 104160
ccaaagcatg ttacaaatgg ggctcaggaa tgtgtttcaa ttagcaaagg aagtgagcta 104220
ggaggtctga gttctgacag gcatgggcag ggggtggaaa agagacagag gccagctggt 104280
gagaaaaggc tcagagagca gcgcgaacta gtccacaggg atgaggcacg ttgccctcag 104340
ccctgagatt ctcaaggagg ctaggacatc ttaaaaaatt ggacttttgc ccatagcagt 104400
gttgaaccat ctcagtttgg tgctaaaggt ctgtggtgga ggcacatttc ttccagcatg 104460
tgggaacttg aggggcaatt ctctttctga ttctacagcg gatgttgtgt agcgttcacc 104520
cactctaggg caatagggac tttctttggt gacttcccag ctacggaatg attagtaata 104580
gctaactcgg ctggttcttc tccatttgcc tgcctcccac ccacccagat tcattctctt 104640
tcttcctttg ccttgccttg cctcttgaga agctgagcct gagggccact tcttttccac 104700
tccctggctt ctcactggat ccagccagcg ggagggaggc tcctgcaaga ggtcggaggc 104760
tggagggaga atgggagtcg ggtgcttcct ctctgctgcc tccctgcttc tctccacagc 104820
ctcagctttc cctgggatct cataacacat cttcttcccc tcccgcttcc tgtccaggct 104880
agtcaagctt ctcactcgcc agcctctggg aaccacagta gccttgaatt gcgctctttt 104940
cccagttcgc acctctgcct ctcctccttg ttcatctgaa gcgaattctg taccctgcca 105000
gaccctgcct gtaacgctga ctgtgctgag tgttgtgacg tgccagaccc tgtccccagc 105060
cctctctgtg cactgactca ctgagtcctt ccaacactta tagatgaggc tggtgttcaa 105120
aaaggttaag atacttgctc gaggccacag agttgaggtt tgaacctagg taattgagct 105180
ctagacccca aacacttaac cactggtcct ttctacctct ctcctagctt gaggtcacat 105240
tgctgaggta cagctaagaa tgagaaagtt gcagattcga agagctcaaa atacatgcca 105300
aaggtttata cactaaagct tatttgtagg aaaatctctc agatcatatt aactcttatt 105360
ttgtgcacaa ttctaacaga taagatactg gatttcccat ctcagtggtt ctcagccttg 105420
gctactcaac acagtcacct ggggagttgc aaactgtcct cttgcctagg ccagtgaaaa 105480
cacaattctg gagatgggac ccaggagatt tcagcatgct gccaacattc agaaccactg 105540
tcctagccca cagcggcaat tactagaagg cagggattac agatggacag gtcgggagat 105600
gtaagtaaag agtagcagct gacagctaca caaagggagg ataaagagtt aaaaaaaaaa 105660
agcaggggga aaaaggttct gatctgggtt catttaatgt ctgggcaaac taccccctagg 105720 tctgcagaca tcttattatt tttattatta cattatactc attattctga gccagttaaa 105780

-continued aaatagaaat attgtcaata tacttgattg aagtaaaggc aatagatacc ttttggaaag 105840
ttgtcttcac cctaaaaggc tacatcatta aggatattct ttaatagggt gaacttgagc 105900
tatctggaag attcacttaa aatatgatat ttccagctga tctgttgatg ccaaataaat 105960
gaggaattgc tgcaggactg cagatgtttg tcagaatact cacacctgct gactttcagc 106020
agatgagaag ttcacttgct cctgattcat gctcacagat gacattttca tatttcttgg 106080
ccctaatgcg ggtgcttgga caaacactag agctccccag gccatggcaa aaacagagga 106140
cgatgccagc ggcgcgttct cctggaaacg gtccgcggca ccgggaaaag cgaaggcttc 106200
gtgtgtctca gcgtgggctg cggtctcccg gttgttattg ttggttgttc tttttggact 106260
ggggttggaa tattccaaca atctgttcct gacagaagac caaacaactt ttatttcttt 106320
cttatgtttc tcgtggctgg tcttcttgtt tacatgcttg cctgcgaaag ctgatgttgt 106380
gatgtgagga tggctcgcag gatatcaagg gtggctcagg gctcccccttt gcattagttg 106440
agaagccggg gccaggcaag gggaaattca acaattgcca ttcccactgc aaacaaacag 106500
ctctcatctc ctcccgctcc ccgcacccct gaaactccat tgctgcttat tccttccctc 106560
cagttcttca aggactctag cactgttttg cgttatctta ccttgaaaac acagatttca 106620
gcattagctc accttgaaaa caaagatgtc ccagagaaac atcgtgggtg gctcccggga 106680
aaggtcttgc agctacagcc ttgtccaggc tcagctcctg cctgggcagg attctcatcc 106740
ttggcctatt gacatttggg gccagatcat tcttcatggt gggggctgcc ttgtgcatta 106800
taggatgttt tgcatcatcc ctggtctcta ccctctagat gtcagttgca tgccttccac 106860
catttttgac agtgaaaaat gtctctattc attgccagtg tcttgtgggg gatgcaatta 106920
cctccagctg agaaacaaca tgccaagggg aagatgtatg gagaccttag ctttccaatt 106980
ccatcagaca ctgggtaccc tggggccaag gaactaaact aacatctcaa ggttgttcac 107040
tccaccactt ggctgtgagg tgtgtgggct gttgtcctct atctaaagta ttttcatgta 107100
agtgaagagt tagacctgtt ttgcatggac cctggattga ctgggaactt tccagcagtc 107160
agaactggcc aggggaaatg agcagcctga ggagtggctg gcccccacca tggggaggac 107220
tgggtgtctt ccatttgctc ctccggtgcc atctccaccc tcttctcccc tgctctgcac 107280
cccagagtct gacctgcagt tattccactg ggcggctcct ctgccctttg gcttccagtt 107340
gagtggagaa ggaagtaaag tctggacatt ttcccctgcc tctcccatcc gtacaaggcc 107400
actgtggctt ggctatgtcc ctcaaccaat ggtcttgact cctgttgggg gccccacgct 107460
tggagccctc ttctgcctcc taggcatggt gagggaggtt tccctgacac tagccctggc 107520
cactgcattg cccttggtgt ttgccaagcc ctggcctcac ttgtagctag tcctggcatc 107580
aaatcctctg agttcctgtt acattaggat aatctgagtg tgtcctgtat gtcttgctgg 107640
gatcttttct aatacaagaa gtcatgggga ttttatattg aggatacatg gaccttcaag 107700
gcctctttga acccacagat tctacgacat gcataagcat tcaatggttg ctcaaacact 107760
agcctgaaaa ggaaaacctt gtcctcttgg ctgagagata atgaatattt attcataact 107820
tcctatattt gtatcattgc tgtggaagaa agataggcat gtttagaatg cccaaatgct 107880
tgtgttgcag atggtatcag ttgttgaacc aagaactacc cttttaagtc ttctttcttg 107940
cttacagaac cctgacttct tccaccttcc tcagagcagc catgtccttt gagaggccct 108000
gggctcttcc ccagccctaa agtgtgatat cgatttctat cattctgcct tccaggattg 108060
tcgtagacat gggtgcatgg tacagttctg ggttcgttga aaagataatt atgcaggagg 108120

-continued ttgctggtaa agtttcttca ctcttagaaa gagacacaat gaaaggctat tccctttatt 108180
ccacctctgg acattggtgt gagaagatgt gatatctgga gctacagcag tccccccgtt 108240
ttttcttttg tttttatctt tttagagaca gggtctccct gtgttgccca ggctggtctc 108300
aaactcctgc actcaaggga tcctcctgcc ttggcttccc aaagtgctgg gattacaggc 108360
atgagccacc acacctggcc aacagggtgg cagagcccaa agatgaagaa atcttggtcc 108420
ttgatatgtt tgagccaatg agataaccaa cctcaggatt actctttttt tatatatttt 108480
tatttttatt tttatcttga gacagactct cgctctgtca cccaggctgg ggtgctgtga 108540
tgtgatctcg gctgactgca aactcctggg ttcaaacaat tcttgtgcct cagcatcctg 108600
ggtagctggg attacaggca cacaccaccc caaccagcta atttttgtat agatagggtt 108660
ttgccatatt ggccaggctt gtctagatct cctggcctca agtgatccac ctgcctcggc 108720
ctcctaaagt gctgggatta cagggatgag ccactgtgcc cggccctcag aattactctt 108780
ctcagagaat tatattatgt gacatcatga atgcttttat tgcttaagct atttttggtc 108840
aagatttctg gtacttgacc tgtagcacaa ggtactttaa tacatggttt caggtgttca 108900
tctcctttaa ttcagtaata aatagtagag attaaaaacg ccatctgaac ctctcagcga 108960
cttttgctca ctccctcctt ggagcatttt tacagtttgg cttacatgtt accatgcttt 109020
ccagatactc ctccgacaac cctggctgtt ccctctcact gtcttttctt ggatgctcct 109080
cttctctttt ctagcaagtc accacatggt gccagtgcca tggctttaat ggccatgcag 109140
acagtgatga ccacaaacgg aagtctctct aaccttgact cttcctctga agcccagctg 109200
tgtgtataca actgcctgct caacatgaac cctggatatc tcatagacaa tgccaacttc 109260
acatgtccag aacagacttg ctgtccctcc tccaaccttc tccatggttc tacatctcag 109320
taaatggcat tctcctttgc tataaccaat tttagagtca ttttttactt ttttcatggc 109380
atggaaccta aaccctacat cccatccttc aacatatatc acatatctgt ttcttgcctc 109440
tttgactact accttccttg ttcatctaag ccaccaatat ctctctcctg agctacggca 109500
acagctcctc gctggctgtc ctgctttccc tctggctccc tggtgatctg ttctaggtat 109560
atcggcccaa gtgatttttc taaataaggt cagatcttgt cactttcctt ctggaactct 109620
ccagtggttt catatctcgc ttggaatata cagaaaagtc gttatgatca cctacaatgc 109680
cctatatggt ttggcctttg gatgcctctc cagcgatctc tttattgcaa ccatacaggc 109740
ttcttttatt ttcctcaaac actttgagca aacttctacc ttatgacctt ggcatttgcc 109800
agtcccgtac ctggaatgtt ctactagctg cccagctgtc gcctcactca ctgttttcaa 109860
gtctctattc aaccattgca gcctcagaaa gaacatcctt aaatactcta tctaaactag 109920
cattcctggc attctccatc tctttaccct attttatttt tattcttgaa atcccttact 109980
ccttgacaac ctattacaac ctttgtgttt atttgctgat tacctgtctc tttggcttgg 110040
atataagctt tgtgggagta gggattttgt tttgttcact actgtgtccc ctgctcttaa 110100
aacaatacct gaccatggtg agagggtggt caggatttgc tgaatgcatg aatgaatgaa 110160
tgaatggctc aaatgccatc ctgttattgt agatcaggga acttgagtag aatcttggtt 110220
acagaggagg gaaaaaggca tttgagacca ttagattcca gagttttcct ctctagcaat 110280
agtcaccaca tggatgatga cctcacccag tgccatggct ttaatgacca tggcaaactc 110340
ttcttgcaag agaggaaaga tttgggatct aataatcttg aatgcctctt tcttgaatct 110400
tgagtgcttt tctctttcta ttactttaat actgtctcct acacacaaag gttaatgatt 110460
gcttttcctt caaagataat tcgtattttt atagggaaca aagtcatcaa gcacagaaat 110520

-continued ggatttccaa ttagacagat tgtgtcagca agccaggagg gagggttcac gtgtgtgtgt 110580
gcaagggtgg atggtagtag tggtgagtga tgagaggcac acagagcctt cctgggtttg 110640
gaaatcatat cacaatataa aaccagtcta gtatgtatga aaggtgatct ggtcacttct 110700
ttactctaga gaaagggcca gagttagtgt agatgcatcc ttatgaaaat gtcatctctc 110760
taaggattgc aggagcaatg aggaaatata attcatacaa tctcctccag ggttttagac 110820
ctcaagatag gccagagaga gattaaggaa gccagtagta aagctaattg tggtggagat 110880
ttgcctatca tggtgagatc ctgcatagag atgtctgaca tagcatctta aatacagcat 110940
ccaaagaatg gaatgttcct gttcagggtc aggcctttta agagcaaacc tactggctgg 111000
gcgcagtgtc agtggctcac gcctgtaatc ccagcacttt gggaggccga ggcaggcaga 111060
tcacgaggtc aggagatcaa gaccatcctg gctaacacgg tgaaaccccg tctctactaa 111120
aaaaaaaaaa aaaaaaaaaa aaagtagctg ggcatggtgg tgggcgcctg tagtcccagc 111180
tactagggag gctgaggcag gagaatggcg tgaacccggg aggtggatgt tgcaatgaga 111240
taagatcgcg ccactgcact ccagcctgag cgacagagca agactctgtc tcaaaaaaat 111300
aaaaaataaa aaataaagaa caaacagacc tacttctagc aaattcagtt cagcttcggt 111360
tattcaaaac agttgagaag catacctgaa ggtgttaacc actagtttgc tacataagcc 111420
aataatatct accctttatt ggatactcat ttgttccaaa tactatgtta agtgctacta 111480
ataataaaat caacaatgat tgctaatatt tatatattaa tataataaat ataatataaa 111540
acttgctaag atttatatat taatataact aatatttatt agttcttata tgacaagaat 111600
agttctaagt ctttagtgag cttattttat tcttatgaag acccttatga gggaggtgct 111660
agtattttct gcattaagct gatcagaaaa ctgagttcta gagagactgt gaatttccca 111720
aggtgattca gttataagtg gtgcagctgg gatttgaacc caggcagttt accttcacaa 111780
ccggtgttac gttaaactgc ataaatgtta aactcactta acattcgtga ctttaggaaa 111840
taggtgctat cgtttgcttt ttatagtccc tgcattgtgt tgctgtaaga agcctaagcc 111900
tctggtgcct ttagcttgtc agtcttgaag gggaaattga tcattttcct gacagtctga 111960
tactgagaag tgatgtactt tgaatacttt gatactgaga aatgatattt tggtgtacag 112020
ttctctgtac accaaaaacc ataaaacaac tgttgagaaa aattaaagaa gatataaata 112080
aatggagaga tataatgtgt tcatgaatcc aaagacttat atcggtaaga tgtcagttct 112140
tcctaaattg atttatagat ttgatatcac cccaatcaaa agcccagtag gctttttttt 112200
gtagaaatga acaaatcgat tctgaacttc atatagaaac acaaaggacc tagaacagca 112260
caaacaaaaa gcaaaacaaa aatcctcaaa aacaaaaatc tttataaaag aagaacaaac 112320
ttggaggatt aatactgccg gatttcaaga attgcaaaac tatactaatc aagacaatgt 112380
gatattggct taaagactga caaatagata agtggaatag aaagaggcct acacacctat 112440
atggacaact gacttttgac aaaggtgcaa agaaacttta gtggagaaac atagttcttt 112500
caacaaatgg tgctagtaca cttggatatc agtattcaaa atagtgcact tcagttcata 112560
tctttcatta tatgaatatt aattcaaagt ggatcagaaa taaatataaa acctaaaact 112620
ataaaaatat aagagaaaat gtttgtgact ttgggtaggc aaggatttct tagttaccac 112680
accaaaagca caatccataa aagaaaaaat taataaatag gacttcataa aaattaaaaa 112740
cacctgctct tctaaagaca ttgttattag actaagaaga caagccagac actggcggaa 112800
aatgtttaca atatataaat ctgataaagt aattgtagcc agaatagata agaaactctc 112860

-continued attactgaat aataagaaaa caaaccaaat agaaaatgga caaaatattt gaccagacat 112920
tttattaatg aggacacaca cagatgacaa ataagcatat gaaaagatgc tcaacatcat 112980
tagtcattag agaaatgcaa attaaagcca ctagaaggta ccactacata cctattagaa 113040
tagcaagaat tagaaggaaa atctgaccat aaaatgtgtt ggcaagggtg aggaggaact 113100
ggaactctca aacactggtg atgggaacat agttaggcag tttcttagga agttaggaat 113160
acactgatca tataatctag tcattgattc ctagattttt atccaagaga aaagaaagcc 113220
tatgccatgc acaccctttt acataaatgt ttttagaatt ttatttctaa ttgcccccaa 113280
ctgggaacaa accaaatatc tatcaaaggt gaatggataa acacactgtg gtccatccgt 113340
atgaagaata acactcagcc ataatgaaaa taaatgaact attgatacat attacaacat 113400
agatacaaat caaagtaact attctgagta taagaagcca gaaaaagggt atataagata 113460
tgtatcattt atataatttt ctggaatatc caaactgatg tatagtgaca gaaagcagat 113520
taacggttgc ctaggaatgg ggctgggggt aggaagcagc agaggtggga ttacaaaggg 113580
gcatgagaaa acttctggag gtgatggatg tgtttgttat cttggttttg gcgatggttc 113640
caccagtgca tatatatatg tcaatgttat caaaatttac tttaattgga ggcttctcta 113700
ctcagtacaa tcatcattaa tatggaactt ttcatggtta tctggttggg ctcacacaat 113760
tttttaaaaa ataaaggtgt aattacagat taaaataatt tatattttca gtatgtgtag 113820
tttatcgtat gtcagttatg cctcaataaa gctgtttaaa gaagccaagt aggctgggcg 113880
cggtggctca cgcttttagt ctcagcactt tgggaggccc aggcaggcgg atccacttga 113940
tatcaggagt tcgagaccag cctggccaac atggcaaaac cccatctcta ctaaaaatac 114000
aaaaatcagc caggcatggt ggcaggtgcc tgtaatccca gacgctcagg aggctgaggc 114060
aggagaattg cttgaacctg gtaggtggag gttggagtta gctgaaatgg tgtcactgta 114120
tgccagtctg ggtggcagag cgagactcca tctcaaaaca aaacaaaaca aaaaccaagt 114180
agttaatgtc tgtggacata ggtttatacg tgtgtgacaa gctggtatga aggtacagta 114240
gtgcacaaat ccacacacac acacacacac acacacagaa cacataaata aaaagtgtta 114300
taagggctac agataacggt cttgagtttt taggcaatat tcttcatccc cttcatccat 114360
tctcctctac gtacttttcc tacacattcc tacttaatgg tctgttgtaa agccttctga 114420
cttggtttca tgtgaaatct actgcctcaa gtgcacaagc ttccagatgg ggttggagtt 114480
gggggcagag agtagcaaag ggataaggtt aagacgctaa cccatcaccc agcaggtaag 114540
aggtgtcact taaccttcca gcttctggaa gttgaatttt gtaatgagct gtcactgtct 114600
ttatcaccta acaattactg caactgagta gggtgggata aaacctggaa aacattactc 114660
tgtcaacagc attgatatct ttgatgaagc tgtctatggc ggggtcccgg gtacagttga 114720
aaattggcac atggcctgtt aaaatggttt aggttctttc cattcctcca ctctgcagac 114780
tgctcctggc ttgtgatatg gcaattgttt ggtcagatca ctagaggtgg tcatgttgtt 114840
agaacatcct gatcttgact ttatatgtgg ctcagtcaaa attacgcagg ctggttcagc 114900
tgcagttcaa gtggcgtatg gcgtgtggcc tggggtgttg ctgggcaaca ttactgcctg 114960
tccagctgca tgccgagggt ggtgtttacc ttaaagagta caccctggtc taaggtctgt 115020
taggctcata aaagtgattt tgttggcgtg cttagggtgg agtcagcaca ccacgtcaga 115080
tataattaaa ttcgtctata caactgacaa gtagaccaga atgtgttgag gcagagctgc 115140
caatagtctc actatgtgag gagccaaatt atcacaaggt tgcttggtgt ccacaggatc 115200
agaacaagtg ctcttaatgg atcttagaat gctgctgtca atggcttgag gcactcttgc 115260

-continued

```
tcacaacagg gaacgtctca taaagggaac catacttttg gtcaacactg ccaagactat 115320
gtttttctta gatgcttcca tgtccaaggg ctttgccatc tagaggggct ttcagaccct 115380
ctgattctcc ttctttcttg cttctttggc tgaccagccc cttctgttca catacctttc 115440
atccaatcag ataacatgga taacatttca tccaatcagg cacaatgcag ccacttggca 115500
ttctgctcac tgacttacaa ccatatattc atcttcctca ttactatacc ccagatcagc 115560
aggactgaag tttaagaagt tcccacactc ttctatttta cagacagatg gatgttttct 115620
tggtttactt ccataattga ctaattgcag ccattttgtt ttactagtgt gtatgtattg 115680
aatgtatgca ttttgctaat ttaactctga aatcttcctt atgtccaagt cctttggagg 115740
tatctaacta gcttgcctct cctctcctgc cattgatttg agtccagact ttgccataaa 115800
ctaacctatg ctcagcaaac gcattcatct tattggcttc aaacaggctg ttaataaaat 115860
ggatacaata tttctgactc acaagaacaa acatttttg aagagctgga acagctagca 115920
tgaaaagaag agcttgagat gaaaaagtga acaatgaagg cacatgtgat tgaattcttc 115980
cactgtactc ttttatatct gacctgtaaa atctaggaag tgtgattata ttttgggaaa 116040
aggcagctaa attaagtaat ataattctgg tactgctata aacctatttt ctattattat 116100
tgttatttga ttttatgtgg taatattcag gttaaatcag caccatactt tgcagccaaa 116160
tggcagatat tttattttat tttatttatt tatttttgag atggagtctc gctatttcgc 116220
ccaggctgga atgcagtggc gcgatcttgg ctcacctcaa cccccacctc ccgggttcac 116280
gccattctcc tgcctcagcc tcccgagtag ctgggactac aggcacctgc caccacgcct 116340
ggctaatttt tgtattttta gtagagacga ggtttcacca tgttacacag gatggtcttg 116400
atctcctgac ctcatgatct gcctgcctca gcttcccaaa gtgctgggat tacaggcgtg 116460
agccactgtg cctggccagc agatattatt tgtatttatt ttctctccct agctgttata 116520
ggtcaggggt ggggagggta gggaaggaga gaaggagatc tcagactgtt aaataatttc 116580
tccaagatcc ttaagaataa gagaaacaat atgcagcatt taattattcc ataccagatc 116640
tccaggtgaa aatctaaaaa ttcaggcaaa aaatcctata gatatataac ctctgtaatg 116700
gtaaagtcag agtttaaaaa aataggtatg taactaactg ttccattagc acttgtgtag 116760
acggttccac gggggcaaag atgcatgcag attttcacac aggagttctt tccactcgta 116820
ttacctccag acagccttac gattccgtta aggagactcc atttgcctat ttgcctgtgt 116880
ccatttcctc attctttagc aggtatttgt tggaagcctc tgttgtttct cacatttgct 116940
cggaactatg agcaggacaa cctttcaaga catatgtttt catgagccac agcgacgctt 117000
gcaagccagg ctgataccat ccagaccttc attcccccca aaggctgtct ccacctttta 117060
agctctcttg acagaatcaa acacaaaaca caagccttag tatgtgactt ctggcctcca 117120
aataaagcat tatggggtat tctgtttcta ttttccttga ctttccccaa agtaatttta 117180
tatcccttag gagccaagaa gcatttccca taattacggt tggctactgg cacttgctcc 117240
ttgaggtatt catctgtgca gctcccagac caagaggcat tgccctggaa ctgcgggttt 117300
tgcagcagag tggtcgtcct cctcctcacc gtggagtcct gcgtagaaga gcaggaaaca 117360
aagctccagc tgtacctcga gaccaaatga gcccttttat ccattaattg gaattaataa 117420
gggtgggcaa gaggcccctg ggtgaacact gcgctgggct gtcactgact agctgtgggt 117480
aacatgtctt ccgagtctca gtcgcctcaa ctgcaaaacc ttaaaaaggg attgaaagaa 117540
aggggcagct aacatctctc cgaggcaggc actgtcagca gctgtgctca tctctacatc 117600
```

-continued

```
tccctgcttt cttcggattt aggttgatga tgcgattgag tgctagacgg tagagtgcca 117660
gtggaagtga tgtactctgc tttctagcct gctccctaac atgtcccaca cactccctct 117720
tgaagaagac ggagtgtttc acatgctgga agtgaaaggc cccgagatac tggagcccat 117780
gatggaagag acccagatcc ccgaggacag ctgtccagga gagtccctga ctggaccacg 117840
agtgagaaca gtgtgttgtg ctgagccact gagcttgtac gatttccttg ctactgcggt 117900
tcactgcagc actatcctcg tgaaggtgct ctactgggtc caaaattctg tgtatctagg 117960
gaatggcaga gcacagggca gaaatagaat gaggtttttt tttttttttt tttttttttg 118020
agacggagtc tcgctctgtc gcccaggctg gagtgcagtg gcacaatctc tgctcactgc 118080
aagctccgcc tcccgggttc acgccattct cctgcctcag cctccccagt agctgggact 118140
acaggcacct gccaccaagc ccagctaatt ttttgtattt ttagtagaga cggggtttca 118200
ccgtagtagc caggatggtc ttgatctcct gacctcgtga tcaacctgcc tcgggctccc 118260
aaagtgctgg gattacaggc gtgagccacc gcgcccggcc agaatgagat ttttaacacg 118320
agcaggaagc actccatgta aacctactgt ttaattggat attgtactca aaggtgcttc 118380
tctaaatgag ccagtgaaaa cccaagtggg cgttggataa tacttaacag atagggttgc 118440
atagtttcag tgtaacggtg cctctgtggg ttacagcacc atggtcaaaa ctggaaaaat 118500
agtttcttag aaacgaataa aggcaaacta tgggaaaatg gtcatggaag gctctctcac 118560
taagaagaag aaaactcaga atgtcttgtt attagcaaca tagatctcca actaaagggc 118620
ttactcatcc ctgcacttgt gatgtctgca tggagatggt gagtacaggg tcacctttga 118680
gttctctgtc attgtcatat ttttgctgtg ctgcttccag aatctttttc atcatgtaat 118740
cagagatagt gattaggtct gggtggttat tgatcatttg gggaaaatag acttacttta 118800
atccttcttc agaatggatt cccacagata aggttttcat ctggacttat ttttactgag 118860
tgaaagtgcc attttcaaga aacccccaaa gctttatatt ttagaataag tgaggcccat 118920
ctatgggaaa agaaagccac agaagacact gaaaaaccac atgacccggt gttaaatcaa 118980
gaaaagcgtc tggtaggcat gggaaagcct gtttaagctt cgaggtcact ttctgcatct 119040
cagctcctgt ttattttctg gaccttggtc agcgtcttct tgacagtgta atttctgcaa 119100
tgcagctgga ctttgtgacc cataatcaaa cccagaaagc cttcagcaat cccatctggg 119160
tgaggggctc cattttgttt ggttgaaatg aaaaagttaa acctccatcc agacatgcct 119220
ctttgcaggc ccaatgactc ttccaccagc aggacacttc gtctttgaat aggcttctca 119280
ttttccagac aagctcaggg gatctgcatc ctccagtaaa atttctgtct gcacaaaatt 119340
gccttttagt ggtgatttat aactcaataa aatgacatct caaaaaggag aattggtttg 119400
agtctataac tgatgtgatt tatgcatgtt ttagttttgg aatacacaga atttatgcaa 119460
tggagagagg tctctgtgat gtgatgtgca gatgtacatc cacagaactc atgacaagga 119520
gggaggtgca aatgtcctca ggcatcctct aagcacagac ctccctgggt tctaatacaa 119580
agaatattct tactgagctc agcctcaagc agagggcttc atgattttct gggtatcaga 119640
aacatccatg gaacttgcta aaattataca ttcctgggct ccaccctaga acccatgaac 119700
tagattcatt aagaatgggg tggggtccag ggatctgtag tttaacaatc tctacaggtg 119760
gttccagtca catacttgag aaaccactcc aagttgagaa acacttgtag tttgtaatca 119820
ttcactgcca atgaactatt tgctgtaaaa aggggaaggg aacaaatgct ttttaaatgc 119880
cttctttgtg tcaagcattg ttgctagaca atctaagtct atgttttttt ttttgtttaa 119940
atcttgcaac agtccaataa gatgggtatt attatattca ttttgcacag gagaaattgg 120000
```

-continued aggttcagag aggttaagaa atattagcaa acagcaagat agagatttga acccagacct 120060
ttctggcgcc acagtgcact tttccactaa cccatgttag cagcccagga ttgggccaaa 120120
tattttcgag tttttaatat gttaccctta gatctactga gagacattgt gagaaatttc 120180
tttgttttct atcccccccct ctcagcttta tcgaagcata tttgacaaat aaaaattgta 120240
tatagttaca gtgtacaaca tgatgctttg atatacatat acattgtgaa ataattacca 120300
caaccaagct aattgaaata tctgtcacct cacaccatga ccgtctatgt gtgtgtgtgt 120360
gcgtgttgag aatatttaag atctactgtg gtagcaagtt tcaagtatat attaaataca 120420
gtatttttaa ccatgtcacc atgttattta ttagattccc aaaacttgtt catcttgtaa 120480
ctgaaaatgt gtactctttg accaacatct ttccaatcct cccagtcccc caacccctgg 120540
taagcacagt tctactttct gcttctatga gtctgtcttt tttagatgcc atatataaag 120600
tgagatcatg tagtatttgt ctttctgtgc ctggcttatt tcactcagca taatgtcctc 120660
caggttcatc cacattgtca caaatgacag gacttccttc ttcttcaagg ctgaatagaa 120720
ttccattgtg taagtgtgtg tgtgtgtgtg tatgtgtgta tgtgtgtgtg tgtatcacat 120780
tttctttatc tgctcatgta ttagtagaat caacacttag gttgattcta tatcctggct 120840
attgtgaata atgttgtaat gaacatggag gtgcatagaa ctctttgagg tactgatttc 120900
atttcctttg gatatatacc cagaagtgga gttactgcta catatgataa ttgtattttt 120960
aaattttgag gaacctgcat gctgtgttcc ataacgacta taccagctaa tatggtttgg 121020
ctctatgtct ctacccaaat ctcatgttga attgtgatct tcagtgttgg gggaggggtc 121080
tggtgggaaa tgttggatca tgggggtgga tttccctttt gctgttctcg tgatagtgag 121140
taagttctca tgagatctgg ttgtttgaga gtgtgtagca cttcccccctt tgctctctcc 121200
ctctcctgtt ccagccatat aggatgtgct ggcttccctt ttgtcttctg ccatgattct 121260
aagtttcctg aggcctctgc agccatgttt cctgtaccgc ctgcagaact gtgagcccat 121320
caaacctctt ttctttataa attacccagt cttaggtagt tctttatagc aatgtaagaa 121380
cgaactaata tatcagttta cattcctacc aacagtatac gtgggttccc ttttcccata 121440
tcctcacaac acttattagt gtttttgatg atagccaact ggggtaagat gatatctcat 121500
tatggttttg atctgtatat ccctgatgat tagtgatacg gtttggctgt gtccccaccc 121560
aaacctcatc ttgaattgta tctcccataa ttcccacatg ttgtgagagg aatctggtgg 121620
gaggtaattg aatcatgggg acgggtcttt cccgtgctgt tcttatggca gtgagtaagt 121680
ctcacaagat ctgatggttt tgtaaagggc agttccacta cacaagctct cttgcctgct 121740
gccatgaaag acgtgccttt gctcctcctt tgccttctgc attgactgtg aggcctcccc 121800
ggccatgtgg aatggtgagt ccattaaacc tctttttcta tataaattac ccagtcttgg 121860
gtaggtcttt attagcagtg tgagaacaga ctaatacaat tagtgatatt gcacaccttt 121920
gtatgtacct cttggccatt tgtatgtctt cttttgacaa atgtcttttc aggttctctg 121980
cccatttatt tagccagatt atgttttatt gttattattg tatgagtgcg ttttattttt 122040
ctgactgtta acccattatc agatggatgg tttgcaaata ttttctccca ttctgtaggg 122100
tgcgagatat ttcttaagaa gataatggta agtccttcca ctcacttgag gaaagtaaat 122160
ttcagatttg tagtggacac tggggtccat gacctgacac ccccacttcag gcttagtcaa 122220
tcattctgtc agctatggaa gggttggcac ctagcagctt gcttcagagt cccctcttga 122280
gattgtcccc agctgaggca cagcacacct cctccctcgg gtggcctgtt tacagtgact 122340

-continued

```
gtctaggaag gggcataaac ttccaactac cttgcctcag ttcagacaac atggaaggac 122400
atcccagctt tggagggcct ctgtgacttg ctggggtctt tatcctgatt tcagcttcct 122460
cctctgccta atcctgcttc ctctcttgcc ttgacagttt cccaggagca ctctccacaa 122520
acttccagca tgccaatctc catctcaaaa tttgcttctc tgggaatgca acctgtggtg 122580
ttgctcaatc aaactgttcc tgtagacaca ttacacccac gttaggtgtg tgatggactg 122640
aattgtgacc cccaccccaa attcatgttg aaactttaac accaaggaac tccaaatgtg 122700
actgtgttta gagatagggt cttcacagaa gtaattaagt taaaatgagg tcacatgggt 122760
gggccctaat ccaatatgac aggagtcctt ataagaagag gagatgagga cacagccacc 122820
cacagaggga agaccacaca gggagaagat gaaggtctac aagtcaagga gagaggcttc 122880
aggagaaatc aaccctgcag acaccttatc ttggacttcc agcctccaga actgtgagag 122940
aataaatttc tgttgtttaa gcccccactc tgtgatacct tgtcatggca gcccaagcag 123000
atacaatagg cggatttaga ggttcttcgt tttgatcctg attctttcac ttttatactt 123060
aaggaacaac tcagaaatct gaacaggtta aattctcttt taagtataat gaagcaggat 123120
ggtaattctc actacatagt gttttcatat tccctacaat aggtcaggat aatcatgttt 123180
ttagagaggt gataaagaat atgcattacc tctcttcatc acatctctct gtttacagca 123240
tttactacaa acctgaggca gatgtaaata cacggtgtgg ataagtacct tggaactgca 123300
gtgaacttgc atttagtggg aaagaatggc aaaatttcct tccttccttt ctttcttcct 123360
tccttccttc ctttccttcc ttcctttcct ttcctttcct ttcctttccc ttccttcctt 123420
ccttccttcc ttccttcctt ccttccttcc tttcttttct ttctttctct tttttgagac 123480
aaagtcttgc tctatcaccc atgctggagt gcagtagcgt gatctgagct cactgcaacc 123540
ttcacctcct gggttcaagc aattctcctg cctcagcctc cggagtagct gggattacag 123600
gtgcacatca ccatgcccgg ctaatttttg tatttttagt agagacatgg tttcgccatc 123660
ttgcccaggc tagtcttgaa ctcctgacct caggcggtcc acccacctcg gcctcccaaa 123720
gtgctggtat tataggcgtg agccaccacg cccagccgat ttggcttttt ttctttagat 123780
aaactataac atgccatgcc tggctgcagg cttcctgccc taatgcaaag gtgaaaaagc 123840
tttgcagttt aatttgtttt gttttttttt ttttttggtt ttcatttttt tctgagccag 123900
cccctttatt ctttattgtc ttcagtggag caatggtaaa tgtttaacta ccagctcttt 123960
gaaaatgaaa taaaacagaa ccatcctggg aaaagaatgc tgcagggtgc cagcctctct 124020
gcagccaggg acagctctcc aggtgtgagg agacctctcc gccttcctcc tcacactgat 124080
attagtgcag ttccctcagg gcttgctttt atttgctgag gcttcttgta aggggtttac 124140
ttttaagagt atttatgagt ttagcacagg cttccccagt gaatttttct gtccatgcct 124200
tcactcatgg tgtcttcatt gtcacctctg gaaccagaaa aatcacagct taaggaagtt 124260
caggtgagtg accaagtcta gccccatcca gattcccaag gctcattctc ccaccaggcc 124320
tttcattatg ctctgtgtct ctcatcttct cccttcaatg atttctttta gctgcactga 124380
cttgactttt tatgtgctat aaaactcagg aagcttcttt tgagggctta gtacgtgcca 124440
aacacaattc taagcaacat gcatgtttaa tcatcacaaa ccctttgagg tcggtactat 124500
tctcattctc atattgtaga tgaagaaact gaggcacaaa gagggttaat aacttgttca 124560
aggccctatt actcaataga ggcaagactg ggattcaaac taggcagtat ggcttctagt 124620
ccgtattttt ttttcttttc tttttttttt tttggagaca gagtctcgct ttgtcgccta 124680
ggttggagtg cagtggtgca atcacagctc actgcaacct ctgcctctgg ggttcaagca 124740
```

-continued

```
attctcatgc ctcagccttc tgaatagctg ttactatagg tgcgcaccac tacacccagc 124800
taatttttct atttttagta gagatggggt ttcactctgt tggtcaggct gctctcgaac 124860
tcctgacctc aacttatctg cccgccttga cctcccaaag tgctgggatt acaggcatga 124920
gccactgcac ccagccccag tccatatttt taaccagcat cctacctgaa aaagagcagt 124980
aggaatatat gtatgcgtag tgtgaagtga tgtgtgtgtg tgagtgtgtg tatctgtgtg 125040
tatgaaaagt taaaataaag tttaataatg gggaaaaaa tcacccagaa gtcatgaaat 125100
taaagacctc aaaggccctt ttgactcaac atagataatt ctaaagcaaa ttaaaaaatt 125160
gaggtggtga aattatatgg tttttaggtt tagaattcca aaagttgaga atcagcatgt 125220
attggaaata ccatagaact aatgttaatt gcagagttac agctggaatg aaatactgac 125280
ttgcttcagg gaatgtttta tctccctgta tctctctgtt tttgtctcag tttagtaatg 125340
ttggctgagt aggtataaaa aatgagaaga gagacatttt ttgtttcact attcatagag 125400
aaattggtat ttatattgaa tggattgaga attcacaaat aaatatagtt tgttccagtt 125460
tggattacta atttggtttg gtggaagcct ctgaagtatc cagttctgtg acagactttt 125520
gccatagaat ctagtactag cgaggattgt taagaggtca ttaccttgac cttaaaacat 125580
cacagtaagc gggctattgt ccaagatgga cgaataggaa cagctccagt ctgcagctcc 125640
cagcaagatt gatgcagaag atgggtgatt tctgcatttc caactgaggc acctgattca 125700
tctcactggg accggttgga cagtggatgc agcccatgga gggtgagctg aagcagggtg 125760
gggcattgcc tcatcaggga aatgcaaggg gttggggtat ttccctttcc tagccaaggg 125820
aagccatgac agactgtacc tggagaaaca gtacactcct gaccaaatac tgtgcttttc 125880
ccacagtctt agcaaccagc agacaagaag ataccctcct gtgccggctc agtgggtccc 125940
acgcccacag agccttgctc actgctagcg ctgcagtctg agatcgacct gcaacgctgc 126000
agcttgaggg ggggaggggc atctgccatt gctgaggctt gagtaaacaa agtgtcacag 126060
tgaaaacaaa gaggccagga agtacaaact gggcagagcc caccacagct cagtaaggcc 126120
tactacttct acagattcca cctctggggt cagggcatag gagaacaaaa ggcagcagac 126180
agcttctgca gacttaaacg tccctgtctg acaactctga agagagcagc ggttctctca 126240
gcatggcatt tgagctccaa gaacggacag actgcctcct caagtgggtc cttgacccct 126300
gtgtagcctg actgggaaac acttcccagt aggggccaac agacacctca aacaggtgag 126360
tgcccccctg ggacgaagct tccagaggaa ggatcaggca gcaatatttg ctgttctgca 126420
gcctccgctg gtgataccca ggcaaacagg gtctggatta gacctccagc aaactccaac 126480
agacctgaag ctgaggggtc tgtaagaagg aaaactaaca aacggaaagg aatagcatca 126540
acatcaacaa aaaggacatc cacaccgaaa ctccatctgt aggtcaccaa tgtcaaagtc 126600
caaaggtaga taaaaccaca aagatgggga gaaaccagag cagaaaagct gaaaattcca 126660
aaaaaacaga gtgcctcttc tcctccaaag gattgcagcc cctcaccagc aaaggaacaa 126720
aacgggacag agaatgagtt tgatgagttg acagaagttg gcttcagaag gtctgtgata 126780
acaaacttct ctgagctaaa ggagcatgtt ctaacccatt gcaaggaagc taaaaacctt 126840
gaaaaaagat tagatgaatg gctaactaga ataaacagtg tagagaagac cttaaatgac 126900
ctgatggagc tgaaaaccac ggcatgagaa cttcatgact catgcacaag attcaatagc 126960
ctattcgatc aagtggaaga aaggatatca gtgattgaag atcaaattaa tgaaataaag 127020
caagaagaga agtttagaga aaaaaagagt aaaaggaaat gaacaaagcc tccaggaaat 127080
```

-continued

```
ataagactat aagaaaagac caaatctacg tttgattggt gtacctgaaa gtgacgggaa 127140
gaatggaatc aagttggaaa acactcttca ggatattatc ctggaaaact tcctcaacct 127200
agcaaggcag gccaacattc aaattcagga aatacagaga acaccacaaa gatactcctc 127260
aagaagagta accccaagac acataattgt cagattcacc aaggttgaaa tgaaagaaaa 127320
aatgttaagg gcagccagag agaaaggtcg ggttacccac aaagggaagc ccatcagact 127380
aacagcggat ctgttggcag aaaccctaca agccagaaga gagtgggggc caatattcaa 127440
cattcttaaa gaaaagaatt ttcaacccag aatctcatat ccagccaaac taagcttcat 127500
aagtgaagga gaaataaaat cctttataga caagcaaatg ctgagagatt ttgtcactac 127560
caggcctgcc ttataagaag agctcctgaa ggaagcacta agcatggaaa ggaataactg 127620
gtactagcca ctgcaaaaac atgccaaatt gtaaagacca ttgatgctat gaagaaactg 127680
catcaattaa caggcaaaat aatgagctaa catcaaaatg acaggatcaa attcacacat 127740
aacaatatta atcttaagtg aaaatgggct aaatgcccca gttaaaagtc acggactggc 127800
aaattggata aagagtcaag acccatgggt gtgctgtatt caggagaccc atttcatgtg 127860
caaagacgca cataggctca aaataaaggg atggaggaag atctaccaaa caaatggaaa 127920
gcaaaaaaaa gcaggggtta caatcctagt ctctgataaa acagacttta aaccaacaaa 127980
gatcaaaaga gacaaagaag gccaccacat aatggtaagg ggatcaattc accaagaaga 128040
gctaactatc ctaaatatat atgcacccaa tacaggagca accagattca taaagcaagt 128100
ccttagagat ctacaaagag acttagactc ccacacaata ataatgggag actttaaaac 128160
cccactgtca gtattagaca gatcaatgag acagaaggtt aacaaggata tcgagggctt 128220
gaactcagct ctgcaccaag tagacctaat agacatctac agaactctcc accccaaatc 128280
aacagaatat acattcttct cagcaccaca ttgcacttat tctaaaattg accacttagt 128340
tggaagtaaa gcactcctca gcaaatgtaa aagaacagaa accacaacaa actctccctg 128400
actacagtgc aatcaaatta gaactcagga ttaataaacc cactcaaaac cacacaacta 128460
catggaaact gaacaacatg ctcctgaatg actactgggt aagtaacgaa atgaaggcag 128520
aaataaagat gttctttgaa accaatgaga aaaaagatgc aacacaccag aatctctggg 128580
atacatttag agcagtgtgt agagggaaat ttatagcact aaatgcatac aagagaaagc 128640
aggaaagatc taaaatcgac actctaacat cacaattaaa agaactagag aagcaagagc 128700
aaacaaattc aacagctagc agaaggcaag aaataacaaa gatcagagca gaactgaagg 128760
agagagagac acaaaaaacc cttcaaaaaa tcaatgaatc caggagctgt tttttaaaa 128820
agatcaacaa aatagataga ctgctagcaa gaccaataaa aaagaaaaga gagaagaatc 128880
aaatagatgc aataaaaaat gataaagggg atatcaccac tgatcccaca gaaatgcaaa 128940
ctaccatcag agaatactat aaacacctct atgcaaataa actagaaaat ctagaagaaa 129000
tggataaatt cctggacaca tacactctct caagactaaa ccaggaagaa attgaatctc 129060
tggattgacc aataacaggc tctgaaattg aggcaataat taatagccta ccaaccaaaa 129120
aaagtccagg accagacaga ttcacagctg aattctacca gaggtacaaa gaggagctgg 129180
taccattcct tctgaaacta tttcaatcaa tagaaaaaag gggaatcctc cctaactcat 129240
tttatgaggc tagaatcatc ctgataccaa agcctggtag agacacaaca aaaaaagata 129300
attttaggcc atatccctga tgaacattga tgcaaaaatc ctcaataaaa tactggcaaa 129360
ccgaatccag cagcacatca aaaagcttat ccaccacgat cacattggct acatccctgg 129420
gatgcaaggc tggttcaaca tacacaaatc tgtaaatgta atccatcaca taaacagaac 129480
```

caatgacaaa aaccacatga tcatctcaat agatgcagaa aaggccttcg ataaaattca 129540
acagcgcttc atgctaaaaa ctctcaataa aataggtatt ggtggaacgt atctcaaaat 129600
aataagagct atttatgaca aacccacagc caatatcata ctgaatggac aaaagctgga 129660
agcattccct ttgaaaaccg gcacaagaca gggatgccct ctctcaccac tcctattcaa 129720
catagtgttg gaagttctgg ctagggaaat caggtaagag aaagaaataa agggtattca 129780
attaggaaag gaggaagtca aattgtccct gcttgcagat gacatgattg tatatttaga 129840
aaaccccatt gtctcagccc aaaatctcct taagctaata agcaacttca gcaaagtttc 129900
aggatacaaa atcaatgtgc aaaaatcaca agcattccta tacaccaata atagacaaac 129960
agagagccaa atcattagtg aactcccatt cacaattact acaaaaagaa taaaatacct 130020
gggaatccaa cttacaaggg acgtgaagga actcttcaag gagaactaca aaccactgct 130080
caatgaaata aaagaggaca caaacaaatg gaagaacatt ccatgttcat ggataggaag 130140
aatcaatatt atgaaaacgt ccatactttc caaggtaatt tatagattca gtgtcatcgc 130200
catcaagcta cctgactttc tttacgtaat tggaaaaaac tacttaaaag aacaaagctg 130260
gaggcatccc gctacctgac ttcaaactat actacaagct agagtaacca aaacagcatg 130320
gtactggtac caaaacagat atatagatca atggaacaga acagaggcct cagaaataac 130380
atcacacatc tacaaccatc tgaactttgg caaacctgaa aaaaacaagc aatattgaaa 130440
gggttcccta tctaataaat ggtgctggga aaactggcta gccatatgta gaaagctgaa 130500
actggatccc ttctttacac cgtatataaa aattaactag aagcattaaa tacttaaatg 130560
taagacctaa cactgtaaaa atcctaaaag aaaacctagg caataccatt caggacatag 130620
acatgggcaa ggacttcatg actaaaatac caaaagcaat ggcaacaaaa gccaaaatag 130680
acaaatggga tctaattaaa ctaaagagct tctgcacagc aaaagaaact accatcagag 130740
tgaacaggca gcctacagaa tgggagaaaa tctttgcagt ctacccatct gaaaaagggc 130800
taatattcag aatctacaaa gaacttaaac aaatttacaa gaaataaaca aacaacccca 130860
tcaaaaagtg ggcaaaggat atgaacagac acttctcaaa agaagacatt tatgcagcca 130920
acagacatat gaaaaaatgc tcatcacttg tcatcagaga aatgcatatc aaaaccacaa 130980
agagatacta tctcacacca gttagaatgg ccatcattaa aaagtcagga aacaacagat 131040
gctggagagg atgtggagaa ataggaaggg ttttacactg ttggtgggag tgtaaactgg 131100
ttcaaccatt gtggaagaca atgtggcggt tcctcaagga tctagaacta gaaataccat 131160
ttgacccagc catcccatta ctgggtatat acccaaagga ttataaatca tgctactata 131220
aggacacatg cacacgtatg tttattgggg cactattcac aatagcaaag acttggaacc 131280
aacccaaata tccatcaatg atagactgga ttgagaaaat gtggcacata tacaccatgg 131340
aatactatgc agtcataaaa aaggatgagt tcatgtcctt tgtagggaca tggataaagc 131400
tggaaaccat cattctaagc aaactatcac aaggacagaa aaccaaacat tgcatgttct 131460
cactcatagg tgggagttga acaatgagaa cacatggaca cagggtgggg aacctcacac 131520
accggggcct gtcagtgggt gggggcctgg gggagatata gcattaggag aaatacctaa 131580
tgtaaatgat gaattgatgg gtgcagcaaa cccacatggc acatgtatac ctatgtaaca 131640
aacctgcacg ttttgcacat gtaccctaga acttaaaata taattaaaaa aacccacagt 131700
gatatgacaa tcaaacttgt ttttaatgcc ttccagggaa atccttttgt tacttatcaa 131760
attatttaaa gaaagcattt cttattatat ttaccttgga acgtttgccc agaaaggaga 131820

-continued

```
ttgggctgtt cttggcttga tacggtgccc agagcttttt tatttgtgtg cagttgatgg 131880
ttgattctct gagatacaga aaacagttga tcgatctcaa tagataaggg aatttacctt 131940
ttttcatttt gagcatgagt tactctatgt gcattttctc atttcatcct ctgaacaatc 132000
ttcctgtcac cattttataa acacagaaac agagattcaa aagggtcagg tcactggctc 132060
caggtcaact ctactactaa acagaaaagc aaggaccaaa attcagatct ttgtgaccct 132120
caatgccact atgccatgcg atgatgcctg cctcttttag aggccaacta ataggtaaaa 132180
ttacatatca tttcttctac tgaattttca taaaaccttt aggaagcctt ggttagatag 132240
aaaaattgat tattttcatc ctacactcta ctccaggcca acttgatttt cttgaggaat 132300
ggccgaatgg aagttgaatg gttgaaggtg actggcaaac agagaaacaa ggcaccaaga 132360
actggctatt tccaaacgtg ggcaatcagc ttctgaatga atagttcagt gagtgtaact 132420
tccaggcttg ctcgggcacc attatgttaa gtggaataat ctatctgcat cccagaagac 132480
tgcttcccca gagatttctg gatggaatag gatgccctgt gggcatcagt gcatccatgt 132540
aaaaaattca cctaacagca aaatctggca gtctaaactt aacagtattt tccccaaatg 132600
ttagttgcag gcccgtatga caaaaaaaca tgatttgtat tattattgca gagaatttag 132660
gctgagcaaa ctggaaaaag gggaatcaca aattgtctgt ttttttctat cagtactcac 132720
ccttgtccac attttgcccc aaggaatgat gcagctctgg atgttggaaa ggacaattcc 132780
ggcgttttac tcttctgacc agtttcttcg ttttcataac tctacttgaa gaacatatga 132840
tgtttgccag tgtctgacat tacggacctc acagcttact gaatctgaaa acaggagata 132900
gagatggaaa ggttggtaag atctgaaaaa aattgagatg cttttcatca tttaagggtt 132960
gcatcatagc agctggaaaa gccaaatcca tagtcttgtg aatggaatcc atcatccatt 133020
cattcatgca atcaaagaaa gcatttatgg ggttcttact atgctttagt tggaacttca 133080
aagacacata aaatatagtc ctgtcctcaa ggatcccaca gtctcactga acaaacaaaa 133140
atacagcaca ataaaatgtt acatcatttc gggtcaaatg tgcagtgggt ctggtgaggg 133200
cacaaaggaa ggtcaatctt gggtggagtc ttgagagatg ggtagacgtt tgccagatgt 133260
tttgtatgga tagtagaggt gagagtgaaa tttccttgcc tataacctac agttttagtc 133320
ttgtcattga tttcattgat tgttttctac tctcccatcc ctgaggcccc accatccccc 133380
tttataccaa cttaatatgt taccactttt atcattttga agccacaaga tgtgcctgac 133440
tctacctctt accagcagct tgtgaaggtc actggagcca tatgcttttc ttgtttccag 133500
aaaaggagaa aaactagtgt tttggaaatg tggcttttaa atagcttaga tgcaaagccc 133560
agaatttgat tttttgggaa aaacatggac tgggctttcg gtgagttagt actggccaat 133620
ttttcactct ctttcaatat cttgcagctg taaggctgtt ttgagatggt gtgtgtgtat 133680
gtatgtgtat gtatttgtag gctatagttg gggtatatat ccttagaaaa accctgatat 133740
ttaaaccaca cggggcacgt gaatatcttt ttgagaattg gtaatgtgaa tctttgtaaa 133800
aggacagtgt tttcctatca agaataagta agaggttgtt ttaaaagggg aagcagaaaa 133860
ataagaagag tgtctggcac ataatagaag ctcagcaaaa aaattaatga acctatgcag 133920
ctgcccttag gaggaagaga agtcctccta gaactccttt ccaaacagga taattgggag 133980
ttggtctcct ttcacttcta ccaggatggg aacagcctcc tgtaatttca gtttgataaa 134040
cgcagtattt atagtcttgg ctaagagggg ggaaaaagga attttcctct gaggcacttg 134100
cagtggctag gcaaggggac acaggcccat gactcatttg ctctgcctga acccatgtgt 134160
ggttacccca gtgtcttggc cccacacagg atggagaaac aaaagggaga tttactgcgt 134220
```

ttccagcgcc ctgtctgtct attgcttctt taggtactca caccttgagg cattttaact 134280
gcccaaggtg tctgtgctta taagacaacc tctcagagct gatttgtcta tggggatacc 134340
ataaactaca gtaccagaaa ttatatatat atatatacac acacacatgt cattaattct 134400
ttactgggaa atataacaca catatagaaa actgtataaa ataaatgtat agcttaataa 134460
attgttataa atttaactgc cacccaggtc aagacataga gtactgccag gactccagaa 134520
gctttccaag agccctttcc agtgcaaccc ctctctttcc cattaaggtg gtactaccct 134580
taccccatgc accggggtct ctgtgttggg ccttgtgctt ttgggcttct ggctgtcctc 134640
cagccatgaa ctttctcaag gggaaagagg tctgtggggc caagagacca tgcccacccg 134700
agatccatgt ctccctttct agaccccgtg ccaaggacca ggacattggg acttcctgtt 134760
cagacgattc caaacctact tcctggtctt tgtgggctct tccttaagtc cttattcctg 134820
acgggggcc tggaagcaga tattcgtaaa aggccatggg tgaaggtaga cttgagggct 134880
caagagtgat acatatgagc accaaggccc ttgggttatg ggatggagca gggctggggc 134940
ataagggtag atggctgggt ctaggggtgg cttcttcctg tggcacatgt tacagcagga 135000
agacccaagc agtccaagaa ttctaaggtc caacgtggtt tctcaggtca ctatgaagag 135060
acatttgtcc aagtaggagg atgggacatc tttttttttt tttttttttt ttttttgata 135120
cgaagtctgg ctctgtcacc caggctggag tgcagtggcg caatctcggc tcactgcaag 135180
ctccgcctcc caggttcacg ccattctcct gcctcagcct cccgagtagc tgggactaca 135240
ggcgcccgcc actacgctgg gctaattttt tgtattttta gtagagacgg ggtttcatcg 135300
tgttagccag gatggtctta atctccttac ctcgtgatcc gcccacctca gcctcccaaa 135360
gtgctgggat tacaggcgtg agccaccgcg cccggccggg acatctttta tttaacagct 135420
tgttagttta atttataatt ttacaatatt tagacccata atatgcagtt ctccatctgt 135480
acttctacct taagccccac aaaaaattgt tttttgtcat gctccaagga atcctgataa 135540
tttattattt gggagaatat caggcattga tcctttgttt taaactcatg ataagaatca 135600
gataatatac attttgaagt gatgtcaaag gaaaagaata attccatatg atatatattg 135660
cagattttta tttgtatata agcaaagcag cgtctaaagt atacttatgt gtcctcaatt 135720
actgaatgtg ccagttgtct gttaacggtg ggcctgccta caggtgacta cctggactgt 135780
tctcgtcatt ccctccttag ttttctctgt gctttactat gtcacttggc actcctatac 135840
aataaagtga cttcccctgt ttttaaactt tggataaatg gatcacagca tatgatcttt 135900
tgtgtcagct tctcccactc agcattaggt ttgagcaatg catctgtgtt attgcctgta 135960
gctgtagttt gtaatttgca ttgctgtatg gtattccact gtatggatat gccaacattt 136020
ttccatccta ttaataatgt tcacagacaa ttgtgttgtt tccagtacta gcccattatg 136080
aataataatg ctacgtagat ctttatctgt ttctgttgtg tttatgtgga attgctggat 136140
gataggtttc cctccatccc tccctgcctt cctgccttcc ttgtttcttt gtgttgccca 136200
ggctgcctca agggattctc ttgcctcagc ctcctgagta gctgggacta caggctcaca 136260
gaaccttgcc tgctttgttt tcagctttaa cagaaaatac caaactgttt ccaaagtggt 136320
cgtatcaatc gatattctca tcaacaaggt ataatagctc ccattgcttc tgacaatgtt 136380
tagtattttt tttaaatgtt gaccattttg tactaggaat aacattagtg tgtcaccacc 136440
cctctaaaac atttatgggt ttttcttctc ctttatttgt atatgaagat actgaagtga 136500
atatggtaac ttggagtttc aagttgactg ctaataacat cagtagaggt atagaatagt 136560

-continued aatatcaata atatttataa taatatccat agtttttatt tgaaatatgg cagctaaggg 136620
aagattggta gtcttagaag attacagcaa taaaatccaa gatgtaaaca gagtcactcc 136680
atactgcatt ttaaagtaac agagaaatga gctgactgat ccaggggata catcgacacg 136740
ccactaggag ggcagctggt accaacctca tcctttcaca ggggtgtgtg tccccagagc 136800
atgctctgag cgttgtggca gcactgagca caaattgctg aattgcccag ctgggaccag 136860
tcaggaccac tgcagaggag ggagaccatc tggggagcct gtcagcctgc agctcattag 136920
tatggcacat ctggcagcat ctgttcctcc aggaagcagc aacagccatg cgctccgaaa 136980
gcaaggggca tgagcaggcc tcttcagcag aaatagccac agcctcctca catgcccact 137040
tccctctctg cccactgaaa cccctgagct tccctacttc accctcctct tgccaatatg 137100
ctcaacctcc ttgccgtttg tccttttaat gcattgccct ggccaaagcc cagctttgga 137160
tgaactcaac tgtttactta ctctgcatca atcgcccagc tattgagcat ggctggcaaa 137220
accacacacc ctgcagatgg tgccactgca acctcagggc caccaatgcc atctagaccc 137280
ttgttactgt caggcagcct tctgtagttc cctggccagc tcaccctcct cttctcctat 137340
ttttctaatt aaaatgagag tagattatct tctgcaatgc tacattgaat ggggcctagt 137400
ctagaaacag caggctgttg cagtttatac acagcggatg tttcaaactt tccccatgtt 137460
tttcaatgtc tctggtttta tttgctgtct ttcttctgag ccccaatctt aaaccctgct 137520
gttaacctca gtaggcagtc tccccacctg ctccacaaag aaagcaggcg ccctctgaaa 137580
tgaacttcct caacttccct cctccacatc tgcagattga cttcacattt caactcatcc 137640
ctttttcctt ccctcatcct tgtaacaata aggaaaatgt gtcctctcat gcccaagtga 137700
atccctccac ctgtcacctg ccactgaatg ccatcctgtc ttgccttcta tgggactttt 137760
ctccatatat gacctctctc ctgacttgct cccagcagtc accccttttcc tttaagaccc 137820 tgaagtcagg ttttccccta gctgactgag tccttcagct cacactcatc caggcagggc 137880
aggagggttg aattgtgtac ccccaaattc atatgttaaa ttcctaaccc ccagtatctc 137940
agaatgggac cttatttgga aataaagtca ttgcagatgt aattagttaa gatgaggtcc 138000
tactagagca gggtgggccc ctcatccaac tggactgatg tccttataaa gaggagcaat 138060
acggagagga aagctgatat gaagaaacat gggcagattc tttccttaca gccctctcaa 138120
gccaccaacc ctaccgaccc gttggtctct cccagcctcc cgagctgtga aacgatcgat 138180
ttctgtttaa gccctgcagt ctgtggtgct ttgtgacagc atccctggga aactgcatta 138240
gaattctgct tactgacttt tccatcttat gcaagttagt ttgtttccct ctctaagctt 138300
caatctcttc atcaagaaaa ggagatacag gagcacttac ctcatgagat gtttgtgaat 138360
attaaataaa aagaaggaag taacatgtta atcacagtgc ctggctgtat tagtttgcta 138420
gagctgccat aataaaatat tacagactgg gtcgggtgca gtggctcacg cctgtaatcc 138480
tagcactttg ggtcgggcgc agaagaaatt ccagttcctc cgttttcact ggtgacagtc 138540
tggtgcttgc tttctctccc tcaccaaccg ggctcttccc aacatccctt gctctaaatc 138600
ctttttccta aacccagtgg cccactttga gtctgacttt acttgacatc tctgcaagat 138660
ttcacaccat tgaccacgtt tcccctttta aatgatgctc tttccttggt gctagtctgt 138720
ctgggtgttt ctcttcacct cccatcatgg cactgagcct ccagttctgt cctcagcctc 138780
ctctactttc accacctgca gccacaactt cagtttccac ctacagcttc aggactcctg 138840
aacctgtctc tccagcccaa gcattctctc cagctggccc tggacagctc cccgtgatgc 138900
ccctctccca ccctgtgctc cacctctcca aaagacacac cccatctgtt aatccaaatg 138960

-continued

```
gatattttca gctttggtct cctctcagtg aatggcacca ccacccacac tagatgctgg 139020
gcctcatcct aatggtttcc attgtccatc ttccccatgg cctcatccta atggtttcca 139080
ttgtctatct tccccatggc tttcaagatg tcctctcgac gatgcctcct gcagtgctct 139140
tgtacctctc cattcctctc tgtccctact gctgtcatgt tcaggccact tccattctca 139200
tctggattac tgcattggcc cttgagactt ggctcatctc tctataaccc tttcttcatg 139260
ctgtagccag agctgatgtc tctaaaatgt caactgtgtc atgtgagttc ccaatctcta 139320
aactttttag tcagctaatg aaattttaat attatggaat tactatggaa atgttttaag 139380
tttgataatg gtattataat tttatattat atatattata tatatatata tatattttta 139440
aagagtcttt gtcttttgaa gattcatact gagtatttgc aggccaataa cccagtgggg 139500
tggggaaagt ggggagacgt aaaacaaggt tttccatgtg ctgagaatta ttgaagctag 139560
gtaattgata ctactctttc tacttttgaa acattctaca ataaaatgtt tttaaaagaa 139620
aatccctaaa cccaagcaaa acaaaaagta ctgcaatgtc tttcttattg ttcttaagac 139680
aatgtccaaa attcttaagg tgactcataa ggccatgcat ggtctggcct ctgtctacct 139740
gtttttcaag tgcaggaccc ctaggactta ttgaaggttt gtgaagtgga tggatggata 139800
gatggattag tgggtagata gatggatggg tagatgaatg gatgggtaga tgaatggatg 139860
gatgaataga tggatggttg gtggatgggt agatagatga atatctagat gggtggatgg 139920
atcaatgggt agatatatga tggatggatg gatggataaa tgaatagata gatggtgggt 139980
ggatggatgg atggatgaat agaaaattgg gtggattgtt gaatggatgg gtggattaat 140040
gaacggatgg atgggtggat agatagtgga tggatggctg agtagatgga tggtggatgg 140100
gtggatggat aggtgaaggg gtggatggat ggatagatga atagatggat gggtgggtgg 140160
gtggatgaat ggaatgatgg atggatggat atatgagtgg gtagatagat ggatggatgg 140220
cagatgaatg aatagatgga tgggtggatg gataggtgaa tgggtggatg gatggataga 140280
tgggtggata gatgaataga tggatgggtg ggtgggtgaa tggaaggatg gatggatgga 140340
tgagtggatg gatggatggg tggaaagaga ataggaaagg atcctatgtt cctaccctca 140400
ctctgcaagt aactttcttt gagacctttg acctctcact ctctttggat ctcagtttcc 140460
tcatttgcga cgggaagagt aaacaagctc attttttagg agaaaggtgc caattttaat 140520
tcttttatta ttttggaagt cacggtaata tttgttttta aaaattgttt cattgttaaa 140580
aaataaaaaa tttacatctt ctggattagg tgacatttca gatccttccc aactgcaata 140640
gactgtgatt atagggaggt tttacaagtt aaaacatatg gatttggaga acacacagca 140700
cagatttttc tcaaaaatcc tgatttaata aaatttattt ttttctagta aaggaacttg 140760
ttataggact tactaacaca attcaatttg taagcctttt aaagacaccc ttataaaaca 140820
ttcgcaaatt agaaaagcag gcttttcttg gaccatatgt tgagatttgg ggtttagaag 140880
tatgctcact gtccacatgg tgcaagcaag cactctacat aaacaggacc tttggatgag 140940
gagatccttg tggattataa ctgtggctgc tccatctttg ttaccccagc tcagcacctg 141000
gtgcatagta agtgctcagt aaaatttggc tttaaatgag gacgtaggat gaagaagact 141060
ctcagtgggg ctctgttaga attttcagtg ataggaaagg aaaataactt ccttccaaag 141120
aaaggagtgg gtggggagaa agctagaaat atggatgaag gaaggcgtac tcttggacca 141180
agcatgggta aaaatggcag gtcttctgcc tgtagggtgt ttctctctat agattgaaat 141240
aagcatgatt gagcaaggca gcttttatgc cccctcaaaa cagcctaggt tcctgatttc 141300
```

-continued

```
ctggctaatc cacttcattt cctacactga ggcttgtgga ccatccagtc tatgtttttt 141360
cttatctctc tttggatgtt tctctagtct gatatctgac ccaggttttc caaacttctg 141420
taactcccat tcaaccatgt gcagctggca gcacatgatg gtattcacag caggaagaac 141480
tgtggcctgc aagtcaggag acctgggctc gactctcagg tgtgcaactt caggcagttc 141540
agccattcct gagtctcagt ttcctcaggc atcaaataaa gagatcagac aaaaatgcat 141600
cctcagtttt gtatcttatt taggttataa cctggatata taattagtgg gataccagaa 141660
aaggccttta tcagttatga atattataaa ttgagtgaag ctctctggtt agcttgtcgc 141720
caaatgagta gtgtcctagg ggaatggaga ctgatctagc tctgtctccc tgatggttct 141780
gccttagggt aattctgggc ccaggatcaa tgcagccaac agaactactt cctgggctgc 141840
taacagtatc tgaagcagag gtctgtagaa actacagaat cactgacttg tcttccttag 141900
caactttatt tcctcaggct gtggagccct accaagattt tgcttgacag ttaatgaggg 141960
agtccttcta ccacgttggg attcacacag tttattttgg taggtaacta aggcagacag 142020
agatcattaa acccttcata aaacagccca tcagccacct gcttgcagag caaaaggctg 142080
ctctttggca ggaaagactg tgttcttcag cccactcttg ggtcccatgc aagattctaa 142140
tgaggttgcc tgtgaaaact ttttggttat gatatatttc tttccatttg tataaaagca 142200
accaataaat accagtgatc ttgtcaggcc atgccaaaga agaatttgtt ggggatttaa 142260
tatcccaatg cattggacat acttgaattt ggctgaacag ccaaattggg tggtttggct 142320
caatttaacc agtttaaatg ttgttggtgt atagctttgc aaatgacttt ggttcttact 142380
gaatgatcac tggaggggat tggcttataa atgaattcaa aatcctcagg tgtgttttaa 142440
agatctacaa aacaagtctc tcctttgttg taaatgggca agactcaata aagagagtga 142500
gatgaaaaga gctattagtt catctgttag ggcatccaaa tatgcaccca gaaggcatag 142560
caacaaataa ttcatgcttt aacatgttct acaaacagca aggtattcca aactactgcc 142620
aaccacctga ccaggaaaaa gggcatggtg gtgatcatga aataattgag ggtaaaaggc 142680
agggttataa gtcctttaaa cccttttgag cttaggtaat gtcttgctgg gcacgtggct 142740
ctgattcttt ctctggtctt tgccagcaga tttttaggaa tctcctggca gaagagcatt 142800
gtttgtggca ccttccactt ctgcagcact cttggatgct gactatttac aaggactttc 142860
aactgcctcc ttcacccatc tggtattaat ttttatttct tcgttattga gtctctgatt 142920
catctctacg cagacctttg agtttcctga aggctttgct tccccagaca gggtgcccca 142980
cccaagtaag ttcacttgct gtttgctttg aggaaagtca ggatctagag ttccccagct 143040
cagagaacaa gactatgact cactttatca tcaaagtcag gatggagagg atttccttca 143100
tctcccttta ctctcactcc cacgtctgat cgtctcatgg gtaatggggt cttggcattt 143160
ctagcttgta ggatctccca gctcccttca ttctgtcctg tgtctccatc tcagttgcct 143220
ctgtcttagc tcacagtctc tctcctggac tgttgcaatt gtcttcatat tgtatcctaa 143280
aggcaatggg gtaggcttgg aaatgctttc agtgggaatt aactcgatca cattttcttg 143340
cataagaatc acactgaaaa tagtcactaa ttcattgaag gggcagttga aatggaggtg 143400
gagagaaatc cattataaag ctatactcca gttgagaatt ataaggaagg ttcggattaa 143460
gctggagaca gggacagtga agaggagagg aaatggatat ttagcaagga gaaccgaaag 143520
agcatagtaa ctgatttgaa ttacaaggtg ggagacggag ccgttggtaa taaatgtctc 143580
ctggataaaa cctctggaga ctgcatggat gctagtatca ttctgagaaa gaagaaatta 143640
agaattaagt ctacgggga aatggtgaat ttgaatgcgg catgttaagt tccagtttca 143700
```

-continued

```
tgtggagact atccaatggg gagagaatct gtaagcagtt atatatccca agtctgagat 143760
tcagagagag agaatgttga agacagagat tttatagtca tgagcctaga gctggcagtt 143820
aaagcaagag agcttataac atctgccaga cagagcttgt taaatgagat agggggccag 143880
gcacggtgac tcacacttgt aatcccagca ctctgagagg ccgaggcggg cagatcacct 143940
caggtcagga gtttgagacc agcctggcca acatggtgaa accccgtctc tactaaaaat 144000
acaaaaatta gctgggtatg ggggtgcggg cctgtgatcc cagctactcg ggaggctgag 144060
gaaggagaat tgcttgaaac tgggaggtgg aggtagcagt gagtactcca gcctgggcta 144120
tagggtgagg ctccgtctca aaaaaataaa ttaaaaaaaa aaaagataga taggaagatg 144180
gtaggatcct ggggactatc actcctagag ggccgcacag agaagagagg cctgaaggag 144240
agattcagga tggtgcgtta ttacacaaag aacagaggaa agaacttgac aattagatta 144300
tgcagattct tgagatcagt ttcaagaaaa tgatggggac aggcgccaac tgccgctggg 144360
ttgacttgtg aatgagagat gagaaactgc agacagtcta gacttctctt tctagaaact 144420
tggctgtaaa gaaaagatga taaacgggaa atgggtgaca gcatgcgtgg ccagtgcacc 144480
cgagaacagg aaggcacacg tgatagttaa ttctatgcgt ccacctgact aggccacagg 144540
atgtccagac atttgggcaa acattattct gggtgttctg agggtgtttt gaaatgagat 144600
taacgtgtaa atcagtaaat tgagtaaagc aggtggccct cccgatgcag gtgggccttg 144660
ttcaatcagt tgaaggcctg aatagaacaa aaaggtggac cttcccctga gcaagagaga 144720
aatcctcctg cttggtcgtc tttgaactag aacattggct ttttctcacc tttggactta 144780
aatggagata tcagatcttc ctgggtctca aacctgctgg cctttgtgct agagctatgt 144840
gatccgctct cctgggttcc agagcctcag acgcagacag gaaccacacc atcagctctc 144900
ttgggtcccc agtttgccaa ctcattctgc agatcttggg acctgcctgc ctccatgatc 144960
acatgagcca agttcttaca agaaatcact ttctaaatat atatgtgtat cttattggtt 145020
ctgagaaccc tgagtaatgc agcacaaaat ggaaaagaaa agagaaaaat agaaaagaag 145080
gaaggaagga ggggtgagag gaaggtgtgg agcgggggat gagaaacaca gcctctgtgc 145140
tttgcaagtg tggggagacg gcgggtcact gcatcattgt ctgtgatcgc tgacggcgtt 145200
gatgactcac tcatgttaca taattagaat tcaccttcag actttgctgt cttaccattt 145260
cgtctcatag aaacaaggct tcctagcttg gcttgttttc ttgttactca ggggctgttg 145320
ctagcataag gtcatactta gaaagctgaa ccctcaataa gattactcag agacttggca 145380
gctttttccc tggccatttt gtctttaagt taaaaaaaaa caacagaaaa cagctcactc 145440
ttctaaaatg acattacaca tcactttgaa atatgtcctg taggccagcc ctgaaatgta 145500
tggtctttct ggacattcat tggagagaag ctctgttttt aaaaatgtaa aaaaaaaaaa 145560
ttgttttact ctaaaagagc gtctctgata acccagtttt taggaaacta ttggctgaaa 145620
agaaacaaca ggagaggtga gaatttgtcc agtttatacc taattcattt ctgccattat 145680
cccattctgg gataacttca gaaaccacga gggccattta accaagagat ttattgggcc 145740
ttagagttca ttatgtttct gccttgtttt tataatgctt ttgttataat attaaagtga 145800
caaagataaa caactttatt tgtggttgtg cagatgccat gtggaatatc tgctcggctt 145860
gaaaagattc ccctggctct tctgcccact cagaacagcg ggacccacat ttcagcttgg 145920
acaacatgac caagctctgc tgttcacagc tgcctggccc aggctgggtg cctggcccca 145980
agttcagggc caacgccctt ttctgggaat ggggaatcaa agcagaaaag catcctgtgc 146040
```

-continued

```
actcacactc tcacacaccc acacactcac atgcacactc acatgcacac taacatacac 146100
acaagtctca cactcacaca cactcatgca ccctcacata cagtcacaca tgcacactca 146160
cacactaaca tgtacacaca cactggtaca cactcacact aacaagcaaa taatcacaca 146220
ctcatgcaca cacacactaa catgcacact cacactaaca tgcggacaca cactaacatg 146280
cggacacaca cactaatatg cactcacact aacgcacaca ctaaccatgc acactcacac 146340
tcacacacac acacactaac atgcacactc acacatgcca cacactaaca tgcacacata 146400
cacaaacatg gacactcaca caaacatgca cacacaaaca tgcacactca cacactaaca 146460
tgcacacaca cactaacatg cacactaaca tgcacactca cgcacactaa catgcacact 146520
cacacactgg tgcacacttg cactaacaag caaatacact cacgcactca tgcacactca 146580
cacactcata cacactaaca tgcacacatg cacacaaagt ctgtctccaa ctgtgaattt 146640
ggtcactatg agcttccacc tttacctgtt gtgaggattg aatagaagag aggaaaaaaa 146700
tatttcaaga aagaagatcc aaatagaagc agcaatgggt gacaggccct gtatccttgg 146760
ctgtcctgtg gtctcccagc tcctggatgc tgtccctcct gggagcacgg ctgcactcct 146820
gcctactgta ccatgagatg tgtccttctt cttacagtga ccacgccctg ccgctctttc 146880
tcccccagtc cactgccaag ctgagttgaa ctgtattttg ttactcacag tcaaaaaaat 146940
cctaattcat taggttacga ttttaaaaat aaaaatatat ctttcttggg ttgtatcata 147000
aagaatcagg tttgagaatt ttgatggttg tggcttggga agtgagaggg ggaacctggt 147060
cttctaatta aataaccttc tatactctct cgcctttttc ttatcccagg aaagcctcag 147120
gaacttgttg caatagggac tgccaggtcc cgttgcacta ttggtggaag agaggtccac 147180
acggtgccta cgataagcga tttgttcgta tctatccaga ctgcaggtgc atacagccac 147240
tcatcctcaa atgccatcct caggagttta tgctgcacac agactggcac atgtgcagga 147300
agacatagtg cagggctacg tgctacaaca ttgttggtga cagcaacata ttggaagcaa 147360
cctgaatttt tgttaataga ggattggcta cataaatgat gctaatctat acaactggag 147420
tactatgatg ccataaaaaa gaatgtacaa ggtctttacg tttggaaaga tctctaagat 147480
ataatggtga gtgaaaagtg taagatgcag agcactgtgt tttacaggct gtcatttggg 147540
ggctgacaac atctattcaa atgtgctttc atatatattg aaagcacttt ggaaggaaaa 147600
acatcaaatc agtaccaatg gtttacttgt gtgtatgaat gtgtgtatgg caggggtggg 147660
gtgggggtag gtggcttagg tacaagacag gaatagcaaa gagacttttt aaccatatac 147720
ctcttaagag gttaaaaaaa aaacctgttg aagcatgtgt tgttaaccat gacagagaga 147780
gagagaatga agggagggag atagggaatg aaagaaaaag agggagggaa atggaggggc 147840
aaagaaagga aggaaggaag aagggaggga cagaaggaag gagggaggga aagaaggaag 147900
gagggaggga aagaaggaag gagggaggga aagaaggaag gagggaggaa ggaagggagg 147960
gagggaggga attggctctt tcctgaagct acagcttaac aaataaaagc gaaggccacc 148020
agcagcgatg gtttgagagg tgaaggatga cgtagtcatg actccgagag ctgaattccc 148080
tgcgcatagt gtgagtgaaa acctgtgtgc gttacatcac agaaagctat tcaaaatgcc 148140
gtgagcccag tgaggtctgc aggacagaca tacaattgct tgcaaacaag tagcaggaca 148200
atgagctttg tttcgtgttt atcggcagat tttctttgcc tctcaaggga gctgggagaa 148260
actcaagtct gaaactcaaa ctcatctcag tcattccttt cccttcaact agacctgaac 148320
ctcaggagat ctggagtatg tgctgaattc tactgggaac tgagccctct gaatattatt 148380
attgttttgc taatactttt tgctggaaag tacatcaaac caggatgtgt tgtacctctt 148440
```

gctttgccag actatttaaa agcaaaagtg accagatatc caacttaagg ctgatccagg 148500
tttttcatga tctagccagg ggagacaaac cttccaggaa agtctctagc gaaggccaag 148560
gattttagaa agtatctgtg aacaaagaaa tgcaatgtta gtgggctaat ttccataatc 148620
aaatgaagct gatgcaagtg ctttgtgaat tgatgcccat caacgagaga ctggataaag 148680
aaaatgtggc acatatacgc catggaatac tatgtagccg taaaaatgaa caagttcatg 148740
tcctttacag ggacatggat gaagctggaa atcatcatcc tcagccaatt aacccaggaa 148800
cagaaaacca aacaccacat gttctcactc ataagtggga gctgaacaat aagaacacgt 148860
gaacacaggg agggaaacat cacatagcag ggcctgttgg tgggccgggg gcaagggaag 148920
ggagagcatt aggacaaata tctaatgcat gcggggctta aaacctagat gacgggttga 148980
taggtgcagc aaaccaccat ggcacacgta tacctgtgta acaaacctgc acattctgca 149040
catgtatccc agaacttaaa aaaaaaaaga aatgctttgt gaattagtca ggttcactga 149100
tgggagcttt ggtcctggca cctgaggact gagctggggg aacccacacc caggctgccc 149160
aaacacacag aggcaggaga ggtcaagggg catctcgtgg gtgtggagtt ttggacacgg 149220
tattgccatt gtcagacatg tggctaagcc tgcaaggatg agagaggaag gaggaaacca 149280
gctcctctca accctgcatc agcctgagtg ctttcaatct ctctcaaccc ttctcctctc 149340
ttttctcttt tctccttccc tccttccctg atggtttgcc aggaagcaca gaataatgga 149400
gttcagtgtt actcaagggg cagtcacctg cacagtcatt accggaatga cgtgtttcat 149460
cagatgtttc aaatcccgat tcttggggcc tgctctaaac ctgcctacca aggctctagg 149520
ggcgaggcct ggggacctgc attgtttgca aacacccaca ggtgattctt acatgcacga 149580
agccagggaa gcattgatag aaaaggtctt agaccagcag ccaaaaaacc caagttcaaa 149640
tccatttact acctgggtgg tcttgggcaa gttacttatt aattcccggc atgggagtca 149700
atactacttt ataggaattt tttataagtt ataggagata cgctgttatg ttataggagt 149760
tatttttttc tctttgaaga ttaaaagaga caaaacatat gacaaggctg gcaaacattg 149820
agctcttgct acatagtagt acacagtgcc ctagagagtt agcaaaggga cggtgagctc 149880
acaaaaatct ttgtaggcct caggatatat atattttgca gtgactttca aggctgatct 149940
aactctcttt ggatgaacac agagcaagga gacttgccca ctgagtgact ttactatacc 150000
cccaggcctt actaacttgc ccaggagtgg ggaatatagt gctagaagga agccaaagca 150060
ataaagagac actttcagaa aagcaggcac tgcaaagaca accattccag ctggaagagc 150120
atgtggtggg agtggcgtcc tctcagacat gatcctctgc agggctcatg ggctcaaagt 150180
cacaggttct caccaagggt gatgatttcc cacagggagc atctagcaac gtctggagac 150240
atttttgtca cagggtaggg aaagggggtt gctactagca tgcagtgaac agaggccaga 150300
gaggctgcta aacatcctac ggtacactgg acagtcttcc acaacagaaa actgtctggc 150360
cccaaatgtt catggtttca aggctgaaaa accctgctct aagctaatgc agaagactta 150420
gtcatgggtg atagaaggag gcccctaggt ggctacaaac ctctgaggga cagccttccg 150480
ctgtggtgtt gcaaagtctc ccagttgcac aaggtcctgg cgtcctgctc attggtggat 150540
caccattaac caccttgcac gtcacatgtt caacatagct agtttcccac ccattcttaa 150600
cgatgataaa tcaggaaaag cattcttaga acactagaaa agcagaagtg tggctctcta 150660
cagggcagcg gggaggttgc ctcactccta gaagatgtct tgtttttacc aagagggtag 150720
agggatgaga ggagctggaa gaccacgctg aggagccacg tccagacaca tgaaacgaac 150780

-continued

```
ctcacagccc cacaaggatg ccggggaggg cactcagtgc ttgggatcag agccacgtgg 150840
ccactggttt ccgatgcccc tttgctagta tctggcttcc gtgattccct tgccttcatt 150900
ttgtggctct ctcctgacac tgccggctga gtgtcttagt taaccagtaa tctggctttt 150960
ctccctccac tttgatcttc ctgtctctgc ctgtctcctc tttcctggca tggcatgtgc 151020
tctcgggctg tacctctggt agtgaatctc tggctgccct ggactcctgc tgtgcacact 151080
gccctgtgtg caggtctgga tgcctggtgt tccttctcag tgcaccgccc gatcccctgg 151140
gatctcttca ccattttcat gcatggtgcc accccacgtg cagggccagc ttcatggcac 151200
gtcacctgtg tgcttgcata ggacttggtg ctcagaagga cttcttgatg ggtttcatgc 151260
tctgcggcca ccgtattaaa attgtaataa tttcctcttg aaacttgtat tttgtaagtg 151320
acttctgatg agacagcatg gaatgagcag aaacacagga gatacgtgtg cctgtccttt 151380
cttgtcaccc tattcacatg gagcattcgc catgaactca gaattctggt gtattcacaa 151440
tgtgtgggag ttcatgaagc ttctaagtga ctcccaagtg tgttttgtct atgactgagt 151500
tagctgggga gggggaggga cactgacagc cctgagaggc cacactttcc atttgaaaac 151560
caaaacttgc ttcaaacaca aaggcagcag tggtattcta agaaacacat atgaccaagg 151620
aaacttggtt tgacctttct tactcatgtt acttctttgc atttgcaaac aacttaaact 151680
gaaaatgaag acacagaaag aaatagaaag ataaggcaac ccataggcct tttttaaatt 151740
cttccttact tgtcagtaag ccaaaggtag agagcattga tagaacgtgc atgtatcagg 151800
ccgggcacgg tggattacgc ctgtaatccc agcactttgg gaggccgagg tggtggatca 151860
cctgaggtca ggagtttgag actagcctgg ccaacatggc aaaaccctgt ctctactaaa 151920
aatacaaaaa ttagcagggt gtggtgccgg gtgcctgtaa tcccagctac tcgggaggct 151980
gaagcatgag aatcatttga acccaggagg cagaggttgc agtgaactga gatcatgcca 152040
ctgcactcca gcctgggtga cagagaggga ctctgtctca aaaaaaaaaa aaaagaatgt 152100
gcattattga gaagcgaaat aaaagcattg aattagtttt gtgcagcatt ttccactgtt 152160
ctggtaagaa tgaaatatgc aaattgcatc atttggaaca atttagcata caaattaaat 152220
gctcttatat tttcgtttaa agctggcttt gcacaatata aagatgaatg gtaagattca 152280
tgctaacaat ttaaaatttt aattttcctt tacttagagt ggcattaaat agcgaataag 152340
aatgatttta aaagccttgt gacaagtcaa aagagagact gcagaagaaa aaaagcggct 152400
tttattttag tacctttcac agcagaggtt gtttttgttc ctgcttttga aaaagggctc 152460
ctacattttc ggtttgcact ggcaaacctt ttaatgaaac agtaaagcaa agttccttac 152520
attaaaaagg agtcattttt aatctcccag tctacataga cccaattttc attttaacaa 152580
gtttcttggc tgggtgcaga ggctcaacgc ctgtaatccc agcactttgg gaggccgagg 152640
cgggcggatc acctgaggcc aggagttcga gatcagtctg gccaacatgg cgaaaccccg 152700
tctctactaa aaatacagaa attagacagg tgtcgtggca catgcctgta atcccagata 152760
cttgggaggt tgaggcagga gaatctcttg aaccctggag gcggaggttg cagtgaaccg 152820
agatcttacc actgtactct agcctgggca acagagcaaa aacctcatct caaaaaaaaa 152880
aaaaaaagga aaaacaaaac aaaaaaaacc ccaagtttct cccaagtccg ctggactttg 152940
ttatcagaag gtcttatgag ccgggtattt agctctgctg tgagttcaaa gcaacacagg 153000
aataaagcac agctgctgaa cccaggtcct ccctgctcat gattatagct tgctgtggga 153060
ctccaccaaa attgcattct gtgtttatgg catctaagaa attcttgaga gtggtactga 153120
tctaccaatt aaacacactg gtatgtttgg ccccatgtgg cagacaagga aaagggttta 153180
```

-continued

```
cattttctta tgggaaatat tttctttctc atgcttaact tttattgttc acagaggttt 153240
tcaaagtatt gccaaagtct atgaacacca ttctggagtc acctggacat tctagacttt 153300
cagagcggca tgggtggtgt tttacattgt attttttttct atccagtgtg gattcatatt 153360
ttttaaatca taaaaattca ccagcttccc tctgcccctc ctggcctttg tcactgagaa 153420
cacaggagca catgggtggc tgtctgaggc ttgggcaagg ccctgggctt gcctggggcc 153480
cagctgcccc tgccccgtac catcttcctt ccccctccac tcaggaacaa aaggtcccac 153540
ggttcaggcc atctggattt ggagctgtca tttatagtcg cccaaacttt gaggatgact 153600
tacttgtgaa aacataagag atgcattcag ataggagaaa caattttgag aaccaggaaa 153660
aagagagaaa gaggtagagt tgtgtggtga gaaaagggat gaattggcag ttggagactt 153720
gggttttagg tagagtgacc atgtaactta ttaatcaaac tggatttctt ttgagagcga 153780
cagggattcc tactggtgat gatgctggga caacaggagc acatagggac tgtactggtg 153840
tggcatggcc accatagttc tagggcatta atcatccaac tgtcagcaag tcacttaaca 153900
tctctgggcc tcaacttttg aagaaagaga caatcggact acaatttcct tagtcctttt 153960
accactaagg acctcttact aatctctctc cacagtcttc ctgatttcaa aattatcata 154020
tcaattaggt actgagtgat atataatgag tgcaagttct gtcaatcaga acttttgtca 154080
gcattgaaat aaccagttat tgcaccgcgt tcatacagtt ttaggcaaaa gaaaacttga 154140
cattttaata cacctgtgag tcctatttaa agtacatcga acagttctga caccatttta 154200
gaaaatgata atagcttttg agtcccctcc agtatcttca cagtcaatag acctcgaagt 154260
ctggaggttg aaagccacgt tactcgatga tctgttggtt tatatccagt tctagtcttc 154320
tctgatcacc tgataacttc agtgcctcat gctataaaac acagacagag aaagacgatg 154380
gaaagtgaaa gagggcctgc tggaagtcag aagctgccgt ccattaatgt gggtccagca 154440
agagggcctg tgtgaagatg ttagatgggg aggcaatccc tcatgctagg gtgcctggac 154500
aaagtttctg cagagggaaa agaggatgct ttgccttggg gcaaatttcc tcctggctta 154560
agtcgtctta atccacacct gggagaattc ttagggtgta ttcacaacat taggagatca 154620
acagggagca ggaatggaac agctgtgcaa cagctatctc tttgcttctc ttccacttat 154680
atgagctcac cctaggggga aaatggacag tcaaaagcct tccacagatc aataacagtg 154740
ggtaaatctg aggtctgcag aatcaaagag tgaaataaat aaagaacagg cctgctgcct 154800
gctcccatgg gtagtactag cattctagtt tctgtggcaa taagcttgca atgtgctcag 154860
tgggggcagt gccacccacc acgtggtgcc tgggagtgcg tgcattggtg ggtggatggt 154920
tgtgacaatg accagaggag gacaccactt gcattctgtg ccctgttgtg tgctggagac 154980
actcccataa ggaagattca tcccacccaa aatgtcaaaa gtatctccac tgagaaacgc 155040
tgaatacaag aatgggcttt acattcatac atatcaggaa ttacttggat cctgtaacag 155100
ggttaaaata atcctggaca acttcctatg gtgccagacc cttgggcaga acttccagat 155160
gaagcagatt gattctaatt gctcctggat aaaagaaaag agcacaggtc atcccagaag 155220
gcactgggca acccacccca agcctaacaa tatattaagt gttgggtgta gggatggctt 155280
ctcttttctc tcaaacttga cagcactgtt gaatcattgt cttcatttac ttatgagatg 155340
attggcattg tcctttaaag cagaacaact tgagctaaag ctaaaggccg gtgtgcagca 155400
gccgggtgac cctttgtctc tactttgcct tccgtgctaa gtgttgactt ctgctgagtt 155460
tgatttcatt catttcagct agacatgtct ggtgaataaa cttcttacca atcttcccct 155520
```

-continued ggaatggttg agtcagctct ggtgtgagtt agtggcccca gaggggagca ggccaagacg 155580
ccctctccat gagatacctc ctaaaaggga agaggtcatt gatgacccac aaaggaggcc 155640
aggaccataa acatttcaga attcagttgt cttaaaatct taaataatga caaacatttg 155700
cttgtttgag ccttttaagt cttcccgtct ttggacttga gccccagtgc ctggctgcag 155760
aattccatgg tgaggcacaa gcatgacatc atgttcagga ggaatgcaca gcacataaag 155820
tcttgcctgg gtcagagaga agtgctaagc cctcaagagg gccctaagac aaatgcacaa 155880
atatggccta gcacatgtca aacacccgtg caagggcaaa catctttatg actttggtcc 155940
tgggaagaga gacccggctt gggattagaa attacagctg acaagctgct gatgaggcag 156000
taatgacatt cagcgtggga atggtcactt tgggaactgg gagcttagca cactaggctc 156060
caagtctcag agtgaagccc ggggcaactc cttcaccttg gctggaataa gttaactcac 156120
cccacaacct gtcccccagg acctttctct gccttccttt ggggttatag gcttccctgc 156180
agttctttag ggttttgacg cacaggacaa tttaacatca agggaatgcc caagttgggg 156240
gaagaatatc tttcttggct ataaatgtta ctctgaaatt cttctcaact gtaatgtttt 156300
aagagcactt acaatgtgcc tgacctgccc tgtgcaatgt ccctcccctc ttagagctta 156360
caactcataa gcacgcttgc agatgtcctc cctgatcccc agagctccag ccaacttcag 156420
tgtaggggtc ccctagggga catttagcaa tgtctcgaga tgttttttga ctgccacaac 156480
tgggtggggg gggcggtggc tgttactggc atgtagggga tagagaccag ggaggcttct 156540
aaacatccta taatgcacag gacatcccca cccccaacaa agaagaatcc agtccaagat 156600
ggcaatagtg ctaagcctga gcaaccctgc actggggagg gccttgcctt tgcataagcc 156660
aagaaggaaa ttacttagat ttgcaccatc caatggggag cttcctgtga gaccagaaat 156720
gatcagtatc tgtgctgtcc gatgtgggag ctaccagcca catgtggtta ttgagtgggt 156780
caaacgtggc cagtgtgact gaggtagtga gttttttatt ttatgtaatt ttaattaatt 156840
aaattgtaat cgtcccatgc aactggtagc tactctgtta ggcagcacga gtccatacag 156900
cgggagctta gatgcactga gatcacctgc cccctagtca gatgtccttt ccactggttt 156960
atgactgaga atccaaagtt agacactcct tctttagcta agactttaac ccgtgttggt 157020
atgacattat ctgtgggagg gagaagacct ttaacttgta aagagctgtt gctaatttaa 157080
tatgactaac ggatctgaaa gatattttgg cgggaacaga gagcactaag aggcctaggg 157140
taaaaaacag gaccccgtga gaatgaccag ggggtaagct tggggagggg ctaactagga 157200
tacactgggg gaggtggaga cataggctag acgtagcaaa ggcaaccagt gctttctttc 157260
ctcatataca ctctgctgag actggaagcc aatcactcag cattctcatc agactcatgt 157320
ctgtgaaaac cagagccaaa gagtgccagg aaagacaagg tccgtgacaa agggcagcct 157380
gtttcctgct ttttctcttc ctccttgtgg cttttagtct aagtccccaa gcactgaaat 157440
attttggtgc ctcctcccat atataaaccc agattaaagc aatactaaac cacaaaacat 157500
aaaatgattt ctttttatca gttataaaat tctggataag tccatgaaag cctcattgtt 157560
ctgactttgg ctggcacccc aagcaagtaa gcaccttgtt gttaacctag cactgcttta 157620
gggtctgagt attagggctg ttttctccgt aatccgttgt ttatctagtc tattgtgcaa 157680
attttcacaa atggaatatt gtgtagatac tctactctac agactctaga gaagaaagtc 157740
agcaacctca cctggtaagc tccacctacc catgtttcta gagaggggaa aaaatagctg 157800
aaacaaatca aaccaaaccc aaaatgctct tttcctcaat gttctgcagg gctcaaatgt 157860
gagcttctgg tagtatcggc tttggtgatc tccatgggga acagtggaga ctgatctcaa 157920
acagtgagtt caccagaatt atggcagtga aggggaactg cggtataaga attgctaaaa 157980
agataaaaat tgttctgtcc agagagacgc aagttgagag agatgtaggg ctgagagaat 158040
agatagttgt gagcatttac tcctccacaa atcatgagtt tttctgaagc aacagggtga 158100
ggcgggggtg gggggtgtgg acaggaaggt agataaattt aaaacagtaa aatagtaaaa 158160
ggaagtatta tataaaacag tgtggcggtg gtgggagtgg ggaggagata tgacttaaga 158220
attttttatc ccaacgctaa agggtgcaaa aataaaaggg ttcaaaaaat gtttaaatgt 158280
aaaatgacag ttccataaca aattattgac tggaggaaac tgaagatgtt taaagctaat 158340
ctcatgagat tagcatagga ggtgctccat ctccttccaa aaacgacccc ttgccattct 158400
ccaaaatgca acacttagac ctgcctgatc atgaatcttt gggtttattt catatggcca 158460
cacttgttgt ggaataaggt caattaaacc tcacgggtaa gtttgcaatt aactgacatt 158520
tgacataagc agcttttacg ggttggtgct gaaacaggct gagaaacaca atccctccct 158580
gggtagaact aggagctttc ctgtggcagc agcaagccca gacatacaga gggctggagg 158640
ggagctgtag ttcaaatgca gtaatagctg tttttaaact gatccgctct aagtctttga 158700
gtgcaatggc tgattattgg gtcaacaaac atgaaaagca ttgtcattgg cccaagtttg 158760
aaccagaagc aacatgtctt tcatgagcat ttaggatgaa agatgtaaga ttagaaaaaa 158820
atgttggtaa cagtgagcat catttgaggg tctttgtaat gtgtgttttg ccctaagagg 158880
aaaagtaagg caagatctat gaaatgtcct tgatcttttt gcaacctaga gttgtaggcc 158940
ctgcattacc ttcatgtttc catttcaaga actgccaggt ttgttttcca atgaaacttt 159000
caactgtcag cttaataaga ctgtgaccat gtggtgcagt gaacaatggt tcaaggacta 159060
cttcactgag tgtgaatttg actacattat gcctattctt aaaatcctta aaattcatca 159120
atggttctcc attacctcca agactgggag tttccttgct aggatgtacc actctcatct 159180
ctcgcctcac attgcgctac gtccgcttct ccaaatgctc caagttctct tgtaacacca 159240
cagccttgca cgtgccatgc cttcatttta gaatcataca tgccttctct acaaaaccat 159300
cctaagcagc tcttgaatta gatgctcctt tgcactctgt gcttaacttg tttacagcac 159360
acgtcgtgtt ctatttgagt gacctcccaa ctaacctgtg agattccaga agctgggtga 159420
gtgtgctctg gaactgattc ttctgctaga tgctgagaac atgtgggcaa tggcacgttc 159480
tcagcatcta gcaccatccc aggcacaagt ggagcagagg tagatctgtg cttgatgatt 159540
gaatggatga gtttcagtga actgtgaatg atggggagct tttcaacaaa gccacactcc 159600
atgttttctc ttcagcagaa taaatgctgc atagaagcgg ttaatagtcc cccttatgtc 159660
agctcagcac atagatatat gaggagtccc acggtttccc ataagccaaa taagacaaag 159720
taaaagcaat aatggtccat acacttcaga aaaaggaagg aaggaaaaaa ggaaggaagg 159780
aagggaggga gggagggagg gaaggaagga aggacaattt tcccatgagt ctactgtcag 159840
tgaaagctat tatttaaata gcattttttt ccgaggcttt gtctatcagc acaaagaaga 159900
aagtgaaata tattgggttc catccatgag attaaaagag gaacatcttt cagttcccaa 159960
tcaatcaaaa gacacaggtt gtgtttcaat cagaagccat ttctgaagag gcacaggagc 160020
gtaggagagt tgtgttaggc aatggaaacc aaactgagcc tgaaatgaaa gcctgggtca 160080
attagtcagt ttctttccca atatctgccc taacattgtc ttctaagttt ttggaaatga 160140
atacgcttta ttattcacct cagctggatt tattgtgcct cacaggtatt gactcctctt 160200
gctcttcctc ctctcgctat ggaaagactg agcagaggaa gtgctcggac aggcatgccc 160260

-continued tcccagaatg caagaaagcc atcaggcaag cggcaggtgc agagaccaca gccagggcca 160320
cacagcctgg agagggactc cctcctggca gggaaggctg tctctacttg ctcctctctg 160380
agaatgctca ccaggtgtgg ctgggggttt tggcagcctg cagctgtgtt taggagggca 160440
tttgctttat ctaccacatc ctttgaggat ttcattgcag gccattttat ccactttaat 160500
gaatgttctg gcagcttgtg aacctggggc tgtgtctgca tgccctgaac agtgcttatg 160560
ttcaccatcg ttgaggttga atgtaacata tattcacaga tccttctgcc acctcctttt 160620
cacaagatgg accctccagt tctggccaaa acaagaagaa agctgtaaaa agaagggctt 160680
tagcccaaaa gttggggttg ctcagttttt ttcctttccc tcatacccca tcagctaatt 160740
aatcacctcc tactgcaatt tataattcct taacagtttt caaatctgtc ctctagatta 160800
gctaaataaa tatagcacat caatcaaaaa tcaagttcta taaagttact aatagggaaa 160860
tatataaagt ggaaaaagct gtttataaaa gtctgagtaa atgactatat atgtacatag 160920
atatgatttt gaaaagaact taataggata cacaaacatt aataagaatg cttatttctg 160980
agtaattaag gggcgatttt gttgtattcc ttatacattt taaatgtttt aatccaaaat 161040
tttttacagt gagtatgtat tatcttttgt catctgaaaa ataacacaaa taaataagtt 161100
aaaatagaat taactgaatt tgtacaaatc ggggaagata agggtgcccc tgttttctct 161160
attcatgcca ccgctaccac tgtttagact attggtcata atttttttct cacctgcaaa 161220
tatctccttg cctgttactt tctcttcagt ttctttcccc attattcatt ctctctgaaa 161280
atattaggtt ggagcaaacg ttaattgcat ttttgcattg ttggaatttg ctgtttgata 161340
ttggaataca ttcttaaata aatgtggtta tgttatacat cattttaatg ggcatttctc 161400
gctttatgtt tttttgctaa tgacttacta cttgctgttt attttatgtt tattttagac 161460
tatggaaatg atgttaaaca aaaagcaaat tcaagcaatt ttttaattca agttcaaaat 161520
gagttgtaaa gcagcagaga caactggcaa catcaacaac acattcggcc caggaaccac 161580
taacaaatgt acagtgcagt ggtggttcaa gaagttttgc aaagaggacg agagccttaa 161640
agatgaggag tgtggcggcc agctgttgga agttgacaat gaccaattga gagcaatcat 161700
taaagctgat cctcttacaa ctacacgaga agttgccgaa gaacttaaca tcgactgttc 161760
tactgttctt tggcatttga agcaaattca aagggtgaaa aagctcggta agtgggtgcc 161820
tcatgagttg actgaaagta aaaaaaatca ccatttggtg gtgttgtctt ttcttattcc 161880
acacaacaac aatgaaccat ttcttgatcg gattgtgaca tgcaatgaaa agtggatttt 161940
atacaacaac gagtgatgac caggtgagtg gttggaccga gaagaagctc caaagcactt 162000
tccaaagcca aacttgcacc aaaatatggt catggtcact gtttggtagt ctgctgccag 162060
tctgatccac tacagctttc tgaatcctgg cgaaatcact acatctgaga agtctgctca 162120
gcaaatcaat gagatgcact gaaaactgca gtggctgcag ctggcattgg tcaacaaaaa 162180
gggacaaatt cttctccaca acaacacccg actgcacgtc atacaaccaa tgcttcaaaa 162240
gttgagcgaa ttgggctaca aagttttgcc tcacccacca tattcacctg acctctcgcc 162300
aaccgactac cacttcttca agcatctcaa caacttttg cttccacaac cagcagtgtg 162360
cagaaaatgc tttccaagtg ttcattgaat cccaaagcac agacctttat gctacaggaa 162420
taaacaaact tatttctcat tggcaaaaat gtgttgatag taattgttcc tatttgaatt 162480
aataaagatg tgtttgagtc tagttataag gatctaaaat tcacagtccc aaaccacaat 162540
tccttttgca ccaatctaat atatttcaaa gaaggaaatc tgaccaagtg gctcctctaa 162600
atcttccagg gtttcctgga ggataaagaa gtcccaaatc ctcaggctga agataagctc 162660

-continued

```
cttcagaagc tcgtctgcac ttgagattta cttccaactc ctgtctccat tcctggtaac 162720
caggagtctg tctgggctcc cccgcttgag acacgacatg ccccaggact cccttttccc 162780
tagtcacctc ctcctgccct cacctccctc agagtcagcc tttcacagtc atctcttatg 162840
acacttctca tagggcacct tccttggcat cgccaagtgg agttaacggt tttctttctg 162900
ccttggtcat ggctctacat ttactatact atagtgatat aattatagcc atgtgccact 162960
tgacgatggg gacgtgttct gagaaatgca ttgttagatg attttgtaat tgtacaaagt 163020
gcatagagtg tactcacaca aacccagatg gtagagccta ctacttaccc aggttatttg 163080
gtctagccta ttgctcctag gctacaaaag tagacagcat gtcactgtac tgaatattgt 163140
agtcaatggc aacacaatgg taagtatttg tgtatgtaaa tacttcctac ctaaacatag 163200
aaaatgttca gtatgaatat ggatataaaa ggtaaaaagt ggcacatctg tatagagcag 163260
ctaccatgaa tggtgcttgc aggactggaa attgctctgg gtgagtcagt gagtgaatgt 163320
gaaggcctcg gacattaccg tacactactg tagactttat aaatactgta catttaggct 163380
acactacatt tatcaaacaa tttttcttac tccaataata aattaccctt agcttactat 163440
aacttcttct actttataaa cttaagaaaa attaaaactt ctttactctt ttgtaattaa 163500
aaagaaagac actagaacac gtattagcct agccctacat ggggtcagga tcagcagtat 163560
tgctgtcttc cacctccaca tcttgccctg ctggaggatc ttcaggggca atgacataca 163620
gggacctgcc atctcctaga atgccttctt ggctgggcgc ggtggctcac acctgtaatc 163680
tcagcacttt gggaggctga ggcaggcgga tcatgaggtc aggagtacga gaccagcatg 163740
gccaatagtt gaaaccctgt ctctactaaa aatacaaaaa ttatctggac gtggtggagc 163800
atgcctgtgg tcccagctac tcaggaggct gaggcagagg aatctcttga acccaggagg 163860
cggaggttgc agtgagccca gatcatgcca ctgcactcca gcctgggtga cagagtgaga 163920
ttctgtctca aaaacaaaaa caaaaacaaa acaatgcctt cttctggaat acttcctgaa 163980
ggacttgcct gagactgttt taaagttaat ttttaaaaat aaggagaaat tgtacactct 164040
aaaataatga ttaaaagtat actatagtaa aaacaaacta gtaaaatagt aattcactat 164100
catcaaatat tatagactgt acacaattat atgttgtggc aatgcagtag ttttgttgac 164160
accagcatca ccacaaacat gtgagcaatg cattattatg tgatgttagg atggctacaa 164220
tgccactagg tgataggaaa ttttcagctt catcatagtc ttgcgggacc acggtcctat 164280
atacggtctg ttgttgactg aagcatagtc acttagtgca tgcctgcatt attttatgtg 164340
tcttttctcc acctgaaggg caggaggatg ttctgtccaa ctccgtccct ggctctcagt 164400
gcagtatcgg gcatcagtag gtgtttaata aacattgctg tgtgcacatg cctttagctg 164460
gcatggatgg ggagggaaga gcaggggatc tgagttttgt ttcatggatt tatcgctcca 164520
acaagctgtt gttcttagtt aagcaagttt aagctctctt ctttcctcag aggatggtag 164580
tgcgttaaaa aatattaagg ttttcaatca taccagcgtg tattcacttt atacatctcg 164640
ggcatgagga gatgcatgtt actatctgtg cttcatagac acatagcaaa aacctcccct 164700
cagtaagcag tttaactctg ggtaagtgtc ccttggtgtc atgagttgag tgctgtcccc 164760
tccaaattct tatgctgaag tcctaagccc cagtgcctca gaatgtcatc ttatctggaa 164820
atagggttgt tgcagatgtc attggttaac ctgaagtcac tagagcacac ccctaatcca 164880
atgactggtg tccttataaa agtggaaaat ttggacataa acacacatgc acacaaggac 164940
agtgacacat gaacatgaaa gcagagatta gggtgatgcc tctacaagcc aaggaatgcc 165000
```

-continued

```
aaagacggcc agcaaacacc agaagttagg agagagccac aggttctccc ttgcagccct 165060
cgaaaggagc caatcctcct gacacccttg atctcagcct tttagtctcc agaactggga 165120
gacaataaat gtttgctgtt taagtcactc agtttgtgtt tttgtttttt aacaacagcc 165180
ctagcaaact aatactctca gggaccctta agtgaagcat cagaaagaag cactttatcc 165240
taaatctccc ttattgaact atcattttga aagccatcat ctgggatgat tctggagccc 165300
tttgcaaatg ggaaaggaat ggacgcattc cagctctttt aaaaattaaa ttaggctgag 165360
cgcagtggct cacacctgta atcccagcac tttgggaggc caaggcaggc agatcacaag 165420
gtcaagagat cgagaccatc ctggccaaca tggtgaaacc ccatatctac taaaaataca 165480
aaaattagct gggtgtagtg gtgtgtgcct gtaatcccag ctacttggga ggctgaggca 165540
ggagaattgc ttgaacctgg gaggcagaag ttgcagtgag cagagattgt gccactgtac 165600
tccagcctgg cgacagagcg agactctgtc tcaaaaaaaa aaaaaaaaaa ttaaactatg 165660
gttgttattt tcttttttcc tattcttttt taatttttc aaccgagaaa taaaactatc 165720
tggatctagg tgcatataca aataaattca aaagatatag actgaaacat aagtctcctg 165780
tttatcttta ttttcagtcc cagctaccca atttccctcc cccagaggca tcctttgtgt 165840
gtgcaacctt atgtatgtgc agatgtacat ttcatttttc tcataattgt catacactat 165900
ataattatct atatattgca tttatcactt tattataaac attggagata actattaaaa 165960
taccaaacat gcctcattct ttttgatgac tgcatagtat ttctttgata gatatatttt 166020
ctgcctattt aaaatacatt ctcagctgac tttctcaatc aaaacaaaca gcatttccaa 166080
ggtaatcact tctcagcctg gatgaggctg agcctttcca ctgctctctc cctcattaaa 166140
taaatggata ctctttttct acttgaggta gttagatatg cctcaacctc tatgaaaacc 166200
tacttttctc atgttttata caggtgtggc caaagtggag cagcttatgt ctgttgtgca 166260
actggtgcat cctgccccac cagatcatat ttcaccaagt ttttctcctc tgatgagcta 166320
tgctaaaaat gatcaattgg acacatgtta tgccagatga aatgtgagac aacattcatt 166380
aatcacaacc tttgattagc gtattcattg ccttcctgtg acctgtgggc cattattcac 166440
tttctcaatt ctgctgcact gagatttcag gacttgactg ggttctctct atttgcattt 166500
ctagaacctt tcttaaattc tcatagaaac aactgggaaa tgcttcttgt taaacaagac 166560
tgtgcttgca tttgtcatct aatttccaaa aataagttaa taaagccatt cagctgtacg 166620
gtaatgatat cctacttctt atggttgatt ccaaatgtga gcttaagggg ataataacca 166680
tgttgaactc ataattttc actttgaatt taagaagctc tttaaacatt agtgatggcc 166740
gcaagttcag gtgaccttca gaattccctt ccctttccac agtctctgta tctaatccat 166800
tcttcaaacc ctaactcatt gcctctcaat agtcttcaaa gatctcctca gcctgaatga 166860
ataacgcctc agccttccct ccttatgcaa gagctgacag catggacctc tacttggctc 166920
taatttcctt cagtcttgtt tttgagatat tttttctatg ccagttgcac atatctcttg 166980
agaatcagaa ttgagtgtgg taccctttat tcacagagta gatcaatgtc aatgtccaca 167040
gggtacagta ataatcatca gacattcagc ctctcagata gtaatagtta acatttgtag 167100
aacgcttact tcatatgcac caggtataat ttagagaatt tgacaggaat tatatgcacc 167160
aggtataatt tagagaattt gacaggaatt atctcattta atcgtcataa tatcttttat 167220
gtaataggta ttcttattat ttccattgta tagaaataaa gaaagacagt tgaagtcact 167280
tgcctaaagt cacacagcca atcagacttc agatgatgtg atcttccaca ctaaggtacc 167340
tgtctcctcg tgagccccaa actctaggaa atgaataaaa actcagccat cgaccttgaa 167400
```

-continued

```
taattcagaa ttttaattag atttgcaagt ttagtcaata gattctctca atggccttct 167460
aattcagcac cctgcttttg tcctggaggt gtttccaaga gctagtgtga ttctgttaaa 167520
acctaaatca gttcttggcc ccaaactttc caatgacttt tcatctcact agagtaaaag 167580
ctagagtgca gataatggcc tatgaagcca aacagtgtct ttcccaccac catgcctctc 167640
tgacctactg tcctactctc tctgtcctta gctctcgtgc tcagccatgt tgcctcccta 167700
ccgttctaag tcaggcaggc atgcttctgc ctcccaccct ttccattgac gtccccctgt 167760
ttgaaactct cttcccctag ttagttatcc cacaatcttc tttggattat gacctgaagg 167820
gacacttctc aggctactga ctgtgatgga atgactagtt tcagactatt tcgtctcctg 167880
taaacaatta gaaaacagga caaggtatgt gaagcaagat agttttcaga caatggaaaa 167940
taaacaacac cagactgcaa aaatggggag aggggagtgt gaggtgagcc ccacagtagt 168000
ccagctgtct gcctggagac ttgagtttga gcagagcaca ggactcttgc tgggctgaag 168060
aggcagggat cagaatctga ggcaactgaa atagctggaa tctgtgcaaa gacaaagccc 168120
tagaagtcct tgcatgcgta tgggaagccc ctccctcagt ccacggctga gggcttgact 168180
gtatatgtgc agggaaaacc atcagaggct tgccagatgt cagctgctat gaggttgaga 168240
ctgaaacagt ataacagagg ttgagaagtt ctgggtgtaa atatgcgaac atttagatta 168300
aaattaaaat tgagttcctc agtcacacta gtcacattga agtgttcaat agccacatgt 168360
ggccagcagc tgtcctattg gatggtgcag acacagaaca ctttcttcat tgcaggtact 168420
attgaagagt gctgagctag agcttctaca atgtaacatt cacaatgccc agtattcaat 168480
gataaatcac tagacataaa aaccaacaaa aaccatacaa gggtagtgta atccatagta 168540
aaaaatgaaa gcaaaggaac tattctaaga tggaccaaat gttggattta gaaaataaag 168600
acattaaaac atatatgttt tacaatatat attcaaaaaa tatattaatt aattagagac 168660
aaatggccct aagttgtgag taaatgagga atttttagta gataaatggg aaccctaaaa 168720
agaaacaaat ggaaattcta gaattgtgca atgcctgaag tgaatcattc atcggaagag 168780
cttgccagca ggttggagat gatagaagaa aaagtgaagt tggagacaca gcagtagaaa 168840
atatcaaatc tgaagaacag aaataaaaaa tattaaggaa aaaatgaaca aagggtcaaa 168900
gacctatgga acaatatcag acagtctaac ttacgtctat ttggtgtccc agaaggagga 168960
gagagagaga gagagcagaa aaaatatctg aagaaatagt ggccaagagc ttcccaaaat 169020
tttaaaaaat gacttaaaaa tccacgaagc ccaagtaaga tgaagataaa ggaagcccca 169080
cctaagtaca tcagtcaaat gactgaacac tgaagataaa gtagaatgtt aaaagcagcc 169140
aaagaaaaag acacatacag aggaacaaag ttaagaatta ttactagtgc tcatcagaaa 169200
cagtagaggc tagaagacaa tgaaacaaca tctttggaga tgtaaaaatc ctattcacac 169260
agaattctat ataaattgaa taaaaatagt cttcaaaatt gaaggtgaaa tgaagacatt 169320
ttcagataag caaaatctga gaagattcat cacaagcaga tctgaactac aggcaatgct 169380
aaaggatgtt cttcagtata aagagaatag taccaggaag aaaccacaca aagaatgaag 169440
agtaatagaa acaataagta actgagtaaa caaattataa aacattcata caatagactc 169500
agtaataaaa aaataatgac tgataaatgc agtaacatgg cttcaactaa ccaaaggaag 169560
ccacattcaa aagacttaac atgcatagtt gcatattaaa ttctaggaca ggaaaaacta 169620
acctataatg atgtaaatag tatctgtggt agcttgagtg ggagtaggag actaaatatg 169680
aaaaagaaag agggacgttt caaggaaatg gaaattttct gtagcttgat tagggtagtg 169740
```

-continued

```
gatgtataca ttagtcaaaa gccactcatc tgtacactta aaatgtggga attttacaga 169800
agataaatta caccatggta acattggctg aaaaaaaaaa ccttaaaaaa ggtaacttcg 169860
gcccagtgcc gtggctcacg tctgtaatcc cagcactttg ggaggctgag gcgggtggat 169920
catgaggtca ggagttcgag accagcctga ctaacatggt gaaaccccgt ttctactaaa 169980
agtacaaaaa attagctggg tgtggtgtca tgcgcctgta atcccagcta ctcaggaggc 170040
tgaggcagga gaattgcttg aatctgggag gcagaggttg cagtgagtgg agatggcgcc 170100
actgcactct agcctgggca acagaaggtg gctctgtctc aaaaaaaaaa aaaagtacct 170160
tctcaatgag gctttccctg agtaccctat ttaaaactgc accccactac tccactactc 170220
cctagcacat atctctgtct aacacactgg atatttttgt cttgctttat attacctcct 170280
agaatgtaac ttccatttgg gcaagaactt ttgcctgtta tgttcagagc tgtggaccat 170340
accaagaaca gtgcctagca caaaatgcat gctcaataaa tttacatgaa tgaatgaata 170400
aaggaatata tgaatgaatg aatttacctt ctttactgct atcagatata agatgagtag 170460
acaggctaaa atcatactgt gaaactcaat atgctgtgaa actcaagaca ccagatttta 170520
gtctaattcc aatttacagg gcaagaaacc taagtaaaag ggtattaaac atagactaaa 170580
tacacgggcc agcagttggc atgctatgtg aggtgcttca tctaggctct tgggtgaact 170640
atagatgttt acaataaagg taaccagata tctgtctgta ctttatccat tggaagatag 170700
gactgtttta gagaattagg ataaggggga gagaagtgaa gttatttctc aagagacagg 170760
gtgagtaggc tgctatctat caccaagcaa tctactacat cctggcctct tttaagtttt 170820
cagtgaatta gtaagtctaa actcttaggt gtagtgggct catgacactt gggttgcata 170880
catctctggc tacaaaaatg tgctgataag aatatgtgat agacataata ttctaacatg 170940
aatgtgagcg caattccaca gttagaaatc tcacataaca tcaaattcca gagagttaaa 171000
aaaattcacc tggtccactc tgttggaaag tccccgttgt tgaagatgtt tatcctggag 171060
aaagagggca ccttcaaagt ggcgaaaggc taagatagga gtgtggacaa aatatcagca 171120
gcatcccatg gcaacacatt cctgtcgtaa gcatcacact cttccaaaga aaagatcaag 171180
ctgcatttaa gtttcaggtg gggcatgttt atttcaggta agcagttgat aaaataagat 171240
tccaatctac aaagtcatgt ggatgactct gcagtgtgtg acctcaatgc cacctccttc 171300
ggggcaaact ccagcctatg gctgatctct actgcaccta gatggcatag cacatgcttt 171360
agcatgtgac tacaatctgc ttggtgctgt gtccaggttg ttagccagca ctgcgcctct 171420
cctcctgtgt ccatcatgag catcagcctc tccagccctg atgttcagaa cacagttacc 171480
ttatctcctc atttgctttt attactaaaa atccctttca tttcttgttt tcccatctct 171540
ctttcttttc ccctactctc cacccattac agagtcagta ttcaaaaaaa agtggagatt 171600
gggaacaggt gtggaaaaga gtcgaagtac tcatacttct catttcaagc ccttctgctg 171660
gttaaaatta taaatgccag gagtcagccc tttcaacaaa aaggaaagga atctggggga 171720
attcttgtgg aagtagagaa gatattatgg aagaaaggta tttttgtaag atcttgtcta 171780
gaatagggcg gtggagaaga gggcttagaa agagggaccg gggtgaggca ggatgagaag 171840
gggagtgaga gtaagagaga aaataaactt acagattctt agagaagaag gagggagaag 171900
aaatccaccc aagggaatat caaagataac tcagcaggga agagctgggg ctagggaatg 171960
agagatgaag atgagctgat ttaatgcttt aaatctaagc caagaaaact gagtgacaag 172020
gaactgtgac atctgtgact tattttgaca gtgtcttgtt ttgggcagtg tgagggagtg 172080
tcagggtttt gagttacttg tacatggagc tgtcttggtt ctcaggacag caatagaaga 172140
```

gatggagcat cgagcaagac agcaggtgag agagagagag tgtgtgtgtg tgtgtgctac 172200
atttgaacac cttaaaggag actcacctcc tgccaactat atgtggagcc aggatctccg 172260
cacatcccta tgctgtgata gctacagggg atcgtggctt cacttccagg ggaaccttag 172320
atcatacaag atgggaactg ctcttagctc tcctgtcttc cgccaccaag tttccaaaga 172380
gacttcctgg agtaggaatg atctttttcac cctcatcaac actggtagag gacttttctc 172440
tgagtagaaa gtacatgaca catcatgcat tggttgcaaa caccaataca gtaggaagta 172500
aagcagcatt ttagctgaga tcgaaggcca agtcagtgtg agagacagag cataaacaat 172560
ttccaagttt atcttgtacc accattccct ggctcatgcc ttgcaggcca actggcctcc 172620
tggttgttcc tcgaacacaa cttctgcacc tgctctgttt gcgtaaaagc tctgatctca 172680
gacctccagg tactctgccc ccaggacctc cctatctaag gcatctccta caacaccatg 172740 tctcatttc aggttcttca tggcacttgc cactctctga catggtctag cgtgtttatt 172800
tatttatttg gctttttttgt gtctccacca ttagcatata agctccatga taacagggat 172860
cttgtctatt ttctccagca ctggggacag tgtctggcac acagaaagtc ttcagaagat 172920
gctctttgaa tgaacaaaca tggctgtgaa tgtaatattt gtacctttta tgttccatgg 172980
aagggttttg ttctgcacta ggtactgatt cagtacattc tcccagtcct actattccat 173040
gtcatgatgg tggcagccct taactgacta aagaatgtgg gagaccagtg ctaacagttc 173100
aagacccacc caaaagagca acgctgttaa ttaagggaac aaatgtctgt ggttcacttt 173160
cgttgtactg ttataagaag gctcggaggc cccccccccc cgaggtgagt ggaaagccct 173220
ctctttactg ggtaaaataa acccaattat gatggataca ctagaattcc caggcaaaga 173280
tgtcttggct ctgtctttga ttcatctcca tagtttctgt ttgaggctgg tctggactct 173340
catcggggaa ggagggggct ggggaggact ggagttatag ataggatctg gactgactgc 173400
tggttgagca gccactttca acttttcaag gctcttgact tgctttgatc actcagccag 173460
tagctgctta gggcagcaac cctgaatttg tgcttagtag ggggctggct catgggcacc 173520
catgtggaga ggatgtgcaa acctcttttc tctgtgggag ctcatgctca gttggcttca 173580
gcccagagca tcttagtcag gactggcctg aaatttgtgt tgtgaaaggt cagccagctt 173640
ctcctgttac ctgctcccca aactccattt ctatgctcca acccccttccc ctcatccttc 173700 atgtatctcc atgggctaag aggccccaaa gcacaactca ccagcctgct ctcctcagcc 173760
ctctccacca tcccctccac tctccagctt cacctcaggt ccttgtgttt ccaccagaag 173820
agcaagccca agaggtgcag ggtggagagg agcactgggg tacaaagtgg agaggagcac 173880
tggggtacaa agatcggatg tctggccact tctttttatt ttcatgagct gcaactttgg 173940
gcaagtcact tctctctgag actcaatttc tttatttata aatctgggat aaaaatcccc 174000
agcctcctac aaaccaaaaa aagccaagga ccagatggat tcacaaccaa attctaccag 174060
atgtacaaag aagagctggt actgaaactg ttcccaaaaa ttgaggagga gggactcctt 174120
cccaactcat tctatgaagc ctgcatcatc ctgataccaa aacctggcag agacacaaca 174180
agaaaaacaa aacaaaacaa acaaacaaaa ataaccactt caggccaata tccttgatga 174240
acattgatgc ataagccctc agcaaaatac tagcaaacct ttccagcagc catcaaaaag 174300
ctaatcaacc acaatcaagt aggctttatc cctgggactc aaggcttgtt caacatgtgc 174360
aaatcaataa atgtgatggg tcaaatagaa ctaaagacaa gacccacgtg atcatctcaa 174420
tagatgaaga aaaagctttc aataaaattc aacatccctt catgttaaaa actctcaaca 174480

-continued

```
aactaggtac tgaagaaaca tacctcaaaa taataagagc catctgtgac aaactcacag 174540
ccagcacatc actgaatggg caaaagctgg aagcattccc cttgaaaact ggagcaagac 174600
aaggatgccc tctctcacca ctcctatgca acatagtatt ggaagctctg gccagggcaa 174660
tcaggcaaga gaagaaataa agggcatcca aataggaaga gaggaagtct atctctgttt 174720
gcagatgaca tgatcctata gctagaaaac cccatagtct ctgcccaaac actccttgag 174780
ctgataagca acttcatcaa agtttcagga tacaaaattg atgtacaaaa attacgagca 174840
ttcctataca ccaacaacag tcaagctgag agcagaacac aatcccatta acaactgcta 174900
caaagagaat aaaataccta ggaaacagct aaccacggag gtgaaagatc tctgcaatga 174960
gaactacaaa acactgctca aagaaatcag agatgacaca aacaaataga aaaatattcc 175020
atactcatag atagaaagaa tcaacatcat taaaatggac atactgccca aagcaattta 175080
cagattcaat gctattccta tcaaactacc aatgacattc ttcacagaat tagaaaaaac 175140
tatttaaaaa ttagtatgga accaaaaaaa gagtctgaat tgccaaagca atcctaagtt 175200
aaaagaacaa agcgggaggt aacacactac ccaacttcaa actatactac agggctacag 175260
taaccaaaac agcatggtac aaaaacagac acgcaggcca atggaacaga atagagagct 175320
cagaaataaa gctgtgcacc tacaatcatc tgatctttga taaagttgac aaaaacaagc 175380
aacagggaaa ggagtcctgt tcaataatgg tgctggaata actggctagg catttacaga 175440
agattgaaac tggatccctt ccttatacta tatacaaaaa tcaactcaag atggactgaa 175500
gagttaaatg taaaacccaa aactataaaa accctgaaag acaacctagg caataccatt 175560
ctgggcttag gaactggcaa agatttcatg acaaagatgc caaaagcaat ctcaacaaaa 175620
gcaaaaattg acaaatggga tctaattaaa ctaatgagct tctgcacagc aaaagaaact 175680
atcaccatag ggaacagacg acctacagaa tgggagaaaa tatttgcaaa ctatgcatct 175740
tacatctgtc taatatccag aacccataag aaactttaac aaatttacaa gaaaaaacaa 175800
cgccattaaa aatttggcaa aggacataaa aagacacttt tcaaaagaag acatacatgt 175860
gaccaacaag catatgaaaa aagcttaatg ccactaatca ttagagaaag gcacatcaaa 175920
actacaatga gatactatct cacaccagtc agaatggcta ttaacaaaaa ataaaaaaat 175980
aacagatgct tgcaagattg tggagaaaag ggaatgctta tataccattg gtgggagtgt 176040
aaattagttc aaccattgtg gaaagcagcg tggtgatttc tcaaaggcct aaagacagac 176100
atacccttg acccagcaat tccattactg ggtatatacc caaagaaata gaaatcattc 176160
catcataaag acacatgcac atgttatgtt tattgtagca ctattcacaa tagccaagac 176220
atggaatcaa ccacaatggc catcaatgat agactggata aagaaaatgt ggtacataca 176280
caccatggaa cgctatgcag ccatattaaa gaatgagagc atgttctttg cagaaacatg 176340
gatggaattg gaagccatta tcctcagcat actaatcggg aacagaaaac caaacactgc 176400
atgttcttac ttataagtgg gagctaaata ataagaacac atggatagat gtggggaaac 176460
aacacacact gggaactaac tgagggtgga gggtgagagg agggagagga gcagaaaaaa 176520
caactaatgg gtactaggtt tagtacctgg gtcaccaaat aatctataca aaatccctca 176580
tgacatgagg ttacctatgt aacaaacctg tatatgtacc cctgaaccta aaataaaagt 176640
taaaaaaata atccttggcc tatctagctt agagaggctc ttagtttgaa agagacaatg 176700
gatggtgtgc aaattgaagg tcacattatc cttctaggct gagatgttca tagttcacag 176760
ttcttcagga gctggcctgg gcaatacagt ttgatctaat acacaataaa ctaattgaca 176820
attggctgtt aatggccaaa gagtgcaagg gttataccat ttacatggca tataaaaaag 176880
```

-continued

```
gtacatatat atctccaatc ttttcatgta catccagtcc taaggaggaa attattacag 176940
gtacaggatt tcagtctgac ctcaagaggc aacatcttat gggaaaagag gcttttgaac 177000
acttaagccg tggttttgac aattgtcctt ttggccatgc tcaagggtat acatacaaag 177060
tcttgtatca tctgggcagg gccaaagatg ctaccacagg ccaccatcac cattacataa 177120
ctcattattt tgcaactctt gcctcatcca aactgtgttt ttctctcagt tcagtttctc 177180
tttcaaagga cctgattaca aattgcaaag gccaggcaga cctgggcaac cccaaacaga 177240
agtctcatca tctgctttgg caacttcctc cgtgactaac tgtgggagca gaaatacaga 177300
ctcacagact ctcagagtgg acaggatctt agaggtcggc gagcttggtc ttccctcaat 177360
gtcactggta catcaacaca atgattggct tattgagccc ctacttagtg ccagaggtca 177420
tggtgggtgc tggaggggat atgactaaga cactgaacaa ggccctgccg ctgacctcac 177480
agtggggaga caggtgagtg agcaagtggt cgggatgccc tgatacacat agcgtaggta 177540
aacactcggg ggctcatgtc agggagtgtc aaccagggtc ggggggtggt cagaaaggcg 177600
tcttgacaga ggtgcagtct ttccacacct ccttgtcttt cttgacatat aatcgacaaa 177660
cacaaattta tacatggtaa tgtgtacaac ttgttttata tatacattgt ggacgccaca 177720
atgatcaagc gaatcagcat ttctatcacc tcacagagtt gccattttct tttgagaagt 177780
ggattcttaa agggagaaaa gaagtgagct ggcaagagat tcacaggtgg aagggagatg 177840
ttccaggaag agtttacagc atgtgcgagg gacatgagcc agaaaggaag agagatggga 177900
agaaggaagg gagagacaga gagggccaag tgaccaggac caggaccagg aaagaaagct 177960
gagctctttg catatttagg gaactgccag gagtccccag gctggaatgt gaagttcaag 178020
gcctggagca gagggagctg agactggaac agtaggatgg accagttcaa gaggggcttc 178080
atggagctgg ggcttcatcc tgatggggtt caggacatat tgcccctgaa aatagaaaat 178140
tggcatttga gaaaacagca aaagcagaaa ggccactctc accttccctt gttctaccct 178200
tctctctgag gccggtcatc agtcccagga aggatttcct gactttcccc tgaagtagga 178260
cattggaccc tggtgtgagt gatgcccgca tactcagagg aaaggaacat cctttttctg 178320
aagacacaag gacacagagg agaatctgag ccaacagatg tggtgacatt ccctccaggt 178380
tatcacccgc tttgctcggt catgcctctc catgactgtc cactcttcat ccaatcgagc 178440
atagcaaata cacaggtttc cctgtttctc tggttcttca tttcccctca aaggcttctg 178500
tgtcatgtaa aacttatatt ctatgcgttt gtatgttctt ctcttgttca tctgtccttc 178560
attatagggg cctcagccat gaatctagca gtgggtgaag acatcttgcc agccctacaa 178620
ttccaaaagc aacaaaggac tcttgagggt tgtgagcaac acagtcattg gggaacacca 178680
gatggctact gaggtttctc cagtggtcca caggtgccag cttctttcac tgtaaggtgg 178740
gtcaagtggt tcacccgtgt gtgttcaagt ggggcccaga gctgcctcca caggcagggt 178800
ccctttccag tctccctgct ctttcatggg ccacgttccc aacctctgaa gactttctga 178860
gcctacccta ccccaagttt ccttttcttc agggttaaca tgtctaatcc cttctccatt 178920
tctctagaaa agtgagttgt ctacaccaca ggcattcctt cagcctctgg gtgtagatgg 178980
agcatacaga tcttgtcctc atgggcagtg tagatgttta cagacactga gcccacttga 179040
tctgctgttt catgatccaa ctcagacatt tgctctttgg ttaactcatt cacccacagc 179100
cgctcggtgg ccggcctttt tctcttctgt tttgcccatt cccctgagaa catacacttt 179160
ttatattgct ttggttaagc ctcaagcata atcatttggt ttctttatac agcttctttc 179220
```

-continued

```
tctgaagcta ggactaccct agtttagata ccctaatgtc caccagcaac atggcatcat 179280
ggtaaggaat ggtcctgcca gtcagaaaga ccagagttta aattttggct gaattatgta 179340
atacttgtgt gacttcaggc aagtgattga aactctttga gcttctgttt cttcatctct 179400
ataaggccat caatatctag ctttgtgagc tgtgaagatc tcagttaata caggtaacat 179460
ccttggtgta tagtagcaca agagatccaa tgcctattaa aaacagaagt gacagcggta 179520
atagcaatca tgatctcgct tttctactta taatctgggt ctcattattt aatcagagcc 179580
tcagtttctc catgtattaa aaaagaataa tagcaactct ttggcagagt tatttgagga 179640
ttcaatggga taaaagcaca tgtggcacac agtaggctct tcaagcacaa atgtgtcctt 179700
ggcttttgcc ctccagtgga ttctcctgcc ctcttgagcg atcacctttg ctgctaggct 179760
ttcgcctcca tctccagatg ttcctgtcgg ggtcccaggc tctttctggg tgaacatcct 179820
ctgagaacat caggatcccc tttttggttg accaagatca aagagttatt tttctgtccc 179880
tgtttttctc tttcctggct gctaggggtt gaattgtgtc ttccttcccc atgaaagggt 179940
atgtgggagt cctatctcct tgcacctgcg aatgtgactt tatttggaaa taagatcttt 180000
gcagatttca tcaagttaag atgaggtcat gaaggtgagc cctgatacaa tatgactgct 180060
gtttttgtaa aaggggaaga gaactctgtg tgaaagagac gcagagggag aaggcggccc 180120
tgtgaagatg gaggcacagg tgtgagagat gctgccacaa gcccaggaat gcccggggct 180180
gctggaagct gaaagaggca aggaaggatc ctccccttga aggttcagaa agagcgtggc 180240
cctgccagca ccttgatttc agactgctgg cctccagaac tgtaagaaaa tctatttctg 180300
tcatctgaag ccacccagtt tatggtactt tgtaacagca gctctgggaa gctgacacag 180360
tggccccact actagttaga gtccatagga ctggaagttc tattagtttg taaaataaac 180420
attcctaaag cccaccttta acgtggaaaa cctggtgact caaattagag atgtattaca 180480
tgattatata gaaattgaaa tagattggat ggaatagggg caggtgatta agaagaaaag 180540
aaaattgcct aaaaaggccc aagccaccac cttgctcatg gataagagaa aacaacttgt 180600
aaaagttgaa agggactcaa atgaatgtca gggcaggaag agtgatgggg gccataattc 180660
aacggtcttg ggggagctgg cattttcatg ctgattaatc taagatttcg gcttgaacaa 180720
gggataaggt ttacagacta aaaattagcc acaaggtata actttacctc tggcttaaca 180780
gaagactgaa agaataaagc aagcagctgt gtcagaactt gccaggcaat gtgaaatact 180840
gtggtttgaa caaagctgag ttgggctgag aatgaattac aggaagaaag gcaggaagaa 180900
aaagaaagag ctctggggct atttattctt tgtgtacagg acgcattgaa gaaagtactg 180960
agtcccacgt caccaaccca gctggaaaac gtgggggcaa ccaaagcaca gagaacatga 181020
gtcaccagct cctcactctc aggagctcca tatttgggag cccagcaaag ggcttatcat 181080
ttttcggatg gagtcccatg ggttctgggg ctgctgctag cttcagctaa atgtggtgcg 181140
tgtcttcaaa attagaactg acaatggtga ccttggagtc ttgcaaccta gtgtttcagg 181200
ggaaaatagt acctagatct cagcagagtg gggatagagg aagacatgga gctgcatgct 181260
gttgcccgtg catcagccaa tcagttggtc agccctcttg aactgtttaa gactaccatg 181320
gacatttgct gttttcacct acccagcatc tgttcctcct ctgcttctag gaaccatctt 181380
ttgactttct tttgggagac ttgcatttct ctcttcttag accctggtgc caggggtggg 181440
tgcatggcca cagtctggac aatcagagta ttccattgtc ctgggggctg caactggttt 181500
agggaagggt catagcacaa gtcagcccaa acagagttca tcctagggac ttttacaaaa 181560
gctactgggg acaagatgcc gtcagctggg ttgctgggag gatgcgggtg tgtggagctg 181620
```

-continued

```
catgtgacca tcttgctatg ggttcaaaga gggaccatgt cctgatgagg tggagcccct 181680
gtatccactt gtgcctgaag ctcttttctg ctacccaagc tgacatactc catccttttg 181740
ttttctttta ctggcaagct aaagagttct gactaataca cagatctcag tagggcacag 181800
taggtgccat agcaaacatc acacaaatat atggaagcca aagagaaaat gcatatggta 181860
tggtgggtct gaagtcagat agaggagaca tggacacagg aatagtccag agtattttag 181920
aatacttaca agtatttcaa aacacataaa ataagggtat tactccctta aatccttctg 181980
gaatgaggga ataaaaacaa atatggtttt taaaaggaaa ccatagtaat ttagtaagaa 182040
cttctcaagg ggctagaaaa atttaaaaaa aaattaaaaa ccaatagtaa tttgaattct 182100
tcttgcagta atatggtata atagcaacaa caacaacaat aataaatcag ccaaaacgca 182160
agaactgtgg gtgtcgtgaa gtctccgacc tagggtgacg aattcatcct ggttggtctg 182220
ggactgtccc tgttttaaaa ctgaacgctc taatttctgg gatgccttta gtcttgggca 182280
gacctgaatg gtcagtcaca tgttttcagg tcattttact tttctgagcc ttggtttctt 182340
catcaatgaa tggggcgtat gtggcaggag gaggaggtgg tgatagaaac atccatgctt 182400
ttcaaaccat atttttgaga gctttaggtt ttttttttta attatttttt tgagacagag 182460
tctcgctctg tcgcccaggc tggagggcag tggcgcgatc tccgctcact gcaagctccg 182520
cctcctgtgt tcacaccatt ctcctgcctc agcctcccca gtagctggga ctacaggcac 182580
ccgccaccac gcccggctaa ttttttgtat tttttagtag agacggggtt tcaccgtgtt 182640
agccaggatg gtctcgatct cctgacctcg tgatctgccc accttggcct cccaaagtcc 182700
tgggattgca ggcgtgagcc accatgcccg gccgagagct ctagattttt actaagagct 182760
gcaacagcca ctgcagaaag gaaagtatga agcaacctcc actccatttc tgctgcagtt 182820
ggagtttctc ttgtatgtgt ttcaattgag atctgcctaa catttgttag gggagtgggg 182880
aaacctgctc tccgagggac caccctctag aattccatga ttttttctct ttgttatggg 182940
gcaaatggct cttatagacc actggttccc acacctgacg gatcctaaga gtcacctggg 183000
aagtcttaaa actaaatact gcctgccaca cctggatatt tctactccgt tggaattggg 183060
tggagccagg gatctgtatt tttacaaaat ctttgcaggt gacatacata taaattattc 183120
acaaatgtcg gtatgctaac tatcattaat aatatattac tttccacaca tctcgcaaat 183180
ggccaggaca catcattgtt tgagacacca tgttcccata catcttaaat tttccgtgca 183240
tcaggaaagc ttgttaaaac acagatggct gggcaccacc cccagggttt ctgtttcagt 183300
aaggctgggc ggggctggaa tttgcattcc taagatactc ccaggtgggc atctgccacc 183360
ttcagtagca tcattttaga ccacaggctc acttgagtgt cttgactggt ctctttaatc 183420
gttggcatca tcataaccca cccccccac cctttcccct ccccctggta tagcactcag 183480
taaattattg atgaataaat gtgtggataa atgttttatg gcctgaatga cgtgaccttt 183540
caaccatctt tctaaagaat attgtgaatt acaccccttc gcatgtaaga aaagtttctg 183600
ctggtatcta aggaatattg tctcatggga cctcagctga ggacatgggt ggggcaacag 183660
gatttcctgc tctcagcttt agagactgtg ctgaatacaa tgaggtgact gaggccttct 183720
gttccggagc ctctagccaa gcccactggg gtctcgttga gccaccattt tttggagctc 183780
cattttgctt cgtttttcac ttttgaaggc cggcagattt ccttttcacc caccaattcc 183840
ttccaggctt tctttagcat gttgtcatat ttaagtcttt aaattgattt gctgggacat 183900
tacacaagcg tcttctggct gctctaaccc tttactcctg tggataaact tgtcattatc 183960
```

-continued

```
cctctggaag ccccaaatga ccactccaac ccctgcgcag gccctgatca cacccgcatc 184020
ctttggcttg tttttcttct ccgttggtgc tgccacagcg gcaggcagct tggcactgtc 184080
tttccacaca tcttccgtag tctgagaaat gtttcttgga ctacagagac ctattcatgg 184140
ccacaaccca gatctcaagg ctaggcacac cccaaataaa gttagaaagg aagagaaagc 184200
cactgaccat tattaacctc taaataggga gcgcccagtc caagttctgc aggaacattc 184260
agagggtgtt taactggctt tgcaactttt atgtaactac ttggaatcag aaacaacacc 184320
cagaaaataa atacaaataa taaagtaact tttaaaaaag attcactctc ttttcaggcg 184380
cttgcttcgg tgctgatcat gcagacctcg attaattagt attcagtccc aatgacccta 184440
agaaaacaag atgtgtgcac aaacaggcag gaagcagtcc ttggaaagag agtttggttc 184500
tgaccagaac ctatacttat ggagaagtaa tcttttctac gtcagttcta caagatcggc 184560
ctagctgaat ggcagtgagt ctgcggtgat gagtgaaagc agccttccct gcctttcttc 184620
cacccaggca gtccctgtgg gtcccgcctc cagaggcagc cattcaacta aagaagctat 184680
ggggccgcat ggtggctcac gcctgtaatc tcagcacttt gggaggccaa ggcgggcgga 184740
tcacgaggtc aggagatcga gatcatcctg gccaacatgg tgaaaccccg tctctactaa 184800
aatacaaaaa attagccggg cgtgcgtgct gcgtgcctgt agtcccagct actcgggagg 184860
ctgaggcagg ggaatcgctt gaatccggaa ggcggaggtt gcagtgagct gagatcacgc 184920
cactgcactc ccagcctggc gacagagcaa gactccgtca aaaaaaaaaa aaaaaaaaaa 184980
aaaaagcaat ggctctgctg ttacataacg tcagcagcac tgtaggaata acaccttttc 185040
cctgatgtca gaagctgcag aaacgcctgc cagtgcagaa cgctcctcca gtgcaaactg 185100
gtctggaagg cttggccatg tgtgccctgg aaagttctgg aatctttttg gtgttggatt 185160
aatggcattc atgtttcaga aaacacctcc aaacctagtt aacaggaaaa ctgttagaga 185220
ataaataaaa cggagcgttt aaaaagtttt ccactgagaa gcagtttgaa gagtcaagtc 185280
accctagagg aaagctgggt attttcttgt aggtagcctt ggaggctttt gtgaacatgg 185340
cgggtggtgg ttgacagggt ggttggagga aggaagaaaa atgacctgcg tgccactctt 185400
aataattgcc tcttgattta gaatcaggac ttttccccct ggttttacaa aatacatgca 185460
gtcttccatg tgaaagatta tgggatgaat ggtgggtggc ggagtgttgc aaggagagac 185520
ttaaacaact cttaccattc ataaagaccg aggaaattca aatactgaga gaggggctaa 185580
gatcacacca tcggcaggca gcaagaatga gaaaggtagc cttgctgtgg cttagctatg 185640
catattatca tgggggagag gcaaactgtg caattcttaa agttcatctt cttagtggtg 185700
agtcaggaac aaatattttg taggagacac gttaagtctg aaaagcttag agagacttga 185760
gagagcttct gtatataaag gagagaattg aaaattcctg ttctactcca tcctgttctg 185820
ttctccaggt ggagtagcaa gctggcaagt cccccagaaa ggaaaggcta gaggggttac 185880
agagacagag agccagcaag ggtttcacgt gggcagggtg gagagatgtc aggggaaggt 185940
atgtatttat ctctgtgtta ggaaactctt ggagaaacaa gctgaagctt tctataaagc 186000
cttcctgttt acccttgaaa gaatcagaag caaatgggcc tttgcccagg aagctacagg 186060
gatcatttgc catatttgga tttctctgag taagaggata gaggaagcct ctgcccaatg 186120
tcctgggatt atgaagacat acccaaatgg cttcagagaa caaatgccta tctgtcccta 186180
tttcactagt taacttttg taaattcaca ttaatagaga taactacaga tatgccagtt 186240
caaagttatc tgtaagttcc tctcattctc tgtacaaact tcacttttgc cccacattct 186300
tctagacatc ttcctttaga aggatgactg gaagtcatga cagcagctcc tcaagggctg 186360
```

-continued

```
cttccgccat ggttaaggca gaatagaata cttttctctt tcataatatc ccaaacaagt 186420
tgccacatgt tgttaaccct gaactccaag gaaacccatc ctataagatt ggtgtccaac 186480
ctgcgaacca ctgtctttgt catgaagatg ttctcctgtt gaaggagttt aatgtgttgg 186540
tgtaccattt tgttgccaga tagcaagtcg tttgagacct gtttcatgcc atgagggaca 186600
aaccacatct tgaagtggcg tggttgacag ttgtgtcaaa acaataaaac aaggcattat 186660
caaataatct tctgaaattt ctgcctatat catgaaagga ggatgtttga tgagcagaag 186720
ttggtgtggg attcataact aaactgtcca tctgtgggag aattctgcag gcttccatca 186780
ctagtgtgtg acacagcaaa gagatgacag tcctattcag ctcccaaatc tgtggttcca 186840
gggcactgct attggaacga ggctcagtct tgggtgccac tcaaaaggga aagtacagat 186900
ggattaaaga gtgatcaagc aaaataaacc cccattaggg tgaagagggt gtgacatatg 186960
aggaaagggt tcaaatgcag aaagcattgt agagcagaag aagaactccc aaaggagagc 187020
atgagcaaga gtctgccagg aatttaagga gagtcttagg gaagagcaga aagtgaataa 187080
cccacacaca ggtgagaact gtgtggtcac cacttagcca ggtgacatgg tttcctctgt 187140
gtccccaccc aaatctcatg tcaaaatgta attcccaatg ttgcaggtgg ggcctggtgg 187200
gaggtgattg tatcatgggg gcagattttt ccctggttgc tgttctcctg atagtgagtg 187260
agttctcatg agatctggtt ggtgagagag cacctccctg ctctctctct tcctcctgct 187320
ccagtcatgg aagatgagct ttctcccctt tcaccttctg ctatgattga aagtttcctg 187380
aggcctcccc agaagctgag cagctgccag catcatgctt cctgtatagc ctgcagaacc 187440
gtgggccaat taaacctctt ttctttataa attacccagt ctcaggtatt tctttatagc 187500
agtgtgagaa ctgactaata catcagggaa ggctaccact ccttgcctac atgcagaatt 187560
caagaaacaa caatgagcac tttggtcctc atattctgcg gacaatggaa gagaaagaac 187620
agaaaaggca tagagcagac tgtccaccca gattctagag gtgagccaaa gtaaaactaa 187680
tgtatcagct tgtttgtgtg tatgactgtg agcgtacatg tgtgtgaggc atgtatggta 187740
catttttctt attgccattt acttttggtg cacttaagct ttattcaaaa agtgaaatag 187800
tggaggaatg gtctccagaa atatgcagct tgttctggaa ataagaaaac aaggctaaag 187860
gtgctaaagg acagctgtgt gctcagacag cagtgtcagg gggtcagagt tgtagggatg 187920
ggggctctgg ttaaagtcca gccaaactct agatcatatc ctctttatct tctgtattag 187980
ggcattcttg cactgctata aggaaatgcc cgagactggg ttaaattggc tcacggttct 188040
gcaggcttta cagaaagctc agaggcttct gcttctgggg aggtctcagg aggcttacaa 188100
tcatggcgga aggtagagta ggagcaggta cgtcacatgg tgaaagcagg agcaagagag 188160
acagacagag tgtcaagggg caggggggag gtaccataca cttttacaca accagatctc 188220
acaagacctc actatcacaa atacagcacc aagccatgag ggatgcacca ccatgatcca 188280
aacacctcct accaggcccc accttcagca ctggagatta caattcaaca tgagattttt 188340
gggtggggac aaaaacctaa actatatcat ccctattcac agcagatggt taggaaatgc 188400
ttatagctga tgagagaaca aaaaccatgt catttttatt taagaaactt aggagtacaa 188460
gaagaacacc tatacaatct aattgcgacc ctaaagaaca acattcagca tcacaatgga 188520
agctctagga gtttgtagga gggagaaagc attgggggct gagatgggct ggggtgttca 188580
agaagtaggt ggtatgtgag ctgagcctgg catatggaga aaaagaagaa attagtctga 188640
gcaaaggcag aggtacagat attcaaggaa tatttgggag attgcataga agaaaaaagt 188700
```

-continued cttcatgaat tgtgctgtgc tgcttgcaat gaactgaatg cttgtatcac ccccaaattt 188760
atatgttgaa gtcccaaccc gcaatgtgat ggtgatagga ggggagggct ttgagaggtg 188820
attacatcat gagggtgaat cctcctgaat ggatgtagtg ccgttatgaa agagatccca 188880
gagagctctc tacctctttt gctgccatgt gagaatacaa tgagaaggca gcaatctgca 188940
acccagagga gggcctcaac aggcacccta tttcagaatg ttagtctcca gaactgtaag 189000
aaataaacat atgatgttta caagccgcct agtctatagt actcggttct agcagtccaa 189060
acttatgagt acactgacat aattccattt tcatccctct ctttctctct cttctgtgtg 189120
ttctgcctct tgctttgcct tttcatgtct tctgccattt attagcatgt gtagactcag 189180
ctagtagcaa ccagggctac catgagcact ttgattctta tattctatga gcttcacatc 189240
ttattttttt atagatgcca ttatttgttc ttcaaattat ggtattaact gcagtcacac 189300
tattctttca ctataactct tgcttgcttt tctcaccaaa gggagatatt tgtgtaggtg 189360
tcaaaatctg gcactgcgtt gactatagtc atccaggaaa tagtcaccta ctcacttggg 189420
atatgtcatg agctgccaga cccaaagatg aagctctttt attaagtgga agtgcattag 189480
catttgagtg ttaatggagc agacctttaa taaacagtca ccatgtgtga attctattct 189540
tggatctatg ggacagaaa tgactaagaa gtttacaaaa tcttcattta ttggaaggga 189600
cagatgtcta acaactaaca atgctaatgc tgaaataaac tattgctcta agactctgtt 189660
tcatcttact ctacaaccat atggcaatct gcattgatga tgcataattt ttaacttaaa 189720
attgaaagga ttcttctagc cctgttccca ttttgaaatc cgtctttgaa aaaaaaaata 189780
ctaaaagata tctaaattgg ttgcagtcaa tgacttcatt tcaatgcata gactttggtg 189840
gtgcaactga tttggcatct actacagttg cttagcattc acagctagct attggacact 189900
ctgctgccct gcccactgac ataaccaaag accagaaaac ctggtgaaag ataagataga 189960
ggtaatccca tgattaaaga gattgattaa ctactttgca ttgggagaag taggtgggag 190020
aaatttcttt gtcagatttt ttttaagcct aaaaatggtt tacaatggga tgatttcaat 190080
tacggcgaga tgattcacta tctagatctt atggaagaaa attcttatgg atttgtggat 190140
acgtatcctg aaaaatgaag gacatcaaca aagcaagcct catggaatgg gggggaagtc 190200
tgaaatatgc tcatgtgggg cattaagtac cagaccataa atgcactctg agtggtttaa 190260
cctgagaaag aagcaaccta atggtgctta tagctccaag aagctctgtc ttcagaacac 190320
aactggaatg aaaggctcca tcttctctga acctgaaaag ggagggaccc accaacaaca 190380
tccccagtta cggtttgaag aaggatgcta ctttgctcat gttagggtga tgtgaataga 190440
tgcatgaacc ttttttgggg atatgtgaat tcagattcca gtttgttcca ttttgactgt 190500
gtagtcattc taaacctgag tatttttttt tctgcataat agtaagggct aaaaaaatct 190560
gtagggcttc ccacaaatta ggcactgttg taagcaacag atatatatat taccttatgt 190620
aatctcacaa caatcaaaag gtagcaagca gtaaagagtt cacatagcag gtctgagact 190680
gctatctcaa tcctgcttgc aaggctggcc cttggctggc atctgggaac atgtgagggg 190740
ttcctgctgg tccgtgatat gagtggctca ctgtgactta actgtgtgtg caaacaacat 190800
ggtttatgct gaacacctgc tttccttctg ggagtctgga atttgtgtac atgccagaca 190860
gagggtgtct aagtgaccag ctccaaatca aaactctggc actaagtatc tactgagctt 190920
ccctagtaga caacatttca tacctgtcat aactcgttgc tggaggagtt aagtatgtcc 190980
tgtgtgactc ccctaggaga ggactcttgg tagctcatgt ctggtttctt ctgttgcttt 191040 ccccttt gct gattctgatt tgtctttgag gtaatagaac ttagctgtgg gcatgtctct 191100

-continued atgatgaatc ctgtgggtcc tcctaatgag tcattgaacc tgggggtggc cttgggaatt 191160
ccccccaaag gtgtgtgaca ttataattat ctccatttta aggtgaggaa gctgattcat 191220
ggagaggtta agtaactata ccaaggccac acagcaggta catggcacaa ctaggatttg 191280
aacccaggca agctgactcc acagcttttg cttgtaaccc ttaaggaggc tccaaagttc 191340
cctcattaag tggttgtgaa tcaaagcagg tgtgttcact cagtacatat taagtgctca 191400
ataaaacata gttactctac tgtattagga tgtaatctcc cgtcccttct acctactaac 191460
tagaaatcta tcatgcattt ttcgccatcc cactaacaag cagaaagtcc ctgaggctga 191520
aatatctttg aagaagaggg agagaaatag aatggatgtc atgctatttt tttaaacaat 191580
aataactatt atggtacagt tcctttataa gccaaatgga gcctctgcat ttcctctcct 191640
ctttccttac ctgatccctg gcctctctca ccctggcacc ggggtaagag cggtgagggt 191700
cagtgtagca ggctgggcat tcagaaaaac tgactggagc aagagttgga ggtgggtggg 191760
cagatttagg ggagctcttc tcatgatggc gactatgttt tctgccactc accccccaga 191820
tgggaacacg ctgtctgaca aacagagtac ttaatgttct gtttgttgaa atcatttctc 191880
aatcaccctc acccctccct acctttcaag tgttctagtt aatgcagaaa catcccgttt 191940
ctttccattg aggaaaccaa gtgaccccaa cattccatag acctattctt gtcctacttt 192000
caaaaaaaaa cagctcttcc tgctgaccgc ctgcctataa taagtcatag cttagttagt 192060
agatctgaat gtcctagtta gagataagtt ggctgaagca cagtacatct acgtgtagaa 192120
tttggaggaa aggactgaag aaagataccg tgatttaaaa acctcatctt caccctacac 192180
tccttgaaat aagtagagaa gcaaagcttc ttatgtatag taagaaatat agattaaaag 192240
gtgaatagca gaagagtggt ggcttggagt tacattaatt gaaatcaaca agaccaaatc 192300
cttccctgca agcacatttt gatgaggtaa aactggaagg agtccatgga tattcagtac 192360
ttaaaaaaaa ggcttgatca taacaaatgc caagaaaaag aagaaagaaa ataaaatggg 192420
gccgggcgca gtggctcacg cctgtaatcc cagcactttg ggaggccgag gtgggcggat 192480
cactttgagc tcaggaattc aagactagcc tggccaacat ggtgaaaccc tgtctctact 192540
aaaaatacaa aaattaggtg gatgtgatgg catgcatctg tagacccaac tactcggggg 192600
gctgaggctg gagaatcact tgagcccagg aggcagaggt tgccgtgagc cgagattgtg 192660
ctactgcact ccagcctgag tgacagagca agagacacag tcaaaaaaag aaagaggctg 192720
ggcgtggtgg ctcacacctg taatcccagc actttgggag gccaaggtgg gcagatcatg 192780
aggtcaggag tttgagacca gcctgaccaa caaggtgaaa cccagtctct attaaaacta 192840
caaaaagtaa ccgggtgtgg tggcatgtgc ctgtaacccc agctactcag caggctgaag 192900
caggagaatc acttgaacct gggaggcaga ggttgcagtg agccgagatt gtgcgtgggt 192960
gacagagtga gagtctgaga aagaaggaag gaaggaagga aggaaggaaa gaaagaaaga 193020
aagagaaaga aagaaaggag aaagacagag agaaagaaag aaagaaatga agaaagaaag 193080
aaagggggag caagacagag agagagagaa ataaaagaag aaagaaaaaa gaaaaagaaa 193140
ggaagaaaga aagaaaaaag aaagaaagag agaaaggaaa agaaagaaga aagaaaaggg 193200
atttaggatg aaaaactggt agtaccaaag ggtcacttca tacttacagt agattttctc 193260
atgggatagc cattagaggt tggcacttta aaagcaatgt atgagaggtg gaaaccaaaa 193320
cagaaactgc ctatcttgaa gtaagatgca ttttagtctg atgaaaacca gcgtcttcac 193380
accaacaacg tgtgctgaaa ggatgcacag caaggagttg cctcgtcatt gaatgagctc 193440

-continued taagcaaatg acttagggga cccaggcttc agtcctagct gtgtcatctg atcagttgcc 193500
caacttcatg tgagttacgt catctttccc accgtgatct cctcagtttc actatctgta 193560
gagtgggaga tacaataaac atgccccagg accactgtga aagtgaaata atatgagtca 193620
atgtgctgtg ttaattgtaa aataatatct aaatcttggc tgttaatatt ttgatccaat 193680
gttgttacct agcaccaaga ttgaagagat aaatcaaaca ttaaaaagaa aacctagatt 193740
agtttttgct gtactgaaca ttaagaaagg agggttacct cgagaggaga accgtataaa 193800
gctcaattaa aaatggaaag ggcactgcag tggactctat gattggtcaa aatattaggc 193860
tttcttcatt aatccttcct ccttggtttg tctggttaaa atcacacaca gtggtctgaa 193920
agtgcagtgg gcatcaatta agatttaggt cagagcctct gaggtagcca gtgatttagt 193980
ttctgggatt aaggaagaca aaagcttacc gatggctgga tgagaataac attcctttct 194040
attgtgatca tcctacatca aggaaatgtt tgaaatttag ggagtctgtt aaagttatta 194100
tatggccgag cttttgaaaa acacagcagc acaaatgtgt tttatcagtc tttactgttg 194160
gtaagaatcc tggagaaagg aaatttgatc agtctcccaa tgcagtttac tccaaaatgg 194220
atcactagtc tagaggacca actgcatcta tcagagtcag atctatctgc caagactccc 194280
cacttccctc accatcattc acacatcctg tgctttcttt gcaaatgata cagactgtca 194340
ttaggtttag agtaagctgc aattagcaag tctctcaact tctcttacaa ggaacttatt 194400
tttagtggaa agttttgtaa tggttcctgt ctaatgttta actcttccct ggagaccaaa 194460
ctccctagct caatcattga cagcaggatt ccaggagtga atggcatccc tttgaaccaa 194520
ctagtgactg taattgctta aacctagcta ctagccattt cggcaccttc tacacagcac 194580
cccttgcaaa taagtccggc agagctatgg aattttggcc tttttgtctg aactctcggg 194640
attgtatgag actggacctt ggttcttaaa agggctcttc agtgtggtca gggctggtga 194700
tcaaaagcat cagtctcagc acctagtcac atgtgttttt cgtgttttcg tggatgaggc 194760
tggttctgtg cttgccaagg tcaagcaact caattaccca gggcctgctt ggaagctact 194820
gtgcgcagtc tggccctcag tggcttctcc ccttgccctt gggccctgat ggctgtttgc 194880
aagctgggaa gaagacacca gggctggggg gtacccagaa acccaaacag atggagaaaa 194940
gtttcaaaaa ggcaaaacaa tgaagatttg cttaatttac agataaaata aaataaacat 195000
aatttaatct atcaactata tttattcctg tggttcttca ttagcacaga aaaattaaga 195060
attgtttata ttttaagagt aatacaatga atctttcttc tattcctgaa tgagtcacac 195120
cgaagtaact accacaactc ttggatacgc tactaatcaa cacacaataa aacaaatgat 195180
cgccatggtt ttccaacttt aaacccactt ggaaaaagtt ccatgctggt gggagctaca 195240
ccaccacgta gctccatacg aatttgttga ctgatgactg acacacagaa gggtctacag 195300
aataataaag gaaagctaac tttaaaaaac cctccttcta tttcatttga gtgcttgtac 195360
atatctgctt atgtttatca tctagtcatg aaatatcatt tcggctttct ttacagaggt 195420
tggggtgaat ttaactggat catttcatgt atcctataag cctttgggtt ttgttttttt 195480
cttgatcttc tggaattctt ttttctgtca aaccctactc attctttaca tcccttctct 195540
tttatgaaaa ctcattccct ctcctcctct tcctcccact agctaatatg tattgagcac 195600
ttaatgtgtc agataccact ttaggtgctg tgtgtgtgtt gactcatgta acattcaaaa 195660
tcatccattg actcataaaa ccttcaaaac caccggtgag gtagggctct tattacctcc 195720
tttgtgcaga tgagaaacag agaaacagaa aagtaaagta atttgctcaa tagcacatgg 195780
caggtgggtg gtacaggttg gatttgaact caggcagttg gttctctctt aagcactcca 195840

-continued

```
accttcttga atctgtccat ttcctgaacc ctgatgatca tttccccaac ttatgttgct 195900
tgatagttgc tttgtgaatg ttcccatgct gcagagaaag aatctcctta gagagtatgc 195960
catgactttc ttacattgct tagaactttt tttttgcttt gccatttatt tttatcaatt 196020
atttattaac aaattaacaa aacaagaaaa caagccaaaa caaaaatggt caaaagataa 196080
gcctgacgag gggagaagaa ttattatttt taagtaaaat aatcttaaaa acacattcct 196140
actgttaaat tttattagga actccccatt tctccaacca ttgctcctgt gtactacaca 196200
acctggcatg catgagtgat tgtgcacgtg tacacacaca gagtttttaa aatttgagcc 196260
agttttcaat cacaaagcaa cgtaaactca tttttaaata tctaaagaca gacaatgtct 196320
actgcagaaa gtgaacctgt cttataaacc caatcccaaa acatttaaaa atatttggga 196380
gtctatattt tgctagactt ttattctaca atgagataga taaaaatggg cttgtactgt 196440
atgttctttt gcatttgttg ctttgtattt gattcacatc ttttcatatc tttgtgtata 196500
tcctctttct tctttttcac cagtagcaca gtattccaaa gtgtggattg ccaaattgta 196560
ataaggaccc tactgatgga cttttggatt gtgttcatgt tttcaatatc atgctcaact 196620
gcatttcaca tagcctcaaa agaaagaaat ctctgctagg tcgaactcaa atagggagtg 196680
ttgggccaag tggctcttct gtgcaattaa gaaagaaatt actcagcaga tagaaagtat 196740
gacatagaag aggctaacac ttctctaact gggtattcag ggaatatcat tagggatgtc 196800
aactgaggta tataaagagt cttttcccta aggaacattt cgtttaatga tgaaatagac 196860
acatctctct gctaaatcat gcttgtggga acccaaggag gccagcccct gaatcacagg 196920
cctgcttaga gtaaaacgct gcaccgaagc tctgctgacg ttttcctatg ctgaagcaag 196980
aagtgaggaa cattgtcttt gaaaaatgct ctgaccaaaa ccattctttg ctctgctatg 197040
tagagtagag ctttgttttt caatcaggct gttattcaaa tgctggagcg gatccaaatt 197100
tgctttcctg aggaaaagtc tgcctttgcc tacagcacgc acacacggct ggaggacggc 197160
tcccacccct gtcctcccaa gacctgcatt ccagtccaaa tggttccctc accgacccac 197220
taggtgcaca aggctctcct caagccgcct tttcttcccc tcacaatctc ctcatgcttt 197280
tctgtgtcct tcccgttttg caagggccat accagcttca cttctgagca ggcttccctg 197340
cttacagaga gcttctttcc ctgcctggta gcacccgtcc ctcacgctca ctggatgatc 197400
cactcactgg ctcactcact cgttccttca gcagatgtcc ctccagcacc tcccatgtgc 197460
caagaacaca gcaggggaca aaataacgtc cttcacccac ccacggagcc aacggttcag 197520
aggcagaaac agaccataag ccagtacgtc agtctgcacg gcgtcgggtg gtgttgagga 197580
caggtgacaa cggggagggt gacagaggtg accccgtggc cattttgcat ggcatgtgag 197640
ggagggctgg cggattgggt gacttgtggc ccagagctga atgaggaagg ggacggagcc 197700
tggcagggat ctcccagaag gtccttccag gcagagggac tgtcagtgca aacgtccggt 197760
gttgggcact ttcttggcct tctgggggaa catcaaagag gccacttagc tccttttaaa 197820
aaaagactat tttttagagc acttttgggt tcacagcaaa attgagaaaa aggtacagag 197880
atttcccata tacctcctgc tcccacatgc acacaggctc tcccactgtc gacctccctc 197940
cacagactgg cacatttgct acaatcaata aacctgcatt gacacatcat tatgacccca 198000
agtctatagt tgacagtagg gttcgcacct ggtggtgtac attctatggg attgggcaaa 198060
tgcacagtga cacgcttcta ccactatcgt atcacgcaga ggactttcac tgccctcaaa 198120
tcttccatgc ctcacctatt catccctccc tccttgcagt ccctgggaac ccctgatctt 198180
```

-continued

```
tttactggta ccctagtttt atcttttcca gaacgttcta gttagaatca tacaatatac 198240
agctttttca gattggcttc tttcacttag caacatattt agctattttt taaatgtgat 198300
ttttgtttta caaacgtatt tgttctttct tcaactcaaa tgtaagattt tttagagcaa 198360
tgggttgaag gttgtagata acaggtgaga aatcgtgatg acgctttctt agaagaattc 198420
ccctctttga ggtacatcaa cgtgtgctac acatccctgt gtcctccagc ccttacctaa 198480
aactttaatt ggattattag ccctagcctg tgacatgcaa atattctaat taaaggctgt 198540
ttttttcttt tttaaaaaaa ttcagtggat acatagtagg tgtatatatt tatgggttat 198600
atgagatgtt ttgatacagg catgcaatgt gtaataatca catcagggta catggggtct 198660
ccatcacctc aagcatttat cctctgtgtt acaaacaatc caattacaat attttagtta 198720
ttttttaatg tacaattaaa ttattttcga ctacggtcat cctgttgtgc tagcaaatac 198780
taggtcttac tcattctttc tatgacttgt actcattatc tatctcccct acctgccccc 198840
cataatcccc cccacccaca acgctaccct tcccagcccc tggtaaccat ccctctattg 198900
tctgtcttta tgagttcaat tattttaatt tttagctccc acaagtaagt gagaacatgt 198960
gaaatttgtc tttctgtgcc tggtttattt cacttaacat aatgaccact agttccatcc 199020
atgttgctgc aaatgactgg atctcattct tttttatggg tgaatagtac tccattgtgt 199080
atatgtacca catttccttt atccatttat ttgttgatgg acacttaggt ttcttccaaa 199140
tcttggcact tgtgaagagt gctgcaataa acacaggact gcagatatgt ctttaatata 199200
ttgatttcct ttcttttggg tatatgtgag tgggattgct ggatcatatg acagctctat 199260
ttttagtttt ttgaggaacc tccaaactgt tctccacagt ggttatacta atttacattc 199320
ccactaacag tatatgaggg ttcccttttc ttcacatcct cagtagaatt tgttattgcc 199380
tgacttttgc atataagcca ttttaactgt ggtgaaatga tatctcattg tagttttgat 199440
ttgcatttct ctgaggatca gtgatgttga gcacctattc atatacctgc ttgccatttg 199500
tatttttcct tttgagaaat aagcctgata ttctttcagg gcataaatta agaatgcaac 199560
cctcctctgc ccatggccac atatatcatg taagagcaat ctggcataga tactccaatt 199620
catttttttt aaatggattc tcagttctaa acaacataaa ccaatgtctt tatttttaat 199680
gcttgtcttt gcttcagtca aaaaaactcc aaaacacaat gaaggaagag gccaattgag 199740
taaaccagtt acttaaagct aacaaagaaa cagacatcat caagcagttc tgtcttccca 199800
aatcaattct tttgaaatca aacaccttcg ttaagtggtt ccttgaactg ttttgccata 199860
aaaattaaaa aaaaaaaact catgaagaaa atgaaataat catgtacaaa ataccttttgt 199920
cactttattt ttaatacaat tgtatgcaat ttgttaattt tcatcatcct ttataactga 199980
attatatgtg cttttgaaag ctacataatg aataacatgt tgtatataat tgttaaaatg 200040
tgtctatggt catcatataa tttagacctg aggtcctcag tagaagacaa agtccaggaa 200100
gtcagaacct ctgttcctct tttcactata ccccaatacc atatgtatat gggagaatgg 200160
atttgattga cttgagttgt atctgcagtg cttcttgaag gcatgaaaac tactgcgagt 200220
gttttaatta ctcaaacctc caccccttcca tatgtaagct tcttgaaaat agggattttg 200280
tctggctggc tttcctgctg aatccccagc acctaatatg gtgcctggcc catacagagt 200340
ccttaacaga tgttcaataa atattaatat ctactaaatt attttctgaa atggatacag 200400
tatctgagat ggttaatttt acgtgttaac ttggctaagc caaggtacct agatattgat 200460
caaacattct tctggatgtc actgcaaagc tatcttcttt aaaagattaa catttaaatg 200520
agtaggcttt gagcaaaaca aatgaccttc cataatgtag gtgggcctcc aatcagttga 200580
```

```
aggccttaat agaaaaaaga gcgacatcca cagagcaaga aggaattcag ctagcagagt 200640
gccttcggac tcaagtagca atgtcagttc ttccctgatc tccagcttgc cagcctgcct 200700
tgctgatttt ggacttgcca gtctccataa ttgtgtgaac caacttcata aaataaatct 200760
ctctctctct ctctctctct atatatatat gtatatatat acacacacac attccattgg 200820
ttctgtttgt ctggagaacc ctaatacacc caccttactc ctttgctcac tcaatgaatc 200880
aatcaatata tgtcatttgc cagggatcac tctcacccat caagacctca caactactaa 200940
agccaaacca gtgatacaac ccctgaagta cactcttgac tttaacttct ccactccggt 201000
ggagtgacaa agagcattac ttccttaatg tttcgacgat tatatgatgc aaagcacctg 201060
catgaggaac aggtgctgag aggacactgt acttgctaaa gccatgtcct gatagtgtga 201120
cagaaggcac cagcatacta ctgtgctttg aggagaaaat gcttcccatg gtgaggctga 201180
gctgctgata gtctcacttc ctctaaatat ttccactctt tacaagtgaa gctgtgggtg 201240
gggaatttca gagtcatgga aactagtcaa aggttactaa aggttcatgg acactactat 201300
ttgataactg tgtggtagct gcatagtcgc atatgctata gaaaaaggtg aatataaaaa 201360
atacatcaat aggaagctta tagatgagca ctatatgaaa tttggttctc ttcaggatca 201420
agcaaagtga tggaccttca tggaacccaa tctgctggtc tggggaacaa tacttttgta 201480
aattaagtat tcatatagaa cttttcccca agggcttatc tggaggggaa gtgacagtga 201540
gagtgaaagc cttaatttgc ccacaatcag catgggctag cccagtcaca aattgtctgt 201600
ccaggaagat tctttttttt ctttttgttt ttatttttta atcttgggga gtcactttag 201660
ccctttcttc ctctcccatt taagacccct tccctccttt gatgtcccct agctaaaacc 201720
tgcttctaac ttgaggcaaa attttcactt ctctgctcaa gtagtttgtg catgaaacag 201780
ggataaattt ggtggcaatt gtgccttctt gaaatcctaa ctctgaacca tcatttttgt 201840
caatgactta gcactgccaa ctgatagaaa tgatagactg tcatacattc atgcaatagg 201900
atactataca gctgtgaaaa tgaattatca acatctcttg gcatcaacat ggataacact 201960
cagaaatatc atgttgaccc tagagcaagt cttggaagaa tgcttatgta tgattatatt 202020
tacttacagt tcccaaacag gcagaaattg actatatgca aattgtatat atacctatgc 202080
atatatgtct atgcatacac ttagacctag gaggccaatc aaaaagtaaa gtaagggaat 202140
gactaacaaa attttaagac aatagttcct tttgtggtag gtgatataat ttggatgttt 202200
gtctcctcca aatctcacgc tgaaatgtga tccacagtgt tagaggtggg gcctagtagg 202260
aggtattgga ttatgggggc agatccctca tgagtggctt agtgctgtcc ctttgatggt 202320
gagtgagttt tcactcagtt aacgcaccca agatctggtt gtttaaagga ctctgggacc 202380
tctcccttct gtccttttct ctctctcttg ccatgtcata tgctggctcc tccttccgcc 202440
atgattgtaa ccttcctgag gcctcacccg aagcagatgc cagcaccatg ctttctgtat 202500
accctgcaga accataagtc aatcaaccct tttttctttt ttctttcttt tttttgagac 202560
ggagtctcac tttatcactc aggctggagt gcagtggcgt gatctcggct cactgcaagc 202620
tccgcctccc gggttcatgc cattctcctg cctcagcctc ctgagtagct gggactacag 202680
gcgcccgtca ccacacccag ctaatttttt gtatttttag tagagacggg ctttcactgt 202740
gttagccagg gtggtctcga tctcctgacc tcgtgatccg cccgtctcgg cctcccaaag 202800
tgctgggatt actggcgtga gccaccgtgc ccggtcccca cttttttttct ttataaatta 202860
cccagccttg ggtatttctt tatagtgatg caaaacggac taacacagaa aattgaaaat 202920
```

-continued

```
tggtactgag aagtggagca ttgctataaa gataactgaa aatgtggaag tgactttgga 202980
acggggtaag ggagaggctg gaagagttta aaggactcag aaaaagacag gaagatgagg 203040
gaaagtttgg aacttcttag agactggtta aatggttgtg accaaaatac tgatacagat 203100
atggacagtg aagttctggc tgatgaggtc tcagatggaa atgagaaagt ttttgggaaa 203160
tggaatgggg tcattcttat tatgccctaa caaagaactt ggttgcactg tatgctctag 203220
ggatctgtgg aagtttgaac ttaagagtga tgacccaggc tacctagtag aggaaatttc 203280
taagcagcaa agcattcaag aggtgacttg gctacttcca gcaacctaaa tcagatatgg 203340
gagcaaagaa gtgacttaac attgaaattt atatttaaaa gggaaacaga gtgtaaaagt 203400
ttgtaaaatt tgcagcctgg ctctgtggta gagaaagaat ccaagcaggt tgtgaaacat 203460
tcacttgcta gagagatgag cataactaaa aggaagccaa tatccaagac aaggcaaaaa 203520
ccctccaaag gcatttcaaa aatcttgagg acagcccctc ccatcaaagg cccagaggct 203580
taggagaaaa gaatggtttc aggggccagg cccagggccc tactgccctg ctgagcttca 203640
gactctggct tcagcctcag ctcaaagggg cccaggtaca gctctggcca cagttctgga 203700
ggacacaagc cataagcctt ggtgattgcc acatggggtt aagtctgcag atgctcagaa 203760
cgcaagtgtg aagaaggctt ggtggcttcc acctagattc cagaggatgt atgggaaagc 203820
ctgggtgctc aggcagaagc ctactgcaga ggcagaggcc ccacagaaaa actctactag 203880
gaaaatgcca ggggaaatgt ggggttggag ctcctacaca gagtccccac cagggcacta 203940
cctagtggag ctgcggaaag ggggctgcca ccctctagaa cccagaatag cagattcact 204000
ggcagcttgc accctttaac tggaaaagca acaagcactc aacttaaacc catgagagca 204060
gccatgtggg ctgcatcctg caaagccaca gggccagagc tgctcaaggc cttaggagtc 204120
cactgttata acagtgtgcc ctaaatgtag gacttggagt caaaggagat tgtattttgg 204180
acctttaaga tttaatgact accctgctag gtttcagatt tgtgtggggc ccctataccc 204240
tttcttttgg ccaatttctc ccttttggaa tggtaatgtt tgcccaatat ctgtaccatc 204300
attgtacctt ggaagtaact aacttgtttt gactttagag tctcataggt ggacagattt 204360
gagtcttaga tgagacacga ctttgtactt gatgctggaa tcaattcaga cttcgggaga 204420
ctactgggag aagatgattg tattttgcaa tgtgagaagg acatcagatt tgggaagcca 204480
ggggcagaat gatatggttt aaacatttgt cccctccaag tctcatgttg aaatgtgatc 204540
cccaattttg gaggtgggat ctagtgggag gtattggagc atgcgggtgg atcccttatg 204600
aatgaattaa caccatctat ttggtgatga gtgagttctt cttcaattag tttacatgag 204660
atctggttgt ttaggccagg cgcagtggct catgcctgta accccagcac tttgggaggc 204720
tgaggtgggt ggatcacctg aggtcaggag ctcaagacca gcctggccaa catgacaaaa 204780
ctccatctct gctaaaaata caaaattttg ctgggtgtgg tggcatgcac gtgtaatccc 204840
agctactcag gaggctgagg caggagaatc acttgaaccc aggaagtgga ggttgcggca 204900
agccaagatt gcaccactgc actccagcct gggtgacaga gtgagattct gtctcaaaaa 204960
aaagatctga ttgtttaaaa gagtgtggca cctcccagct ttcttgctcc cactcttgcc 205020
atgtgatgct ggctcccccct tcatctttca ccatgactgt aagcttccag aggcctcacc 205080
agaagcagat gccagcacca tgcttcctat acagcctgca gaaccatgag ccaattaaac 205140
ctttttcttt tgcagattac ccagcctcag gtatttatag ccacacaaac atagaccaac 205200
ccagtgggca ttgggagaga aggatacaat tgtttagggg cacacagcag gctttcaggg 205260
ttgggtagtg gggtaacagg tggatgtgta tttatgtttt tattcctatg attatttaga 205320
```

-continued

```
atatatggat accttatata tactttttttg tagtataaaa tgttacaata tttaaaaatt 205380
ttttcaagct aaatttatct aaattattca ccctcatgta tcactttcct tggaaagtag 205440
agggttttgt agctgttcaa aaaaatttat cattcattga cctctagtta agtgaattac 205500
agaccttcac gaaccagagc ttctaatctg aagcaaaagt gaaaaggaat gcagatgaag 205560
aaatacctcc acccgtcccc tcagctcaca ttgctgagtt acatcggagc ctcatggatt 205620
cttacctagg gtggaactac catacaatgg agcttgtgtt gtacccattt ttaggtgtct 205680
atactaccct gcatcactgc tgggacgttt gggagccact gtgggcaaag tgaagttgta 205740
tattttgaag accaaaaaag cctgtagcta acaagggcag cttggacccc tgcttcctgg 205800
gatatccaaa atccatacaa ttccagccca gtggcacagg ccaggcaggc cctgggtgga 205860
aggcactggg agatgcagcc atgcccttga ggagcctgcg ttctagtggg gctttcctag 205920
tcttctctta atcaaacccc attttccagg gtttgccata ttctgtgtgc tgtcaggact 205980
gtcagcaacg tttttctttt aaattaactc acttttgggc cgggcgcagt ggctcatgcc 206040
tgtaatccca gcactttggg aggctaaggt gggcgggtca cctgaggtca ggagttcgag 206100
accagcttgg ccaacatggt gaaaccccat ctctactaaa aacacaaaaa ttagccaggt 206160
gtgatggtgg gcacctgcaa tcccagctac ttgggaggct gaggcaagag aatcacttga 206220
acctgggagg cagaagttgc agtgagccac actgcactct agcctgggtg acagagtgag 206280
actttgtctc aaaaataata atagtaataa taaattcact tttttaaaac ttaaagattt 206340
atattttaaa agaaatgttt ataccattcc tacaaattaa aaaaaaaaca ggccgttgtg 206400
gtttaatata aggtaaccat aaaaagcaaa tacaggaaaa taaagccatg ctattaattt 206460
gtagctagct accagtgcct gttgatggct cctagcctca gatcgacttt ctcttgttaa 206520
aacagtaagg agccaagagt tagagtagct ttaagatcag gttcaatgtg atttcatgct 206580
ctatctatgt atcttgtgct atataaaatt ctcctatttg tgttccacac ttcagaaatt 206640
ttcatcaaat gagttgtgaa ggtgacagat aagcaggaca aagtgaaggt catttgcagt 206700
aggacgcatc ttcgtgctgt gcgggtttgc atggagacat gtcaagccta aggtgctctc 206760
catgctgtgc ctgtgccctt tctccaagcc aaatccagaa gaggaggagg aggatcttcc 206820
cccactacaa cccttgaatg gatatgtggg aaatcaaaac tcagagtcta aggtcaaatg 206880
gagatggagc tgatcattgg aaaacagacg actaaactct ttaagtacct acagtagtag 206940
gtggccggtg gtcttagctt gggttccccc agaagtagac cccaatgcag agttcgagga 207000
catgtagttt aagaaatgat cccaggaagc attgatgggg agtgaaggag tatccaggga 207060
aggagagaag ccatgaaggg ccccgccact gtgggcaact ggagcttgat tccgtgtaga 207120
ttattccact caagactgag ggagctggaa tatttacagc ctttgaggag ttcatttctg 207180
ggaattttcg tctgcccttt gggcaattac agttgtccct gtgtggcttg gagaaagctc 207240
tcaggtcatg agataaagac tcaggttgtc agcagccagc tcagtcacag tgaggcctgg 207300
aggagggagg caggacactg actacttcgg ataccccttc tctgccagat gcttaaatgt 207360
ttgctattca atctaatcct taccacagcc attcaagata gctctttccc cttatttaca 207420
tgtagaggaa gaggcaccgg gaattacatc atgtgaccct tacagcctgt cctctcctac 207480
acctctgctt ttatatcttc ctagtcatcg tcttcttctt cttcttcttc ttcttcttga 207540
gacaggatct cactctgtca cccaagctgc agtgcagtgg tgcaatcata gctcactgca 207600
gcctcgacct cctgggctcc agcaatcctc ccgccttagc ctcctgcata gccgggacta 207660
```

-continued

```
taggcataca ccaccgtgcc cagctatctt gtttaagtgg tgacgtacaa agtgacagcc 207720
actaaatagc tgttaaataa actaaccgat taacaagaaa tggtggagcg ctagctaaac 207780
actgatttca catcctttct tttccaccaa ctccactttc cgcattctta gaaccaggaa 207840
tgtcctcgaa agtaaccaag cttggaagaa aacagaaaca aagaagaaaa ctatttggca 207900
gattcccagt attctgtcat ggacaattgc tcttcacacc ccatgctggg tgggaaacca 207960
gcttctgggc aggggaagga gggactcccc atgcaggagt ttaaatgact agagcgccta 208020
ctctcacttc tcaacacaag caaagggaaa agattggtgg ccgatctctg catagcttag 208080
aattatgtat aacccttca gaacgattgt cccctttatg attacagatg gtcttcattt 208140
tgaaaaaatt tcagcaagat aaaaaatttg cctcaagtcc ttggtggaag aaaggcaatt 208200
gaatgaatga atgaaggaag aaatgaatga atgggctaag tgaaagaata aacatagaga 208260
aaagtaaggg tggagctctt gggcggctca ctatggacag ggagaacaca gtgtgctgtc 208320
acttgtcctc agccccttgg agatgatcct aatgactaca gggataggac acgcacagaa 208380
tccaatcctc agtcaccatt tctcgccagt caggactcat gtccaaagag gctgaaaagg 208440
acgtaaatga ttctaatcca ccataaagaa taagtgacgg cccacacttt gaagtactga 208500
aataattcag gaaaaataaa agcttagttg ctgtcaggta agctctctga cgacagtagg 208560
aagaggggag gggccatgta cttacacacc aggaagcatc tacccagaac aatttcataa 208620
gtagaaatca tgctggtttg aatgttgcac taaaaccagc acctccaggt caacttggag 208680
accgggagtc actcattcct cttctggggc atgtggaggt cctccctgcc ccagttgagg 208740
agtgttcaca gtggggaaac accaccagat gtctggcacc aactcaggaa gtaggagcct 208800
gaatgagtcc ctcctctccc acaggccaca gcaagtggct gagaactcac ccaagtgtag 208860
gatggaaccg ctggtggatc atcttgcctc cccgacgctc tggccctctc tgggcaggcg 208920
ggcgggaggt gacagctagt cctgctgcat gctcatgttt ccctctccat gcagcgagcg 208980
gacttgcttc tagaggcagc tgtaagcatt tccctactga gcaaccacac acgtcggatg 209040
tgagtggcat atgtatgtgt gtgtttttcc ttccggttgc tgtgaggtga tgttgtcttg 209100
gttcatttcc tctctgtgct tcttcttttt tttctctgtc atactttctg attcgctgag 209160
gacactttgt agtttaggga caggtaagaa agcttgttct catctggcct ctttgctatt 209220
tttagaaagg taggtgatct ttaaattcgt attgcaagga aatttgtcaa aatgtattct 209280
tctaagtggc ataagctccc tcctaggccg cactgaagca aaagttaggc tatttccaag 209340
ccaactgaat tgggatttta tggttttatg gactcagtat gttgcaaagg gttccactat 209400
taattgacat gaaacattct ttcctatgac aagtacttat tgagcttgta cactggaata 209460
gacaccatgc tagaggctag gtgctcagag agtttcctac ttacaatgtg gtatggaagc 209520
ctagatctgt gtatgtagaa gggaattcga aagcccaaac cctttgtctt cttcattctg 209580
tgctttcaag tagcagacaa gtggctctga gacaagcctc ctgggtttga attatggctc 209640
tgctctttaa acacttctgg cctttctgtg ccacggcctc ctcatctgta aaatgggaac 209700
agtcacagga ttgttgtgag aattaagtga attagtacat gtaaagcact ccaagaatgc 209760
ctggcacaaa tagagtaagc gcaatataag tgtttgccgt gatcattcgt ggcaactttg 209820
tattattatc agctgagatc tttgctattt tcctaccctt cctcattttc cactccttgc 209880
tcatgcctag caaacgactt ggggacatag agggttgaga ggaaagagag agaggaggtt 209940
tgataatgga tgttccccaa atgatcctgt ggtgcttgat gtttctgctc caactccttc 210000
ctgctccatc atgaagacaa agaaagggct gcccttggtc ccacccatca gactcagctc 210060
```

-continued

```
atgtatgttg cactcttgtg gcatctcttt tgttgttgtt gttgttgttt gttttgtttt 210120
gttttgtttt aattttctgt aagacttctc tgaaattcat ttatttttaa atgtttgagc 210180
tggttcaaat cttgctaaag aatattctgc tcatacaaag gtgccacact taaagcaata 210240
aacactcagc tcagtgccat gtacactggg tcttatgaag aaatcaatga caagaacatc 210300
gatattaatc atcatatatt gtatatattg tatacatata ttgtacctgt taagtgcaat 210360
taacaatatt cagcaaggta tgcttttatt cttctttcct ctctttcttt ctccttacaa 210420
aaccattctt gagtacatgc tatgtatcca catcgttcca gatttgagct agaattattc 210480
tactctgaag tttttatttt ataatacaga gtgtttataa taaattgatg gaggtagaga 210540
agtctggata gtacatgttt tatcaaaacg tccttttatg cttttcccct tataccgtat 210600
caggtaagga attattttct tcatcaggca tttaattagt ataactttaa atgtacaaac 210660
tttagaaaac ataattaata attttgtagt atgacttgaa tattaatgcc atcaaattgt 210720
ctgcataagt cagttacact ctagagatat taaaaatgct aagcttgggc tccttttaca 210780
taaaatactt gagactgaca accttattat cctgaactct gtttttttcat cttcatccta 210840
tggcttcatt tcccacttcc agctgcctgg acctcccact gctgagtttt tcagaacaga 210900
gagcgagcga gcatgtcctt caaggcaaac tcaggaactg agactttgtc caaaaacaga 210960
tcagacttat tttagaaaaa caagttaaat atttttccca tttgcaaaga tgccggtttt 211020
ctatgtctgt tttcctactt acagtgttag attttcttct tcttctttgg tttattttct 211080
ttttgattag tagcaggtta tgctgcatgt caacattttg gcaaaccaca gatgattctg 211140
acaaaaaaca aacaacttta atttctaatc actctatcca ttgaggacag ggcttacatt 211200
ttcatcttca tttaaaccag cttcttgact gctttaatta gctccttcat gccatctcag 211260
ttagctggaa tcttagcttg caccacaaaa tgctttataa ctacctgtga agcagtagcc 211320
aaaccccagg caactgtttt gaatttgtta tggaggtctg gtccaaggag cagctgttgt 211380
atggagtgga ggatgaggat gggggaagga aaagtaagga gaatttgaga agactcaaag 211440
gttgagaaat ctatggccaa agtgtgtgca catgtgtgtg tgcatgtgtg cacgcatgca 211500
catgtgtcta tttatgattc catttgcttg actcattccc ctccacgatg gaagacagta 211560
tgagccatgg ggaatcaact gcccactgag gaatttaaat gaaaatgctc aagggctggt 211620
ctggcaaatt ttaagaacaa agttgtctag aattataatg gatgcctcct cccttcttgg 211680
gaatgggagt ttgtcttgtg gttttcattt ttagatgagg aaatcagagc tcaaaaagat 211740
cccgttcatt ttttcccatt cattaactat cgcatacctg cgaagtctcc tgagctttcc 211800
tgggcattct cgatacctcg ctccacagga caccctccag aaacctgtag ctcagtggga 211860
gataagccag caagatagct gtttctgttc attagttaat tcatgatctt aaaagcatta 211920
tttaacatgg gctaaaataa ataaaaaaga aatgagaatc agtttctccc ctaagagaga 211980
tgatagtctg gaaggcatgg aagaatgagc cttattcacc ttcctcttct gctctcttgc 212040
ccttataaac ctccttttct ctctcccta acaggacacc tttgtctttt gcctgtctat 212100
tctcccagtc cctcagccaa gtcctgggct ctctagccct cctacattgc cagaactcca 212160
tgacctattt cagcaatgtg tataatgtag atttccttgc tcttgttctt ccattttcca 212220
cccatgtcat gcaccagagc tatccagact tactggggaa agttaataag gcaacttgtt 212280
tccttgcaaa ttctccccaa taatcttaac tgaggccctt ctgctgctca agaattttcc 212340
ttctcatctc ctgctgtctg tcaggtcccc tgtggtatcc cttctagacc tttctcatgt 212400
```

-continued

```
tctaaaagct ctaagcctag ctgttgcctc ctgttatgcc tggggtaagg tctcatgatg 212460
ggaactcttt caggatgcct caagatccct gcagtttcac catttcttcc atactgttcc 212520
ccattctctg tccattcttc agtcctttga attacagctt caagcatcac cacccaatta 212580
ataatgatag taagagctat cattttaaat ttatattagc aggaggcaaa caacattggc 212640
aaagatgaaa ccattcttct agtcatagaa cagctgtttg agaaaacacg ggcacctgga 212700
agagcaaaag gaagaaagac tgaacacttt taaagacaga agtgatgcca aattgtaaag 212760
attctgactt attggaagca ttcattgcat ttaggcatct tgcaaacacg tatttctcca 212820
tggtttacac cctgtttgcc tacccttcca ctacataata accatctttg acttctcaaa 212880
aaatacttgg taaaacttaa ttagtgctaa tttctctata actttaaaat aaaattttaa 212940
aatctacaag taataaattt atcttgtaaa gaactaacat tgcagatgag gttctccaaa 213000
gtgtctttgc ccatcagccc tagttttaat tttctctctt gctttgccca cagagaacct 213060
ttgctatcgg tttgaggtac attctactaa gacattttca ggcattcata taaatatatg 213120
tcaccactgc caatttgcag ttgtgcacat gtgtactacc cttgcccttg agcattgcat 213180
gtgcacacaa acagaacctg atactgaaac catcatactg tactatcctc ggtttctgag 213240
ggaactgtat aaactgccgt tctggtttca catgaaacag caacttggaa acaacatctt 213300
attcacgaga atgtaaaaaa caaaactgca ttgctgcttt agatggttga acaggtgagg 213360
ctcctcagtt tatctgaatc ttgtccattt gttttctaaa tacatagaaa tgtggattca 213420
catccagctg atttacctct gggtagagat tcctggatca aatactaaag atctatttgc 213480
catttgataa agtgattttt gggattgttc ctttttgcct tcacaatcac ctagctaaaa 213540
agtcaaatca caaccctccc ctgatatata cataagctgc ccctgacaat gaccccagac 213600
acggggaggg atgccaagtg ctgggattat ttacatccac ttttttctct acaatgactg 213660
actgtttacc tctctccttc cttgggcgtt tcccttatcc tgactctcat agcagcctcc 213720
atttcacagt gccatactgt gggttaacta ctttctaaat tgagaaatat tttttactga 213780
tccctagtag ttaaaactgc agcactccct gtttgttccc tttagttttt atacaatgat 213840
tttttctcta agacaataga aatttaaact ggaaatccaa cttacccttc ctctattttc 213900
accacaactt ttcttataaa caaacaccta tgtccatatt ttcctggcag tcctaactca 213960
gttccttggt tccatcttct tctttgcctc tttctcttct ttctttcttt cttttttttt 214020
tgagacagag ttttgttctt gtcgcccagg ctggagtgca atggcgcgat ctcggctcac 214080
cgcaacctcc gcctcccggg ttcaagtgat tctcctgcct cagcctccca agaagctggg 214140
attacaggca tgcgccacca tgcccggcta attttttgta tttttagta gagacggggt 214200
ttctccatgt tggtcaggct ggtctcgaac tcccgacctc aggtgatccg cccaccttgg 214260
cctcccaaag tgctgggatt acaggcgtga gccaccgcgc ccggcctctc ttctttcttt 214320
catactcagt tttcctaaga aatttgtcta cacttcatac ctccacttcc acactttcca 214380
ttccttcctt cctcactgca ttccttccat cctgacatct ggtccatgcc tccagctctc 214440
cgctgaaatc atctttgcta aggtcaccct caggaacctg gatgataaac cggtagacac 214500
tacaaagtct ttttctctgc tgcattggaa gtggttgagc aattctttcc tctcagaccc 214560
ctctctactt ctttggagga cacctcttgc cttggttccc ctctttctgg ttcagtacac 214620
tccaccactt actgctacgg tgattcaccc ttgggcatca cacattttca ctcttctgct 214680
ttctgtatgg gtaggttcat cccatttaaa agagggacct tctcttccca cacttccatt 214740
tgtcctagtt catttgcatt gctataaagg aatacttgag gctggtcatt tataaagaaa 214800
```

-continued agagctttat ttggctcatt gttctgctgg gctgtacaag tcgcatggtg ccattgcttg 214860
ggggagggac aggagggcct cagggagctt ccagtcatgt tggaagagga agggaagctt 214920
gcatgtgcag agatcaggtg atgagagagg aagcaagaaa gggcggaagt gccaggctct 214980
ttttaacaac cagctcttgt gggaactaat agattaaaaa cccactcacc accctgtcaa 215040
gggaagacac taatctaatc tgcactaatg aagggtctgc acccatgacc caaacacctt 215100
caatccagcc ccactttcaa cattgggggt taaatttcag catgagattt ggagggacaa 215160
acatccaaac tattgtcttt tgcctgtctg ttctcccagt cattacccat gtcattaccg 215220
tattctcagt ccctctgccc caaaacactg cagatctttt ccccactgca tcttcaatcc 215280
aaccagtcac catattctgt gttgttgtct ttttaaatta aatctcaaat ccaatcttgt 215340
tgacgcattc agttccctct ctgtgtgtcc cttgccactt tcttagttta gacgttaatt 215400
gctcagactg ttacaacaat tccaagctgt gaggtcctct tctagcctct atagaacact 215460
gttaggaaca cggtaggtgc tatggttcag atttttgtgt ccccccccaaa attcatatgt 215520
tggaacctaa ttcttaaggt gttattatta ggaagtgggg catttgagag gtgattagga 215580
gatgaggaca gtgtcctgat gaatggaatt agtcccctta taaaagaggc ctgaaggagt 215640
cttttgctcc tctcaccaca tgcagaccca gctggaaggc actatctatg aggaagaggg 215700
acctcagcag acactgaatc tgctggcgcc ttgatcttag acttccagcc tccactactg 215760
ggagcaatca ctttctgttg tttgtaagtt actcagtcct agttatttgg tatagcagcc 215820
tgaatgggcc aatacaccag gtcctcagga gatattaatt gaatgaacat cttcaaaata 215880
ttagatactt ccatagacaa acttcatatc ttctcatgtt cactttctgc ttaaagactt 215940
ttgccaactt cctgttgcct acaaaataga attgaaatga ctgtgctggt gaatggcagt 216000
ccactcttct ctttacattc tctcctgcct tgtccacctc tgcagtgccc ttcaccttcc 216060
catcacatca aactgtgatt cacccttggg ccccacacat gttcatgctc ctgctttctc 216120
tggataagtt catcccattt aaaccagggg ccagccttct cgtcccatac ttccatttgt 216180
ctcagtccat ttgtgttgct ataaagaaat acctgaggct gctaatttat taaacattga 216240
ggctgctctc ggtcccctcc tattccataa tttctcatgg ttatggcatg taaaggctgt 216300
tcccctgcct agaatgccct ttctccttgt ctttctggca accccttggt atcccctgga 216360
cagagtcttc ctttcctcct tcactgtcac caggccctct attaatcaca taatgtcaca 216420
atagtgtatc tccattccct ggactttgag gctccagagg gcagggaact gttgtttatt 216480
cattctggag accaaactaa acattttaca aagtagtcca tggaggtctc ttatcagaat 216540
cacctatgag gctggttaaa tgtagattcc caggctctgt gactcaactg ccaaattctg 216600
tttgtcttgg tcgtgggact gtcctaggca aatcttacgg acatgaatgt ttgagaacac 216660
ttctacagca tccaacaaat atttgatgaa taaaaacttg attaaaaaag tactgagatc 216720
cctgctccta aaattctgct ctatttcctt cattcctctg gggtgtagtt tggctgggga 216780
caggcccagg tatttggctc agtcatagat caaagtgacc taaatgggaa acagctgtgc 216840
gttattcccc aaccatgtca cgcaagtacc tattgtcctg tccaaaacgc caaattaggt 216900
ttagggccat tcaaattccg gaagatggtt ggctgtgata agaactaaca aattcttgct 216960
caagtggaaa ctggttttgc agggcatact ctgcattttt aactcactaa agccaagttc 217020
ttaagtttaa gtggttcgta agtatcttct aatgagctgc acggttccat ttgctgtgcc 217080
tatcatcggt attgataact ctagtatcag ctagtagccc tcacctgttg acactgagtg 217140

-continued

```
gattgtgaat gagctttttt agactttaga tgagactgct gggagactgt aatgataggc 217200

aagccttgtt ttggccacaa actctctaaa atgtcctttt taatcttgag ctctagcaac 217260

acaattttga gatctgtcat aatgcaccat accagaaccc acgaagactt tacaaaacat 217320

acatcatctg aatgacctca agactacacg acaacacata tttgttgtat ttgttattta 217380

ccaaatatgt atgtattatg tatcattact taccagccaa tgaaatcttt tctttttttt 217440

tttttctttc tttttttttt ttttgagaca gaatcttgca gaatcttgct ctgttgccag 217500

gctggagtgc agtggcatga tctctgctca ctgcaacctc cgcctcccag ttcaagtgat 217560

tctcctgcct cagactcccg agtagctggg attacaggtg caagccacca tgcccggcta 217620

attttttgt atttttagt agagatgggg tttcaccata ttagccagga tggtcttgaa 217680

ctcctgacct cgtgatccac ccggcttggc ttcccaaagt gctgggacta caggcttgag 217740

ccatcacgcc cggccaatga aatcttttaa aaattccata tagatgccgc agttccactt 217800

cgggatatat atatcctaag gacttgaaat tatgttgaag agatatctgt actcccatgt 217860

ttactgcagc actgtttata atagctaaaa taggaaattt tcctgtgtcc atcagtgaac 217920

gaatggataa agaaaatgtg gtatatacac acaatggaat acaatttagc cttaaaaaga 217980

aagaaatcct ataatttgca acaacaggga tggatatgga agacattatg ctaagtgaaa 218040

taagccaggc acagaaagac aaatactgcc tgctctcact catatgtgga atctagaata 218100

atttaactaa tagagagcaa aatgatggta aaatgatttt tgctccaaat aatgtaaaaa 218160

taccagaggc tggaggtcag ggaatgggga ggtggtggta aaggggtaga aagttagaca 218220

agaggaataa atgataagta tttaagggga tggatatgtt aattagcttg attccaacat 218280

tcctcgttgt atacatacac cataacatca ctgtgcaccc tataattata tctgattata 218340

atttgtaaaa aaaataaata aaaggacaca taaaaatgta gaaacacact gatatcatat 218400

acaggtgaat acatatttgt atctgagata tggaaaataa agacaccagg agtgatttga 218460

aattgctctt tctggttcct ttgtggagga gttaagacct gtctatggca tccaagaaga 218520

aacaggatat ggattggcaa ttaagccacc agctggattg ctcagataat gccacagtta 218580

ggtggagcct tagaggtcat ctaactttat ttagtacata ttacttattc tttaacattt 218640

ccatcatttc tttattacac aaataacaca cagtcgttat tgaaaccaga aaaaagaaat 218700

aatttgaaaa gatgacaaaa ccaatgttac attggagaat acattctttt agacattttc 218760

ccatgcatat gtagtgttag ccatcagaat gtattagttt tctattgctg ctgtaacaag 218820

ttactgcaaa cttaacagct taaaacaaca caaatctgtt atattacagt tctataggtt 218880

aaaagtttaa cacaggttta acagggctaa agctggggtg tttggcaggc tgtgttcctc 218940

ctctttaggt tgggaagaat ctgcttcctt gcctttttcc agcttctaga ggccatccac 219000

attccttggt tcacggcccc ttcctctatc ttgaaagcca gtagtgcagc           219050
```

<210> SEQ ID NO 2
<211> LENGTH: 201
<212> TYPE: DNA
<213> ORGANISM: Homo sapiens

<400> SEQUENCE: 2

```
ccaaaatttt ttacagtgag tatgtattat cttttgtcat ctgaaaaata acacaaataa     60

ataagttaaa atagaattaa ctgaatttgt acaaatcggg saagataagg gtgcccctgt    120

tttctctatt catgccaccg ctaccactgt ttagactatt ggtcataatt tttttctcac    180

ctgcaaatat ctccttgcct g                                              201
```

<210> SEQ ID NO 3
<211> LENGTH: 201
<212> TYPE: DNA
<213> ORGANISM: Homo sapiens

<400> SEQUENCE: 3
atactctttt tctacttgag gtagttagat atgcctcaac ctctatgaaa acctactttt 60
ctcatgtttt atacaggtgt ggccaaagtg gagcagctta ygtctgttgt gcaactggtg 120
catcctgccc caccagatca tatttcacca agtttttctc ctctgatgag ctatgctaaa 180
aatgatcaat tggacacatg t 201

<210> SEQ ID NO 4
<211> LENGTH: 201
<212> TYPE: DNA
<213> ORGANISM: Homo sapiens

<400> SEQUENCE: 4
aaaataatcc ttggcctatc tagcttagag aggctcttag tttgaaagag acaatggatg 60
gtgtgcaaat tgaaggtcac attatccttc taggctgaga ygttcatagt tcacagttct 120
tcaggagctg gcctgggcaa tacagtttga tctaatacac aataaactaa ttgacaattg 180
gctgttaatg gccaaagagt g 201

<210> SEQ ID NO 5
<211> LENGTH: 201
<212> TYPE: DNA
<213> ORGANISM: Homo sapiens

<400> SEQUENCE: 5
ggtggtgttg tcttttctta ttccacacaa caacaatgaa ccatttcttg atcggattgt 60
gacatgcaat gaaaagtgga ttttatacaa caacgagtga ygaccaggtg agtggttgga 120
ccgagaagaa gctccaaagc actttccaaa gccaaacttg caccaaaata tggtcatggt 180
cactgtttgg tagtctgctg c 201

<210> SEQ ID NO 6
<211> LENGTH: 201
<212> TYPE: DNA
<213> ORGANISM: Homo sapiens

<400> SEQUENCE: 6
aaaatgcttt ccaagtgttc attgaatccc aaagcacaga cctttatgct acaggaataa 60
acaaacttat ttctcattgg caaaaatgtg ttgatagtaa wtgttcctat ttgaattaat 120
aaagatgtgt ttgagtctag ttataaggat ctaaaattca cagtcccaaa ccacaattcc 180
ttttgcacca atctaatata t 201

<210> SEQ ID NO 7
<211> LENGTH: 201
<212> TYPE: DNA
<213> ORGANISM: Homo sapiens

<400> SEQUENCE: 7
tacatgcctt ctctacaaaa ccatcctaag cagctcttga attagatgct cctttgcact 60
ctgtgcttaa cttgtttaca gcacacgtcg tgttctattt ragtgacctc ccaactaacc 120
tgtgagattc cagaagctgg gtgagtgtgc tctggaactg attcttctgc tagatgctga 180

-continued

```
gaacatgtgg gcaatggcac g                                           201

<210> SEQ ID NO 8
<211> LENGTH: 201
<212> TYPE: DNA
<213> ORGANISM: Homo sapiens

<400> SEQUENCE: 8

aggtagatct gtgcttgatg attgaatgga tgagtttcag tgaactgtga atgatgggga    60

gcttttcaac aaagccacac tccatgtttt ctcttcagca raataaatgc tgcatagaag   120

cggttaatag tccccttat gtcagctcag cacatagata tatgaggagt cccacggttt   180

cccataagcc aaataagaca a                                           201

<210> SEQ ID NO 9
<211> LENGTH: 201
<212> TYPE: DNA
<213> ORGANISM: Homo sapiens

<400> SEQUENCE: 9

aatgaaagcc tgggtcaatt agtcagtttc tttcccaata tctgccctaa cattgtcttc    60

taagtttttg gaaatgaata cgctttatta ttcacctcag ytggatttat tgtgcctcac   120

aggtattgac tcctcttgct cttcctcctc tcgctatgga aagactgagc agaggaagtg   180

ctcggacagg catgccctcc c                                           201

<210> SEQ ID NO 10
<211> LENGTH: 201
<212> TYPE: DNA
<213> ORGANISM: Homo sapiens

<400> SEQUENCE: 10

aatattaggt tggagcaaac gttaattgca tttttgcatt gttggaattt gctgtttgat    60

attggaatac attcttaaat aaatgtggtt atgttataca wcattttaat gggcatttct   120

cgctttatgt ttttttgcta atgacttact acttgctgtt tattttatgt ttattttaga   180

ctatggaaat gatgttaaac a                                           201

<210> SEQ ID NO 11
<211> LENGTH: 201
<212> TYPE: DNA
<213> ORGANISM: Homo sapiens

<400> SEQUENCE: 11

gacatgcccc aggactccct tttccctagt cacctcctcc tgccctcacc tccctcagag    60

tcagcctttc acagtcatct cttatgacac ttctcatagg scaccttcct tggcatcgcc   120

aagtggagtt aacggttttc tttctgcctt ggtcatggct ctacatttac tatactatag   180

tgatataatt atagccatgt g                                           201

<210> SEQ ID NO 12
<211> LENGTH: 17
<212> TYPE: DNA
<213> ORGANISM: Homo sapiens

<400> SEQUENCE: 12

ggggcaccct tatcttg                                                 17

<210> SEQ ID NO 13
<211> LENGTH: 18
```

<212> TYPE: DNA
<213> ORGANISM: Homo sapiens

<400> SEQUENCE: 13
aggggcaccc ttatcttc 18

<210> SEQ ID NO 14
<211> LENGTH: 25
<212> TYPE: DNA
<213> ORGANISM: Homo sapiens

<400> SEQUENCE: 14
ccaaaatttt ttacagtgag tatgt 25

<210> SEQ ID NO 15
<211> LENGTH: 18
<212> TYPE: DNA
<213> ORGANISM: Homo sapiens

<400> SEQUENCE: 15
ccagttgcac aacagacg 18

<210> SEQ ID NO 16
<211> LENGTH: 18
<212> TYPE: DNA
<213> ORGANISM: Homo sapiens

<400> SEQUENCE: 16
ccagttgcac aacagaca 18

<210> SEQ ID NO 17
<211> LENGTH: 25
<212> TYPE: DNA
<213> ORGANISM: Homo sapiens

<400> SEQUENCE: 17
ctttccactg ctctctccct catta 25

<210> SEQ ID NO 18
<211> LENGTH: 23
<212> TYPE: DNA
<213> ORGANISM: Homo sapiens

<400> SEQUENCE: 18
acattatcct tctaggctga gac 23

<210> SEQ ID NO 19
<211> LENGTH: 23
<212> TYPE: DNA
<213> ORGANISM: Homo sapiens

<400> SEQUENCE: 19
acattatcct tctaggctga gat 23

<210> SEQ ID NO 20
<211> LENGTH: 24
<212> TYPE: DNA
<213> ORGANISM: Homo sapiens

<400> SEQUENCE: 20
aacagccaat tgtcaattag ttta 24

<210> SEQ ID NO 21

-continued

```
<211> LENGTH: 24
<212> TYPE: DNA
<213> ORGANISM: Homo sapiens

<400> SEQUENCE: 21

ggattttata caacaacgag tgac                                             24


<210> SEQ ID NO 22
<211> LENGTH: 25
<212> TYPE: DNA
<213> ORGANISM: Homo sapiens

<400> SEQUENCE: 22

tggattttat acaacaacga gtgat                                            25


<210> SEQ ID NO 23
<211> LENGTH: 21
<212> TYPE: DNA
<213> ORGANISM: Homo sapiens

<400> SEQUENCE: 23

ggcagcagac taccaaacag t                                                21


<210> SEQ ID NO 24
<211> LENGTH: 601
<212> TYPE: DNA
<213> ORGANISM: Homo sapiens

<400> SEQUENCE: 24

agttctataa agttactaat agggaaatat ataaagtgga aaaagctgtt tataaaagtc      60

tgagtaaatg actatatatg tacatagata tgattttgaa aagaacttaa taggatacac     120

aaacattaat aagaatgctt atttctgagt aattaagggg cgattttgtt gtattcctta     180

tacattttaa atgttttaat ccaaaatttt ttacagtgag tatgtattat cttttgtcat     240

ctgaaaaata acacaaataa ataagttaaa atagaattaa ctgaatttgt acaaatcggg     300

saagataagg gtgcccctgt tttctctatt catgccaccg ctaccactgt ttagactatt     360

ggtcataatt tttttctcac ctgcaaatat ctccttgcct gttactttct cttcagtttc     420

tttccccatt attcattctc tctgaaaata ttaggttgga gcaaacgtta attgcatttt     480

tgcattgttg gaatttgctg tttgatattg gaatacattc ttaaataaat gtggttatgt     540

tatacatcat tttaatgggc atttctcgct ttatgttttt ttgctaatga cttactactt     600

g                                                                     601
```